(12) United States Patent
Gu et al.

(10) Patent No.: US 11,396,495 B2
(45) Date of Patent: Jul. 26, 2022

(54) AMINE COMPOUND FOR INHIBITING SSAO/VAP-1 AND USE THEREOF

(71) Applicant: SUNSHINE LAKE PHARMA CO., LTD., Guangdong (CN)

(72) Inventors: Zheng Gu, Dongguan (CN); Jianhao Li, Dongguan (CN); Zheng Li, Dongguan (CN); Weihua Wang, Dongguan (CN); Haoxiong Qin, Dongguan (CN); Xuli Wang, Dongguan (CN); Jianyu Liu, Dongguan (CN); Yingjun Zhang, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 0 days.

(21) Appl. No.: 16/770,474

(22) PCT Filed: Dec. 28, 2018

(86) PCT No.: PCT/CN2018/124953
§ 371 (c)(1),
(2) Date: Jun. 5, 2020

(87) PCT Pub. No.: WO2019/129213
PCT Pub. Date: Jul. 4, 2019

(65) Prior Publication Data
US 2020/0377461 A1 Dec. 3, 2020

(30) Foreign Application Priority Data
Dec. 29, 2017 (CN) .......................... 201711469017.1

(51) Int. Cl.
| | | |
|---|---|---|
| *C07D 215/227* | (2006.01) | |
| *C07D 217/24* | (2006.01) | |
| *C07D 239/88* | (2006.01) | |
| *C07D 279/02* | (2006.01) | |
| *C07D 401/04* | (2006.01) | |
| *C07D 405/04* | (2006.01) | |
| *C07D 405/06* | (2006.01) | |
| *C07D 413/06* | (2006.01) | |
| *C07D 417/04* | (2006.01) | |

(52) U.S. Cl.
CPC ....... *C07D 215/227* (2013.01); *C07D 217/24* (2013.01); *C07D 239/88* (2013.01); *C07D 279/02* (2013.01); *C07D 401/04* (2013.01); *C07D 405/04* (2013.01); *C07D 405/06* (2013.01); *C07D 413/06* (2013.01); *C07D 417/04* (2013.01)

(58) Field of Classification Search
CPC ............ C07D 215/227; C07D 217/24; C07D 239/88; C07D 279/02; C07D 401/04; C07D 405/04; C07D 405/06; C07D 413/06; C07D 417/04
See application file for complete search history.

(56) References Cited

U.S. PATENT DOCUMENTS

| | | | |
|---|---|---|---|
| 4,943,593 | A | 7/1990 | Palfreyman et al. |
| 4,965,288 | A | 10/1990 | Palfreyman et al. |
| 5,021,456 | A | 6/1991 | Palfreyman et al. |
| 5,182,297 | A | 1/1993 | Palfreyman et al. |
| 5,252,608 | A | 10/1993 | Palfreyman et al. |
| 8,426,587 | B2 | 4/2013 | McDonald et al. |
| 9,302,986 | B2 | 4/2016 | Deodhar et al. |
| 9,815,782 | B2 | 11/2017 | Deodhar et al. |
| 10,160,723 | B2 | 12/2018 | Deodhar et al. |
| 2006/0025438 | A1 | 2/2006 | Salter-Cid et al. |
| 2007/0078157 | A1 | 4/2007 | Salter-Cid et al. |
| 2007/0293548 | A1 | 12/2007 | Wang et al. |
| 2009/0203764 | A1 | 8/2009 | Wang et al. |
| 2011/0269811 | A1 | 11/2011 | Wang et al. |
| 2012/0172392 | A1 | 7/2012 | Salter-Cid et al. |
| 2019/0071396 | A1 | 3/2019 | Deodhar et al. |
| 2020/0087248 | A1 | 3/2020 | Zhu et al. |
| 2021/0070750 | A1 * | 3/2021 | Wu ...................... C07D 213/82 |

FOREIGN PATENT DOCUMENTS

| | | | | |
|---|---|---|---|---|
| WO | WO-2018196677 A1 * | 11/2018 | ............. | A61K 31/18 |
| WO | WO-2019101086 A1 * | 5/2019 | ............. | A61K 31/437 |
| WO | WO-2020069330 A2 * | 4/2020 | ............. | C07D 235/12 |
| WO | WO-2020233583 A1 * | 11/2020 | ............. | C07D 401/04 |

OTHER PUBLICATIONS

National Center for Biotechnology Information. PubChem Substance Record for SID 164207142, 16064-25-8, Source: AstaTech, Inc., https://pubchem.ncbi.nlm.nih.gov/substance/164207142. Available Oct. 25, 2013. (Year: 2013).*
Issa; Curr Drug Metab. 2017, 18, 556-565. doi:10.2174/1389200218666170316093301. (Year: 2017).*
Horvath, Sci. Rep. 2017, 7, 39863. doi: 10.1038/srep39863 (Year: 2017).*
Schilter; Respiratory Research 2015, 16, 42. DOI: 10.1186/s12931-015-0200-z (Year: 2015).*
Sole; Biol Cell 2011, 103, 543-557. doi: 10.1042/BC20110049 (Year: 2011).*
Ucar; Turk J Biochem 2004, 29, 247-254. (Year: 2004).*

(Continued)

*Primary Examiner* — Daniel R Carcanague
(74) *Attorney, Agent, or Firm* — Oliff PLC

(57) ABSTRACT

An amine compound serving as a semicarbazide-sensitive amine oxidase (SSAO) and/or vascular adhesion protein-1 (VAP-1) inhibitor, a pharmaceutical composition, and an application thereof in medicines that can be used for treating inflammation and/or inflammation related diseases, diabetes and/or a disease related diabetes, psychiatric disorder, ischemic disease, vascular disease, fibrosis, or tissue transplant rejection.

22 Claims, No Drawings

(56) References Cited

OTHER PUBLICATIONS

Mar. 28, 2019 Search Report issued in International Patent Application No. PCT/CN2018/124953.
Mar. 28, 2019 Written Opinion of the International Searching Authority issued in International Patent Application No. PCT/CN2018/124953.

* cited by examiner

AMINE COMPOUND FOR INHIBITING SSAO/VAP-1 AND USE THEREOF

CROSS-REFERENCE TO RELATED APPLICATION

This application claims the priority and benefits of Chinese Patent Application No. 201711469017.1, filed with the State Intellectual Property Office of China on Dec. 29, 2017, which is incorporated herein by reference in its entirety.

FIELD OF THE INVENTION

The invention belongs to the pharmaceutical field, specifically, it relates to an amine compound as an inhibitor of semicarbazide sensitive amine oxidase (SSAO) and/or vascular adhesion protein-1 (VAP-1), preparation method thereof, a pharmaceutical composition containing the compound and pharmaceutical uses of the compound or pharmaceutical composition thereof. More in particular, the invention relates to the compound having Formula (I) or a pharmaceutically acceptable salt thereof, or a stereoisomer, a geometric isomer, and a pharmaceutical composition containing the compound, further relates to use of the compound and pharmaceutical composition in the manufacture of a medicament for preventing, treating or lessening inflammation and/or a disease related inflammation, diabetes and/or a disease related diabetes, a mental disorder, an ischemic disease, a vascular disease, fibrosis or tissue transplant rejection.

BACKGROUND OF THE INVENTION

Amine oxidase (AO) is a kind of protein with special biological functions, which exists widely in organisms, for example, in higher animals such human and microbial cells. It can metabolize various endogenous or exogenous monoamines, diamines and polyamines. There are two main kinds of amine oxidases that are well known. One is copper-containing amine oxidases, which mainly include semicarbazide-sensitive amine oxidase (SSAO) and diamine oxidase (DAO); the other is flavin-containing oxidases, which mainly include monoamine oxidase and polyamine oxidase. Wherein semicarbazide-sensitive amine oxidase (SSAO) is an amine oxidase which contains divalent copper ions, takes 6-hydroxydopoquinone as coenzyme, and is particularly sensitive to semicarbazide, mainly exists in the form of dimer. Diamine oxidase (DAO) is mainly expressed in kidney, placenta, intestine and seminal vesicle (Elmore et al, 2002). It only acts on diamine, especially histamine, so it is also called histamine oxidase. Monoamine Oxidase A (MAO-A) and Monoamine Oxidase B (MAO-B) are present in the mitochondria of most cell types and use covalently bound flavin adenine dinucleotide (FAD) as the cofactor. Polyamine oxidase is another FAD-dependent amine oxidase which oxidatively deaminates spermine and spermidine. SSAO is different from MAO-A and MAO-B in terms of their substrates, inhibitors, cofactors, subcellular localization and function, it is a copper dependent amine oxidase that uses substances other than FAD, such as trihydroxyphenylalanine quinone (TPQ), as cofactors.

SSAO widely exists in mammalian tissues containing rich vascular, mainly in two forms, one is soluble form, mainly exists in circulating blood; the other is membrane binding form, widely distributes in organs and tissues, especially in fat cells, vascular endothelial cells and smooth muscle cells. SSAO is a multifunctional enzyme, and its pathophysiological functions vary with the tissue distribution of SSAO. In adipocytes and smooth muscle cells, SSAO can promote the transference of glucose transporter 4 (GLUT4) from adipocytes to cell membrane, and then regulate glucose transport. In endothelial cells, SSAO exists in the form of vascular adhesion protein-1 (VAP-1), which mediates the adhesion and exudation of leukocytes and endothelial cells and plays a role in inflammatory.

VAP-1 is an endothelial adhesion molecule with dual functions. On the one hand, it is an adhesion molecule of lymphocytes, which promotes the adhesion of lymphocytes to vascular endothelium; on the other hand, VAP-1 has the function of enzyme, which can catalyze the primary amine convert to the corresponding aldehyde. VAP-1 is encoded by AOC3 gene located on human chromosome 17. VAP-1 protein may exist in plasma as solute, and also may exist on the surface of endothelial cells, adipocytes and smooth muscle cells in membrane bound form. Cloning of VAP-1 antigen revealed that it belongs to semicarbazide sensitive amine oxidase (Smith D. J, Salmi m, Bono P, et al. *J I. J expmed*, 1998, 188 (1): 17-27), which has the same structure as SSAO. Therefore, in recent years, researchers usually study SSAO by equating it with VAP-1. Therefore, the present invention describes the protein as SSAO/VAP-1

Inflammation is the first response of the immune system to infection or irritation. The movement of leukocytes into tissue circulation is important for this process. Inappropriate inflammatory response can lead to local inflammation of other healthy tissues, which can lead to diseases such as rheumatoid arthritis, inflammatory bowel disease, multiple sclerosis, asthma, chronic obstructive pulmonary disease (COPD), eczema, psoriasis, etc. Leukocytes first adhere to the endothelium by binding with adhesion molecules before they pass through the vessel wall. Membrane-bound SSAO/VAP-1 is abundantly expressed in vascular endothelial cells such as high-efficiency vein endothelial cells (HVE) of lymphoid organs, and also expressed in hepatic sinusoidal endothelial cells (HSEC), smooth muscle cells and adipocytes. SSAO/VAP-1 contains sialic acid, which can induce cell adhesion, regulate leukocyte transport, participate in granulocyte exosmosis, and increase its level in the process of inflammation. The migration of neutrophils from blood to an inflammatory site is realized through the combination of adhesion molecules and vascular endothelial cells. It was found that the SSAO/VAP-1 activity in vivo of pneumonia transgenic mice overexpressing SSAO/VAP-1 was increased, the accumulation of tissue protein-formaldehyde was formed, and the inflammatory cells in bronchoalveolar lavage fluid increased significantly When SSAO/VAP-1 selective inhibitor was used to inhibit its activity, neutrophils, macrophage inflammatory protein 1-α and tumor necrosis factor-α in bronchoalveolar lavage fluid were reduced significantly, indicating that the deamination mediated by SSAO/VAP-1 has a significant effect on the occurrence and development of pneumonia (Smith D J, Salmi M, Bono P, et al, *J Exp Med*, 1998, 188: 17-27).

In the glucose transport system, insulin stimulates uptake and utilization of glucose by insulin sensitive tissues such as adipose tissue, myocardium, skeletal muscle by promoting the transfer of glucose transporter (GLUT) from the interior of the cell to its cell membrane. GLUT4 is an important GLUT subtype involved in glucose transport, which is mainly stored in the cytoplasm in the form of vesicles. In the study of the mechanism of SSAO/VAP-1 promoting glucose transportation and GLUT4 transference in adipocytes, Enrique-Tarancon et al. found that SSAO/VAP-1 in rat adipocytes was mainly expressed on the membrane surface of adipocytes in the form of membrane binding, and 18%-24% SSAO/VAP-1 in rat adipocytes, 3T3-L1 adipocytes and GLUT4 vesicles in rat skeletal muscle cells (Enrique-Tarancon G, Marti L, Morin N, et al. *J Biol Chem,* 1998, 273(14): 8025-8032). Mercader et al. administered FVB/N male mice with an inhibitor of SSAO/VAP-1 carbamide in drinking water for a long time, which found that the body mass index and body mass of FVB/N mice decreased by 31% and 15%, indicating that SSAO/VAP-1 inhibitor can inhibit fat deposition, reduce body mass and play an important role in regulating fat metabolism (Mereader J, Iffiu-Soltesz Z, Bour S, et al, *J Obes,* 2011, 2011:475-786).

The thickness of elastic layer of vascular wall is positively correlated with the ratio of SSAO/VAP-1 to elastin, which indicates that SSAO/VAP-1 may be involved in the organization of elastic fibers, and the characteristics and quantity of elastic fibers are important factors affecting the mechanical properties of arterial walls and the differentiation of vascular smooth muscle cells. The increase of SSAO/VAP-1 activity can lead to the destruction of the elastic fiber structure of aortic membrane, accompanied by the decrease of the grade of maturity of the elastin component and the increase of collagen, and finally the expansion of the aorta. The overexpression of SSAO/VAP-1 in smooth muscle can reduce arterial elasticity and impair the blood pressure regulating ability. The study found that although rodents are usually less prone to atherosclerosis, some mouse breeds, such as C57BL/6 mice, still have atherosclerotic plaques after administration of high cholesterol diet causing atherosclerosis. The activity of SSAO/VAP-1 was significantly increased in C57BL/6 mice which were prone to atherosclerosis. The deamination mediated by SSAO/VAP-1 may exist in the process of atherosclerosis and vascular disease.

In conclusion, SSAO/VAP-1 inhibitors have enzyme and adhesion activity and a significant correlation with incremental regulation in many inflammatory disorders, which make it a therapeutic target for all of the above diseases, and it has a good prospect of pharmaceutical development.

SUMMARY OF THE INVENTION

The present invention provides a novel compound having a good inhibition of SSAO/VAP-1 activity, the compound and a pharmaceutical composition thereof can be used in the manufacture of a medicament for preventing, treating or lessening inflammation and/or a disease related inflammation, diabetes and/or a disease related diabetes, a mental disorder, an ischemic disease, a vascular disease, fibrosis or tissue transplant rejection, in particular for preventing, treating or lessening nonalcoholic steatohepatitis in a patient.

In one aspect, provided herein is a compound having Formula (I) or a stereoisomer, a geometric isomer, a tautomer, an N-oxide, a solvate, a metabolite, a pharmaceutically acceptable salt or a prodrug thereof,

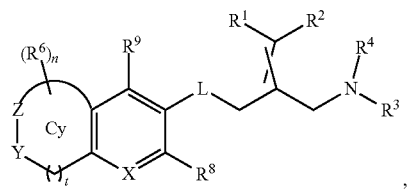

(I)

wherein
Y is —CH$_2$—, —S(=O)—, —S(=O)$_2$— or —C(=O)—;
Z is —N(R$^5$)— or —N=;
X is —N= or —C(R$^7$)—;
L is —O—, —S— or —NH—;
ring Cy is 5- to 8-membered heterocyclyl or 5- to 8-membered heteroaryl;
each R$^6$ is independently H;
R$^5$ is H, D, F, Cl, Br, I, CN, NO$_2$, =O, —C(=O)R$^a$, —C(=O)OR$^b$, —C(=O)NR$^c$R$^d$, —SR$^e$, —S(=O)$_2$R$^e$, —S(=O)R$^e$, —S(=O)$_2$NR$^c$R$^d$, —NR$^f$C(=O)R$^a$, —NR$^f$S(=O)$_2$R$^e$, —NR$^c$R$^d$, —OR$^b$, R$^b$O—C$_{1-4}$ alkylene, R$^b$O—C(=O)—C$_{1-4}$ alkylene, R$^d$R$^c$N—C$_{1-4}$ alkylene, C$_{1-6}$ haloalkyl, C$_{1-6}$ alkyl, C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, 5- to 6-membered heteroaryl or (5- to 10-membered heteroaryl)-C$_{1-4}$ alkylene, wherein each of the C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, 5- to 6-membered heteroaryl and (5- to 10-membered heteroaryl)-C$_{1-4}$ alkylene is independently unsubstituted or substituted with 1, 2, 3 or 4 substituents, the substituent is independently selected from D, F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, C$_{6-10}$ aryl, 5- to 10-membered heteroaryl, C$_{1-6}$ haloalkyl, C$_{1-6}$ alkoxy, C$_{1-6}$ alkylamino or C$_{1-6}$ haloalkoxy; each of the C$_{1-6}$ alkyl and C$_{6-10}$ aryl is independently substituted with 1, 2, 3 or 4 substituents, the substituent is independently selected from F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, 5- to 10-membered heteroaryl, C$_{1-6}$ haloalkyl, C$_{1-6}$ alkoxy, C$_{1-6}$ alkylamino or C$_{1-6}$ haloalkoxy;
each of R$^8$ and R$^9$ is independently H, D, Br, I, CN, NO$_2$, —C(=O)R$^a$, —C(=O)OR$^b$, —C(=O)NR$^c$R$^d$, —OH, NH$_2$, R$^b$O—C$_{1-4}$ alkylene, R$^d$R$^c$N—C$_{1-4}$ alkylene, C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl or 5- to 8-membered heteroaryl, wherein each of the C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl and 5- to 8-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
R$^7$ is H, D, F, Cl, Br, I, CN, NO$_2$, —C(=O)R$^a$, —C(=O)OR$^b$, —C(=O)NR$^c$R$^d$, —OH, NH$_2$, R$^b$O—C$_{1-4}$ alkylene, R$^d$R$^c$N—C$_{1-4}$ alkylene, C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl or 5- to 8-membered heteroaryl, wherein each of the C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl and 5- to 8-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
R$^1$ is H, D, F, Cl, Br, I, C$_{1-6}$ alkyl, —C(=O)OR$^b$, —C(=O)R$^a$, —OC(=O)R$^a$, —OC(=O)OR$^b$, —NR$^f$C(=O)R$^a$, —NR$^f$S(=O)$_2$R$^e$, —C(=O)NR$^c$R$^d$, —S(=O)$_2$NR$^c$R$^d$, —S(=O)$_2$R$^e$, —SR$^e$ or —S(=O)R$^e$, wherein the C$_{1-6}$ alkyl is unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

$R^2$ is F, Cl, Br, I, $C_{1-6}$ alkyl, —C(=O)$OR^b$, —C(=O)$R^a$, —OC(=O)$R^a$, —OC(=O)$OR^b$, —$NR^f$C(=O)$R^a$, —$NR^f$S(=O)$_2R^e$, —C(=O)$NR^cR^d$, —S(=O)$_2NR^cR^d$, —S(=O)$_2R^e$, —$SR^e$ or —S(=O)$R^e$, wherein the $C_{1-6}$ alkyl is unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

each of $R^3$ and $R^4$ is independently H, D, $C_{1-6}$ alkyl, $C_{1-6}$ haloalkyl, $C_{3-6}$ cycloalkyl, 3- to 6-membered heterocyclyl, $C_{6-10}$ aryl, 5- to 6-membered heteroaryl or

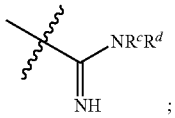

;

wherein each of the $C_{1-6}$ alkyl, $C_{1-6}$ haloalkyl, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

or, $R^3$ and $R^4$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

each $R^a$, $R^b$, $R^c$, $R^d$, $R^e$ and $R^f$ is independently H, D, —OH, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, wherein each of the $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

or, $R^c$ and $R^d$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

n is 0, 1, 2, 3 or 4;

t is 0, 1, 2, 3 or 4;

with the exception of the compounds:

6-[(E)-2-(aminomethyl)-3-fluoro-allyloxy]-3,4-dihydro-2H-isoquinolin-1-one,

6-[(Z)-2-(aminomethyl)-3-fluoro-allyloxy]-3,4-dihydro-2H-isoquinolin-1-one,

7-[(E)-2-(aminomethyl)-3-fluoro-allyloxy]-3,4-dihydro-2H-isoquinolin-1-one,

7-[(Z)-2-(aminomethyl)-3-fluoro-allyloxy]-3,4-dihydro-2H-isoquinolin-1-one,

5-[(Z)-2-(aminomethyl)-3-fluoro-allyloxy]isoindolin-1-one,

5-[(E)-2-(aminomethyl)-3-fluoro-allyloxy]isoindolin-1-one,

7-[(E)-2-(aminomethyl)-3-fluoro-allyloxy]-2,3,4,5-tetrahydro-2-benzoazepin-1-one and 7-[(Z)-2-(aminomethyl)-3-fluoro-allyloxy]-2,3,4,5-tetrahydro-2-benzoazepin-1-one.

In other embodiments, wherein ring Cy is 5-membered heterocyclyl, 6-membered heterocyclyl, 5-membered heteroaryl or 6-membered heteroaryl.

In other embodiments, wherein ring Cy is

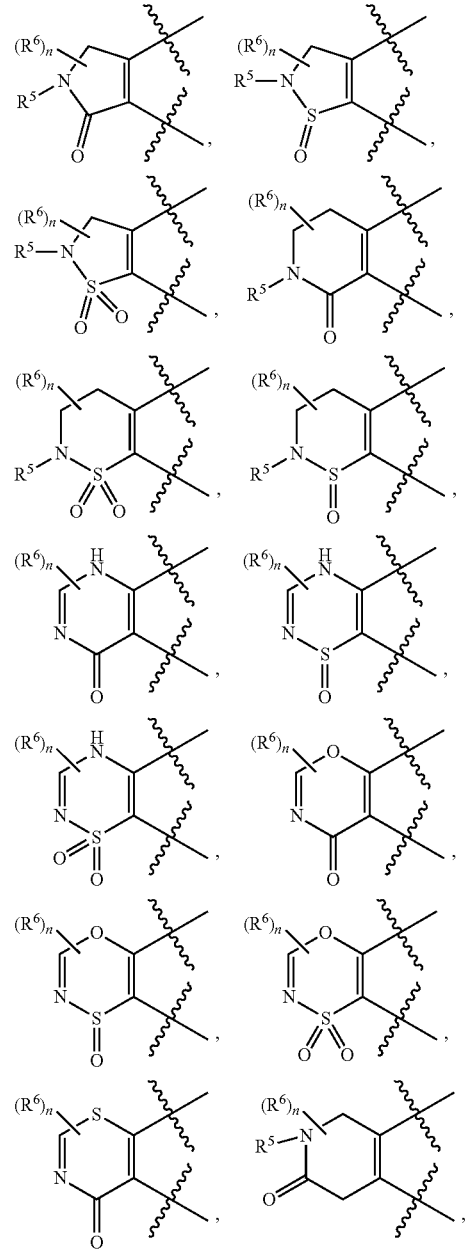

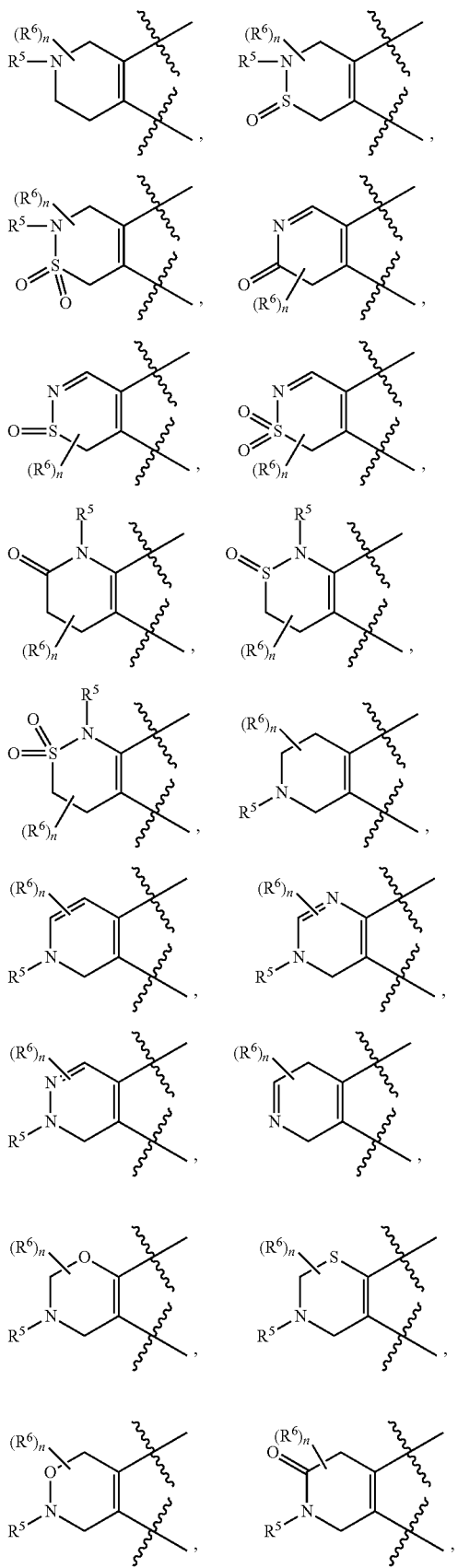

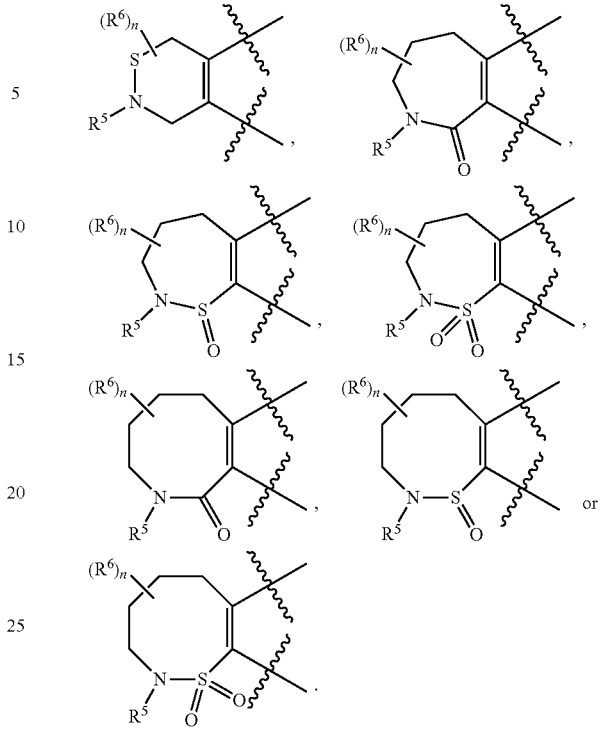

In other embodiments, wherein $R^5$ is H, D, F, Cl, Br, I, CN, $NO_2$, =O, —C(=O)$R^a$, —C(=O)O$R^b$, —C(=O)N$R^cR^d$, —S$R^e$, —S(=O)$_2R^e$, —S(=O)$R^e$, —S(=O)$_2$N$R^cR^d$, —N$R^f$C(=O)$R^a$, —N$R^f$S(=O)$_2R^e$, —N$R^cR^d$, —O$R^b$, $R^b$O—$C_{1-2}$ alkylene, $R^b$O—C(=O)—$C_{1-2}$ alkylene, $R^dR^c$N—$C_{1-2}$ alkylene, $C_{1-4}$ haloalkyl, $C_{1-4}$ alkyl, $C_{2-4}$ alkenyl, $C_{2-4}$ alkynyl, $C_{3-6}$ cycloalkyl-$C_{1-2}$ alkylene, 3- to 6-membered heterocyclyl, (3- to 6-membered heterocyclyl)-$C_{1-2}$ alkylene, $C_{6-10}$ aryl, 5- to 6-membered heteroaryl or (5- to 6-membered heteroaryl)-$C_{1-2}$ alkylene, wherein each of the $C_{2-4}$ alkenyl, $C_{2-4}$ alkynyl, $C_{3-6}$ cycloalkyl-$C_{1-2}$ alkylene, 3- to 6-membered heterocyclyl, (3- to 6-membered heterocyclyl)-$C_{1-2}$ alkylene, 5- to 6-membered heteroaryl and (5- to 6-membered heteroaryl)-$C_{1-2}$ alkylene is independently unsubstituted or substituted with 1, 2, 3 or 4 substituents, the substituent is independently selected from D, F, Cl, Br, I, CN, $NO_2$, —O$R^b$, —N$R^cR^d$, —C(=O)O$R^b$, $C_{1-4}$ alkyl, $C_{3-6}$ cycloalkyl, 3- to 6-membered heterocyclyl, $C_{6-10}$ aryl, 5- to 6-membered heteroaryl, $C_{1-4}$ haloalkyl, $C_{1-4}$ alkoxy, $C_{1-4}$ alkylamino or $C_{1-4}$ haloalkoxy; each of the $C_{1-4}$ alkyl and $C_{6-10}$ aryl is independently substituted with 1, 2, 3 or 4 substituents, the substituent is independently selected from D, F, Cl, Br, I, CN, $NO_2$, —O$R^b$, —N$R^cR^d$, —C(=O)O$R^b$, $C_{1-4}$ alkyl, $C_{3-6}$ cycloalkyl, 3- to 6-membered heterocyclyl, 5- to 6-membered heteroaryl, $C_{1-4}$ haloalkyl, $C_{1-4}$ alkoxy, $C_{1-4}$ alkylamino or $C_{1-4}$ haloalkoxy;

In still other embodiments, wherein $R^5$ is H, D, F, Cl, Br, I, CN, $NO_2$, =O, —C(=O)$R^a$, —C(=O)OH, —C(=O)OCH$_3$, —C(=O)OCH$_2$CH$_3$, —C(=O)OCH$_2$CH$_2$CH$_3$, —C(=O)OCH(CH$_3$)$_2$, —C(=O)NH$_2$, —S$R^e$, —S(=O)$_2R^e$, —S(=O)$R^e$, —S(=O)$_2$N$R^cR^d$, —NHC(=O)$R^a$, —NHS(=O)$_2R^e$, NH$_2$, —OH, $R^b$O—$C_{1-2}$ alkylene, $R^b$O—C(=O)—$C_{1-2}$ alkylene, trifluoromethyl, methyl, ethyl, n-propyl, i-propyl, vinyl, propynyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-$C_{1-2}$ alkylene, phenyl, naphthyl, $C_{6-10}$ aryl-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl or (5- to 6-membered heteroaryl)-$C_{1-2}$ alkylene, wherein each of the vinyl, propynyl, $C_{3-6}$ cycloalkyl-$C_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-$C_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl and (5- to 6-membered heteroaryl)-$C_{1-2}$ alkylene is independently unsubstituted or substituted with 1, 2, 3 or 4 substituents, the substituent is independently selected from D, F, Cl, Br, I, CN, $NO_2$, —OH, —$OCH_3$, —$OCH_2CH_3$, —O-methylene-phenyl, $NH_2$, —C(=O)OH, —C(=O)$OCH_3$, —C(=O)$OCH_2CH_3$, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy; each of the methyl, ethyl, n-propyl, i-propyl, phenyl and naphthyl is independently unsubstituted or substituted with 1, 2, 3 or 4 substituents, the substituent is independently selected from D, F, Cl, Br, I, CN, $NO_2$, —OH, —$OCH_3$, —$OCH_2CH_3$, —O-methylene-phenyl, $NH_2$, —C(=O)OH, —C(=O)$OCH_3$, —C(=O)$OCH_2CH_3$, —C(=O)$OCH_2CH_2CH_3$, —C(=O)OCH($CH_3$)$_2$, —C(=O)$OCH_2CH_2CH_2CH_3$, —C(=O)OC($CH_3$)$_3$, —C(=O)$OCH_2$Ph, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy.

In other embodiments, each of $R^8$ and $R^9$ is independently H, D, Br, I, CN, $NO_2$, —C(=O)$R^a$, —C(=O)$OR^b$, —C(=O)$NR^cR^d$, —OH, $NH_2$, $R^bO$—$C_{1-2}$ alkylene, $R^dR^cN$—$C_{1-2}$ alkylene, $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl or 5- to 6-membered heteroaryl, wherein each of the $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, $NO_2$, —OH, $NH_2$, $C_{1-4}$ alkyl, $C_{1-4}$ haloalkyl, $C_{1-4}$ alkoxy, $C_{1-4}$ alkylamino or $C_{1-4}$ haloalkoxy;

In other embodiments, $R^7$ is H, D, F, Cl, Br, I, CN, $NO_2$, —C(=O)$R^a$, —C(=O)$OR^b$, —C(=O)$NR^cR^d$, —OH, $NH_2$, $R^bO$—$C_{1-2}$ alkylene, $R^dR^cN$—$C_{1-2}$ alkylene, $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl or 5- to 6-membered heteroaryl, wherein each of the $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, $NO_2$, —OH, $NH_2$, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, each of $R^8$ and $R^9$ is independently H, D, Br, I, CN, $NO_2$, —C(=O)$R^a$, —C(=O)OH, —C(=O)$OCH_3$, —C(=O)$OCH_2CH_3$, —C(=O)$NH_2$, —OH, $NH_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, $NO_2$, —OH, $NH_2$, methyl, ethyl, n-propyl, i-propyl, trifluoromethyl, methoxy, ethoxy, methylamino, trifluoromethoxy or difluoromethoxy.

In still other embodiments, $R^7$ is H, D, F, Cl, Br, I, CN, $NO_2$, —C(=O)$R^a$, —C(=O)OH, —C(=O)$OCH_3$, —C(=O)$OCH_2CH_3$, —C(=O)$NH_2$, —OH, $NH_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, $NO_2$, —OH, $NH_2$, methyl, ethyl, n-propyl, i-propyl, trifluoromethyl, methoxy, ethoxy, methylamino, trifluoromethoxy or difluoromethoxy.

In still other embodiments, $R^1$ is H, D, F, Cl, Br, I, methyl, ethyl, i-propyl, n-propyl, —C(=O)OH, —C(=O)$OCH_3$, —C(=O)$OCH_2CH_3$, —C(=O)$R^a$, —OC(=O)$R^a$ or —OC(=O)$OR^a$, wherein each of the methyl, ethyl, i-propyl and n-propyl is independently unsubstituted or substituted with 1, 2, 3 or 4 substituents, the substituent is independently selected from D, F, Cl, Br, I, CN, $NO_2$, —OH, $NH_2$, methyl, ethyl, n-propyl, i-propyl.

In still other embodiments, $R^2$ is F, Cl, Br, I, methyl, ethyl, i-propyl, n-propyl, —C(=O)OH, —C(=O)$OCH_3$, —C(=O)$OCH_2CH_3$, —C(=O)$R^a$, —OC(=O)$R^a$ or —OC(=O)$OR^a$, wherein each of the methyl, ethyl, i-propyl and n-propyl is independently unsubstituted or substituted with 1, 2, 3 or 4 substituents, the substituent is independently selected from D, F, Cl, Br, I, CN, $NO_2$, —OH, $NH_2$, methyl, ethyl, n-propyl, i-propyl.

In other embodiments, wherein each of $R^3$ and $R^4$ is independently H, D, methyl, ethyl, n-propyl, i-propyl, $C_{1-4}$ haloalkyl, cyclopropyl, cyclobutyl, 5- to 6-membered heterocyclyl, phenyl or 5- to 6-membered heteroaryl or

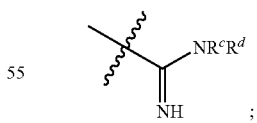

wherein each of the methyl, ethyl, n-propyl, i-propyl, $C_{1-4}$ haloalkyl, cyclopropyl, cyclobutyl, 5- to 6-membered heterocyclyl, phenyl or 5- to 6-membered heteroaryl is independently unsubstituted or substituted with 1, 2, 3 or 4 substituents, the substituent is independently selected from D, F, Cl, Br, I, CN, —OH, $NH_2$, methyl, ethyl, n-propyl, i-propyl, trifluoromethyl, methoxy or ethoxy;

or, $R^3$ and $R^4$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

In other embodiments, wherein each $R^a$, $R^b$, $R^c$, $R^d$, $R^e$ and $R^f$ is independently H, D, —OH, trifluoromethyl, difluoromethyl, methyl, ethyl, i-propyl, n-propyl, n-butyl, t-butyl, methoxy, ethoxy, cyclopropyl, cyclobutyl, cyclopentyl, cyclohexyl, $C_{3-6}$ cycloalkyl-$C_{1-2}$ alkylene, 5- to 6-membered heterocyclyl, (5- to 6-membered heterocyclyl)-$C_{1-2}$ alkylene, phenyl, phenyl-methylene, 5- to 6-membered heteroaryl or (5- to 6-membered heteroaryl)-$C_{1-2}$ alkylene, wherein each of the difluoromethyl, methyl, ethyl, i-propyl, n-propyl, n-butyl, t-butyl, methoxy, ethoxy, cyclopropyl, cyclobutyl, cyclopentyl, cyclohexyl, $C_{3-6}$ cycloalkyl-$C_{1-2}$ alkylene, 5- to 6-membered heterocyclyl, (5- to 6-membered heterocyclyl)-$C_{1-2}$ alkylene, phenyl, phenyl-methylene, 5- to 6-membered heteroaryl or (5- to 6-membered heteroaryl)-$C_{1-2}$ alkylene is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

or, $R^c$ and $R^d$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy.

In other embodiments, the present invention provides a compound having Formula (II) or a stereoisomer, a geometric isomer, a tautomer, an N-oxide, a solvate, a metabolite, a pharmaceutically acceptable salt or a prodrug thereof,

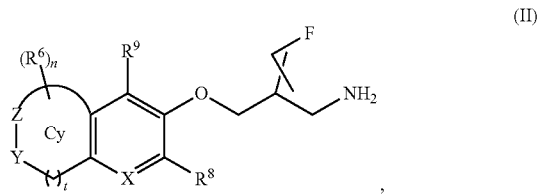

(II)

wherein ring Cy, $R^6$, $R^8$, $R^9$, X, Y, Z, t and n are as defined herein.

In other embodiments, wherein the pharmaceutically acceptable salt is hydrochloride, hydrobromide or mesylate.

In other aspect, provided herein is a pharmaceutical composition comprising the compound disclosed herein.

In some embodiments, the pharmaceutical composition disclosed herein further comprises a pharmaceutically acceptable carrier, excipient, adjuvant, medium or a combination thereof.

In other aspect, provided herein is use of the compound or the pharmaceutical composition disclosed herein in the manufacture of a medicament for inhibiting SSAO/VAP-1.

In other aspect, provided herein is use of the compound or the pharmaceutical composition disclosed herein in the manufacture of a medicament for preventing, treating or lessening a disease related to SSAO/VAP-1 protein or regulated by SSAO/VAP-1 in a subject.

In other aspect, provided herein is a method of inhibiting SSAO/VAP-1 comprising administering to the subject a therapeutically effective amount of the compound or the pharmaceutical composition disclosed herein.

In other aspect, provided herein is a method of preventing, treating or lessening a disease related to SSAO/VAP-1 protein or regulated by SSAO/VAP-1 comprising administering to the subject a therapeutically effective amount of the compound or the pharmaceutical composition disclosed herein.

In other aspect, provided herein is the compound or the pharmaceutical composition disclosed herein for use in inhibiting SSAO/VAP-1.

In other aspect, provided herein is the compound or the pharmaceutical composition disclosed herein for use in preventing, treating or lessening a disease related to SSAO/VAP-1 protein or regulated by SSAO/VAP-1.

In some embodiments, wherein the disease related to SSAO/VAP-1 protein or regulated by SSAO/VAP-1 is inflammation and/or a disease related inflammation, diabetes and/or a disease related diabetes, a mental disorder, an ischemic disease, a vascular disease, fibrosis or tissue transplant rejection.

In other embodiments, wherein the inflammation and/or a disease related inflammation disclosed herein is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis.

In other embodiments, wherein the diabetes and/or a disease related diabetes disclosed herein is type I diabetes, type II diabetes, X syndrome, diabetic retinopathy, diabetic nephropathy, diabetic neuropathy or diabetic macular edema.

In other embodiments, wherein the mental disorder disclosed herein is severe depression, bipolar depression or attention deficit hyperactivity disorder.

In other embodiments, wherein the ischemic disease disclosed herein is apoplexia and/or a complication thereof, myocardial infarction and/or a complication thereof or damage of inflammatory cells to tissues after apoplexia.

In other embodiments, wherein the fibrosis disclosed herein is hepatic fibrosis, cystic fibrosis, renal fibrosis, idiopathic pulmonary fibrosis or radiation-induced fibrosis.

In other embodiments, wherein the vascular disease disclosed herein is atherosclerosis, chronic heart failure or congestive heart failure.

In still other embodiments, wherein the arthritis disclosed herein is osteoarthritis, rheumarthritis, rheumatoid arthritis or juvenile rheumatoid arthritis.

In still other embodiments, the systemic inflammatory response syndrome disclosed herein is systemic inflammatory sepsis.

In still other embodiments, the inflammatory bowel disease disclosed herein is irritable bowel syndrome.

In still other embodiments, the hepatopathy disclosed herein is a liver autoimmune disease, autoimmune hepatitis, primary biliary cirrhosis, sclerosing cholangitis, autoimmune cholangitis, an alcoholic liver disease or a non-alcoholic fatty liver disease.

In still other embodiments, the non-alcoholic fatty liver disease disclosed herein is nonalcoholic simple fatty liver, nonalcoholic steatohepatitis, cryptogenic cirrhosis or primary liver cancer related to nonalcoholic fatty liver disease.

In still other embodiments, the respiratory disease disclosed herein is asthma, acute lung injury, acute respiratory distress syndrome, lung inflammation, a chronic obstructive pulmonary disease, bronchitis or bronchiectasis.

In still other embodiments, the eye disease disclosed herein is uveitis, iritis, retinitis, autoimmune ophthalmia, inflammation driven by angiogenesis and/or lymphogenesis, macular degeneration.

In still other embodiments, the skin disease disclosed herein is contact dermatitis, skin inflammation, psoriasis or eczema.

In still other embodiments, the neuritis disclosed herein is Parkinson's disease, Alzheimer's disease, vascular dimentia, multiple sclerosis, chronic multiple sclerosis.

The foregoing merely summarizes certain aspects disclosed herein and is not intended to be limiting in nature. These aspects and other aspects and embodiments are described more fully below.

EXAMPLES

The invention provides an amine compound having SSAO/VAP-1 inhibition activity, a preparation method thereof and a pharmaceutical use. Skilled in the art can learn from this article to properly improve the process parameters to implement the preparation method. Of particular note is that all similar substitutions and modifications to the skilled person is obvious, and they are deemed to be included in scope of the present invention.

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The invention is not limited to the methods and materials described herein, in the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

Unless otherwise stated, the terms of the invention used in specification and claims have the definitions blow.

The term "comprise" is an open expression, it means comprising the contents disclosed herein, but don't exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "unsubstituted or substituted". The term "optional" or "optionally" refers to that a subsequently described event or circumstance may but need not occur, and that the description includes instances where the event or circumstance occurs and instances in which it does not. Generally speaking, unless otherwise indicated, an optionally substituted group may have a substituent at each substitutable position of the group. When more than one position in a given structure can be substituted with more than one substituent selected from a specified group, the substituent may be either the same or different at each position. Wherein the substituent may be, but are not limited to, D, F, Cl, Br, I, CN, $NO_2$, —C(=O)$R^a$, —C(=O)O$R^b$, —C(=O)N$R^cR^d$, —OC(=O)O$R^b$, —OC(=O)$R^a$, —S$R^e$, —S(=O)$_2R^e$, —S(=O)$R^e$, —S(=O)$_2$N$R^cR^d$, —N$R^f$C(=O)$R^a$, —N$R^f$S(=O)$_2R^c$, —O$R^b$, —N$R^cR^d$, $R^b$O-alkylene, $R^dR^c$N-alkylene, alkyl, haloalkyl, haloalkoxy, alkylamino, alkoxy, alkenyl, alkynyl, cycloalkyl, cycloalkyl-alkylene, carbocyclyl, carbocyclyl-alkylene, heterocyclyl, heterocyclyl-alkylene, aryl, aryl-alkylene, heteroaryl, heteroaryl-alkylene and

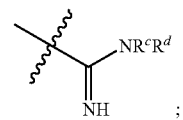

;

wherein each $R^a$, $R^b$, $R^c$, $R^d$, $R^e$ and $R^f$ are as defined herein.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is especially $C_1$ alkyl (methyl), $C_2$ alkyl (ethyl), $C_3$ alkyl, $C_4$ alkyl, $C_5$ alkyl and $C_6$ alkyl disclosed independently, and "5- to 6-membered heteroaryl" refers to 5-membered heteroaryl and 6-membered heteroaryl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "halogen" refers to F (fluorine), Cl (chlorine), Br (bromine), or I (iodine).

The term "alkyl" or "alkyl group" refers to a saturated linear or branched-chain monovalent hydrocarbon radical containing 1 to 20 carbon atoms. Unless otherwise indicated, the alkyl group contains 1-20 carbon atoms; in some embodiments, the alkyl group contains 1-10 carbon atoms; in other embodiments, the alkyl group contains 1-8 carbon atoms; in still other embodiments, the alkyl group contains 1-6 carbon atoms; in yet other embodiments, the alkyl group contains 1-4 carbon atoms; in yet other embodiments, the alkyl group contains 1-2 carbon atoms. The alkyl group containing 1 to 6 carbon atoms described herein is a lower alkyl group.

Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, n-heptyl and n-octyl, etc. The alkyl group may be optionally substituted with one or more substituents disclosed herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. Such examples include methylene (—CH$_2$—), ethylene (including —CH$_2$CH$_2$— or —CH(CH$_3$)—), isopropylene (including —CH(CH$_3$)CH$_2$— or —CH(CH$_3$)CH$_3$—), and the like. Wherein, the alkylene group may be optionally substituted with one or more substituents disclosed herein.

The term "alkenyl" refers to linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. In some embodiments, the alkenyl contains 2 to 8 carbon atoms. In other embodiments, the alkenyl contains 2 to 6 carbon atoms. In still other embodiments, the alkenyl contains 2 to 4 carbon atoms. Some non-limiting examples of the alkenyl include vinyl (—CH=CH$_2$), propenyl (—CH$_2$CH=CH$_2$, —CH=CHCH$_3$), butenyl (—CH=CHCH$_2$CH$_3$, —CH$_2$CH=CHCH$_3$, —CH$_2$CH$_2$CH=CH$_2$, —CH=C(CH$_3$)$_2$, —CH=C(CH$_3$)$_2$, —CH$_2$C(CH$_3$)=CH$_2$), pentenyl (—CH$_2$CH$_2$CH$_2$CH=CH$_2$, —CH$_2$CH$_2$CH=CHCH$_3$, —CH$_2$CH$_2$CH=CHCH$_3$, —CH$_2$CH=CHCH$_2$CH$_3$, —CH=CHCH$_2$CH$_2$CH$_3$, —CH$_2$CH$_2$C(CH$_3$)=CH$_2$, —CH$_2$CH=C(CH$_3$)$_2$, —CH=CHCH(CH$_3$)$_2$, —C(CH$_2$CH$_3$)=CHCH$_3$, —CH(CH$_2$CH$_3$)CH=CH$_2$), and the like.

The term "alkynyl" refers to a linear or branched monovalent hydrocarbon radical containing 2 to 12 carbon atoms, at least one site of unsaturation is a carbon-carbon, sp triple bond. In some embodiments, the alkynyl contains 2 to 8 carbon atoms. In other embodiments, the alkynyl contains 2 to 6 carbon atoms. In still other embodiments, the alkynyl contains 2 to 4 carbon atoms. Some non-limiting examples of the alkynyl group include ethynyl (—C≡CH), 1-propynyl (—C≡C—CH$_3$), 2-propynyl (—CH$_2$C≡CH), 1-butynyl, 2-butynyl, 1-pentynyl, 2-pentynyl, 3-methyl-1-butynyl, 1-hexynyl, 1-heptynyl and 1-octynyl, etc. The alkynyl group may be optionally and independently substituted with one or more substituents disclosed herein.

The term "alkoxy" or "alkyl-oxy" refers to an alkyl group attached to the parent molecular moiety via an oxygen atom, i.e. alkyl-O—, wherein the alkyl group has the definition as described herein. In some embodiments, the alkoxy group contains 1-20 carbon atoms; in some embodiments, the alkoxy group contains 1-10 carbon atoms; in other embodiments, the alkoxy group contains 1-8 carbon atoms; in still other embodiments, the alkoxy group contains 1-6 carbon atoms; in yet other embodiments, the alkoxy group contains 1-4 carbon atoms; in yet other embodiments, the alkoxy group contains 1-3 carbon atoms. Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substituents disclosed herein.

The term "alkylamino" refers to "N-alkylamino" and "N,N-dialkylamino" wherein amino groups are independently substituted with one alkyl radical or two alkyl radicals, respectively. In some embodiments, the alkylamino group is lower alkylamino group having one or two alkyl groups of 1 to 6 carbon atoms attached to nitrogen atom. In other embodiments, the alkylamino group is lower alkylamino group having 1 to 3 carbon atoms. In other embodiments, the alkylamino group is lower alkylamino group having 1 to 2 carbon atoms. Suitable alkylamino radical may be mono or dialkylamino, some non-limiting examples of such group include N-methylamino, N-ethylamino, N,N-dimethylamino and N,N-diethylamino, and the like.

The term "haloalkyl" refers to an alkyl group substituted with one or more halogen atoms. In some embodiments, the haloalkyl group contains 1-10 carbon atoms; in other embodiments, the haloalkyl group contains 1-8 carbon atoms; in still other embodiments, the haloalkyl group contains 1-6 carbon atoms; in yet other embodiments, the haloalkyl group contains 1-4 carbon atoms; in yet other embodiments, the haloalkyl group contains 1-3 carbon atoms. In yet other embodiment, the haloalkyl group contains 1-2 carbon atoms. Some non-limiting examples of the haloalkyl group include, fluoromethyl (—$CH_2F$), difluoromethyl (—$CHF_2$), trifluoromethyl (—$CF_3$), fluoroethyl (—$CHFCH_3$, —$CH_2CH_2F$), difluoroethyl (—$CF_2CH_3$, —$CFHCFH_2$, —$CH_2CHF_2$), pentafluoroethyl, fluoropropyl (—$CHFCH_2CH_3$, —$CH_2CHFCH_3$, —$CH_2CH_2CH_2F$), difluoropropyl (—$CF_2CH_2CH_3$, —$CFHCFHCH_3$, —$CH_2CH_2CHF_2$, —$CH_2CF_2CH_3$, —$CH_2CHFCH_2F$), trifluoropropyl, 1,1-dichloroethyl, 1,2-dichloropropyl, and the like. Wherein, the haloalkyl group may be optionally substituted with one or more substituents disclosed herein.

The term "haloalkoxy" refers to an alkoxy group substituted with one or more halogen atoms, In some embodiments, the haloalkoxy group contains 1-10 carbon atoms; in other embodiments, the haloalkoxy group contains 1-8 carbon atoms; in still other embodiments, the haloalkoxy group contains 1-6 carbon atoms; in yet other embodiments, the haloalkoxy group contains 1-4 carbon atoms; in yet other embodiments, the haloalkoxy group contains 1-3 carbon atoms; in yet other embodiments, the haloalkoxy group contains 1-2 carbon atoms. Some non-limiting examples of the haloalkoxy group include trifluoromethoxy, difluoromethoxy, etc. Wherein, the haloalkoxy group may be optionally substituted with one or more substituents disclosed herein.

The term "carbocyclyl" may be used alone or as a large part of "carbocyclylalkyl" or "carbocyclylalkoxy", it refers to a nonaromatic carbon ring system having 3 to 14 ring carbon atoms, which is saturated or contains one or more units of unsaturation. The terms "carbon ring", "carbocyclyl" or "carbocyclic" can be used interchangeably here. In some embodiments, the ring carbon atom number of the carbocyclyl is 3 to 12; in other embodiments, the ring carbon atom number of the carbocyclyl is 3 to 10; in other embodiments, the ring carbon atom number of the carbocyclyl is 3 to 8; in other embodiments, the ring carbon atom number of the carbocyclyl is 3 to 6; in other embodiments, the ring carbon atom number of the carbocyclyl is 5 to 6; in other embodiments, the ring carbon atom number of the carbocyclyl is 5 to 8. In yet other embodiments, the ring carbon atom number of the carbocyclyl is 6 to 8. The "carbocyclyl" includes a monocyclic, bicyclic, or polycyclic fused ring, spiro ring or bridged ring system, and a polycyclic ring system containing one carbocyclic ring fused with one or more non-aromatic carbocyclic ring, or one or more aromatic ring, or a combination thereof, wherein the linked group or point exists on carbocyclic ring. The bicyclic carbocyclyl groups includes bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share three or four adjacent ring atoms. Spiro bicyclic system contains two ring which share one ring atom. Some non-limiting examples of the cycloaliphatic group include cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged bicyclic carbocyclyl group includes, but are not limited to, bicyclo[2.2.2]octyl, bicyclo[2.2.1]heptyl, bicyclo[3.3.1]nonyl, bicyclo[3.2.3]nonyl, and the like.

The term "cycloalkyl" refers to a saturated ring having 3 to 12 ring carbon atoms as a monocyclic, bicyclic, or tricyclic ring system, which has one or more attachments attaching to the rest of the molecule. In some embodiments, the cycloalkyl group is a ring system containing 3 to 10 ring carbon atoms, e.g. $C_{3-10}$ cycloalkyl. In other embodiments, the cycloalkyl group is a ring system containing 3 to 8 ring carbon atoms, e.g. $C_{3-8}$ cycloalkyl. In other embodiments, the cycloalkyl group is a ring system containing 5 to 8 ring carbon atoms, e.g. $C_{5-8}$ cycloalkyl. In still other embodiments, the cycloalkyl group is a ring system containing 3 to 6 ring carbon atoms, e.g. $C_{3-6}$ cycloalkyl. In yet other embodiments, the cycloalkyl group is a ring system containing 5 to 6 ring carbon atoms, e.g. $C_{5-6}$ cycloalkyl. Examples of cycloalkyl group include, but are not limited to, cyclopropyl, cyclobutyl, cyclopentyl, cyclohexyl, and the like. The cycloalkyl radical is independently unsubstituted or substituted with one or more substituents described herein.

The term "heterocyclyl" may be used alone or as a large part of heterocyclylalkyl or heterocyclylalkoxy, it refers to a saturated or partially unsaturated non-aromatic monocyclic, bicyclic or tricyclic ring containing 5-10 ring atoms of which at least one ring atom is selected from nitrogen, sulfur and oxygen, wherein the heterocyclyl is non-aromatic, and without any aromatic ring, and of which may has one or more attachments attached to the rest of the molecule. The term "heterocyclyl" comprises monocyclyl, bicyclyl or fused, spiral, or bridged polyheterocyclic ring system. Biheterocyclyl radical includes bridged biheterocyclyl, fused biheterocyclyl and spiro biheterocyclyl. The terms "heterocycle", "heterocyclyl", or "heterocyclic ring" are used interchangeably herein. Unless otherwise specified, the heterocyclyl group may be carbon or nitrogen linked, and a —$CH_2$— group can be optionally replaced by a —C(=O)— group. In which, the sulfur can be optionally oxygenized to S-oxide. and the nitrogen can be optionally oxygenized to N-oxide. In some embodiments, the heterocyclyl group is a 5- to 7-membered ring system; in other embodiments, the heterocyclyl group is a 5- to 10-membered ring system; in other embodiments, the heterocyclyl group is a 5- to 8-membered ring system; in other embodiments, the heterocyclyl group is a 6- to 8-membered ring system; in other embodiments, the heterocyclyl group is a 5- to 6-membered ring system; in other embodiments, the heterocyclyl group is a 4-membered ring system; in other embodiments, the heterocyclyl group is a 5-membered ring system; in other embodiments, the heterocyclyl group is a 6-membered ring system; in other embodiments, the heterocyclyl group is a 7-membered ring system; in other embodiments, the heterocyclyl group is a 8-membered ring system. In some embodiments, the heterocyclyl group may be a 5-10, 5-8, 5-6, 5- or 6-membered ring system containing at least one degree of unsaturation. In other embodiments, the heterocyclyl group may be a 5-10, 5-8, 5-6, 5- or 6-membered ring system containing one or two degrees of unsaturation, and the ring system contains 1, 2 or 3 heteroatoms selected from N, O or S.

Examples of the heterocyclyl group include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3- dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, tetrahydropyrrolyl, dihydropyrrolyl, tetrahydropyridyl, tetrahydropyrimidinyl, tetrahydropyrazinyl, tetrahydropyridazinyl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized is sulfolanyl and 1,1-dioxo-thiomorpholinyl. Some non-limiting examples of the bridged heterocyclyl group include, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "m-membered", where m is an integer typically describes the number of ring-forming atoms in a moiety where the number of ring-forming atoms is m. For example, piperidinyl is an example of a 6 membered heterocyclyl and 1,2,3,4-tetrahydro-naphthalene is an example of a 10 membered carbocyclyl group. As another example, "5-10 membered heterocyclyl" refers to heterocyclyl consisted of 5, 6, 7, 8, 9 or 10 atoms.

The term "aryl" used alone or as a great part of "arylalkyl", "arylalkoxy", refers to monocyclic, bicyclic and tricyclic aromatic carbon ring systems having a total of 6 to 14 ring members, or 6 to 12 ring members, or 6 to 10 ring members, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, naphthyl and anthracene. The aryl group may be optionally unsubstituted or substituted with one or more substituents disclosed herein.

The term "heteroaryl" used alone or as a great part of "heteroarylalkyl" or "heteroarylalkoxy", refers to monocyclic, bicyclic and tricyclic aromatic ring systems having 5 to 10 ring members, and in which at least one ring contains one or more heteroatoms, wherein each ring contains 5 to 7 ring members, wherein at least one ring in the system is aromatic, and that has a single point or multipoint of attachment to the rest of the molecule. Unless otherwise specified, the heteroaryl group can attach to the rest of the molecular via any reasonable attachments (such as carbon atom of CH, or nitrogen atom of NH). When —CH$_2$-group exists in heteroaryl, the —CH$_2$— can be optionally substituted with —C(=O)—. The term "heteroaryl" and "heteroaromatic ring" or "heteroaromatic compound" can be used interchangeably herein. In other embodiments, "heteroaryl" is a heteroaryl group consisting of 5 to 8 atoms that has 1, 2, 3 or 4 heteroatoms independently selected from O, S and N; in other embodiments, "heteroaryl" is a heteroaryl group consisting of 5 to 7 atoms that has 1, 2, 3 or 4 heteroatoms independently selected from O, S and N; in other embodiments, "heteroaryl" is a heteroaryl group consisting of 5 to 6 atoms that has 1, 2, 3 or 4 heteroatoms independently selected from O, S and N; in other embodiments, "heteroaryl" is a heteroaryl group consisting of 5 atoms that has 1, 2, 3 or 4 heteroatoms independently selected from O, S and N; in other embodiments, "heteroaryl" is a heteroaryl group consisting of 6 atoms that has 1, 2, 3 or 4 heteroatoms independently selected from O, S and N.

In other embodiment, some non-limiting examples of heteroaryl group include the following monocyclic group: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl, 1,3,5-triazinyl, and the following bicycles or tricycles, but are not limited to: indolinyl, 1,2,3,4-tetrahydroisoquinolinyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), phenoxathiinyl, bibenzoimidazolyl, bibenzofuryl, bibenzothienyl, and the like. The heteroaryl group is optionally substituted with one or more substituents disclosed herein.

The term "heteroatom" refers to oxygen, sulfur, nitrogen, phosphorus and silicon, including any oxidized form of nitrogen, sulfur, or phosphorus; the quaternized form of any basic nitrogen (primary, secondary, tertiary amines and quaternary ammonium salts); or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "nitro" refers to —NO$_2$.
The term "mercapto" refers to —SH.
The term "hydroxy" refers to —OH.
The term "amino" refers to —NH$_2$.
The term "cyano" refers to —CN.
The term "carboxy" refers to —C(=O)OH.
The term "carbonyl", whether used alone or with other terms, such as "aminocarbonyl", "acyloxy", denotes —(C=O)—.

The term "D" refers to deuterated, i.e. $^2$H.

As described herein, a bond drawn from a substituent R to the center of one ring within a ring system represents substitution of the substituent R at any substitutable position on the ring attached to it. For example, formula a represents that any substitutable position on ring A may be optionally substituted by n R, but any substitutable position on ring B can not be substituted by R; when ring A is a double ring, any substitutable position on any ring of ring A may be substituted by R; as another example, formula b represents that any substitutable position on ring C may be substituted by R, as shown in formulas b-1 to b-3:

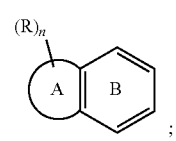

a

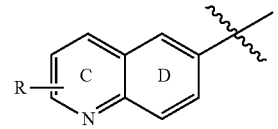

b

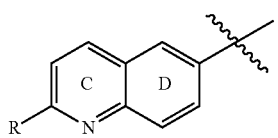

b-1

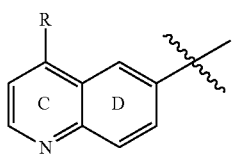

b-2

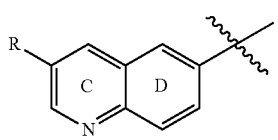

b-3

As described herein, "⤳" refers to a double bond, the bond-bonded structure may be "cis isomer", "trans isomer" or "mixture of cis isomer and trans isomer in any proportion"; for example, formula e represents formula e-1, formula e-2 or mixture of both (e-1 and e-2) in any proportion:

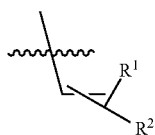

e

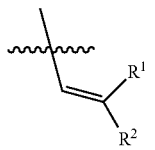

e-1

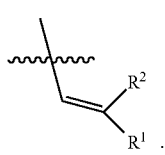

e-2

As described herein, "any two R together with the carbon or nitrogen atoms to which they are attached, form ring" means that any two R together with the carbon or nitrogen atoms to which they are attached, can form a spiral ring, a bridge ring or a fused ring.

As described herein, a specific group on the ring is represented by a letter, indicating that the position of the group represented by the letter is determined. As shown in formula f, the position of group J and group K on the ring F is fixed, that is, group J is directly connected with benzene ring, group K is directly connected with group J, wherein the bond between Group K and J is a single bond, and the bond connected with "arc" part of F ring may be a single bond or a double bond; and the "arc" part of F ring may be a bond, an atom/group or a combination of atoms/groups, and its position, degree of saturation of bond, atomic types and number of atoms are all not limited.

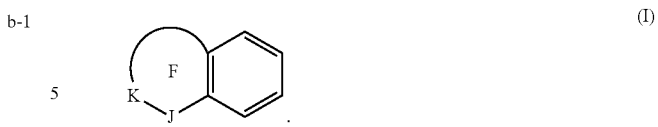

(f)

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl, benzoyl, benzyl, p-methoxybenzyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxymethy-1, 2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "leaving group" or "LG" refers to an atom or functional group separated from a larger molecule in a chemical reaction, and it is a term applied in nucleophilic substitution reaction and elimination reaction. In the nucleophilic substitution reaction, the reactant attacked by the nucleophile is called the substrate, and the atom or group breaking out with a pair of electrons from the substrate molecule is called the leaving group. Some non-limited examples of common leaving groups include halogen atoms, ester groups, sulfonic ester groups, nitro groups, azido groups or hydroxyl groups, etc.

The phrase "pharmaceutically acceptable" refers to that the substance or composition must be chemically and/or toxicologically compatible with the other ingredients comprising a formulation, and/or the mammal being treated therewith. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., Remington's Pharmaceutical Sciences, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

The term "pharmaceutical composition" refers to a mixture of one or more of the compounds described herein, or physiologically/pharmaceutically acceptable salts or prodrugs thereof, and other chemical components, such as physiologically/pharmaceutically acceptable carriers, excipients, diluents, adjuvants, vehicles, and other additional therapeutic agents, such as anti-diabetic agents, antihyperglycemic agents, antiadipositas agents, antihypertensive agents, antiplatelet agents, antiatherosclerotic agents, lipid-lowering agents, anti-inflammatory agents, etc. The purpose of the pharmaceutical composition is to facilitate administration of a compound to an organism.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., Prodrugs as Novel Delivery Systems, Vol. 14, A.C.S. Symposium Series; Roche, et al. ed., Bioreversible Carriers in Drug Design, American Pharmaceutical Association and Pergamon Press, 1987; Rautio et al., Prodrugs: Design and Clinical Applications, Nature Reviews Drug Discovery, 2008, 7, 255-270, and Hecker et al., Prodrugs of Phosphates and Phosphonates, J. Med. Chem., 2008, 51, 2328-2345.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The term "pharmaceutically acceptable salt" refers to organic or inorganic salts of a compound disclosed herein. Pharmaceutically acceptable salts are well known in the art. For example, the pharmaceutically acceptable salts are described in detail in Berge et al., J. Pharmacol Sci, 1977, 66: 1-19, which is incorporated herein by reference in its entirety.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If the compound contains a double bond, the substituent may be cis-(Z) or trans-(E) configuration.

Therefore, as the invention described, the compound disclosed herein may exist in the form of any possible isomer, such as rotational isomer, atropisomer, tautomer, or a mixture thereof, i.e., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric isomers, optical isomers, diastereoisomers, racemate, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, UK, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques:

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{13}C$, $^{14}C$, $^{15}N$, C, $^{16}O$, $^{17}O$, $^{31}P$, $^{32}P$, $^{36}S$, $^{17}F$ and $^{37}Cl$, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^3H$ or $^{14}C$ are incorporated, are useful in drug and/or substrate tissue distribution assays. Because of easy preparation and detection, isotopes such as tritiated, i.e., $^3H$, and carbon-14, i.e., $^{14}C$ are preferred. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. Therefore, the heavier isotopes may be preferred in somewhere.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, different optically active compounds are called stereoisomers and are identical except that they are mirror images of one another. A specific stereoisomer may be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers and geometric (conformational) isomers as well as mixtures thereof such as racemic mixtures, form part of the present invention.

Unless otherwise specified, the Formula described herein also contains all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures of the present compounds are within the scope disclosed herein.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

The term "geometric isomer" is also known as "cis-trans isomer", which is caused by the double bond (including the double bond of olefin, C=N double bond and N=N double bond) or the single bond of ring carbon atom can not rotate freely.

As used herein, the term "subject" refers to an animal. Typically, the animal is a mammal. As used herein, the term "subject" refers to an animal. Typically, the animal is a mammal. The subject also refers to for example, primates (e.g., humans), cows, sheep, goats, horses, dogs, cats, rabbits, rats, mice, fish, birds and the like. In certain embodiments, the subject is a primate. In other embodiments, the subject is a human.

The term "subject" can be used interchangeably with "patient" in the invention. The term "subject" and "patient" refer to animals (e.g., birds such as chicken, quail or turkey, or mammals), specially mammals including non-primates (e.g., cattle, pigs, horses, sheep, rabbits, guinea pigs, rats, dogs, cats and mice) and primates (e.g., monkeys, chimpanzees and humans), more specially humans. In some embodiments, the subject is a non-human animal, such as livestock (e.g., horses, cattle, pigs or sheep) or pet (e.g., dogs, cats, guinea pigs or rabbits). In other some embodiments, the "patient" refers to a human. In one embodiment, "patient" refers to a human.

The term "syndrome X", also known as conditions, diseases of metabolic syndrome, the disorders are detailed in Johannsson et al., *J. Clin. Endocrinol. Metab.*, 1997; 82, 727-734, which is incorporated herein by reference.

"Inflammatory disorder/disease" as used herein refers to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" or "Inflammatory" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with the compounds disclosed herein encompass disorders associated with reactions of the specific defense system as well as with reactions of the nonspecific defense system.

"Allergy" used herein refers to any symptom, tissue damage or loss of tissue function causing allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Additionally, unless otherwise stated, structures depicted herein are also meant to include compounds that differ only in the presence of one or more isotopically enriched atoms.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Description of Compounds of the Invention

The present invention provides a compound having a good inhibition of SSAO/VAP-1 activity, and used in the manufacture of a medicament for treating inflammation and/or a disease related inflammation, diabetes and/or a disease related diabetes, a mental disorder, an ischemic disease, a vascular disease, fibrosis or tissue transplant rejection, in particular for treating nonalcoholic steatohepatitis in a patient. The present invention also provides a method of preparing such compounds and pharmaceutical compositions containing these compounds, and a method of using these compounds or combinations to prepare medicament for treating the diseases above in mammals, especially in humans. Compared with the existing similar compounds, the compound of the invention not only has good pharmacological activity, but also has excellent pharmacokinetic properties in vivo and pharmacodynamic properties in vivo. At the same time, the compound of the invention has high selectivity for SSAO/VAP-1. The preparation method of the compound is simple and easy, the process is stable, and is suitable for the commercial manufacturing. Therefore, the compound provided by the invention has better druggability compared with the existing similar compound.

Specifically:

In one aspect, provided herein is a compound having Formula (I) or a stereoisomer, a geometric isomer, a tautomer, an N-oxide, a solvate, a metabolite, a pharmaceutically acceptable salt or a prodrug thereof,

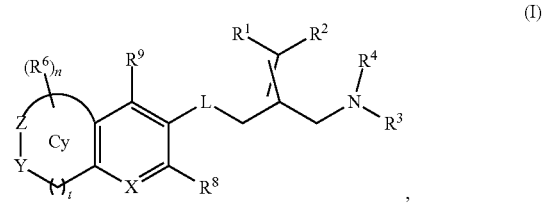

wherein ring Cy, $R^1$, $R^2$, $R^3$, $R^4$, $R^6$, $R^8$, $R^9$, X, Y, Z, L, t and n are as defined herein.

with the exception of the compounds:
6-[(E)-2-(aminomethyl)-3-fluoro-allyloxy]-3,4-dihydro-2H-isoquinolin-1-one,
6-[(Z)-2-(aminomethyl)-3-fluoro-allyloxy]-3,4-dihydro-2H-isoquinolin-1-one,
7-[(E)-2-(aminomethyl)-3-fluoro-allyloxy]-3,4-dihydro-2H-isoquinolin-1-one,
7-[(Z)-2-(aminomethyl)-3-fluoro-allyloxy]-3,4-dihydro-2H-isoquinolin-1-one,
5-[(Z)-2-(aminomethyl)-3-fluoro-allyloxy]isoindolin-1-one,
5-[(E)-2-(aminomethyl)-3-fluoro-allyloxy]isoindolin-1-one,
7-[(E)-2-(aminomethyl)-3-fluoro-allyloxy]-2,3,4,5-tetrahydro-2-benzoazepin-1-one and
7-[(Z)-2-(aminomethyl)-3-fluoro-allyloxy]-2,3,4,5-tetrahydro-2-benzoazepin-1-one.

In some embodiments, wherein
Y is —CH$_2$—, —S(=O)—, —S(=O)$_2$— or —C(=O)—;
Z is —N($R^5$)— or —N=;
X is —N= or —C($R^7$)=;
L is —O—, —S— or —NH—;
ring Cy is 5- to 8-membered heterocyclyl or 5- to 8-membered heteroaryl;
each $R^6$ is independently H;
$R^5$ is H, D, F, Cl, Br, I, CN, NO$_2$, =O, —C(=O)$R^a$, —C(=O)O$R^b$, —C(=O)NR$^c$R$^d$, —SR$^e$, —S(=O)$_2$R$^e$, —S(=O)R$^e$, —S(=O)$_2$NR$^c$R$^d$, —NR$^f$C(=O)R$^a$, —NR$^f$S(=O)$_2$R$^e$, —NR$^c$R$^d$, —OR$^b$, R$^b$O—C$_{1-4}$ alkylene, R$^b$O—C(=O)—C$_{1-4}$ alkylene, R$^d$R$^c$N—C$_{1-4}$ alkylene, C$_{1-6}$ haloalkyl, C$_{1-6}$ alkyl, C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, 5- to 6-membered heteroaryl or (5- to 10-membered heteroaryl)-C$_{1-4}$ alkylene, wherein each of the C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, 5- to 6-membered heteroaryl and (5- to 10-membered heteroaryl)-C$_{1-4}$ alkylene is independently unsubstituted or substituted with 1, 2, 3 or 4 substituents, the substituent is independently selected from D, F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, C$_{6-10}$ aryl, 5- to 10-membered heteroaryl, C$_{1-6}$ haloalkyl, C$_{1-6}$ alkoxy, C$_{1-6}$ alkylamino or C$_{1-6}$ haloalkoxy; each of the C$_{1-6}$ alkyl and C$_{6-10}$ aryl is independently substituted with 1, 2, 3 or 4 substituents, the substituent is independently selected from F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, 5- to 10-membered heteroaryl, $C_{1-6}$ haloalkyl, $C_{1-6}$ alkoxy, $C_{1-6}$ alkylamino or $C_{1-6}$ haloalkoxy;

each of $R^8$ and $R^9$ is independently H, D, Br, I, CN, $NO_2$, —C(=O)$R^a$, —C(=O)O$R^b$, —C(=O)N$R^cR^d$, —OH, $NH_2$, $R^b$O—$C_{1-4}$ alkylene, $R^dR^c$N—$C_{1-4}$ alkylene, $C_{1-6}$ alkyl, $C_{1-6}$ haloalkyl, $C_{1-6}$ haloalkoxy, $C_{3-6}$ cycloalkyl, 3- to 8-membered heterocyclyl, $C_{6-10}$ aryl or 5- to 8-membered heteroaryl, wherein each of the $C_{1-6}$ alkyl, $C_{1-6}$ haloalkyl, $C_{1-6}$ haloalkoxy, $C_{3-6}$ cycloalkyl, 3- to 8-membered heterocyclyl, $C_{6-10}$ aryl and 5- to 8-membered heteroaryl is independently unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

$R^7$ is H, D, F, Cl, Br, I, CN, $NO_2$, —C(=O)$R^a$, —C(=O)O$R^b$, —C(=O)N$R^cR^d$, —OH, $NH_2$, $R^b$O—$C_{1-4}$ alkylene, $R^dR^c$N—$C_{1-4}$ alkylene, $C_{1-6}$ alkyl, $C_{1-6}$ haloalkyl, $C_{1-6}$ haloalkoxy, $C_{3-6}$ cycloalkyl, 3- to 8-membered heterocyclyl, $C_{6-10}$ aryl or 5- to 8-membered heteroaryl, wherein each of the $C_{1-6}$ alkyl, $C_{1-6}$ haloalkyl, $C_{1-6}$ haloalkoxy, $C_{3-6}$ cycloalkyl, 3- to 8-membered heterocyclyl, $C_{6-10}$ aryl and 5- to 8-membered heteroaryl is independently unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

$R^1$ is H, D, F, Cl, Br, I, $C_{1-6}$ alkyl, —C(=O)O$R^b$, —C(=O)$R^a$, —OC(=O)$R^a$, —OC(=O)O$R^b$, —N$R^f$C(=O)$R^a$, —N$R^f$S(=O)$_2R^e$, —C(=O)N$R^cR^d$, —S(=O)$_2$N$R^cR^d$, —S(=O)$_2R^e$, —S$R^e$ or —S(=O)$R^e$, wherein $C_{1-6}$ alkyl is unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

$R^2$ is F, Cl, Br, I, $C_{1-6}$ alkyl, —C(=O)O$R^b$, —C(=O)$R^a$, —OC(=O)$R^a$, —OC(=O)O$R^b$, —N$R^f$C(=O)$R^a$, —N$R^f$S(=O)$_2R^e$, —C(=O)N$R^cR^d$, —S(=O)$_2$N$R^cR^d$, —S(=O)$_2R^e$, —S$R^e$ or —S(=O)$R^e$, wherein $C_{1-6}$ alkyl is unsubstituted or substituted with 1, 2, 3 or 4 substituents, the substituent is independently selected from D, F, Cl, Br, I, CN, $NO_2$, —OH, $NH_2$, $C_{1-6}$ alkyl, $C_{1-6}$ haloalkyl, $C_{1-6}$ alkoxy, $C_{1-6}$ alkylamino or $C_{1-6}$ haloalkoxy;

each of $R^3$ and $R^4$ is independently H, D, $C_{1-6}$ alkyl, $C_{1-6}$ haloalkyl, $C_{3-6}$ cycloalkyl, 3- to 6-membered heterocyclyl, $C_{6-10}$ aryl, 5- to 6-membered heteroaryl or

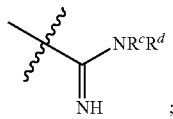

wherein each of the $C_{1-6}$ alkyl, $C_{1-6}$ haloalkyl, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

or, $R^3$ and $R^4$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

each $R^a$, $R^b$, $R^c$, $R^d$, $R^e$ and $R^f$ is independently H, D, —OH, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, wherein each of the $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

or, $R^c$ and $R^d$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, $NH_2$, $C_{1-6}$ alkyl, $C_{1-6}$ haloalkyl, $C_{1-6}$ alkoxy or $C_{1-6}$ alkylamino;

n is 0, 1, 2, 3 or 4;
t is 0, 1, 2, 3 or 4.

In other embodiments, wherein ring Cy is 5-membered heterocyclyl, 6-membered heterocyclyl, 5-membered heteroaryl or 6-membered heteroaryl.

In other embodiments, wherein ring Cy is

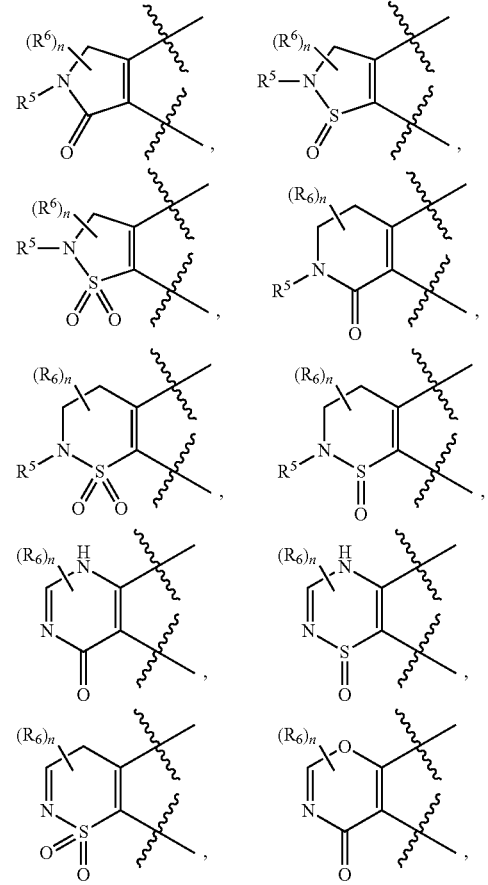

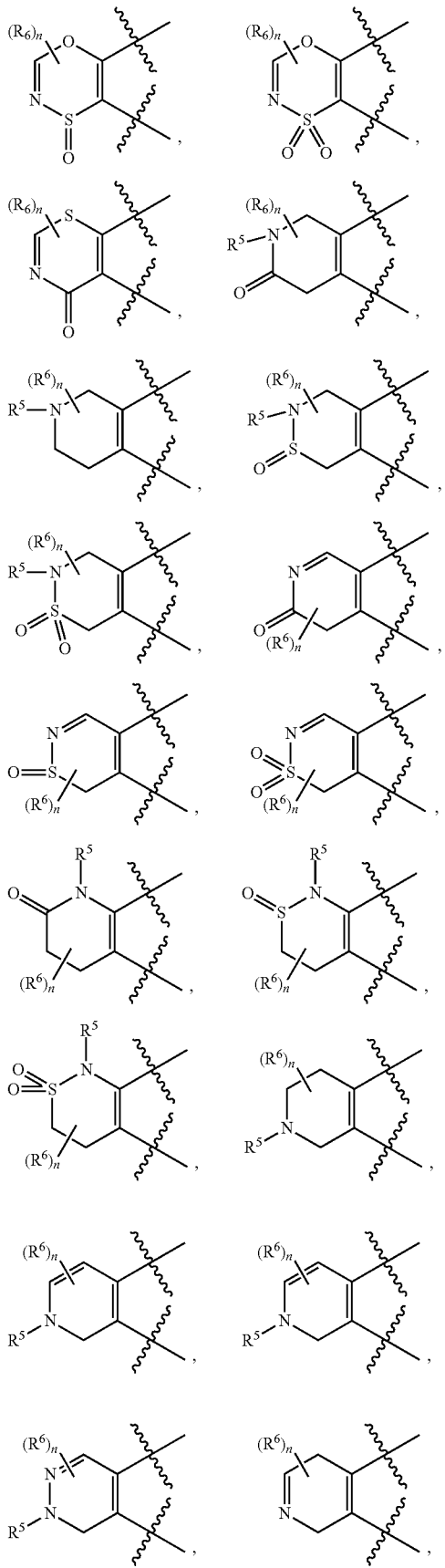

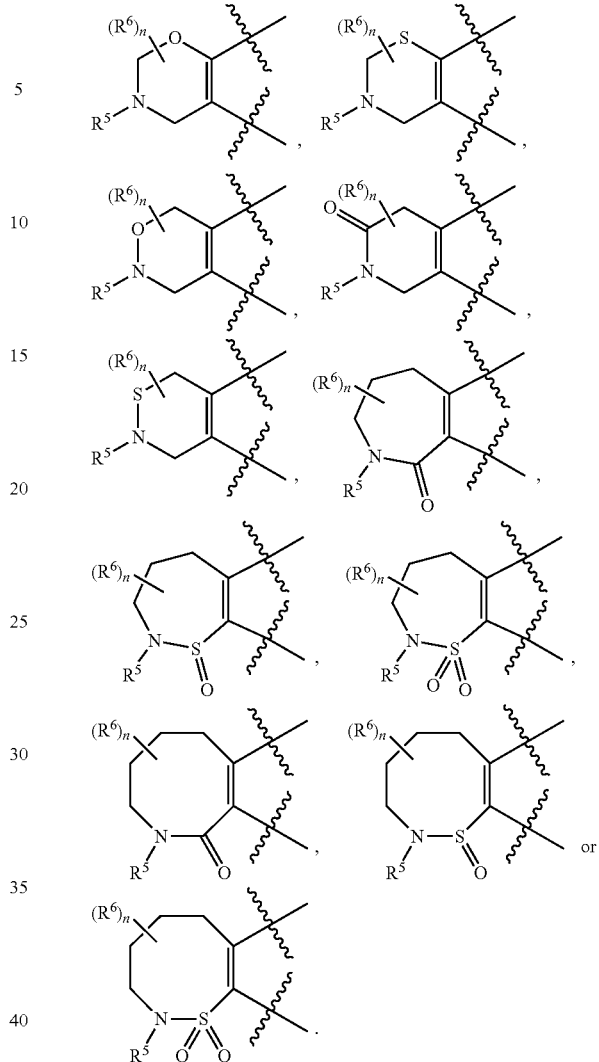

In other embodiments, $R^5$ is H, D, F, Cl, Br, I, CN, $NO_2$, =O, $-C(=O)R^a$, $-C(=O)OR^b$, $-C(=O)NR^cR^d$, $-SR^e$, $-S(=O)_2R^e$, $-S(=O)R^e$, $-S(=O)_2NR^cR^d$, $-NR^fC(=O)R^a$, $-NR^fS(=O)_2R^e$, $-NR^cR^d$, $-OR^b$, $R^bO-C_{1-2}$ alkylene, $R^bO-C(=O)-C_{1-2}$ alkylene, $R^dR^cN-C_{1-2}$ alkylene, $C_{1-4}$ haloalkyl, $C_{1-4}$ alkyl, $C_{2-4}$ alkenyl, $C_{2-4}$ alkynyl, $C_{3-6}$ cycloalkyl-$C_{1-2}$ alkylene, 3- to 6-membered heterocyclyl, (3- to 6-membered heterocyclyl)-$C_{1-2}$ alkylene, $C_{6-10}$ aryl, 5- to 6-membered heteroaryl or (5- to 6-membered heteroaryl)-$C_{1-2}$ alkylene, wherein each of the $C_{2-4}$ alkenyl, $C_{2-4}$ alkynyl, $C_{3-6}$ cycloalkyl-$C_{1-2}$ alkylene, 3- to 6-membered heterocyclyl, (3- to 6-membered heterocyclyl)-$C_{1-2}$ alkylene, 5- to 6-membered heteroaryl and (5- to 6-membered heteroaryl)-$C_{1-2}$ alkylene is independently unsubstituted or substituted with 1, 2, 3 or 4 substituents, the substituent is independently selected from D, F, Cl, Br, I, CN, $NO_2$, $-OR^b$, $-NR^cR^d$, $-C(=O)OR^b$, $C_{1-4}$ alkyl, $C_{3-6}$ cycloalkyl, 3- to 6-membered heterocyclyl, $C_{6-10}$ aryl, 5- to 6-membered heteroaryl, $C_{1-4}$ haloalkyl, $C_{1-4}$ alkoxy, $C_{1-4}$ alkylamino or $C_{1-4}$ haloalkoxy; each of the $C_{1-4}$ alkyl and $C_{6-10}$ aryl is independently substituted with 1, 2, 3 or 4 substituents, the substituent is independently selected from D, F, Cl, Br, I, CN, $NO_2$, $-OR''$, $-NR^cR^d$, $-C(=O)OR''$, $C_{1-4}$ alkyl, $C_{3-6}$ cycloalkyl, 3- to 6-membered heterocyclyl, 5- to 6-membered heteroaryl, $C_{1-4}$ haloalkyl, $C_{1-4}$ alkoxy, $C_{1-4}$ alkylamino or $C_{1-4}$ haloalkoxy.

In still other embodiments, wherein $R^5$ is H, D, F, Cl, Br, I, CN, $NO_2$, =O, —C(=O)$R^a$, —C(=O)OH, —C(=O)OCH$_3$, —C(=O)OCH$_2$CH$_3$, —C(=O)OCH$_2$CH$_2$CH$_3$, —C(=O)OCH(CH$_3$)$_2$, —C(=O)NH$_2$, —SR$^e$, —S(=O)$_2$R$^e$, —S(=O)R$^e$, —S(=O)$_2$NR$^c$R$^d$, —NHC(=O)R$^a$, —NHS(=O)$_2$R$^e$, NH$_2$, —OH, R$^b$O—C$_{1-2}$ alkylene, R$^b$O—C(=O)—C$_{1-2}$ alkylene, trifluoromethyl, methyl, ethyl, n-propyl, i-propyl, vinyl, propynyl, $C_{3-6}$ cycloalkyl-C$_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-C$_{1-2}$ alkylene, phenyl, naphthyl, $C_{6-10}$ aryl-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl or (5- to 6-membered heteroaryl)-C$_{1-2}$ alkylene, wherein each of the vinyl, propynyl, $C_{3-6}$ cycloalkyl-C$_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl and (5- to 6-membered heteroaryl)-C$_{1-2}$ alkylene is independently unsubstituted or substituted with 1, 2, 3 or 4 substituents, the substituent is independently selected from D, F, Cl, Br, I, CN, $NO_2$, —OH, —OCH$_3$, —OCH$_2$CH$_3$, —O-methylene-phenyl, NH$_2$, —C(=O)OH, —C(=O)OCH$_3$, —C(=O)OCH$_2$CH$_3$, —C(=O)OCH$_2$CH$_2$CH$_3$, —C(=O)OCH(CH$_3$)$_2$, —C(=O)OCH$_2$CH$_2$CH$_2$CH$_3$, —C(=O)OC(CH$_3$)$_3$, —C(=O)OCH$_2$Ph, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy; each of the methyl, ethyl, n-propyl, i-propyl, phenyl and naphthyl is independently unsubstituted or substituted with 1, 2, 3 or 4 substituents, the substituent is independently selected from D, F, Cl, Br, I, CN, $NO_2$, —OH, —OCH$_3$, —OCH$_2$CH$_3$, —O-methylene-phenyl, NH$_2$, —C(=O)OH, —C(=O)OCH$_3$, —C(=O)OCH$_2$CH$_3$, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy.

In still other embodiments, wherein each of $R^8$ and $R^9$ is independently H, D, Br, I, CN, $NO_2$, —C(=O)R$^a$, —C(=O)OR$^b$, —C(=O)NR$^c$R$^d$, —OH, NH$_2$, R$^b$O—C$_{1-2}$ alkylene, R$^d$R$^c$N—C$_{1-2}$ alkylene, $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl or 5- to 6-membered heteroaryl, wherein each of the $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, $NO_2$, —OH, NH$_2$, $C_{1-4}$ alkyl, $C_{1-4}$ haloalkyl, $C_{1-4}$ alkoxy, $C_{1-4}$ alkylamino or $C_{1-4}$ haloalkoxy;

In still other embodiments, $R^7$ is H, D, F, Cl, Br, I, CN, $NO_2$, —C(=O)R$^a$, —C(=O)OR$^b$, —C(=O)NR$^c$R$^d$, —OH, NH$_2$, R$^b$O—C$_{1-2}$ alkylene, R$^d$R$^c$N—C$_{1-2}$ alkylene, $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl or 5- to 6-membered heteroaryl, wherein each of the $C_{1-4}$ alkyl, $C_{1-4}$ haloalkyl, $C_{1-4}$ haloalkoxy, $C_{3-6}$ cycloalkyl, 3- to 6-membered heterocyclyl, $C_{6-10}$ aryl and 5- to 6-membered heteroaryl is independently unsubstituted or substituted with 1, 2, 3 or 4 substituents, the substituent is independently selected from D, F, Cl, Br, I, CN, $NO_2$, —OH, NH$_2$, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, each of $R^8$ and $R^9$ is independently H, D, Br, I, CN, $NO_2$, —C(=O)R$^a$, —C(=O)OH, —C(=O)OCH$_3$, —C(=O)OCH$_2$CH$_3$, —C(=O)NH$_2$, —OH, NH$_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, $NO_2$, —OH, NH$_2$, methyl, ethyl, n-propyl, i-propyl, trifluoromethyl, ethoxy, ethoxy, methylamino, trifluoromethoxy or difluoromethoxy.

In still other embodiments, $R^7$ is H, D, F, Cl, Br, I, CN, $NO_2$, —C(=O)R$^a$, —C(=O)OH, —C(=O)OCH$_3$, —C(=O)OCH$_2$CH$_3$, —C(=O)NH$_2$, —OH, NH$_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, $NO_2$, —OH, NH$_2$, methyl, ethyl, n-propyl, i-propyl, trifluoromethyl, methoxy, ethoxy, methylamino, trifluoromethoxy or difluoromethoxy.

In still other embodiments, $R^1$ is H, D, F, Cl, Br, I, $C_{1-4}$ alkyl, —C(=O)OR$^b$, —C(=O)R$^a$, —OC(=O)R$^a$, —OC(=O)OR$^b$, —NR$^f$C(=O)R$^a$, —NR$^f$S(=O)$_2$R$^e$, —C(=O)NR$^c$R$^d$, —S(=O)$_2$NR$^c$R$^d$, —S(=O)$_2$R$^e$, —SR$^e$ or —S(=O)R$^e$, wherein the $C_{1-4}$ alkyl is unsubstituted or substituted with 1, 2, 3 or 4 substituents, the substituent is independently selected from D, F, Cl, Br, I, CN, $NO_2$, —OH, NH$_2$, $C_{1-4}$ alkyl, $C_{1-4}$ haloalkyl, $C_{1-4}$ alkoxy, $C_{1-4}$ alkylamino or $C_{1-4}$ haloalkoxy.

In still other embodiments, $R^1$ is H, D, F, Cl, Br, I, methyl, ethyl, i-propyl, n-propyl, —C(=O)OH, —C(=O)OCH$_3$, —C(=O)OCH$_2$CH$_3$, —C(=O)R$^a$, —OC(=O)R$^a$ or —OC(=O)OR$^a$, wherein each of the methyl, ethyl, i-propyl and n-propyl is independently unsubstituted or substituted with 1, 2, 3 or 4 substituents, the substituent is independently selected from D, F, Cl, Br, I, CN, $NO_2$, —OH, NH$_2$, methyl, ethyl, n-propyl, i-propyl.

In still other embodiments, $R^2$ is F, Cl, Br, I, $C_{1-4}$ alkyl, —C(=O)OR$^b$, —C(=O)R$^a$, —OC(=O)R$^a$, —OC(=O)OR$^b$, —NR$^f$C(=O)R$^a$, —NR$^f$S(=O)$_2$R$^e$, —C(=O)NR$^c$R$^d$, —S(=O)$_2$NR$^c$R$^d$, —S(=O)$_2$R$^e$, —SR$^e$ or —S(=O)R$^e$, wherein the $C_{1-4}$ alkyl is unsubstituted or substituted with 1, 2, 3 or 4 substituents, the substituent is independently selected from D, F, Cl, Br, I, CN, NO$_2$, —OH, NH$_2$, C$_{1-4}$ alkyl, C$_{1-4}$ haloalkyl, C$_{1-4}$ alkoxy, C$_{1-4}$ alkylamino or C$_{1-4}$ haloalkoxy;

In still other embodiments, R$^2$ is F, Cl, Br, I, methyl, ethyl, i-propyl, n-propyl, —C(=O)OH, —C(=O)OCH$_3$, —C(=O)OCH$_2$CH$_3$, —C(=O)R$^a$, —OC(=O)R$^a$ or —OC(=O)OR$^a$, wherein each of the methyl, ethyl, i-propyl and n-propyl is independently unsubstituted or substituted with 1, 2, 3 or 4 substituents, the substituent is independently selected from D, F, Cl, Br, I, CN, NO$_2$, —OH, NH$_2$, methyl, ethyl, n-propyl, i-propyl.

In still other embodiments, each of R$^3$ and R$^4$ is independently H, D, C$_{1-4}$ alkyl, C$_{1-4}$ haloalkyl, C$_{3-6}$ cycloalkyl, 5- to 6-membered heterocyclyl, C$_{6-10}$ aryl, 5- to 6-membered heteroaryl or

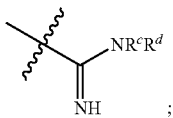

wherein each of the C$_{1-4}$ alkyl, C$_{1-4}$ haloalkyl, C$_{3-6}$ cycloalkyl, 5- to 6-membered heterocyclyl, C$_{6-10}$ aryl and 5- to 6-membered heteroaryl is independently unsubstituted or substituted with 1, 2, 3 or 4 substituents, the substituent is independently selected from D, F, Cl, Br, I, CN, —OH, NH$_2$, C$_{1-4}$ alkyl, C$_{1-4}$ haloalkyl, C$_{1-4}$ alkoxy or C$_{1-4}$ alkylamino;

or, R$^3$ and R$^4$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, C$_{1-4}$ alkyl, C$_{1-4}$ haloalkyl, C$_{1-4}$ alkoxy or C$_{1-4}$ alkylamino.

In other embodiments, wherein each of R$^3$ and R$^4$ is independently H, D, methyl, ethyl, n-propyl, i-propyl, C$_{1-4}$ haloalkyl, cyclopropyl, cyclobutyl, 5- to 6-membered heterocyclyl, phenyl or 5- to 6-membered heteroaryl or

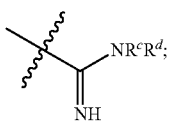

wherein each of the methyl, ethyl, n-propyl, i-propyl, C$_{1-4}$ haloalkyl, cyclopropyl, cyclobutyl, 5- to 6-membered heterocyclyl, phenyl or 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

or, R$^3$ and R$^4$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

In other embodiments, wherein each R$^a$, R$^b$, R$^c$, R$^d$, R$^e$ and R$^f$ is independently H, D, —OH, trifluoromethyl, difluoromethyl, methyl, ethyl, i-propyl, n-propyl, n-butyl, t-butyl, methoxy, ethoxy, cyclopropyl, cyclobutyl, cyclopentyl, cyclohexyl, C$_{3-6}$ cycloalkyl-C$_{1-2}$ alkylene, 5- to 6-membered heterocyclyl, (5- to 6-membered heterocyclyl)-C$_{1-2}$ alkylene, phenyl, phenyl-methylene, 5- to 6-membered heteroaryl or (5- to 6-membered heteroaryl)-C$_{1-2}$ alkylene, wherein each of the difluoromethyl, methyl, ethyl, i-propyl, n-propyl, n-butyl, t-butyl, methoxy, ethoxy, cyclopropyl, cyclobutyl, cyclopentyl, cyclohexyl, C$_{3-6}$ cycloalkyl-C$_{1-2}$ alkylene, 5- to 6-membered heterocyclyl, (5- to 6-membered heterocyclyl)-C$_{1-2}$alkylene, phenyl, phenyl-methylene, 5- to 6-membered heteroaryl and (5- to 6-membered heteroaryl)-C$_{1-2}$ alkylene is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

or, R$^e$ and R$^d$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy.

In other embodiments, the present invention provides a compound having Formula (II) or a stereoisomer, a geometric isomer, a tautomer, an N-oxide, a solvate, a metabolite, a pharmaceutically acceptable salt or a prodrug thereof,

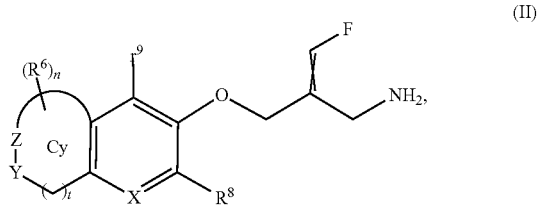

wherein ring Cy, R$^6$, R$^8$, R$^9$, X, Y, Z, t and n are as defined herein.

In other aspect, the present invention provides a compound having one of the following structures or a stereoisomer, a geometric isomer, a tautomer, an N-oxide, a solvate, a metabolite, a pharmaceutically acceptable salt or a prodrug thereof,

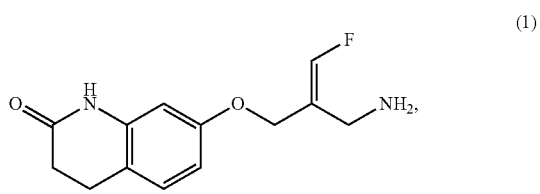

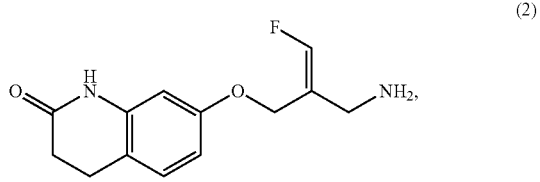 [SMILES: NC/C(=C/F)COc1ccc2c(c1)NC(=O)CC2 ; Cl]

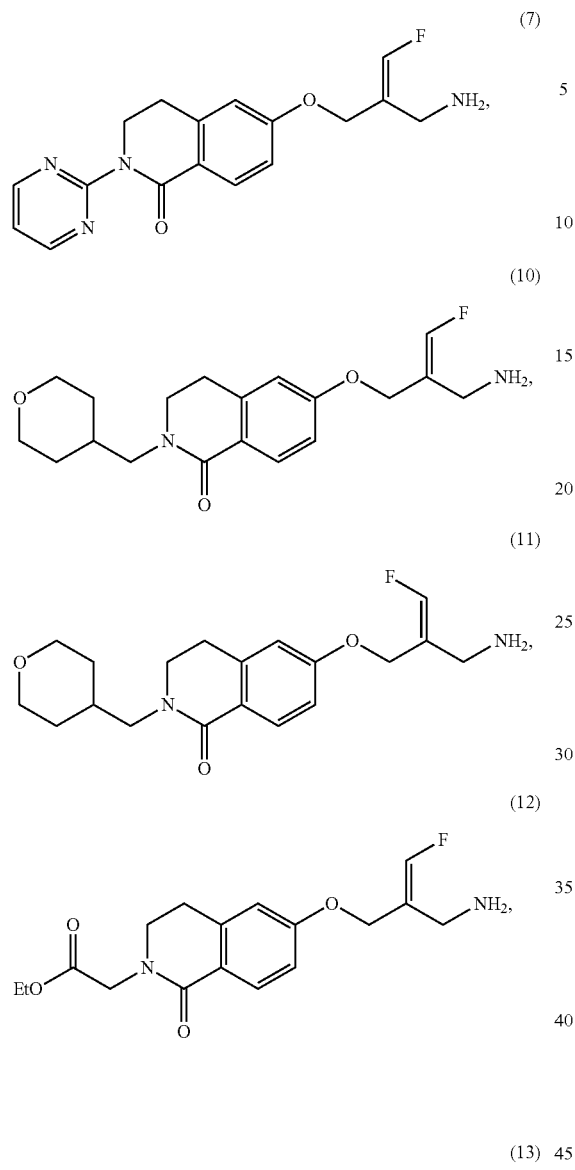
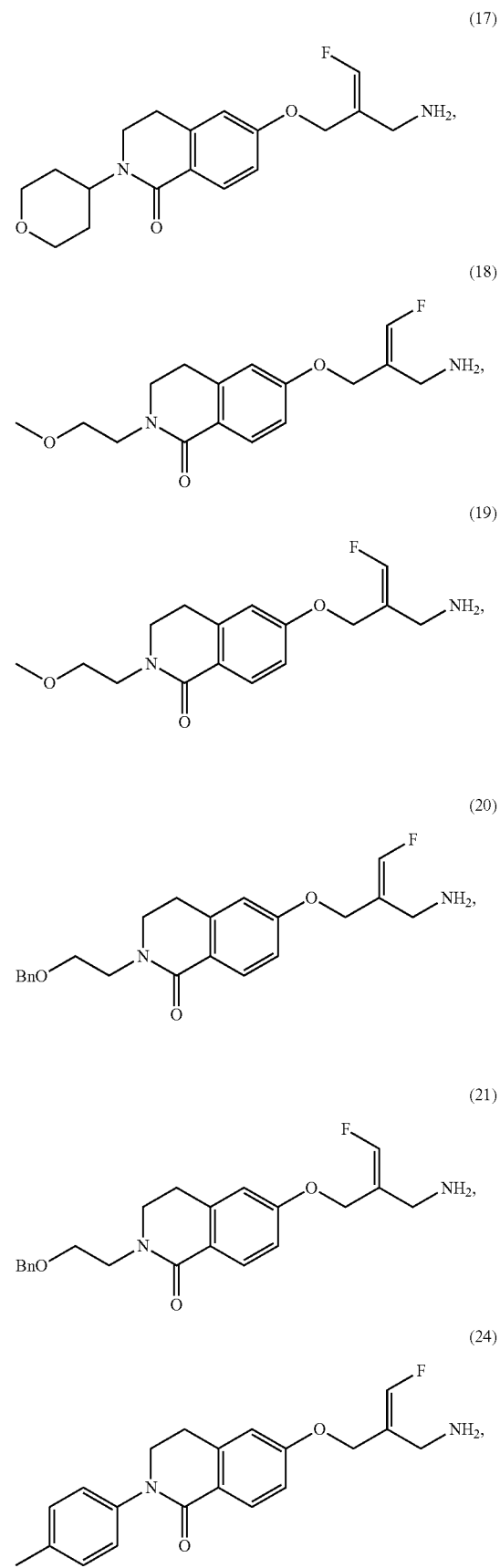

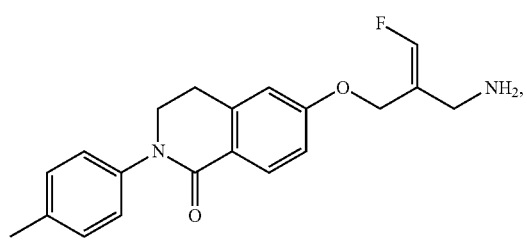
(25)
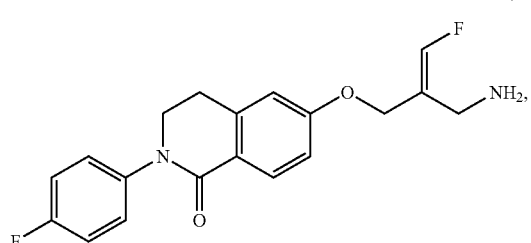
(26)
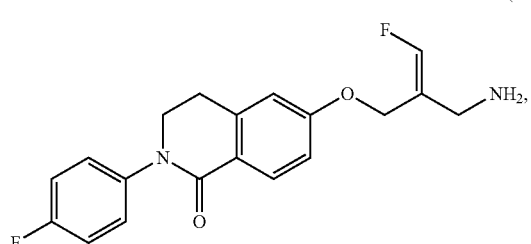
(27)
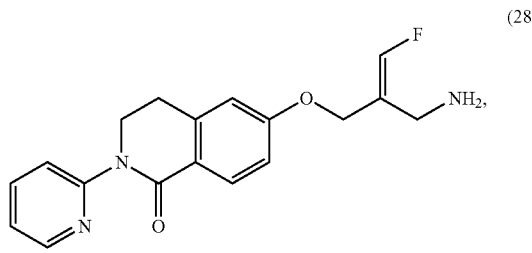
(28)
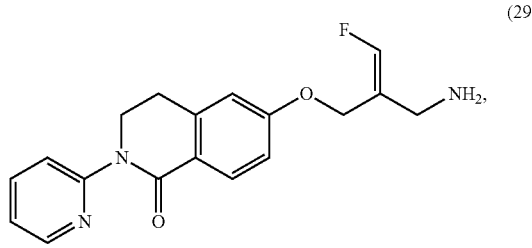
(29)
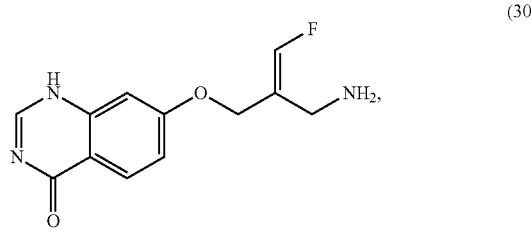
(30)
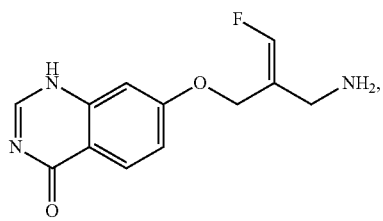
(31)
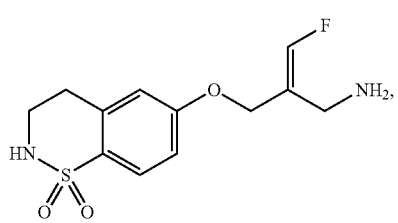
(32)
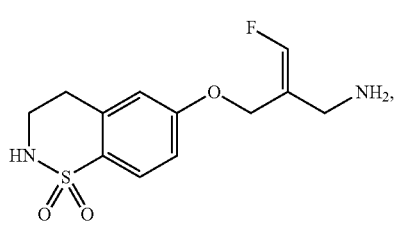
(33)
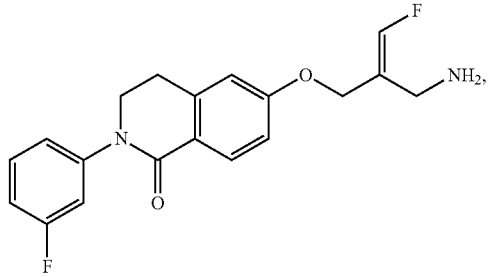
(34)
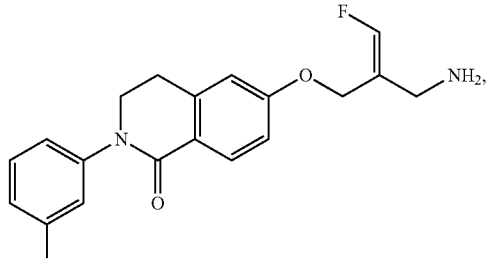
(35)
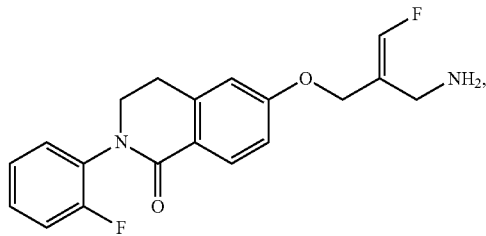
(36)

(37) 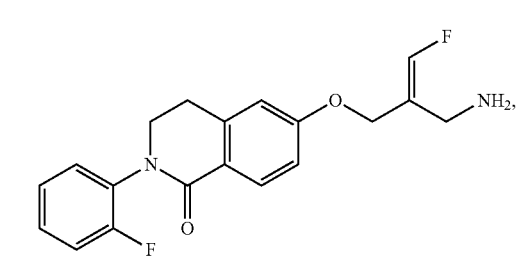
(38) 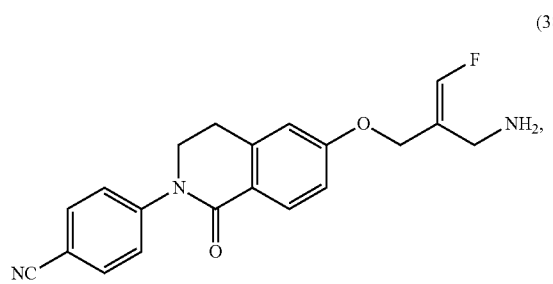
(39) 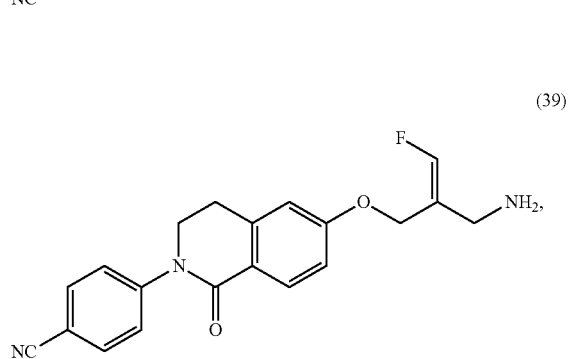
(40) 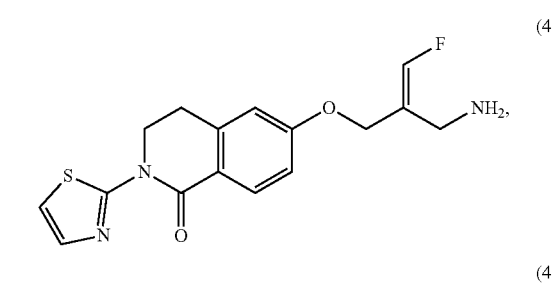
(41) 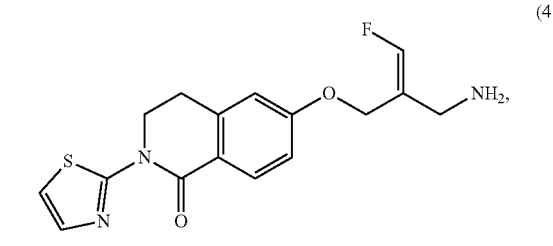
(42) 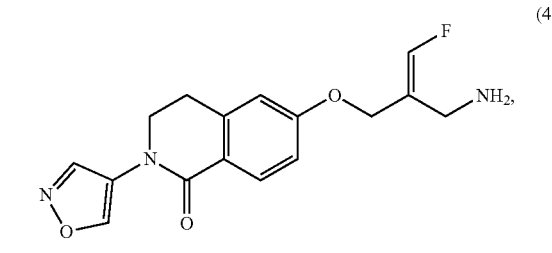
(43) 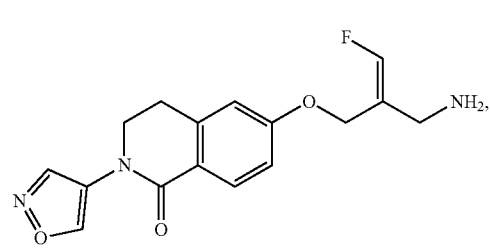
(44) 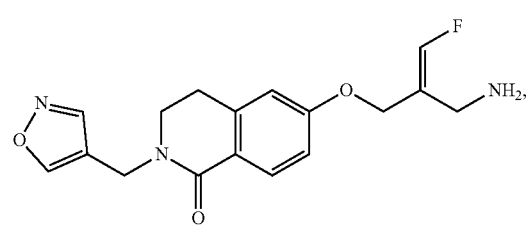
(45) 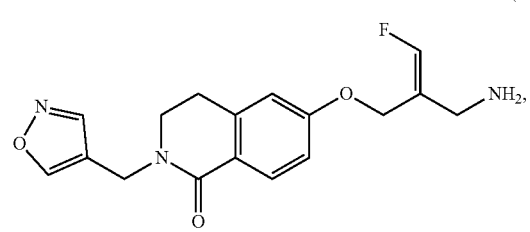
(46) 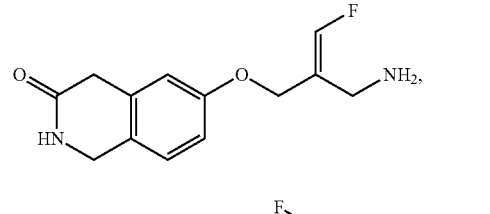
(47) 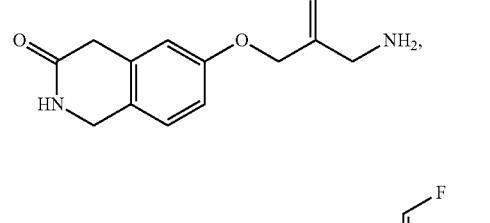
(48) 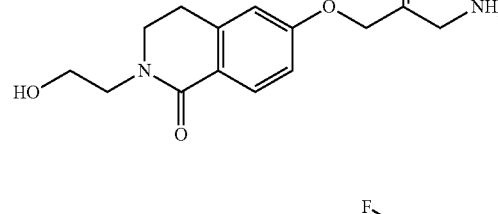
(49) 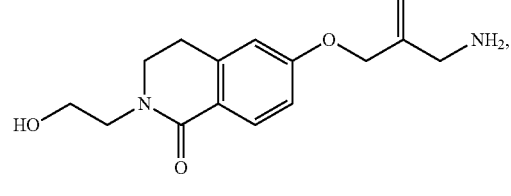

(50) 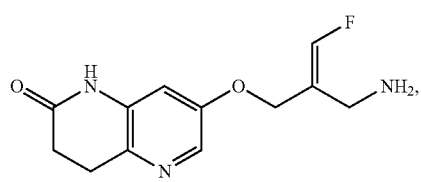
(51) 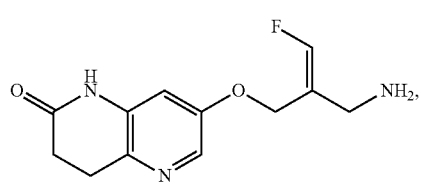
(52) 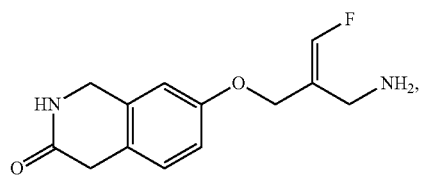
(53) 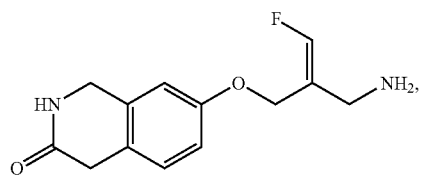
(54) 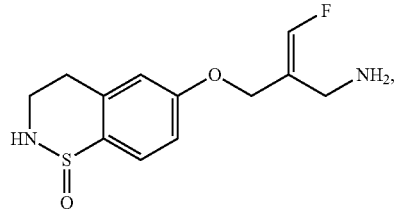
(55) 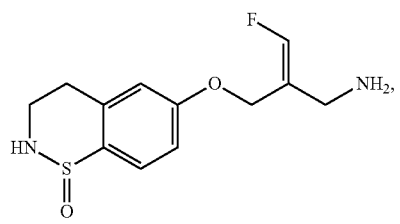
(56) 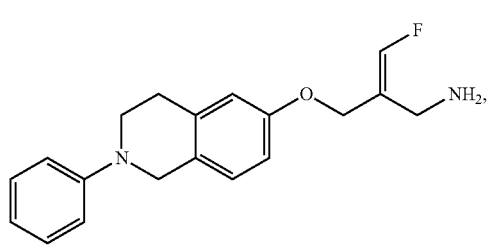
(57) 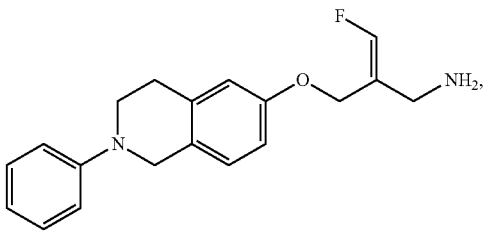
(58) 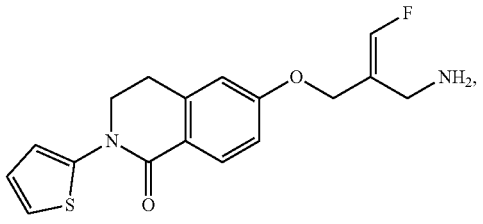
(59) 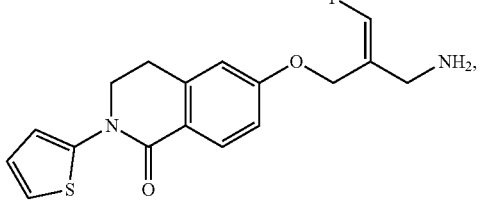
(60) 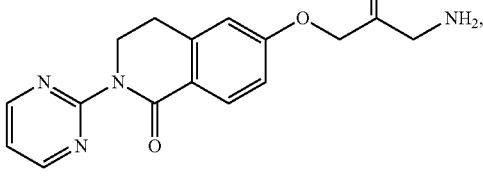
(61) 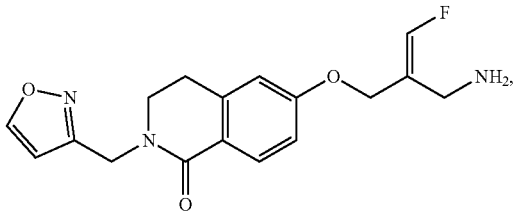
(62) 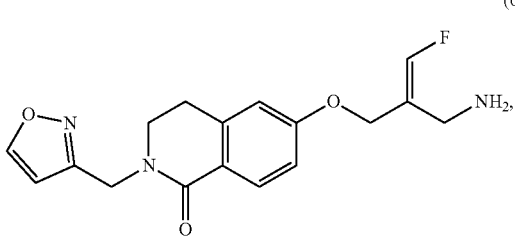
(63) 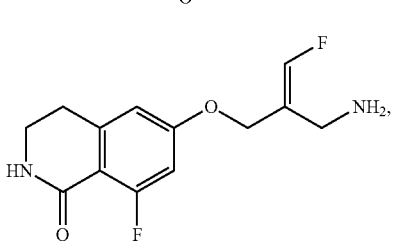

(64) (65) (66) (67) (68) (69) (70) (71) (72) (73) (74) (75)

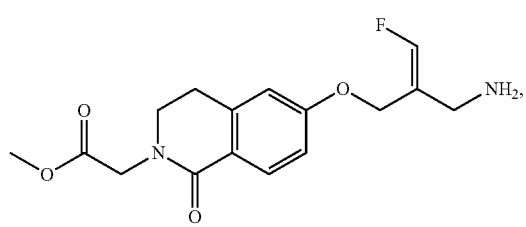
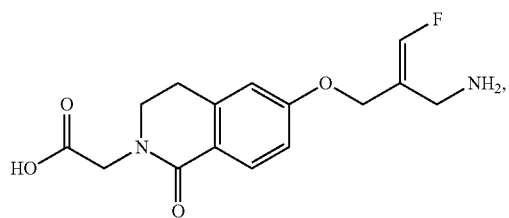
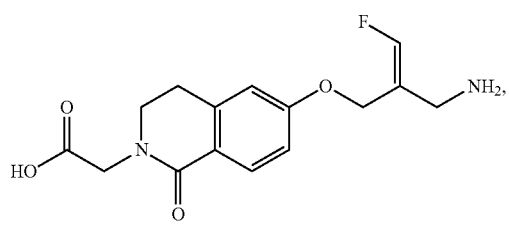
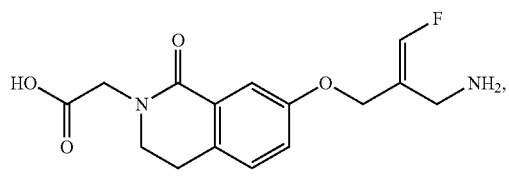

In still other embodiments, wherein the pharmaceutically acceptable salt is hydrochloride, hydrobromide or mesylate.

In other aspect, provided herein is a pharmaceutical composition comprising the compound disclosed herein.

In some embodiments, the pharmaceutical composition disclosed herein further comprises a pharmaceutically acceptable carrier, excipient, adjuvant, medium or a combination thereof.

In certain embodiments, the pharmaceutical composition provided herein further comprises one or more therapeutic agents.

In other embodiments, the therapeutic agent disclosed herein is a SSAO/VAP-1 inhibitor.

In other embodiments, the pharmaceutical composition of the invention is in the form of a liquid, solid, semi-solid, gel or spray.

In other embodiments of the pharmaceutical composition, the therapeutic agent is Vapaliximab, PRX-167700, BTT-1023, ASP-8232, PXS-4728A or RTU-1096.

In other aspect, provided herein is use of the compound or the pharmaceutical composition disclosed herein in the manufacture of a medicament for inhibiting SSAO/VAP-1.

In other aspect, provided herein is use of the compound or the pharmaceutical composition disclosed herein in the manufacture of a medicament for preventing, treating or lessening a disease related to SSAO/VAP-1 protein or regulated by SSAO/VAP-1 in a subject.

In certain embodiments, wherein the disease disclosed herein related to SSAO/VAP-1 protein or regulated by SSAO/VAP-1 is inflammation and/or a disease related inflammation, diabetes and/or a disease related diabetes, a mental disorder, an ischemic disease, a vascular disease, fibrosis or tissue transplant rejection.

In other embodiments, wherein the inflammation and/or a disease related inflammation disclosed herein is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis.

In still other embodiments, wherein the diabetes and/or a disease related diabetes disclosed herein is type I diabetes, type II diabetes, X syndrome, diabetic retinopathy, diabetic nephropathy, diabetic neuropathy or diabetic macular edema.

In still other embodiments, wherein the mental disorder disclosed herein is severe depression, bipolar depression or attention deficit hyperactivity disorder.

In still other embodiments, wherein the ischemic disease disclosed herein is apoplexia and/or a complication thereof, myocardial infarction and/or a complication thereof or damage of inflammatory cells to tissues after apoplexia.

In still other embodiments, wherein the fibrosis disclosed herein is hepatic fibrosis, cystic fibrosis, renal fibrosis, idiopathic pulmonary fibrosis or radiation-induced fibrosis.

In still other embodiments, wherein the vascular disease disclosed herein is atherosclerosis, chronic heart failure or congestive heart failure.

In still other embodiments, wherein the arthritis disclosed herein is osteoarthritis, rheumarthritis, rheumatoid arthritis or juvenile rheumatoid arthritis.

In still other embodiments, the systemic inflammatory response syndrome disclosed herein is systemic inflammatory sepsis.

In still other embodiments, the inflammatory bowel disease disclosed herein is irritable bowel syndrome.

In still other embodiments, the hepatopathy disclosed herein is a liver autoimmune disease, autoimmune hepatitis, primary biliary cirrhosis, sclerosing cholangitis, autoimmune cholangitis, an alcoholic liver disease or a non-alcoholic fatty liver disease.

In still some embodiments, the non-alcoholic fatty liver disease disclosed herein is nonalcoholic simple fatty liver, nonalcoholic steatohepatitis, cryptogenic cirrhosis or primary liver cancer related to nonalcoholic fatty liver disease.

In still other embodiments, the respiratory disease disclosed herein is asthma, acute lung injury, acute respiratory distress syndrome, lung inflammation, a chronic obstructive pulmonary disease, bronchitis or bronchiectasis.

In still other embodiments, the eye disease disclosed herein is uveitis, iritis, retinitis, autoimmune ophthalmia, inflammation driven by angiogenesis and/or lymphogenesis, macular degeneration.

In still other embodiments, the skin disease disclosed herein is contact dermatitis, skin inflammation, psoriasis or eczema.

In still other embodiments, the neuritis disclosed herein is Parkinson's disease, Alzheimer's disease, vascular dimentia, multiple sclerosis, chronic multiple sclerosis.

In certain embodiments, the disease disclosed herein is cancer.

In other aspect, the invention relates to a method for inhibiting SSAO/VAP-1 activity by using the compound or pharmaceutical composition of the invention, the method comprises administering an effective therapeutic amount of the compound or pharmaceutical composition to a subject in need.

In other aspect, the invention relates to a method for preventing or treating the following diseases by using the compound or pharmaceutical composition of the invention, the method comprises administering an effective therapeutic amount of the compound or pharmaceutical composition to an subject, wherein the disease is inflammation and/or a disease related inflammation, diabetes and/or a disease related diabetes, a mental disorder, an ischemic disease, a vascular disease, fibrosis or tissue transplant rejection. And, the compounds or pharmaceutical compositions thereof can be co-administered with other therapies or therapeutic agents. The co-administration can be performed simultaneously, sequentially, or in a certain time interval.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the attending doctor in accordance with specific conditions. For example, when the compound or pharmaceutical composition of the present invention is administrated intravenously, the administration may be once a week or even longer intervals.

In other aspect, provided herein is the compound or the pharmaceutical composition disclosed herein for use in inhibiting SSAO/VAP-1 activity.

In other aspect, the invention relates to the compound or the pharmaceutical composition disclosed herein for use in preventing, treating the following diseases, lessening the development or seizure of the following diseases, wherein the disease is inflammation and/or a disease related inflammation, diabetes and/or a disease related diabetes, a mental disorder, an ischemic disease, a vascular disease, fibrosis or tissue transplant rejection.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compound of the invention also embraces the salts thereof, and the salts are not necessarily pharmaceutically acceptable salts, and which may be useful as intermediates for preparing and/or purifying compounds of the invention and/or for separating enantiomers of compounds of the invention.

Pharmaceutically acceptable acid addition salts can be formed with inorganic and organic acid.

Pharmaceutically acceptable base addition salts can be formed with inorganic and organic bases.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have the structure depicted by the general formula given in the present invention, except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2H$, $^3H$, $^{11}C$, $^{13}C$, $^{14}C$, $^{15}N$, $^{18}F$, $^{31}P$, $^{32}P$, $^{36}S$, $^{37}Cl$, $^{125}I$, respectively.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

Pharmaceutical Composition of the Compound of the Invention and Preparations and Administration Provided herein is pharmaceutical composition, which comprises the compound of the invention or examples or a stereoisomer, a geometric isomer, a tautomer, an N-oxide, a solvate, a metabolite, a pharmaceutically acceptable salt or a prodrug thereof. The pharmaceutical composition further comprises at least one pharmaceutically acceptable carriers, excipients, adjuvants, vehicles, or a combination thereof, and optionally other treating and/or preventing ingredients. In one embodiment, the pharmaceutical composition comprises an effective amount of at least one pharmaceutically acceptable carriers, excipients, adjuvants or vehicles. The amount of the compound in the compositions disclosed herein is an effective and detectable amount for inhibiting SSAO/VAP-1 activity in biological samples or patients.

A pharmaceutically acceptable carrier may contain inert ingredients which do not unduely inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as Tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds or compositions of the present invention can be administered by any suitable means, and the compounds and the pharmaceutically acceptable compositions described above can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated.

Liquid formulations for oral administration include, but not limited to, pharmaceutically acceptable emulsions, micro-emulsion, solution, suspension, syrup and elixir. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Addition to inert diluents, the oral compositions can also contain adjuvants such as wetting agents, emulsifiers or suspending agent, sweeteners, flavorings and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carriers, such as sodium citrate or calcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, controlled release coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the pharmaceutical compositions may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per Use of the Compounds and Pharmaceutical Compositions The compound or the pharmaceutical composition disclosed herein can be use in the manufacture of a medicament for inhibiting SSAO/VAP-1.

The compound or the pharmaceutical composition disclosed herein can be used in preventing, treating or lessening a disease related to SSAO/VAP-1 protein or regulated by SSAO/VAP-1, the disease is inflammation and/or a disease related inflammation, diabetes and/or a disease related diabetes, a mental disorder, an ischemic disease, a vascular disease, fibrosis or tissue transplant rejection.

The compound or the pharmaceutical composition disclosed herein can be used in the manufacture of a medicament for preventing, treating or lessening a disease related to SSAO/VAP-1 protein or regulated by SSAO/VAP-1, the disease is inflammation and/or a disease related inflammation, diabetes and/or a disease related diabetes, a mental disorder, an ischemic disease, a vascular disease, fibrosis or tissue transplant rejection.

Provided herein is a method of treating, preventing or lessening a disease related to SSAO/VAP-1 protein or regulated by SSAO/VAP-1, and wherein the method comprises administering to the patent a therapeutically effective amount of the compound or the pharmaceutical composition described herein to a patient in need of treatment. The disease is inflammation and/or a disease related inflammation, diabetes and/or a disease related diabetes, a mental disorder, an ischemic disease, a vascular disease, fibrosis or tissue transplant rejection. And, the compounds or pharmaceutical compositions thereof can be co-administered with other therapies or therapeutic agents. The co-administration can be performed simultaneously, sequentially, or in a certain time interval.

Besides being useful for human treatment, these compounds are also useful for veterinary treatment of animals such as companion animals, exotic animals and farm animals, including mammals, rodents, and the like. In other embodiments, the animals disclosed herein include horses, dogs, and cats. As used herein, the compounds disclosed herein include the pharmaceutically acceptable derivatives thereof.

An "effective amount" or "effective dose" of the compound or pharmaceutically acceptable composition is an amount that is effective in treating or lessening the severity of one or more of the aforementioned disorders. The compounds and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The compounds and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

day). When multiple daily doses are used, the unit dosage form can be the same or different for each dose.

General Synthetic Procedures and Detection Method

For the purpose of describing the invention, the following examples are listed. It should be understood that, the invention is not limited to these examples, and the present invention only provides the method to practice the invention.

In the present invention, if the chemical name of the compound doesn't match the corresponding structure, the compound is characterized by the corresponding structure.

In the specification, the compound number in the examples, the compound number in the claims or the compound number in other positions in the specification are independent of each other. Wherein the compound in the activity test examples is the compound in the preparation examples with the same compound number.

Generally, the compounds disclosed herein may be prepared by methods described herein, wherein the substituents are as defined for Formula (I) or (II) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compounds were identified by nuclear magnetic resonance (e.g., $^1$H-NMR, $^{13}$C-NMR or/and $^{19}$F-NMR). $^1$H-NMR, $^{13}$C-NMR, $^{19}$F-NMR chemical shifts (δ) were recorded as ppm ($10^{-6}$). Measure of $^1$H-NMR, $^{13}$C-NMR, $^{19}$F-NMR are performed, respectively, on Bruker Ultrashield—400 nuclear magnetic resonance spectrometer and Bruker Avance III HD 600 nuclear magnetic resonance spectrometer using deuterated chloroform ($CDCl_3$), deuterated methanol ($CD_3OD$) or deuterated DMSO (DMSO-$d_6$) as a solvent. TMS (0 ppm) or chloroform (7.25 ppm) is as the reference standard. When peak multiplicities were reported, the following abbreviations were used: s (singlet), d (doublet), t (triplet), m (multiplet), br (broadened), dd (doublet of doublets), dt (doublet of triplets), td (triplet of doublets), brs (broadened singlet). Coupling constants J, when given, were reported in Hertz (Hz).

Novasep pump 250 high performance liquid chromatography is generally used for preparation, purification or separation.

LC-MS spectra were determined on Agilen-6120 Quadrupole LC/MS mass spectrometer.

The silica gel used in column chromatography generally was Qingdao Ocean Chemical Factory 300 to 400 mesh silica gel.

The starting materials of the present invention were known or purchased from Shanghai Accela Company, Energy Company, J&K, Alfa Company and the like, or they could be prepared by the conventional synthesis methods in the prior art.

Unless otherwise stated, the reactions disclosed herein were carried out in a nitrogen atmosphere.

The term "nitrogen atmosphere" refers to such an atmosphere that a reaction flask was equipped with a balloon or a stainless steel autoclave filled with about 1 L nitrogen.

The term "hydrogen atmosphere" refers to such an atmosphere that a reaction flask was equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature;

Unless otherwise stated, the room temperature was from 20° C. to 30° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compounds.

The elution system of column chromatography comprised: A: petroleum ether and ethyl acetate, B: dichloromethane and ethyl acetate, C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

HPLC refers to High Performance Liquid Chromatography.

HPLC was determined on Agilent 1200 DAD high pressure liquid chromatography spectrometer (Zorbax Eclipse Plus C18 150×4.6 mm chromatographic column).

The test condition of HPLC: the run time was 15-20 minutes (min); the column temperature was 35° C.; the detection was carried out at the wavelength of 210 nm and 254 nm using PDA detector;

Mobile phase: phase A: pH 2.5 potassium dihydrogen phosphate phase B: acetonitrile flow rate: 1.0 mL/min And the gradient of Mobile phase was in the Table A.

TABLE A

| Time | Gradient of Mobile Phase A | Gradient of Mobile Phase B |
|---|---|---|
| 0 min | 90% | 10% |
| 15 min | 30% | 70% |

The LC/MS/MS system used in biological analysis test comprises Agilent 1200 series vacuum degassing furnace, binary pumps, well-plate autosampler, thermostatted column compartment, the Agilent G6430 Triple Quadru pole Mass Spectrometer with an electrosprayionization (ESI) source. Quantitative analysis was carried out using MRM mode. The parameters for MRM transitions are in the Table B.

TABLE B

| Multiple Reaction Monitoring | 490.2 → 383.1 |
|---|---|
| Fragmentor | 230 V |
| Capillary voltage | 55 V |
| Temperature of dryer | 350° C. |
| Nebulizer | 0.28 MPa |
| Drying gas flow rate | 10 L/min |

An Agilent XDB-C18, 2.1×30 mm, 3.5 μM column was used for the analysis. 5 μL of the samples were injected. Analysis condition: The mobile phase was 0.1% formic acid in water (A) and 0.1% formic acid in methanol (B). The flow rate was 0.4 mL/min. And the gradient of mobile phase was in the Table C.

TABLE C

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 μL of the samples were injected.

The following abbreviations are used throughout the specification:

DMSO-$d_6$ dimethyl sulfoxide-$d_6$
CDCl$_3$ chloroform-d
CD$_3$OD methyl alcohol-d4
Ac: acetyl
Bn: Benzyl
Et: ethyl;
Me: methyl;
Ms: methylsulfonyl;
Boc: tert-butoxycarbonyl
PMB: p-methoxybenzyl;
% wt, mass %: weight percent;
mL milliliter;
μL: microlitre;
mol/L: moles per liter;
mol: mole;
mmol: millimole;
g: gram;
h: hour, hours;
H$_2$: hydrogen;
min: minute, minutes;
N$_2$: nitrogen;
MPa: mega pascal;
atm: standard atmospheric pressure.

General Synthetic Procedures

Typical synthetic procedures for preparing the compounds of the present invention disclosed are shown in the following scheme 1. Unless otherwise stated, each ring Cy, $R^6$, X, $R^8$, $R^9$, Y, Z, t and n are as defined herein, PG is amino protecting group, LG is leaving group.

Scheme 1:

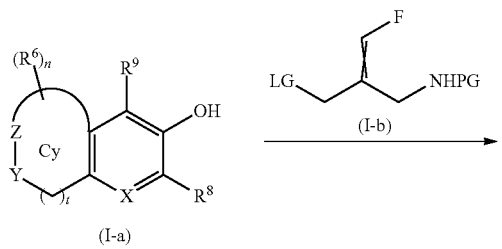

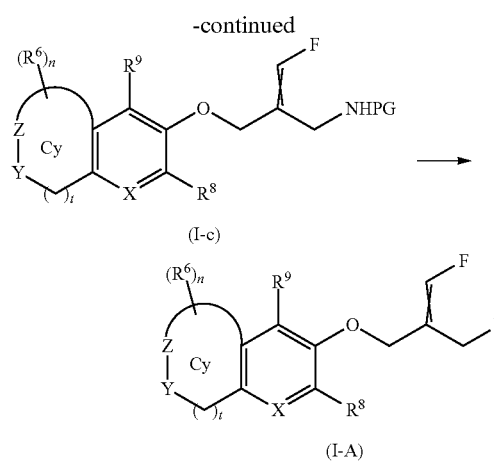

The compound having formula (I-A) can be prepared by the general synthesis method described in scheme 1, and the specific steps can refer to the examples. Compound (I-a) undergoes a nucleophilic reaction with compound (I-b) under alkaline conditions to give compound (I-c); an amino protecting group PG of compound (I-c) can be removed to give the target compound having formula (I-A). In general, free amino compounds, i.e. the target compounds having formula (I-A), are converted into acid addition salts for facilitate treatment and improvement of chemical stability.

Some non-limited examples of the acid addition salts include hydrochloride, hydrobromate and methanesulphonate.

EXAMPLES

Preparation Example

Example 1 7-[(E)-2-(aminomethyl)-3-fluoro-allyloxy]-3,4-dihydro-1H-quinolin-2-one hydrochloride 1

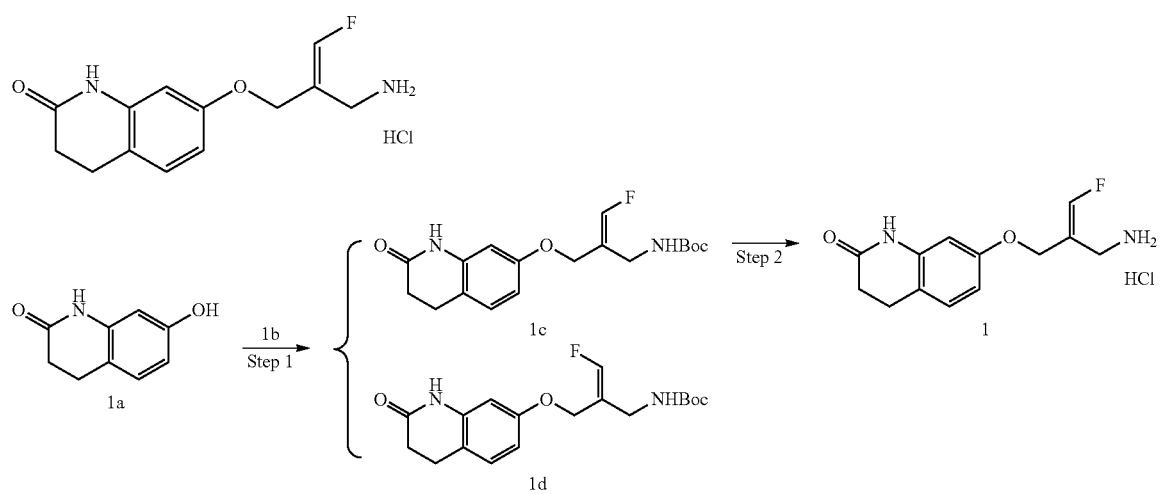

Step 1 t-butyl N—[(E)-3-fluoro-2-[(2-oxo-3,4-dihydro-1H-quinolin-7-yl)oxymethyl]allyl]carbamate 1c and t-butyl N—[(Z)-3-fluoro-2-[(2-oxo-3,4-dihydro-1H-quinolin-7-yl) oxymethyl]allyl]carbamate 1d To a solution of 7-hydroxy-3,4-dihydro-1H-quinolin-2-one 1a (0.40 g, 2.5 mmol) in N,N-dimethyl formamide (5 mL) were added t-butyl N-[2-(bromomethyl)-3-fluoro-allyl] carbamate 1b (0.73 g, 2.7 mmol) and potassium carbonate (0.68 g, 4.9 mmol). The mixture was stirred at 50° C. for 15 hours. After the mixture was cooled to rt, ethyl acetate (20 ml) and water (10 ml) were added and which was stirred for 10 min. The water phase was separated and extracted with ethyl acetate (15 mL×3). The combined organic phases were washed with water (15 mL) and saturated sodium chloride solution (15 mL), and dried over anhydrous sodium sulfate. The mixture was filtered by suction filtration, the filtrate was concentrated, the residue was purified by silica gel column chromatography (petroleum ether/ethyl acetate (v/v)=2/1) to give the title compound 1c (0.56 g, yield: 65%) and 1d (0.20 g, yield: 23%), both are white solid.

MS (ESI, pos. ion) m/z: 373.1 [M+Na]$^+$.

Step 2 7-[(E)-2-(aminomethyl)-3-fluoro-allyloxy]-3,4-dihydro-1H-quinolin-2-one hydrochloride 1 t-Butyl N—[(E)-3-fluoro-2-[(2-oxo-3,4-dihydro-1H-quinol-7-yl)oxymethyl]allyl]carbamate 1c (0.20 g, 0.57 mmol)

was dissolved in hydrogen chloride-ethyl acetate solution (10 mL, 4 mol/L). The mixture was stirred at rt for 0.5 hour. The mixture was concentrated to give the title compound 1 (0.16 g, yield: 99%, HPLC: 90.04%) as a white solid.

MS (ESI, pos. ion) m/z: 251.1 [M−Cl]+;

1H NMR (400 MHz, CD3OD) δ (ppm) 7.23 (d, J=73.5 Hz, 1H), 7.11 (s, 1H), 6.66 (dd, J=8.3, 2.5 Hz, 1H), 6.56 (d, J=2.4 Hz, 1H), 4.60 (d, J=3.4 Hz, 2H), 3.83 (s, 2H), 2.89 (t, J=7.5 Hz, 2H), 2.55 (t, J=7.5 Hz, 2H);

19F NMR (376 MHz, CD3OD) δ (ppm) −123.62.

Example 2 7-[(Z)-2-(aminomethyl)-3-fluoro-allyloxy]-3,4-dihydro-1H-quinolin-2-one hydrochloride 2

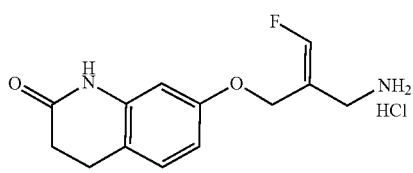

The title compound 2 (45 mg, yield: 99%, HPLC: 84.07%) was obtained according to the method described in step 2 of example 1 by using t-butyl N—[(Z)-3-fluoro-2-[(2-oxo-3,4-dihydro-1H-quinolin-7-yl)oxymethyl]allyl]carbamate 1d (55 mg, 0.16 mmol) instead of compound 1c.

MS (ESI, pos. ion) m/z: 251.1 [M−Cl]+;

1H NMR (400 MHz, CD3OD) δ (ppm) 7.13 (d, J=8.3 Hz, 1H), 7.11 (d, J=81.2 Hz, 1H), 6.67 (dd, J=8.3, 2.5 Hz, 1H), 6.58 (d, J=2.4 Hz, 1H), 4.80 (d, J=2.2 Hz, 2H), 3.70 (s, 2H), 2.90 (t, 2H), 2.55 (t, 2H);

19F NMR (376 MHz, CD3OD) δ (ppm) −121.79.

Example 3 6-[(E)-2-(aminomethyl)-3-fluoro-allyloxy]-3,4-dihydro-2H-isoquinolin-1-one hydrochloride 3 and 6-[(Z)-2-(aminomethyl)-3-fluoro-allyloxy]-3,4-dihydro-2H-isoquinolin-1-one hydrochloride 4

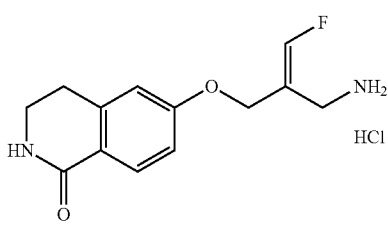

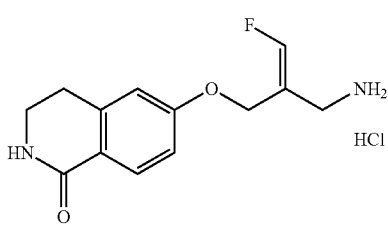

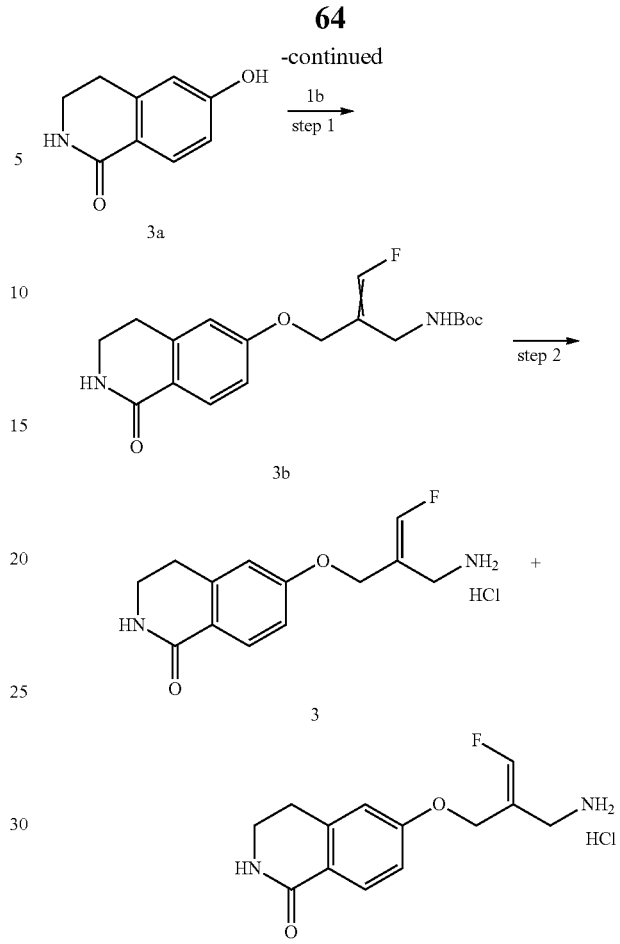

Step 1 t-butyl N-[3-fluoro-2-[(1-oxo-3,4-dihydro-2H-isoquinolin-6-yl)oxymethyl]allyl]carbamate 3b t-Butyl N-[2-(bromomethyl)-3-fluoro-allyl]carbamate 1b (0.50 g, 1.9 mmol) was dissolved in N,N-dimethylformamide (10 mL), then potassium carbonate (0.29 g, 2.1 mmol) and 6-hydroxy-3,4-dihydro-2H-isoquinolin-1-one 3a (0.20 g, 1.2 mmol) were added, the resulting mixture was stirred at 40° C. for 11 hours. To the reaction mixture was added water (15 mL) to quench the reaction, and the mixture was extracted with ethyl acetate (30 mL×2). The combined organic layers were washed with saturated sodium chloride solution (50 mL), dried over anhydrous sodium sulfate, and filtered by suction filtration. The filtrate was concentrated to give the title compound 3b (0.41 g, yield: 61%) as yellow oil. The crude product was used in the next step without further purification.

MS (ESI, pos. ion) m/z: 373.1 [M+Na]+.

Step 2 6-[(E)-2-(aminomethyl)-3-fluoro-allyloxy]-3,4-dihydro-2H-isoquinolin-1-one hydrochloride 3 and 6-[(Z)-2-(aminomethyl)-3-fluoro-allyloxy]-3,4-dihydro-2H-isoquinolin-1-one hydrochloride 4 t-Butyl N-[3-fluoro-2-[(1-oxo-3,4-dihydro-2H-isoquinolin-6-yl)oxymethyl]allyl]carbamate 3b (0.35 g, 1.0 mmol) was dissolved in hydrogen chloride-ethyl acetate solution (15 mL, 4 mol/L), the mixture was stirred at rt for 1 hour. The reaction mixture was concentrated, the residue was purified, and reacted with hydrogen chloride-ethyl acetate solution to give the title compound 3 (0.15 g, yield: 52%, HPLC: 97.43%) and 4 (51 mg, yield: 17%, HPLC: 97.80%), both are white solid.

Compound 3:

MS (ESI, pos. ion) m/z: 251.1 [M−Cl]⁺;

¹H NMR (400 MHz, DMSO-d₆) δ (ppm) 8.32 (s, 3H), 7.86-7.69 (m, 2H), 7.33 (d, J=81.9 Hz, 1H), 6.94 (dd, J=11.0, 2.4 Hz, 2H), 4.69 (d, J=3.1 Hz, 2H), 3.60 (d, J=5.0 Hz, 2H), 3.35 (t, J=5.7 Hz, 2H), 2.87 (t, J=6.5 Hz, 2H).

Compound 4:

MS (ESI, pos. ion) m/z: 251.1 [M−Cl]⁺;

¹H NMR (400 MHz, DMSO-d₆) δ (ppm) 8.32 (s, 3H), 7.86-7.69 (m, 2H), 7.33 (d, J=81.9 Hz, 1H), 6.94 (dd, J=11.0, 2.4 Hz, 2H), 4.69 (d, J=3.1 Hz, 2H), 3.60 (d, J=5.0 Hz, 2H), 3.35 (t, J=5.7 Hz, 2H), 2.87 (t, J=6.5 Hz, 2H).

Example 4 6-[(E)-2-(aminomethyl)-3-fluoro-allyloxy]-2-phenyl-3,4-dihydroisoquinolin-1-one hydrochloride 5

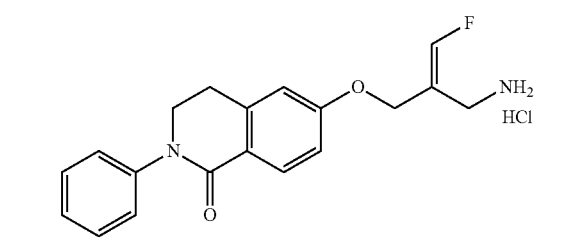

5

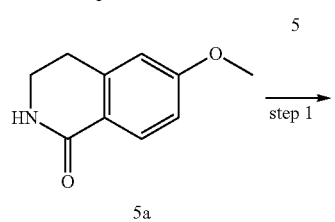

5a

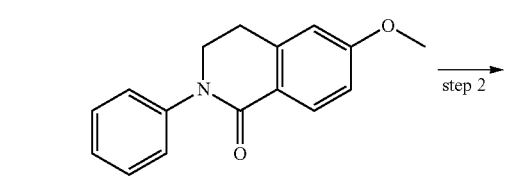

5b

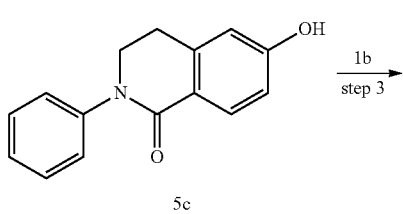

5c

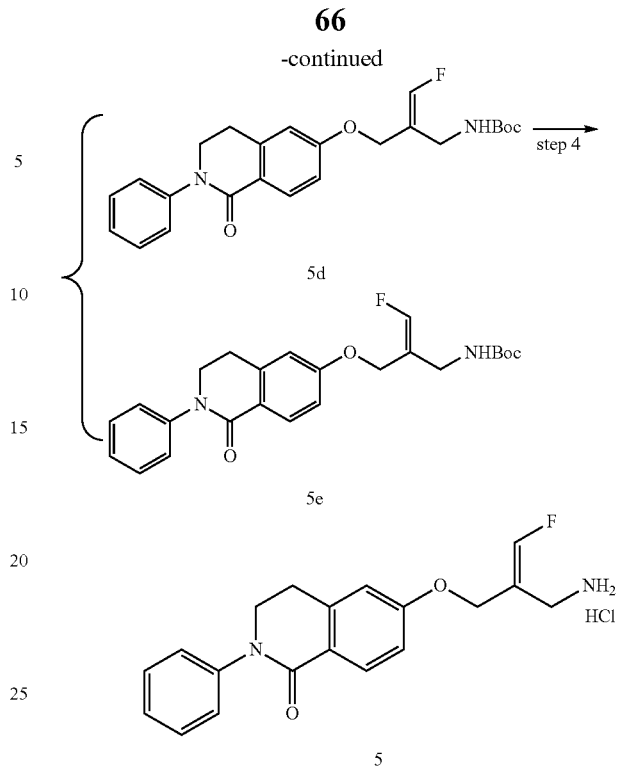

Step 1
6-methoxy-2-phenyl-3,4-dihydroisoquinolin-1-one 5b 6-(Methoxy)-3,4-dihydro-1(2H)-isoquinolinone 5a (0.55 g, 3.10 mmol) was dissolved in N,N-dimethylformamide (15 mL), and then iodobenzene (1.20 g, 5.76 mmol), cuprous iodide (0.07 g, 0.40 mmol) and potassium carbonate (0.45 g, 3.20 mmol) were added, the resulting mixture was refluxed at 150° C. for 48 hours. The reaction was quenched with water (10 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 5b (0.50 g, yield: 64%) as a white solid.

MS (ESI, pos. ion) m/z: 254.1 [M+H]⁺.

Step 2
6-hydroxy-2-phenyl-3,4-dihydroisoquinolin-1-one 5c

6-Methoxy-2-phenyl-3,4-dihydroisoquinolin-1-one 5b (0.50 g, 1.97 mmol) was dissolved in dichloromethane (20 mL), the mixture was cooled to 0° C. and boron tribromide (1.00 mL, 10.55 mmol) was added dropwise, the resulting mixture was stirred at 0° C. for 2 hours. The reaction mixture was poured into ice-water (20 mL) to quench the reaction, when the ice melt, a lot of solid precipitated out. The mixture was filtered by suction filtration to give the title compound 5c (0.27 g, yield: 57%) as a white solid.

MS (ESI, pos. ion) m/z: 240.2 [M+H]⁺.

Step 3 t-butyl N—[(E)-3-fluoro-2-[(1-oxo-2-phenyl-3,4-dihydroquinolin-6-yl)oxymethyl]allyl]carbamate 5d and t-butyl N—[(Z)-3-fluoro-2-[(1-oxo-2-phenyl-3,4-dihydroquinol-6-yl)oxymethyl]allyl]carbamate 5e To a solution of 6-hydroxy-2-phenyl-3,4-dihydroisoquinolin-1-one 5c (0.27 g, 1.13 mmol) in N,N-dimethyl formamide (15 mL) were added t-butyl N-[2-(bromomethyl)-3-fluoro-allyl]carbamate 1b (0.30 g, 1.12 mmol) and cesium carbonate (0.60 g, 1.84 mmol), the resulting mixture was stirred at rt for 1.5 hours. The reaction was quenched with water (10 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 5d (75 mg, yield: 16%) and 5e (35 mg, yield: 7.3%), both are white solid.

MS (ESI, pos. ion) m/z: 427.1 [M+H]$^+$.

Step 4 6-[(E)-2-(aminomethyl)-3-fluoro-allyloxy]-2-phenyl-3,4-dihydroisoquinolin-1-one hydrochloride 5 t-Butyl N—[(E)-3-fluoro-2-[(1-oxo-2-phenyl-3,4-dihydroisoquinolin-6-yl)oxymethyl]allyl]carbamate 5d (75 mg, 0.55 mmol) was dissolved in ethyl acetate solution, and then hydrogen chloride-ethyl acetate solution (2 mL, 4 mol/L) was added, the mixture was stirred at rt for 1 hour. The mixture was concentrated to give the title compound 5 (60 mg, yield: 94%, HPLC: 90.04%) as a white solid.

MS (ESI, pos. ion) m/z: 327.0 [M−Cl]$^+$;
$^1$H NMR (400 MHz, DMSO-d$_6$) δ (ppm) 8.36 (s, 3H), 7.90 (d, J=9.2 Hz, 1H), 7.52-7.33 (m, 4H), 7.34-7.18 (m, 2H), 7.08-6.94 (m, 2H), 4.74 (d, J=2.5 Hz, 2H), 3.94 (t, J=6.4 Hz, 2H), 3.62 (s, 2H), 3.11 (t, J=6.3 Hz, 2H).

Example 5 6-[(Z)-2-(aminomethyl)-3-fluoro-allyloxy]-2-phenyl-3,4-dihydroisoquinolin-1-one hydrochloride 6

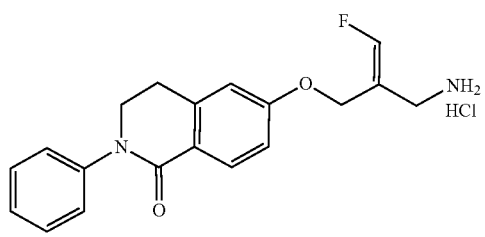

6

The title compound 6 (20 mg, yield: 67%, HPLC: 86.15%) as a white solid was obtained according to the method described in step 4 of example 4 by using t-butyl N—[(Z)-3-fluoro-2-[(1-oxo-2-phenyl-3,4-dihydroisoquinol-6-yl)oxymethyl]allyl]carbamate 5e (35 mg, 0.08 mmol) instead of compound 5d.

MS (ESI, pos. ion) m/z: 327.3 [M−Cl]$^+$;
$^1$H NMR (400 MHz, DMSO-d$_6$) δ (ppm) 8.35 (s, 3H), 7.89 (d, J=9.3 Hz, 1H), 7.40 (t, J=6.2 Hz, 4H), 7.24 (s, 1H), 7.16 (s, 1H), 7.00 (s, 2H), 4.84 (s, 2H), 3.94 (s, 2H), 3.54 (s, 2H), 3.10 (s, 2H).

Example 6 6-[(E)-2-(aminomethyl)-3-fluoro-allyloxy]-2-(pyrimidin-2-yl)-3,4-dihydro isoquinolin-1-one hydrochloride 7

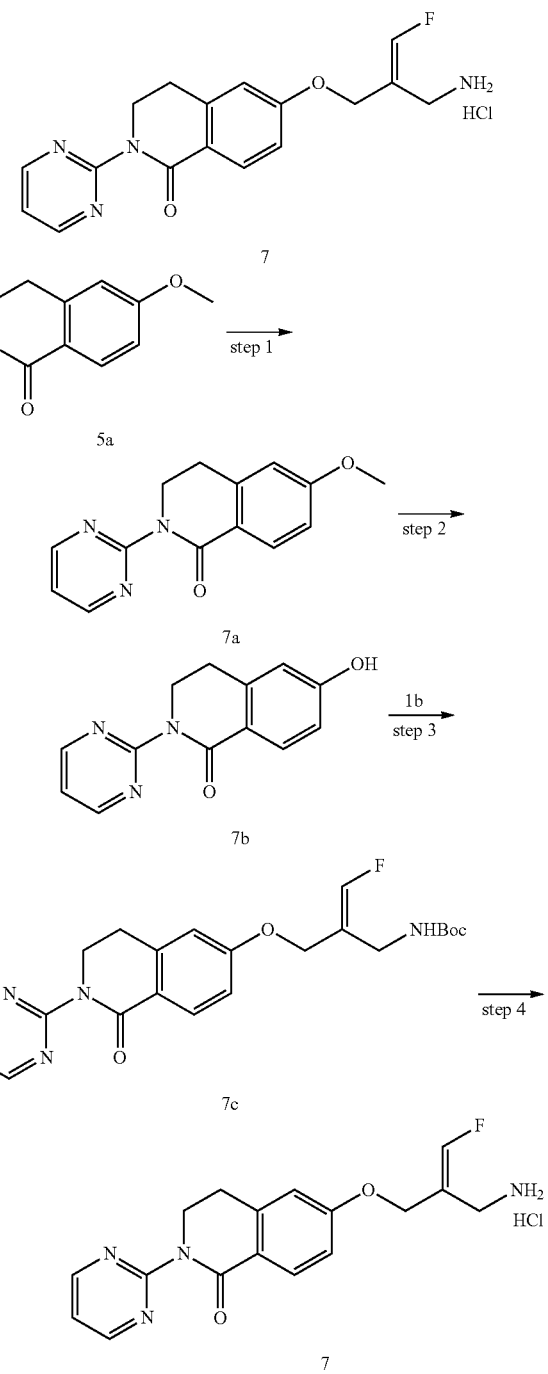

Step 1 6-methoxy-2-(pyrimidin-2-yl)-3,4-dihydroisoquinolin-1-one 7a

To a 50 mL two-neck flask were added 6-(methoxy)-3,4-dihydro-2H-isoquinolin-1-one 5a (0.20 g, 1.1 mmol), 2-chloropyrimidine (0.160 g, 1.40 mmol), tris(dibenzylideneacetone)dipalladium (0.053 g, 0.056 mmol) and 4,5-bis (diphenylphosphino)-9,9-dimethylxanthene (0.10 g, 0.17 mmol) in turn, then 1,4-dioxane (3 mL) was added under N₂, the mixture was stirred at 100° C. for 16 hours. The mixture was cooled to rt and diluted with dichloromethane (20 mL), filtered through celite. The filtrate was concentrated, and the residue was purified by silica gel column chromatography (petroleum ether/ethyl acetate (v/v)=1/3) to give the title compound 7a (0.25 g, yield: 90%) as a yellow solid.

MS (ESI, pos. ion) m/z: 256.0 [M+H]⁺;

¹H NMR (400 MHz, CDCl₃) δ (ppm) 8.73 (d, J=4.7 Hz, 2H), 8.20 (d, J=8.7 Hz, 1H), 7.08 (t, J=4.8 Hz, 1H), 6.88 (dd, J=8.6, 1.7 Hz, 1H), 6.72 (s, 1H), 4.24 (t, J=6.3 Hz, 2H), 3.86 (s, 3H), 3.11 (t, J=6.2 Hz, 2H).

Step 2 6-hydroxy-2-(pyrimidin-2-yl)-3,4-dihydroisoquinolin-1-one 7b

At −10° C. and under N₂, boron tribromide (1.2 mL, 12.6 mmol) was added dropwise into a solution of 6-methoxy-2-(pyrimidin-2-yl)-3,4-dihydroisoquinolin-1-one 7a (0.267 g, 1.05 mmol) in dichloromethane (10 mL), the mixture was moved to rt and stirred for 2 hours. The mixture was cooled to −10° C., and methanol (6 mL) was added slowly. The resulting mixture was concentrated to give the title compound 7b (0.25 g, yield: 99%) as an orange solid, the crude product was used in the next step without further purification.

MS (ESI, pos. ion) m/z: 242.2 [M+H]⁺.

Step 3 t-butyl N—[(E)-3-fluoro-2-[(1-oxo-2-(pyrimidin-2-yl)-3,4-dihydroisoquinolin-6-yl)oxymethyl] allyl]carbamate 7c To a solution of 6-hydroxy-2-(pyrimidin-2-yl)-3,4-dihydroisoquinolin-1-one 7b (0.25 g, 1.0 mmol) and t-butyl N-[2-(bromomethyl)-3-fluoro-allyl]carbamate 1b (0.30 g, 1.1 mmol) in N,N-dimethylformamide (5 mL) was added potassium carbonate (0.43 g, 3.1 mmol). The reaction mixture was stirred at 40° C. in an oil bath for 8 hours. To the reaction was added water (20 mL) and ethyl acetate (20 mL), the mixture was stirred for 10 min. The water phase was extracted with ethyl acetate (20 mL×2). The combined organic phases were washed with water (20 mL) and saturated sodium chloride solution (20 mL) and concentrated. The residue was purified by silica gel column chromatography (petroleum ether/ethyl acetate (v/v)=1/3) to give a white solid, then further purified by recrystallization with ethyl acetate/petroleum ether (v/v=1/4, 5 mL) to give the title compound 7c (0.15 g, yield: 33%) as a white solid.

MS (ESI, pos. ion) m/z: 429.3 [M+H]⁺;

¹H NMR (400 MHz, CDCl₃) δ (ppm) 8.74 (d, J=4.8 Hz, 2H), 8.20 (d, J=8.7 Hz, 1H), 7.10 (t, J=4.8 Hz, 1H), 6.94-6.82 (m, 1H), 6.77 (d, J=81.7 Hz, 1H), 6.75 (dd, J=7.6, 1.9 Hz, 1H), 4.76 (s, 1H), 4.50 (d, J=2.9 Hz, 2H), 4.24 (t, J=6.3 Hz, 2H), 4.01 (d, J=4.8 Hz, 2H), 3.10 (t, J=6.2 Hz, 2H), 1.41 (s, 9H);

¹⁹F NMR (376 MHz, CDCl₃) δ (ppm) −128.20.

Step 4 6-[(E)-2-(aminomethyl)-3-fluoro-allyloxy]-2-(pyrimidin-2-yl)-3,4-dihydroisoquinolin-1-one hydrochloride 7 t-Butyl N—[(E)-3-fluoro-2-[(1-oxo-2-(pyrimidin-2-yl)-3,4-dihydroquinol-6-yl)oxymethyl]allyl]carbamate 7c (0.14 g, 0.33 mmol) was dissolved in dichloromethane (2 mL), and then hydrogen chloride-ethyl acetate solution (10 mL, 4 mol/L) was added, the mixture was stirred at rt for 1.5 hours.

The mixture was concentrated to give the title compound 7 (0.10 g, yield: 84%, HPLC: 82.9%) as a white solid.

MS (ESI, pos. ion) m/z: 329.3 [M−Cl]⁺;

¹H NMR (400 MHz, CD₃OD) δ (ppm) 9.09 (d, J=5.1 Hz, 2H), 8.19 (d, J=8.7 Hz, 1H), 7.69 (t, J=5.2 Hz, 1H), 7.29 (d, J=81.0 Hz, 1H), 7.13 (dd, J=8.6, 2.0 Hz, 1H), 7.09 (s, 1H), 4.79 (d, J=3.2 Hz, 2H), 4.58 (t, J=6.1 Hz, 2H), 3.87 (s, 2H), 3.26 (t, J=6.1 Hz, 2H);

¹⁹F NMR (376 MHz, CD₃OD) δ (ppm) −122.36.

Example 7 6-[(E)-2-(aminomethyl)-3-fluoro-allyloxy]-2-methyl-3,4-dihydroisoquinolin-1-one hydrochloride 8

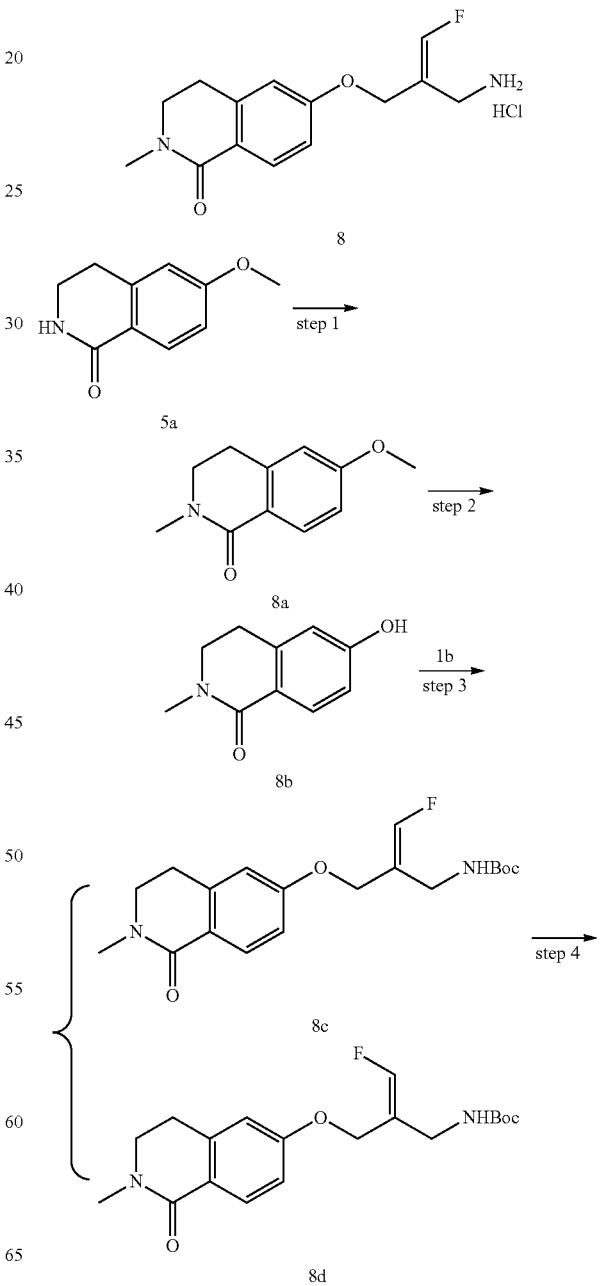

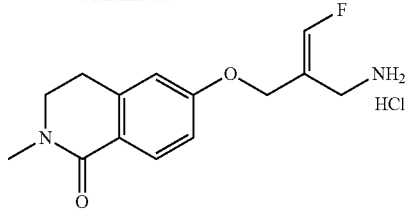

8

Step 1
6-methoxy-2-methyl-3,4-dihydroisoquinolin-1-one 8a

At 0° C., a solution of 6-(methoxy)-3,4-dihydro-2H-isoquinolin-1-one 5a (0.50 g, 2.8 mmol) in N,N-dimethylformamide (10 mL) was added into a solution of sodium hydride (0.14 g, 3.3 mmol, 60% wt) in N,N-dimethylformamide (5 mL), the resulting mixture was stirred at rt for 30 min, and then iodomethane (0.2 mL, 3.3 mmol) was added, the resulting mixture was further stirred for 5 hours. The mixture was poured into ice-water (20 mL) to quench the reaction. The resulting mixture was extracted with ethyl acetate (30 mL×2). The combined organic phases were washed with saturated sodium chloride solution (50 mL), dried over anhydrous sodium sulfate, filtered by suction filtration. The filtrate was concentrated. The residue was purified by silica gel column chromatography (ethyl acetate/petroleum ether (v/v)=1/3) to give the title compound 8a (0.46 g, yield: 87%) as light yellow oil.

$^1$H NMR (400 MHz, DMSO-d$_6$) δ 7.79 (d, J=8.6 Hz, 1H), 6.87 (dd, J=8.6, 2.5 Hz, 1H), 6.83 (d, J=2.2 Hz, 1H), 3.80 (s, 3H), 3.50 (t, J=6.7 Hz, 2H), 2.99 (s, 3H), 2.94 (t, J=6.7 Hz, 2H).

Step 2
6-hydroxy-2-methyl-3,4-dihydroisoquinolin-1-one 8b

At −20° C., boron tribromide (0.8 mL, 8 mmol) was added dropwise into a solution of 6-methoxy-2-methyl-3,4-dihydroisoquinolin-1-one 8a (513 mg, 7.8 mmol) in dichloromethane (40 mL), the mixture was stirred at rt for 3 hours. The reaction mixture was poured into ice-water (30 mL) to quench the reaction. The mixture was filtered by suction filtration, the filter cake was washed with water (10 mL) to give the title compound 8b (310 mg, yield: 65%) as an off-white solid.

MS (ESI, pos. ion) m/z: 178.1 [M+H]$^+$.

Step 3 t-butyl N—[(E)-3-fluoro-2-[(2-methyl-1-oxo-3,4-dihydroisoquinolin-6-yl)oxymethyl]allyl]carbamate 8c and t-butyl N—[(Z)-3-fluoro-2-[(2-methyl-1-oxo-3,4-dihydroisoquinolin-6-yl)oxymethyl]allyl]carbamate 8d To a solution of 6-hydroxy-2-methyl-3,4-dihydroisoquinolin-1-one 8b (0.24 g, 1.3 mmol) in N,N-dimethyl formamide (5 mL) was added potassium carbonate (0.28 g, 2.0 mmol), after the mixture was stirred for 5 min, t-butyl N-[2-(bromomethyl)-3-fluoro-allyl]carbamate 1b (0.24 g, 1.3 mmol) was added, the resulting mixture was stirred at rt for 3.5 hours. The mixture was poured into water (10 mL) to quench the reaction. The resulting mixture was extracted with ethyl acetate (15 mL×2). The combined organic phases were washed with saturated sodium chloride solution (30 mL), dried over anhydrous sodium sulfate, filtered by suction filtration. The filtrate was concentrated. The residue was purified by silica gel column chromatography (ethyl acetate/petroleum ether (v/v)=1/3) to give the title compound 8c (0.21 g, yield: 42%) and 8d (94 mg, yield: 19%), both are colorless oil.

MS (ESI, pos. ion) m/z: 365.1 [M+H]$^+$.

Step 4 6-[(E)-2-(aminomethyl)-3-fluoro-allyloxy]-2-methyl-3,4-dihydroisoquinolin-1-one hydrochloride 8

Hydrogen chloride-ethyl acetate solution (5 mL, 4 mol/L) was added into a solution of t-butyl N—[(E)-3-fluoro-2-[(2-methyl-1-oxo-3,4-dihydroisoquinolin-6-yl)oxymethyl]allyl] carbamate 8c (0.20 g, 0.55 mmol) in ethyl acetate (2 mL), the mixture was stirred at rt for 2 hour and concentrated to give the title compound 8 (0.16 g, yield: 96%, HPLC: 98.83%) as an off-white solid.

MS (ESI, pos. ion) m/z: 265.1[M−Cl]$^+$;

$^1$H NMR (400 MHz, DMSO-d$_6$) δ (ppm) 8.44 (s, 3H), 7.80 (d, J=8.5 Hz, 1H), 7.32 (d, J=82.0 Hz, 1H), 6.99-6.86 (m, 2H), 4.71 (d, J=3.0 Hz, 2H), 3.58 (d, J=4.8 Hz, 2H), 3.51 (t, J=6.6 Hz, 2H), 2.99 (s, 3H), 2.95 (t, J=6.6 Hz, 2H).

Example 8 6-[(Z)-2-(aminomethyl)-3-fluoro-allyloxy]-2-methyl-3,4-dihydroisoquinolin-1-one hydrochloride 9

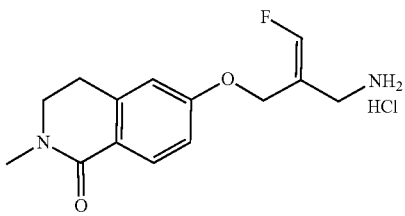

9

The title compound 9 (35 mg, yield: 92%, HPLC: 96.05%) as an off-white solid was obtained according to the method described in step 4 of example 7 by using t-butyl N—[(Z)-3-fluoro-2-[(2-methyl-1-oxo-3,4-dihydroisoquinolin-6-yl)oxymethyl]allyl]carbamate 8d (46 mg, 0.13 mmol) instead of compound 8c.

MS (ESI, pos. ion) m/z: 265.3[M−Cl]$^+$;

$^1$H NMR (400 MHz, DMSO-d$_6$) δ (ppm) 8.34 (s, 3H), 7.81 (d, J=8.5 Hz, 1H), 7.24 (d, J=82.1 Hz, 1H), 7.00-6.88 (m, 2H), 4.79 (s, 2H), 3.51 (d, J=6.6 Hz, 4H), 3.00 (s, 3H), 2.95 (t, J=6.6 Hz, 2H).

Example 9 6-[(E)-2-(aminomethyl)-3-fluoro-allyloxy]-2-(tetrahydropyranyl-4-methylene)-3,4-dihydroisoquinolin-1-one hydrochloride 10

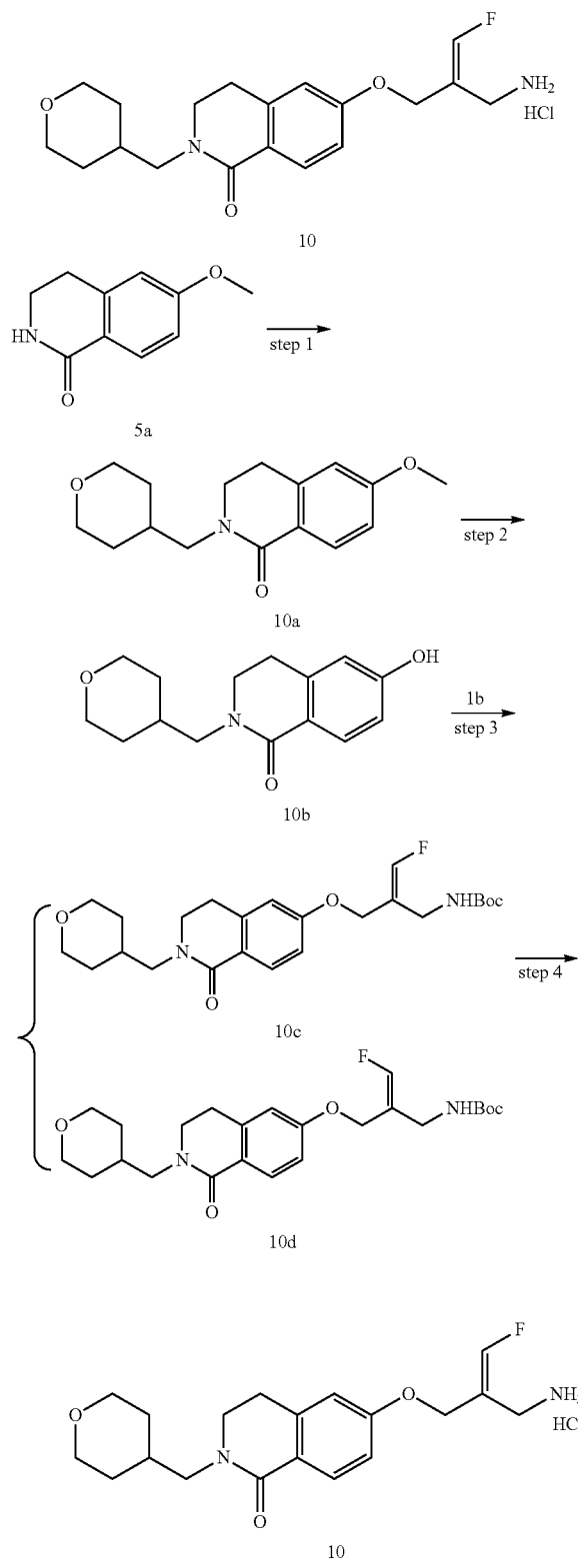

Step 1 6-methoxy-2-(tetrahydropyranyl-4-methylene)-3,4-dihydroisoquinolin-1-one 10a At 0° C., to a solution of sodium hydride (0.45 g, 11.25 mmol, 60% wt) in N,N-dimethylformamide (15 mL) was added a solution of 6-methoxy-3,4-dihydro-2H-isoquinolin-1-one 5a (1.70 g, 9.59 mmol) in N,N-dimethylformamide (15 mL) dropwise, the resulting mixture was stirred at 0° C. for 1 hour, and then 4-(bromomethyl)-tetrahydropyrane (1.80 g, 10.10 mmoL) was added dropwise, the mixture was stirred at rt for 34 hours. To the reaction mixture was added water (20 mL) to quench the reaction, and the mixture was extracted with ethyl acetate (60 mL). The organic layer was washed with saturated sodium chloride solution (50 mL×2), dried over anhydrous sodium sulfate, and filtered by suction filtration. The filtrate was concentrated to give the title compound 10a (0.95 g, yield: 36%) as a white solid.

MS (ESI, pos. ion) m/z: 276.1 [M+H]$^+$.

Step 2 6-hydroxy-2-(tetrahydropyranyl-4-methylene)-3,4-dihydroisoquinolin-1-one 10b 6-Methoxy-2-(tetrahydropyranyl-4-methylene)-3,4-dihydroisoquinolin-1-one 10a (0.95 g, 3.50 mmol) was dissolved in dichloromethane (20 mL), the mixture was cooled to 0° C. and boron tribromide (1.00 mL, 10.00 mmol) was added dropwise, the resulting mixture was stirred at 0° C. for 0.6 hour. The reaction mixture was poured into ice-water (20 mL) to quench the reaction, when the ice melt, after the mixture was warmed to rt, the mixture was filtered by suction filtration to give the title compound 10b (0.55 g, yield: 61%) as an off-white solid.

MS (ESI, pos. ion) m/z: 262.2 [M+H]$^+$.

Step 3 t-butyl N—[(E)-3-fluoro-2-[[1-oxo-2-(tetrahydropyranyl-4-methylene)-3,4-dihydro isoquinolin-6-yl]oxymethyl]allyl]carbamate 10c and t-butyl N—[(Z)-3-fluoro-2-[[1-oxo-2-(tetrahydropyranyl-4-methylene)-3,4-dihydroisoquinolin-6-yl]oxymethyl]allyl]carbamate 10d To a solution of 6-hydroxy-2-(tetrahydropyranyl-4-methylene)-3,4-dihydroisoquinolin-1-one 10b (1.0 g, 2.86 mmol) and t-butyl N-[2-(bromomethyl)-3-fluoro-allyl]carbamate 1b (0.55 g, 2.10 mmol) in N,N-dimethylformamide (10 mL) was added cesium carbonate (1.00 g, 3.07 mmol), the mixture was stirred at rt for 1 hour. The reaction was quenched with water (10 mL). The resulting mixture was extracted with ethyl acetate (30 mL). The organic phase was washed with saturated sodium chloride solution (30 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 10c (39 mg, yield: 4%) and 10d (50 mg, yield: 5%), both are colorless oil.

MS (ESI, pos. ion) m/z: 449.1 [M+H]$^+$.

Step 4 6-[(E)-2-(aminomethyl)-3-fluoro-allyloxy]-2-(tetrahydropyranyl-4-methylene)-3,4-dihydroisoquinolin-1-one hydrochloride 10 t-Butyl N—[(E)-3-fluoro-2-[[1-oxo-2-(tetrahydropyranyl-4-methylene)-3,4-dihydro isoquinolin-6-yl]oxymethyl] allyl]carbamate 10c (0.15 g, 0.41 mmol) was dissolved in ethyl acetate (2 mL), and then hydrogen chloride-ethyl acetate solution (2 mL, 4 mol/L) was added, the mixture was stirred at rt for 30 min. The mixture was concentrated to give the title compound 10 (30 mg, yield: 89%, HPLC: 82.10%) as a colorless oil.

MS (ESI, pos. ion) m/z: 349.1 [M−Cl]+;

$^1$H NMR (400 MHz, DMSO-d$_6$) δ (ppm) 8.25 (s, 3H), 7.81 (d, J=8.6 Hz, 1H), 7.34 (d, J=82.1 Hz, 1H), 6.95 (dd, J=8.6, 2.3 Hz, 1H), 6.91 (s, 1H), 4.69 (d, J=2.9 Hz, 2H), 3.84 (d, J=9.1 Hz, 2H), 3.61 (s, 2H), 3.52 (t, J=6.4 Hz, 2H), 3.35 (s, 2H), 3.27 (t, J=11.7 Hz, 2H), 2.93 (t, J=6.4 Hz, 2H), 1.92 (s, 2H), 1.53 (d, J=11.9 Hz, 2H), 1.20 (s, 1H).

Example 10 6-[(Z)-2-(aminomethyl)-3-fluoro-allyloxy]-2-(tetrahydropyranyl-4-methylene)-3,4-dihydroisoquinolin-1-one hydrochloride 11

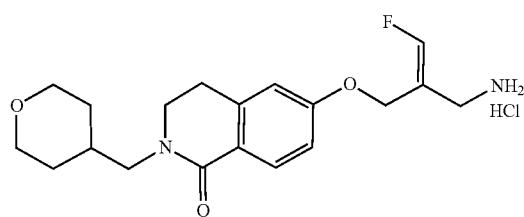

11

The title compound 11 (40 mg, yield: 93%, HPLC: 82.43%) as colorless oil was obtained according to the method described in step 4 of example 9 by using t-butyl N—[(Z)-3-fluoro-2-[[1-oxo-2-(tetrahydropyranyl-4-methylene)-3,4-dihydroquinol-6-yl]oxymethyl]allyl]carbamate 10d (50 mg, 0.11 mmol) instead of compound 10c.

MS (ESI, pos. ion) m/z: 349.3 [M−Cl]+;

$^1$H NMR (400 MHz, DMSO-d$_6$) δ (ppm) 8.23 (s, 3H), 7.81 (d, J=8.6 Hz, 1H), 7.24 (d, J=82.1 Hz, 1H), 7.02-6.93 (m, 1H), 6.92 (s, 1H), 4.79 (s, 2H), 3.91-3.77 (m, 2H), 3.52 (d, J=12.0 Hz, 4H), 3.35 (s, 2H), 3.26 (t, J=11.2 Hz, 2H), 2.93 (t, J=6.2 Hz, 2H), 1.92 (s, 2H), 1.53 (d, J=12.6 Hz, 2H), 1.24 (s, 1H).

Example 11 ethyl 2-[6-[(E)-2-(aminomethyl)-3-fluoro-allyloxy]-1-oxo-3,4-dihydro isoquinolin-2-yl]acetate hydrochloride 12

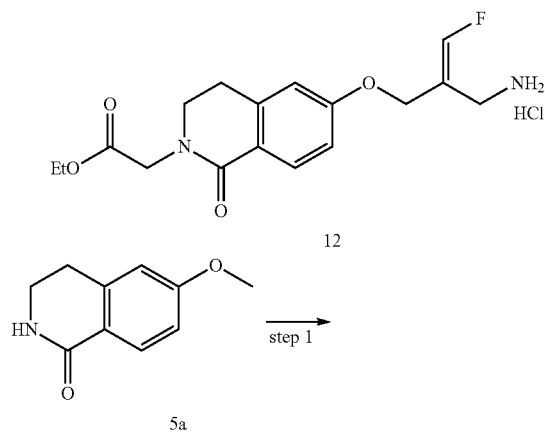

12

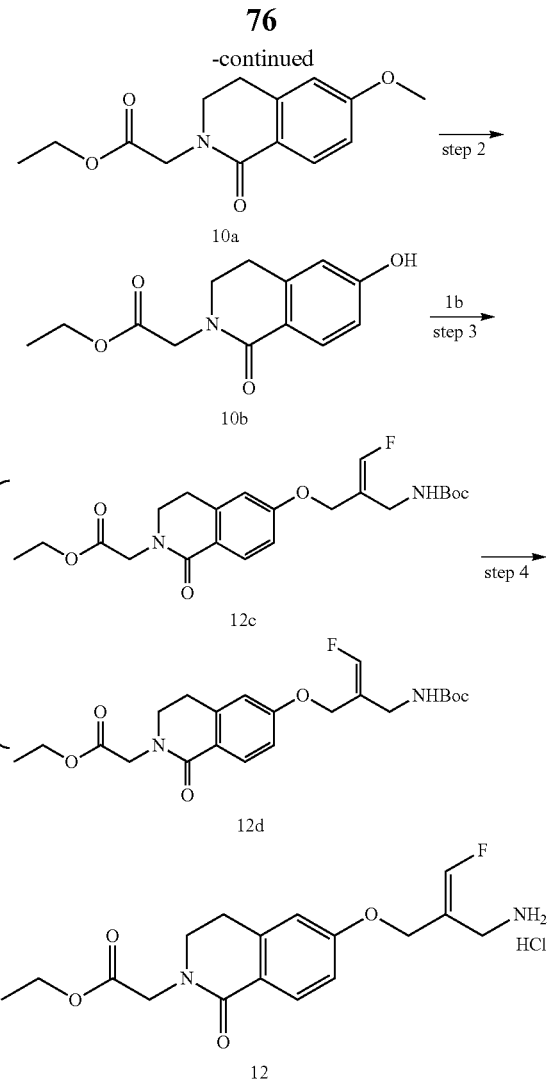

Step 1 ethyl 2-(6-methoxy-1-oxo-3,4-dihydroisoquinolin-2-yl)acetate 12a

At 0° C., a solution of 6-(methoxy)-3,4-dihydro-2H-isoquinolin-1-one 5a (500 mg, 2.8 mmol) in N,N-dimethylformamide (15 mL) was added into a solution of sodium hydride (0.14 g, 3.3 mmol, 60% wt) in N,N-dimethylformamide (5 mL), the resulting mixture was stirred at rt for 30 min, and then ethyl 2-bromoacetate (0.4 mL, 3.3 mmol) was added, the resulting mixture was further stirred for 22 hours. The mixture was poured into ice-water (20 mL) to quench the reaction. The resulting mixture was extracted with ethyl acetate (30 mL×2). The combined organic phases were washed with saturated sodium chloride solution (50 mL), dried over anhydrous sodium sulfate, filtered by suction filtration. The filtrate was concentrated. The residue was purified by silica gel column chromatography (ethyl acetate/petroleum ether (v/v)=1/3) to give the title compound 12a (0.40 g, yield: 55%) as a white solid.

$^1$H NMR (400 MHz, DMSO-d$_6$) δ (ppm) 7.79 (d, J=8.5 Hz, 1H), 6.94-6.83 (m, 2H), 4.26 (s, 2H), 4.12 (q, J=7.1 Hz, 2H), 3.81 (s, 3H), 3.61 (t, J=6.6 Hz, 2H), 2.97 (t, J=6.5 Hz, 2H), 1.21 (t, J=7.1 Hz, 3H).

Step 2 ethyl 2-(6-hydroxy-1-oxo-3,4-dihydroisoquinolin-2-yl)acetate 12b

At −10° C., boron tribromide (0.4 mL, 4 mmol) was added dropwise into a solution of ethyl 2-(6-methoxy-1-oxo-3,4-dihydroisoquinolin-2-yl)acetate 12a (360 mg, 1.4 mmol) in dichloromethane (15 mL), the mixture was stirred at rt for 7 hours. The mixture was cooled to 0° C., and ethanol (2 mL) precooled to 0° C. was added dropwise to quench the reaction. Ethyl acetate (50 mL) and water (20 mL) were added to the mixture in turn. The organic phase was washed with saturated sodium chloride solution (30 mL), dried over anhydrous sodium sulfate, filtered by suction filtration. The filtrate was concentrated. The residue was purified by silica gel column chromatography (ethyl acetate/petroleum ether (v/v)=1/1) to give the title compound 12b (190 mg, yield: 56%) as an off-white solid.

$^1$H NMR (400 MHz, DMSO-$d_6$) δ (ppm) 10.08 (s, 1H), 7.70 (d, J=8.5 Hz, 1H), 6.71 (dd, J=8.5, 2.1 Hz, 1H), 6.64 (s, 1H), 4.24 (s, 2H), 4.12 (q, J=7.1 Hz, 2H), 3.58 (t, J=6.6 Hz, 2H), 2.90 (t, J=6.5 Hz, 2H), 1.21 (t, J=7.1 Hz, 3H).

Step 3 ethyl 2-[6-[(E)-2-[(tert-butoxycarbamate)methyl]-3-fluoro-allyloxy]-1-oxo-3,4-dihydroisoquinolin-2-yl]acetate 12c and ethyl 2-[6-[(Z)-2-[(tert-butoxycarbamate)methyl]-3-fluoro-allyloxy]-1-oxo-3,4-dihydroisoquinolin-2-yl]acetate 12d Potassium carbonate (0.10 g, 0.73 mmol) was added to a solution of ethyl 2-(6-hydroxy-1-oxo-3,4-dihydroisoquinolin-2-yl)acetate 12b (0.14 g, 0.56 mmol) in N,N-dimethylformamide (10 mL), after stirring for 5 min, t-butyl N-[2-(bromomethyl)-3-fluoro-allyl]carbamate 1b (0.18 g, 0.67 mmol) was added, the resulting mixture was stirred at rt for 1.5 hours, and water (10 mL) was added to quench the reaction, the mixture was extracted with ethyl acetate (15 mL×2). The combined organic layers were washed with saturated sodium chloride solution (30 mL), dried over anhydrous sodium sulfate, filtered by suction filtration. The filtrate was concentrated. The residue was purified by silica gel column chromatography (ethyl acetate/petroleum ether (v/v)=1/3) to give the title compound 12c (0.065 g, yield: 26%, HPLC: 99.72%) and 12d (0.12 g, yield: 49%, HPLC: 98.78%), both are colorless oil.

MS (ESI, pos. ion) m/z: 381.3 [M−55]$^+$.

Step 4 ethyl 2-[6-[(E)-2-(aminomethyl)-3-fluoro-allyloxy]-1-oxo-3,4-dihydroisoquinolin-2-yl]acetate hydrochloride 12

Hydrogen chloride-ethyl acetate solution (2 mL, 4 mol/L) was added into a solution of ethyl 2-[6-[(E)-2-[(tert-butoxycarbamate)methyl]-3-fluoro-allyloxy]-1-oxo-3,4-dihydroisoquinolin-2-yl]acetate 12c (65 mg, 0.15 mmol) in ethyl acetate (5 mL), the mixture was stirred at rt for 2.5 hours and concentrated to give the title compound 12 (50 mg, yield: 88%, HPLC: 97.26%) as an off-white solid.

MS (ESI, pos. ion) m/z: 337.1 [M−Cl]$^+$;

$^1$H NMR (400 MHz, DMSO-$d_6$) δ (ppm) 8.24 (s, 3H), 7.82 (d, J=8.6 Hz, 1H), 7.34 (d, J=81.9 Hz, 1H), 6.96 (dd, J=14.3, 5.7 Hz, 2H), 4.70 (s, 2H), 4.27 (s, 2H), 4.13 (q, J=7.1 Hz, 2H), 3.62 (d, J=7.2 Hz, 4H), 2.98 (t, J=6.4 Hz, 2H), 1.21 (t, J=7.1 Hz, 3H).

Example 12 ethyl 2-[6-[(Z)-2-(aminomethyl)-3-fluoro-allyloxy]-1-oxo-3,4-dihydro isoquinolin-2-yl]acetate hydrochloride 13

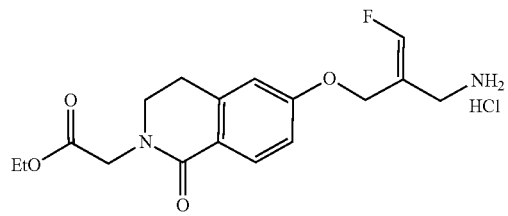

The title compound 13 (89 mg, yield: 85%, HPLC: 97.21%) as an off-white solid was obtained according to the method described in step 4 of example 11 by using ethyl 2-[6-[(Z)-2-[(tert-butoxycarbamate)methyl]-3-fluoro-allyloxy]-1-oxo-3,4-dihydroisoquinolin-2-yl]acetate 12d (120 mg, 0.27 mmol) instead of compound 12c.

MS (ESI, pos. ion) m/z: 337.1 [M−Cl]$^+$;

$^1$H NMR (400 MHz, DMSO-$d_6$) δ (ppm) 8.27 (s, 3H), 7.81 (d, J=8.5 Hz, 1H), 7.24 (d, J=82.1 Hz, 1H), 7.03-6.83 (m, 2H), 4.81 (s, 2H), 4.26 (s, 2H), 4.12 (q, J=7.0 Hz, 2H), 3.62 (t, J=6.2 Hz, 2H), 3.54 (s, 2H), 2.99 (d, J=6.1 Hz, 2H), 1.21 (t, J=7.1 Hz, 3H).

Example 13 7-[(E)-2-(aminomethyl)-3-fluoro-allyloxy]-3,4-dihydro-2H-isoquinolin-1-one hydrochloride 14

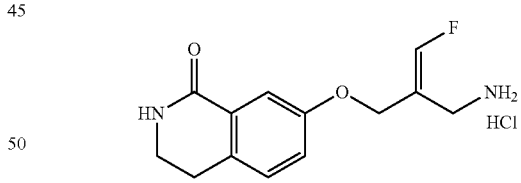

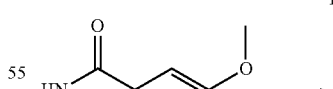

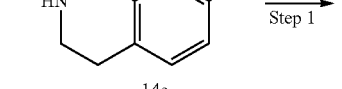

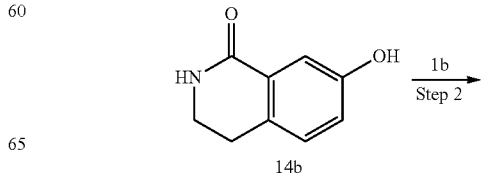

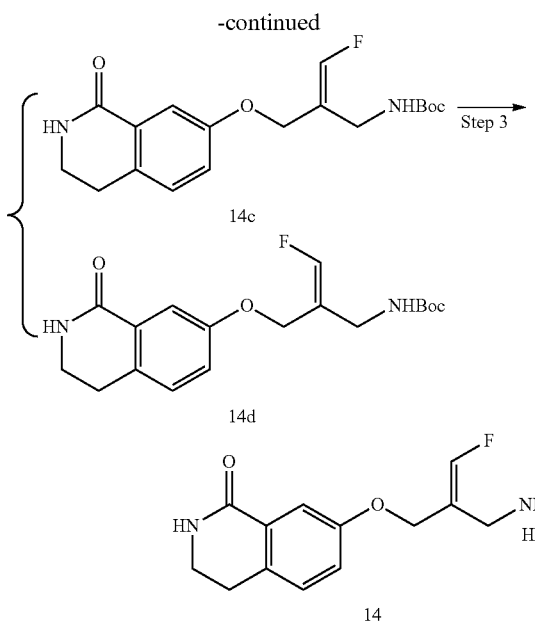

Step 1 7-hydroxy-3,4-dihydro-2H-isoquinolin-1-one 14b

At 0° C. and under N₂, boron tribromide (0.94 mL, 9.8 mmol) was added dropwise into a solution of 7-methoxy-3,4-dihydro-2H-isoquinolin-1-one 14a (0.70 g, 4.0 mmol) in dichloromethane (10 mL), the mixture was stirred at rt for 2 hours. The reaction mixture was cooled to 0° C., ethanol (4 mL) was added slowly to quench the reaction, the mixture was concentrated to give the title compound 14b (0.64 g, yield: 99%) as an orange solid.

MS (ESI, pos. ion) m/z: 164.1 [M+H]$^+$.

Step 2 tert-butyl N—[(E)-3-fluoro-2-[(1-oxo-3,4-dihydro-2H-isoquinolin-7-yl)oxymethyl]allyl]formate 14c and tert-butyl N—[(Z)-3-fluoro-2-[(1-oxo-3,4-dihydro-2H-isoquinolin-7-yl) oxymethyl]allyl] formate 14d To a solution of 7-hydroxy-3,4-dihydro-2H-isoquinolin-1-one 14b (0.51 g, 3.1 mmol) and t-butyl N-[2-(bromomethyl)-3-fluoro-allyl]carbamate 1b (1.0 g, 3.7 mmol) in N,N-dimethylformamide (5 mL) was added potassium carbonate (0.87 g, 6.2 mmol). The mixture was stirred at 90° C. under N₂ for 23 hours. After the mixture was cooled to rt, water (30 ml) and ethyl acetate (20 ml) were added and which was stirred for 5 min. The water phase was separated and extracted with ethyl acetate (15 mL×3). The combined organic phases were washed with water (20 mL) and saturated sodium chloride solution (20 mL), and dried over anhydrous sodium sulfate. The mixture was filtered by suction filtration, the filtrate was concentrated, the residue was purified by silica gel column chromatography (petroleum ether/ethyl acetate (v/v)=3/1) to give the title compound 14c (0.16 g, yield: 14%) and 14d (0.14 g, yield: 13%), both are white solid.

MS (ESI, pos. ion) m/z: 351.3 [M+H]$^+$;

Compound 14c: $^1$H NMR (400 MHz, CDCl₃) δ (ppm) 7.59 (d, J=2.7 Hz, 1H), 7.13 (d, J=8.3 Hz, 1H), 7.02 (dd, J=8.3, 2.7 Hz, 1H), 6.75 (d, J=82.1 Hz, 1H), 6.00 (br, 1H), 4.76 (br, 1H), 4.48 (d, J=3.4 Hz, 2H), 4.00 (d, J=4.1 Hz, 2H), 3.54 (td, J=6.6, 2.8 Hz, 2H), 2.94 (t, J=6.6 Hz, 2H), 1.42 (s, 9H);

Compound 14d: $^1$H NMR (400 MHz, CDCl₃) δ (ppm) 7.63 (d, J=2.6 Hz, 1H), 7.13 (d, J=8.3 Hz, 1H), 7.03 (dd, J=8.3, 2.7 Hz, 1H), 6.73 (d, J=82.4 Hz, 1H), 6.27 (br, 1H), 4.83 (br, 1H), 4.73 (d, J=2.2 Hz, 2H), 3.77 (s, 2H), 3.54 (td, J=6.6, 2.7 Hz, 2H), 2.93 (t, J=6.5 Hz, 2H), 1.42 (s, 9H).

Step 3 7-[(E)-2-(aminomethyl)-3-fluoro-allyloxy]-3,4-dihydro-2H-isoquinolin-1-one hydrochloride 14

Hydrogen chloride-ethyl acetate solution (5 mL, 4 mol/L) was added into a solution of tert-butyl N—[(E)-3-fluoro-2-[(1-oxo-3,4-dihydro-2H-isoquinolin-7-yl)oxymethyl]allyl] formate 14c (0.16 g, 0.45 mmol) in dichloromethane (2 mL), the mixture was stirred for 1 hour and concentrated to give the title compound 14 (0.13 g, yield: 99%, HPLC: 99.70%) as a white solid.

MS (ESI, pos. ion) m/z: 251.1 [M−Cl]$^+$;

$^1$H NMR (400 MHz, CD₃OD) δ (ppm) 7.55 (d, J=2.5 Hz, 1H), 7.29 (d, J=8.4 Hz, 1H), 7.24 (d, J=81.6 Hz, 1H), 7.17 (dd, J=8.3, 2.7 Hz, 1H), 4.66 (d, J=3.3 Hz, 2H), 3.84 (s, 2H), 3.50 (t, J=6.7 Hz, 2H), 2.94 (t, J=6.7 Hz, 2H);

$^{19}$F NMR (376 MHz, CD₃OD) δ (ppm) −123.41.

Example 14 7-[(Z)-2-(aminomethyl)-3-fluoro-allyloxy]-3,4-dihydro-2H-isoquinolin-1-one hydrochloride 15

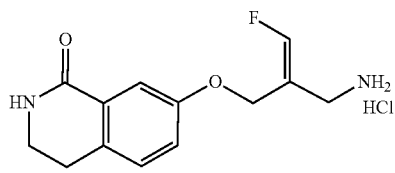

15

The title compound 15 (0.11 g, yield: 99%, HPLC: 99.99%) as a white solid was obtained according to the method described in step 3 of example 13 by using tert-butyl N—[(Z)-3-fluoro-2-[(1-oxo-3,4-dihydro-2H-isoquinolin-7-yl)oxymethyl]allyl]formate 14d. (120 mg, 0.27 mmol) instead of compound 14c.

MS (ESI, pos. ion) m/z: 251.1 [M−Cl]$^+$;

$^1$H NMR (400 MHz, CD₃OD) δ (ppm) 7.58 (d, J=2.2 Hz, 1H), 7.29 (d, J=8.4 Hz, 1H), 7.25-6.99 (m, 2H), 4.88 (overlap, 2H), 3.72 (s, 2H), 3.50 (t, J=6.7 Hz, 2H), 2.95 (t, J=6.7 Hz, 2H); $^{19}$F NMR (376 MHz, CD₃OD) δ (ppm) −121.53.

Example 15 6-[(E)-2-(aminomethyl)-3-fluoro-allyloxy]-2-(tetrahydropyran-4-yl)-3,4-dihydroisoquinolin-1-one hydrochloride 16

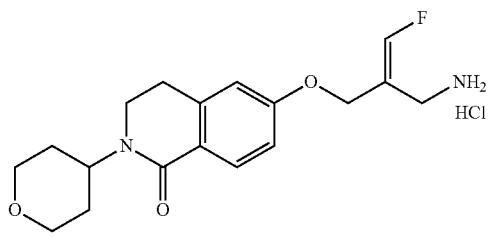

16

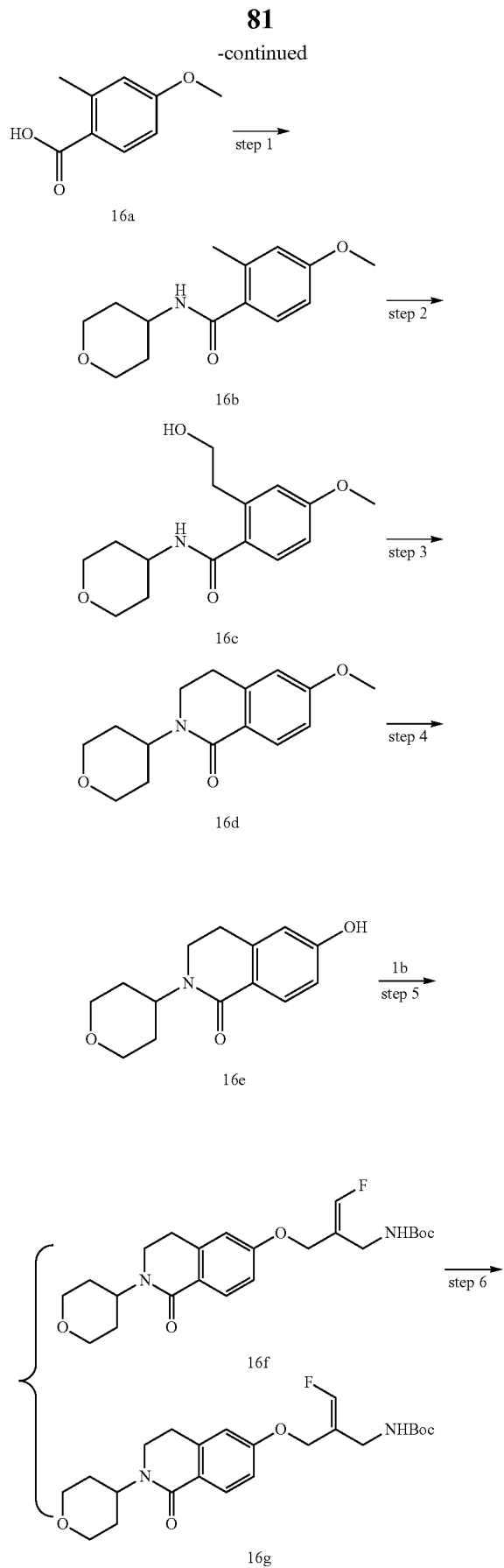

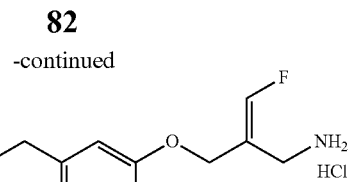

Step 1 4-methoxy-2-methyl-N-(tetrahydropyran-4-yl)-benzamide 16b

4-Methoxy-2-methyl-benzoic acid 16a (5.00 g, 30.10 mmol) was dissolved in a mixture of dichloromethane (60 mL) and N,N-dimethylformamide (15 mL), and then 4-aminotetrahydropyrane (3.50 g, 33.90 mmol), triethylamine (5.00 mL, 35.50 mmol) and 2-(7-azobenzotriazole)-N,N,N,N-tetramethylurea hexafluorophosphate (12.00 g, 30.00 mmol) were added at 0° C., the mixture was stirred at rt for 5 hours. The mixture was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 16b (5.20 g, yield: 69%) as a white solid.

MS (ESI, pos. ion) m/z: 250.3 $[M+H]^+$.

Step 2 2-(2-hydroxyethyl)-4-methoxy-N-(tetrahydropyran-4-yl)-benzamide 16c

Under $N_2$, 4-methoxy-2-methyl-N-(tetrahydropyran-4-yl)-benzamide 16b (4.00 g, 16.00 mmol) and diisopropylamine (250 mg, 2.46 mmol) were dissolved in anhydrous tetrahydrofuran (100 mL), and at −78° C., n-butyllithium in cyclohexane (35 mL, 53 mmol, 1.5 mol/L) was added dropwise, and then the mixture was stirred at 0° C. for 1 hour. The mixture was cooled to −78° C., and paraformaldehyde (3.50 g, 37.70 mmol) was added slowly, then the mixture was warmed to 0° C. and stirred for 3 hours. The mixture was quenched by adding water (50 mL), the organic layer was washed with saturated sodium chloride solution (100 mL×2), dried over anhydrous sodium sulfate, filtered by suction filtration. The filtrate was concentrated. The residue was purified by silica gel column chromatography (petroleum ether/ethyl acetate (v/v)=1/1) to give the title compound 16c (2.80 g, yield: 63%) as a white solid.

MS (ESI, pos. ion) m/z: 280.1 $[M+H]^+$.

Step 3 6-methoxy-2-(tetrahydropyran-4-yl)-3,4-dihydroisoquinolin-1-one 16d 2-(2-Hydroxyethyl)-4-methoxy-N-(tetrahydropyran-4-yl)-benzamide 16c (0.90 g, 3.20 mmol) was dissolved in tetrahydrofuran (20 mL), then triphenylphosphine (1.50 g, 5.66 mmol) and diisopropyl azodicarboxylate (1.20 g, 5.82 mmol) were added at 0° C., the mixture was stirred at rt for 20 hours. The mixture was concentrated. The residue was purified by silica gel column chromatography (petroleum ether/ethyl acetate (v/v)=3/1) to give the title compound 16d (0.60 g, yield: 71%) as a white solid.

MS (ESI, pos. ion) m/z: 262.2 [M+H]+.

Step 4 6-hydroxy-2-(tetrahydropyran-4-yl)-3,4-dihydroisoquinolin-1-one 16e

6-Methoxy-2-(tetrahydropyran-4-yl)-3,4-dihydroisoquinolin-1-one 16d (0.60 g, 2.30 mmol) was dissolved in dichloromethane (15 mL), the mixture was cooled to 0° C. and boron tribromide (2.00 mL, 8.00 mmol) was added, the resulting mixture was stirred at 0° C. for 1 hour. The reaction was quenched by adding ice, the mixture was filtered by suction filtration after the ice melting to give the title compound 16e (0.45 g, yield: 79%) as a white solid.

MS (ESI, pos. ion) m/z: 248.3 [M+H]+.

Step 5 t-butyl N—[(E)-3-fluoro-2-[(1-oxo-2-(tetrahydropyran-4-yl)-3,4-dihydroisoquinolin-6-yl) oxymethyl]allyl]carbamate 16f and t-butyl N—[(Z)-3-fluoro-2-[(1-oxo-2-(tetrahydropyran-4-yl)-3,4-dihydroisoquinolin-6-yl)oxymethyl]allyl]carbamate 16g To a solution of 6-hydroxy-2-(tetrahydropyran-4-yl)-3,4-dihydroisoquinolin-1-one 16e (0.45 g, 1.80 mmol) and t-butyl N-[2-(bromomethyl)-3-fluoro-allyl]carbamate 1b (0.50 g, 1.86 mmol) in N,N-dimethylformamide (10 mL) was added cesium carbonate (1.00 g, 3.00 mmol), the mixture was stirred at rt for 2 hours. The reaction was quenched with water (10 mL). The resulting mixture was extracted with ethyl acetate (20 mL). The organic phase was washed with saturated sodium chloride solution (20 mL×3), dried over anhydrous sodium sulfate, filtered by suction filtration. The filtrate was concentrated. The residue was purified by silica gel column chromatography (petroleum ether/ethyl acetate (v/v)=1/1) to give the title compound 16f (34 mg, yield: 4%) and 16 g (73 mg, yield: 10%), both are colorless oil.

MS (ESI, pos. ion) m/z: 248.3 [M+H]+.

Step 6 6-[(E)-2-(aminomethyl)-3-fluoro-allyloxy]-2-(tetrahydropyran-4-yl)-3,4-dihydro isoquinolin-1-one hydrochloride 16 t-Butyl N—[(E)-3-fluoro-2-[(1-oxo-2-(tetrahydropyran-4-yl)-3,4-dihydroisoquinolin-6-yl) oxymethyl]allyl]carbamate (34 mg, 0.08 mmol) was dissolved in ethyl acetate (2 mL), and then hydrogen chloride-ethyl acetate solution (2 mL, 4 mol/L) was added, the mixture was stirred at rt for 30 min. The mixture was concentrated to give the title compound 16 (28 mg, yield: 97%, HPLC: 93.41%) as a white solid.

MS (ESI, pos. ion) m/z: 335.4 [M−Cl]+;
$^1$H NMR (400 MHz, DMSO-d$_6$) δ (ppm) 8.04 (s, 3H), 7.84 (d, J=8.5 Hz, 1H), 7.35 (d, J=82.1 Hz, 1H), 7.01-6.86 (m, 2H), 4.66 (s, 3H), 3.94 (d, J=7.2 Hz, 2H), 3.62 (s, 2H), 3.50-3.42 (m, 4H), 2.90 (t, J=6.0 Hz, 2H), 1.79 (dd, J=11.9, 4.5 Hz, 2H), 1.50 (d, J=13.6 Hz, 2H).

Example 16 6-[(Z)-2-(aminomethyl)-3-fluoro-allyloxy]-2-(tetrahydropyran-4-yl)-3,4-dihydroisoquinolin-1-one hydrochloride 17

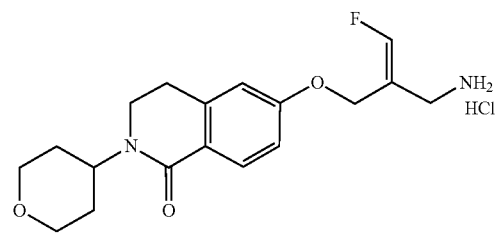

The title compound 17 (60 mg, yield: 96%, HPLC: 91.13%) as a white solid was obtained according to the method described in step 6 of example 15 by using t-butyl N—[(Z)-3-fluoro-2-[(1-oxo-2-(tetrahydropyran-4-yl)-3,4-dihydro isoquinolin-6-yl)oxymethyl]allyl]carbamate 16 g (73 mg, 0.17 mmol) instead of compound 16f.

MS (ESI, pos. ion) m/z: 335.2 [M−Cl]+;
$^1$H NMR (400 MHz, DMSO-d$_6$) δ (ppm) 8.19 (s, 3H), 7.83 (d, J=8.5 Hz, 1H), 7.23 (d, J=82.1 Hz, 1H), 7.10-6.81 (m, 2H), 4.79 (s, 2H), 4.75-4.60 (m, 1H), 3.94 (dd, J=11.1, 3.8 Hz, 2H), 3.53 (s, 2H), 3.39 (s, 4H), 2.89 (t, J=6.4 Hz, 2H), 1.78 (qd, J=12.3, 4.5 Hz, 2H), 1.50 (d, J=9.8 Hz, 2H).

Example 17 6-[(E)-2-(aminomethyl)-3-fluoro-allyloxy]-2-(2-methoxyethyl)-3,4-dihydro isoquinolin-1-one hydrochloride 18

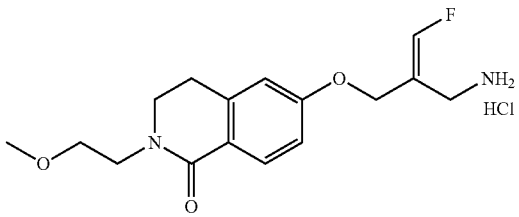

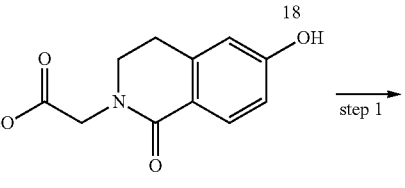

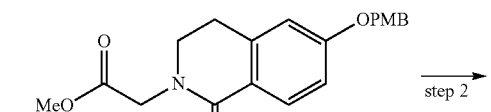

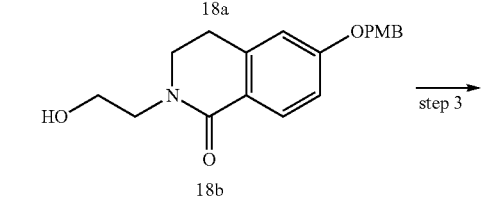

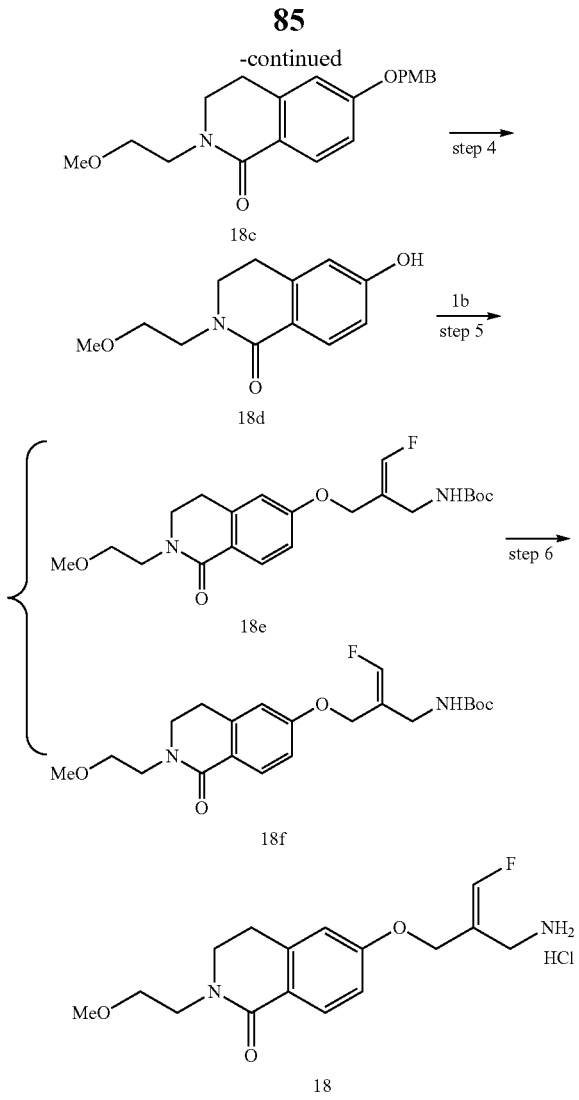

Step 1 methyl 2-[6-[(4-methoxyphenyl)methoxy]-1-oxo-3,4-dihydroisoquinolin-2-yl]acetate 18a Ethyl 2-(6-hydroxy-1-oxo-3,4-dihydroisoquinolin-2-yl)acetate 12b (0.85 g, 3.61 mmol), cesium carbonate (2.0 g, 6.1 mmol) were added to acetonitrile (20 mL), then 4-methoxybenzyl bromide (1.5 mL, 10 mmol) was added, the mixture was stirred at rt for 3.5 hours. To the mixture was added saturated sodium chloride solution (15 mL), and the resulting mixture was extracted with ethyl acetate (25 mL×3), the combined organic layers were dried over anhydrous sodium sulfate, filtered by suction filtration. The filtrate was concentrated. The residue was purified by silica gel column chromatography (petroleum ether/ethyl acetate (v/v)=5/1) to give the title compound 18a (1.0 g, yield: 78%) as a white solid.

$^1$H NMR (400 MHz, DMSO-$d_6$) δ (ppm) 7.78 (d, J=8.5 Hz, 1H), 7.39 (d, J=8.6 Hz, 2H), 6.97 (d, J=2.8 Hz, 2H), 6.94 (d, J=3.1 Hz, 2H), 5.08 (s, 2H), 4.27 (s, 2H), 3.76 (s, 3H), 3.66 (s, 3H), 3.60 (t, J=6.5 Hz, 2H), 2.96 (t, J=6.5 Hz, 2H).

Step 2 2-(2-hydroxyethyl)-6-[(4-methoxyphenyl)methoxy]-3,4-dihydroisoquinolin-1-one 18b Methyl 2-[6-[(4-methoxyphenyl)methoxy]-1-oxo-3,4-dihydroisoquinolin-2-yl]acetate 18a (1.0 g, 2.80 mmol) was dissolved in tetrahydrofuran (20 mL), and lithium aluminium hydride (0.13 g, 3.43 mmol) was added slowly at −10° C. in portions, the mixture was stirred for 15 min, and then saturated sodium hydroxide solution (10 mL) was added to the reaction mixture, the reaction solution became clear. To the mixture was added saturated sodium chloride solution (20 mL), and the resulting mixture was extracted with ethyl acetate (25 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 18b (0.80 g, yield: 87%) as a white solid.

$^1$H NMR (400 MHz, DMSO-$d_6$) δ (ppm) 7.77 (d, J=8.5 Hz, 1H), 7.38 (d, J=8.6 Hz, 2H), 6.95 (d, J=8.7 Hz, 2H), 6.91 (d, J=6.3 Hz, 2H), 5.06 (s, 2H), 3.76 (s, 3H), 3.56 (dd, J=12.6, 5.8 Hz, 4H), 3.50 (t, J=5.5 Hz, 2H), 2.90 (t, J=6.5 Hz, 2H).

Step 3 2-(2-methoxyethyl)-6-[[4-[(4-methoxyphenyl)methoxy]-3,4-dihydroisoquinolin-1-one 18c 2-(2-Hydroxyethyl)-6-[(4-methoxyphenyl)methoxy]-3,4-dihydroisoquinolin-1-one 18b (0.20 g, 0.46 mmol) was dissolved in tetrahydrofuran (6 mL), sodium hydride (73 mg, 1.83 mmol) was added at −10° C., the mixture was stirred for 10 min, and then iodomethane (80 μL, 1.29 mmol) was added, the reaction mixture was moved to rt and stirred for 1.5 hours. To the mixture was added slowly saturated sodium chloride solution (15 mL) at 0° C. to quench the reaction, and the resulting mixture was extracted with ethyl acetate (25 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 18c (89 mg, yield: 40%) as a white solid.

$^1$H NMR (400 MHz, CDCl$_3$) δ (ppm) 8.00 (d, J=8.6 Hz, 1H), 7.34 (d, J=8.6 Hz, 2H), 6.91 (d, J=8.5 Hz, 3H), 6.72 (d, J=2.1 Hz, 1H), 5.01 (s, 2H), 3.81 (d, J=2.3 Hz, 3H), 3.71 (t, J=5.3 Hz, 2H), 3.66-3.57 (m, 4H), 3.34 (d, J=2.5 Hz, 3H), 2.92 (t, J=6.6 Hz, 2H).

Step 4 6-hydroxy-2-(2-methoxyethyl)-3,4-dihydroisoquinolin-1-one 18d 2-(2-Methoxyethyl)-6-[[4-[(4-methoxyphenyl)methoxy]-3,4-dihydroisoquinolin-1-one 18c (200 mg, 0.59 mmol) was dissolved in a mixture of trifluoroacetic acid (4.0 mL) and dichloromethane (4.0 mL), the mixture was stirred at rt for 30 min. To the mixture was added potassium carbonate until gas evolution has ceased, and the resulting mixture was extracted with ethyl acetate (15 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 18d (90 mg, yield: 69%) as a white solid.

Step 5 t-butyl N—[(E)-3-fluoro-2-[[2-(2-methoxyethyl)-1-oxo-3,4-dihydroisoquinolin-6-yl]oxymethyl]allyl]carbamate 18e and t-butyl N—[(Z)-3-fluoro-2-[[2-(2-methoxyethyl)-1-oxo-3,4-dihydroisoquinolin-6-yl]oxymethyl]allyl]carbamate 18f To a solution of 6-hydroxy-2-(2-methoxyethyl)-3,4-dihydroisoquinolin-1-one 18d. (90.1 mg, 0.41 mmol) and t-butyl N-[2-(bromomethyl)-3-fluoro-allyl]carbamate 1b (131 mg, 0.49 mmol) in N,N-dimethylformamide (6 mL) was added cesium carbonate (400 mg, 1.23 mmol), the mixture was stirred at rt for 12 hours. To the mixture was added saturated sodium chloride solution (15 mL), and the resulting mixture was extracted with ethyl acetate (15 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 18e (40.2 mg, yield: 24%) and 18f (29.2 mg, yield: 18%)

Step 6 6-[(E)-2-(aminomethyl)-3-fluoro-allyloxy]-2-(2-methoxyethyl)-3,4-dihydroisoquinolin-1-one hydrochloride 18 t-Butyl N—[(E)-3-fluoro-2-[[2-(2-methoxyethyl)-1-oxo-3,4-dihydroisoquinolin-6-yl]oxymethyl]allyl]carbamate 18e (61.6 mg, 0.15 mmol) was dissolved in hydrogen chloride-ethyl acetate solution (4 mL, 4 mol/L) at 0° C., the mixture was stirred at rt for 4.5 hours. The mixture was concentrated to give the title compound 18 (50 mg, yield: 96%, HPLC: 94.4%) as a white solid.

MS (ESI, pos. ion) m/z: 309.2 [M−Cl]$^+$;

$^1$H NMR (600 MHz, DMSO-d$_6$) δ (ppm) 8.23 (s, 3H), 7.80 (d, J=8.5 Hz, 1H), 7.23 (d, J=78.0 Hz, 1H), 6.98-6.92 (m, 1H), 6.91 (s, 1H), 4.78 (s, 2H), 3.60 (t, J=5.5 Hz, 2H), 3.58-3.48 (m, 6H), 3.26 (s, 3H), 2.91 (t, J=6.3 Hz, 2H).

Example 18 6-[(Z)-2-(aminomethyl)-3-fluoro-allyloxy]-2-(2-methoxyethyl)-3,4-dihydro isoquinolin-1-one hydrochloride 19

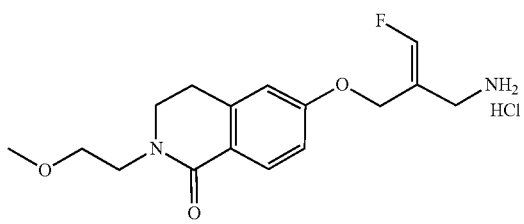

19

The title compound 19 (37 mg, yield: 98%, HPLC: 92.74%) as a white solid was obtained according to the method described in step 6 of example 17 by using t-butyl N—[(Z)-3-fluoro-2-[[2-(2-methoxyethyl)-1-oxo-3,4-dihydroisoquinolin-6-yl]oxymethyl]allyl]carbamate 18f (44.8 mg, 0.110 mmol) instead of compound 18e.

MS (ESI, pos. ion) m/z: 309.2 [M−Cl]$^+$;

$^1$H NMR (600 MHz, DMSO-d$_6$) δ (ppm) 8.24 (s, 3H), 7.80 (d, J=8.6 Hz, 1H), 7.33 (d, J=78.0 Hz, 1H), 6.94 (dd, J=8.6, 2.3 Hz, 1H), 6.89 (d, J=2.0 Hz, 1H), 4.68 (d, J=2.5 Hz, 2H), 3.61 (t, J=5.5 Hz, 4H), 3.56 (t, J=6.6 Hz, 2H), 3.50 (t, J=5.6 Hz, 2H), 3.26 (s, 3H), 2.91 (t, J=6.5 Hz, 2H).

Example 19 6-[(E)-2-(aminomethyl)-3-fluoro-allyloxy]-2-(2-benzyloxyethyl)-3,4-dihydro isoquinolin-1-one hydrochloride 20

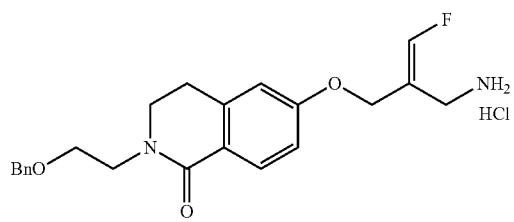

20

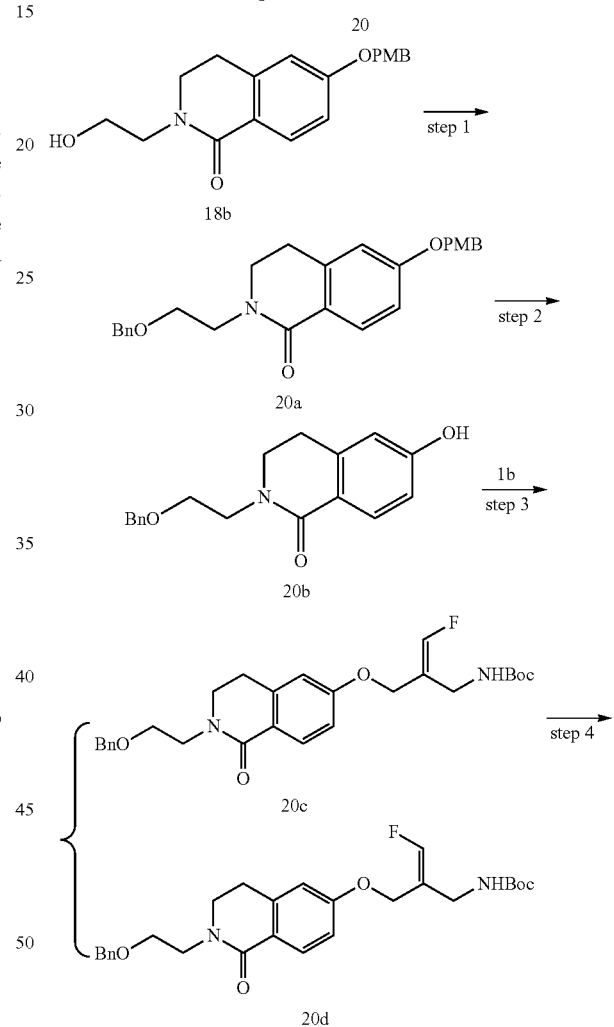

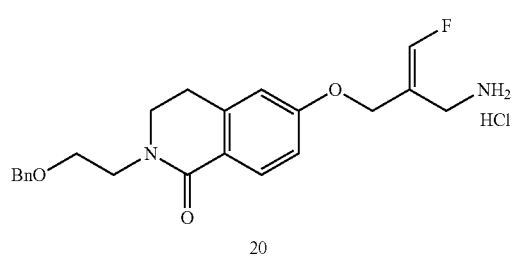

20

Step 1 2-(2-benzyloxyethyl)-6-[(4-methoxyphenyl) methoxy]-3,4-dihydroisoquinolin-1-one 20a 2-(Hydroxyethyl)-6-[(4-methoxyphenyl)methoxy]-3,4-dihydroisoquinolin-1-one 18b (400 mg, 1.22 mmol) was dissolved in tetrahydrofuran (10 mL), sodium hydride (110 mg, 2.75 mmol) was added at −10° C., the mixture was stirred for 10 min, and then benzyl bromide (220 µL, 1.85 mmol) was added, the reaction mixture was moved to rt and stirred for 12 hours. To the mixture was added slowly saturated sodium chloride solution (15 mL) at 0° C., and the resulting mixture was extracted with ethyl acetate (25 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 20a (121 mg, yield: 24%) as a white solid.

Step 2 6-hydroxy-2-(2-benzyloxyethyl)-3,4-dihydroisoquinolin-1-one 20b 2-(2-Benzyloxyethyl)-6-[(4-methoxyphenyl)methoxy]-3,4-dihydroisoquinolin-1-one 20a (120 mg, 0.29 mmol) was dissolved in a mixture of trifluoroacetic acid (2 mL) and dichloromethane (2 mL), the mixture was stirred at rt for 30 min. The reaction was quenched with water (10 mL), to the mixture was added potassium carbonate until gas evolution has ceased, and the resulting mixture was extracted with ethyl acetate (15 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 20b (60 mg, yield: 70%) as a white solid.

Step 3 t-butyl N—[(E)-3-fluoro-2-[[2-(2-benzyloxyethyl)-1-oxo-3,4-dihydroisoquinolin-6-yl]oxymethyl]allyl]carbonate 20c and t-butyl N—[(Z)-3-fluoro-2-[[2-(2-benzyloxyethyl)-1-oxo-3,4-dihydroisoquinolin-6-yl]oxymethyl]allyl]carbonate 20d To a solution of 6-hydroxy-2 (2 benzyloxyethyl)-3,4-dihydroisoquinolin-1-one 20b (174 mg, 0.59 mmol) and t-butyl N-[2-(bromomethyl)-3-fluoro-allyl]carbamate (188 mg, 0.70 mmol) in N,N-dimethylformamide (5.0 mL) was added cesium carbonate (573 mg, 1.76 mmol), the mixture was stirred at rt for 12 hours. To the mixture was added saturated sodium chloride solution (15 mL), and the resulting mixture was extracted with ethyl acetate (15 mL×3), the combined organic layers were dried over anhydrous sodium sulfate, filtered by suction filtration. The filtrate was concentrated. The residue was purified by silica gel column chromatography (petroleum ether/ethyl acetate (v/v)=1/1) to give the title compound 20c (71 mg, yield: 25%) and 20d (29 mg, yield: 22%), both are white solid.

Step 4 6-[(E)-2-(aminomethyl)-3-fluoro-allyloxy]-2-(2-benzyloxyethyl)-3,4-dihydroisoquinolin-1-one hydrochloride 20 t-Butyl N—[(E)-3-fluoro-2-[[2-(2-benzyloxyethyl)-1-oxo-3,4-dihydroisoquinolin-6-yl]oxymethyl]allyl]carbonate 20c (71 mg, 0.15 mmol) was dissolved in hydrogen chloride-ethyl acetate solution (4 mL, 4 mol/L), the mixture was stirred at rt for 4.5 hours. The mixture was concentrated to give the title compound 20 (48 mg, yield: 78%, HPLC: 98.83%) as a white solid.

MS (ESI, pos. ion) m/z: 385.2 [M−Cl]$^+$;
$^1$H NMR (400 MHz, DMSO-d$_6$) δ (ppm) 8.28 (s, 3H), 7.80 (d, J=8.6 Hz, 1H), 7.33 (d, J=82.1 Hz, 1H), 7.36-7.24 (m, 5H), 6.94 (d, J=8.7 Hz, 1H), 6.90 (s, 1H), 4.69 (s, 2H), 4.50 (s, 2H), 3.70-3.56 (m, 8H), 2.89 (dd, J=11.8, 6.6 Hz, 2H).

Example 20 6-[(Z)-2-(aminomethyl)-3-fluoro-allyloxy]-2-(2-benzyloxyethyl)-3,4-dihydro isoquinolin-1-one hydrochloride 21

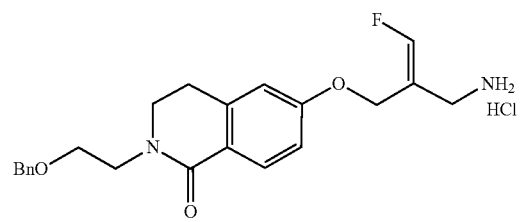

The title compound 21 (50 mg, yield: 93%, HPLC: 96.05%) as a white solid was obtained according to the method described in step 4 of example 19 by using t-butyl N—[(Z)-3-fluoro-2-[[2-(2-benzyloxyethyl)-1-oxo-3,4-dihydroisoquinolin-6-yl]oxymethyl]allyl]carbonate 20d (62 mg, 0.13 mmol) instead of compound 20c.

MS (ESI, pos. ion) m/z: 385.3 [M−Cl]$^+$;
$^1$H NMR (400 MHz, DMSO-d$_6$) δ (ppm) 8.05 (s, 3H), 7.81 (d, J=8.6 Hz, 1H), 7.36-7.22 (m, 5H), 7.23 (d, J=82.1 Hz, 1H), 6.95 (dd, J=8.6, 2.3 Hz, 1H), 6.91 (s, 1H), 4.77 (s, 2H), 4.50 (s, 2H), 3.61 (ddd, J=24.7, 14.8, 8.0 Hz, 8H), 2.91 (t, J=6.4 Hz, 2H).

Example 21 6-[(E)-2-(aminomethyl)-3-fluoro-allyloxy]-2-cyclopentyl-3,4-dihydro isoquinolin-1-one hydrochloride 22

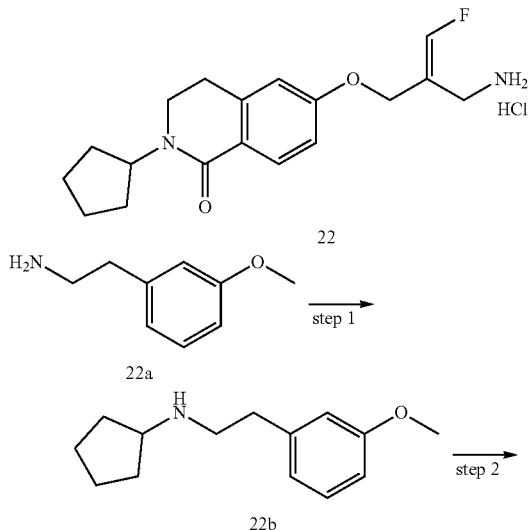

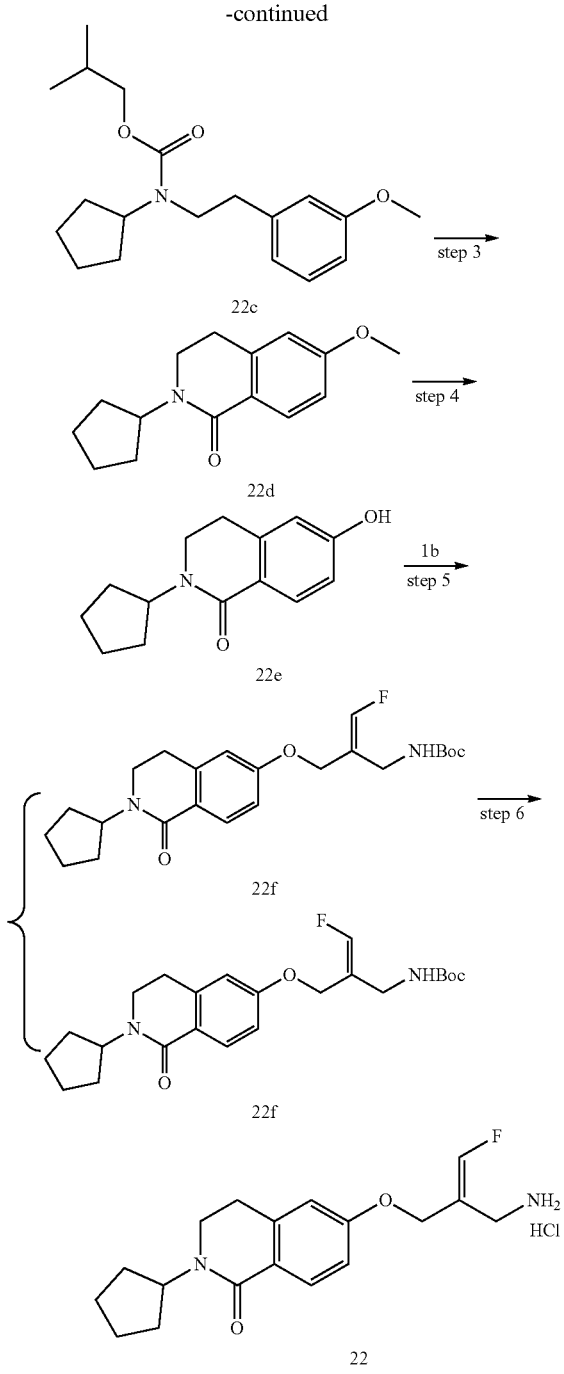

purified by silica gel column chromatography (petroleum ether/ethyl acetate (v/v)=1/1) to give the title compound 22b (1.13 g, yield: 39.8%) as yellow oil.

MS (ESI, pos. ion) m/z: 220.1 [M+H]$^+$;

$^1$HNMR (400 MHz, CDCl$_3$) δ (ppm) 7.23 (t, J=7.9 Hz, 1H), 6.83 (d, J=7.6 Hz, 1H), 6.78 (d, J=7.4 Hz, 2H), 3.82 (s, 3H), 3.09 (p, J=6.9 Hz, 1H), 2.92-2.86 (m, 2H), 2.81 (t, J=6.6 Hz, 2H), 1.85 (dt, J=11.8, 6.0 Hz, 2H), 1.67 (dt, J=13.0, 8.1 Hz, 2H), 1.61-1.48 (m, 2H), 1.41-1.18 (m, 3H).

Step 2 isobutyl N-cyclopentyl-N-[2-(3-methoxyphenyl)ethyl]carbamate 22c

N-[2-(3-Methoxyphenyl)ethyl]cyclopentylamine 22b (1 g, 4.56 mmol) was dissolved in acetonitrile (20 mL), then triethylamine (1.6 mL, 11 mmol) was added, and isobutyl chloroformate (0.7 mL, 5 mmol) was added at 0° C., the mixture was stirred at rt for 24 hours. The reaction was quenched with water (50 mL). The resulting mixture was extracted with ethyl acetate (100 mL×2). The combined organic phases were washed with saturated sodium chloride solution (100 mL×2), dried over anhydrous sodium sulfate, filtered by suction filtration. The filtrate was concentrated. The residue was purified by silica gel column chromatography (petroleum ether/ethyl acetate (v/v)=15/1) to give the title compound 22c (1.3 g, yield: 89%) as light yellow oil.

MS (ESI, pos. ion) m/z: 320.2 [M+H]$^+$;

$^1$H NMR (400 MHz, CDCl$_3$) δ (ppm) 7.24 (t, J=7.9 Hz, 1H), 6.80 (dd, J=14.2, 7.5 Hz, 3H), 3.92 (d, J=6.5 Hz, 2H), 3.82 (s, 3H), 3.37-3.26 (m, 2H), 2.90-2.77 (m, 2H), 2.11-1.93 (m, 1H), 1.90-1.78 (m, 2H), 1.70 (d, J=15.8 Hz, 3H), 1.62-1.46 (m, 4H), 1.00 (d, J=6.7 Hz, 6H).

Step 3 2-cyclopentyl-6-methoxy-3,4-dihydroisoquinolin-1-one 22d

To isobutyl N-cyclopentyl-N-[2-(3-methoxyphenyl)ethyl]carbamate 22c (1.3 g, 4.1 mmol) was added polyphosphate (5 mL), the mixture was stirred at 120° C. for 2 hours and cooled to rt, ice-water (20 mL) was added, the resulting mixture was adjusted with saturated sodium bicarbonate solution to pH 7, and extracted with ethyl (50 mL×2). The combined organic layers were washed with saturated sodium chloride solution (20 mL×3) and dried over anhydrous sodium sulfate, filtered by suction filtration. The filtrate was concentrated. The residue was purified by silica gel column chromatography (petroleum ether/ethyl acetate (v/v)=1/1) to give the title compound 22d (200 mg, yield: 20%) as yellow oil.

MS (ESI, pos. ion) m/z: 246.3 [M+H]$^+$.

Step 4 2-cyclopentyl-6-hydroxy-3,4-dihydroisoquinolin-1-one 22e

2-Cyclopentyl-6-methoxy-3,4-dihydroisoquinolin-1-one 22d (730 mg, 3.0 mmol) was dissolved in dichloromethane (10 mL), and then boron tribromide (1.2 mL, 12 mmol) was added dropwise at 0° C., the resulting mixture was stirred at rt for 1 hour. The reaction mixture was poured into ice-water (30 mL) to quench the reaction, and the mixture was extracted with ethyl acetate (60 mL×2). The combined organic layers were washed with saturated sodium chloride solution (30 mL), dried over anhydrous sodium sulfate, and Step 1 N-[2-(3-methoxyphenyl)ethyl]cyclopentylamine 22b 2-(3-Methoxyphenyl)ethylamine 22a (2 g, 13 mmol) was dissolved in N,N-dimethylformamide (50 mL), then potassium hydroxide (1.8 g, 32 mmol) and cyclopentane iodide (3.14 g, 15.5 mmol) were added, the resulting mixture was stirred at rt for 24 hours. The reaction was quenched with water (80 mL). The resulting mixture was extracted with ethyl acetate (80 mL×3). The combined organic phases were washed with saturated sodium chloride solution (50 mL×3), dried over anhydrous sodium sulfate, filtered by suction filtration. The filtrate was concentrated. The residue was filtered by suction filtration. The filtrate was concentrated to give the title compound 22e (688 mg, yield: 99%) as yellow oil.

MS (ESI, pos. ion) m/z: 232.2 [M+H]+.

Step 5 t-butyl N—[(E)-2-[(2-cyclopentyl-1-oxo-3,4-dihydroisoquinolin-6-yl)oxymethyl]-3-fluoro-allyl] carbamate 22f and t-butyl N—[(Z)-2-[(2-cyclopentyl-1-oxo-3,4-dihydroisoquinolin-6-yl) oxymethyl]-3-fluoro-allyl]carbamate 22 g To a solution of 2-cyclopentyl-6-hydroxy-3,4-dihydroisoquinolin-1-one 22e (0.69 g, 2.97 mmol) and t-butyl N-[2-(bromomethyl)-3-fluoro-allyl]carbamate 1b (0.72 g, 2.67 mmol) in N,N-dimethylformamide (20 mL) was added cesium carbonate (1.9 g, 5.7 mmol), the mixture was stirred at rt for 24 hours. To the reaction was added water (20 mL). The resulting mixture was extracted with ethyl acetate (50 mL×2). The combined organic phases were washed with saturated sodium chloride solution (20 mL×2), dried over anhydrous sodium sulfate, filtered by suction filtration. The filtrate was concentrated. The residue was purified by silica gel column chromatography (petroleum ether/ethyl acetate (v/v)=1/1) to give the title compound 22f (0.14 g, yield: 12%) and 22 g (0.17 g, yield: 14%), both are white solid.

MS (ESI, pos. ion) m/z: 419.3 [M+H]+.

Step 6 6-[(E)-2-(aminomethyl)-3-fluoro-allyloxy]-2-cyclopentyl-3,4-dihydroisoquinolin-1-one hydrochloride 22 t-Butyl N—[(E)-2-[(2-cyclopentyl-1-oxo-3,4-dihydroisoquinolin-6-yl)oxymethyl]-3-fluoro-allyl]carbamate 22f (0.14 g, 0.34 mmol) was dissolved in methanol, and then hydrogen chloride-methanol solution (2 mL, 5 mol/L) was added, the mixture was stirred at rt for 1 hour. The mixture was concentrated to give the title compound 22 (0.10 g, yield: 85%, HPLC: 85.23%) as a white solid.

MS (ESI, pos. ion) m/z: 319.1 [M−Cl]+;
1H NMR (400 MHz, DMSO-d6) δ (ppm) 8.43 (s, 3H), 7.70 (d, J=23.4 Hz, 2H), 7.26 (d, J=82.1 Hz, 1H), 6.93 (s, 1H), 4.81 (s, 2H), 3.54 (s, 2H), 3.34 (t, J=5.9 Hz, 2H), 3.28-3.18 (m, 1H), 2.84 (t, J=5.9 Hz, 2H), 1.96-1.83 (m, 2H), 1.78-1.55 (m, 4H), 1.51 (d, J=15.7 Hz, 2H).

Example 22 6-[(Z)-2-(aminomethyl)-3-fluoro-allyloxy]-2-cyclopentyl-3,4-dihydro isoquinolin-1-one hydrochloride 23

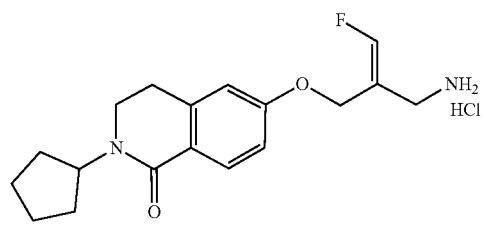

23

The title compound 23 (0.12 g, yield: 79%, HPLC: 96.05%) as a white solid was obtained according to the method described in step 6 of example 21 by using t-butyl N—[(Z)-2-[(2-cyclopentyl-1-oxo-3,4-dihydroisoquinolin-6-yl)oxymethyl]-3-fluoro-allyl]carbamate 22 g (0.17 g, 0.42 mmol) instead of compound 22f.

MS (ESI, pos. ion) m/z: 319.1 [M−Cl]+;
1H NMR (400 MHz, DMSO-d6) δ (ppm) 8.36 (s, 3H), 7.68 (s, 2H), 7.32 (d, J=81.7 Hz, 1H), 6.92 (s, 1H), 4.70 (s, 2H), 3.61 (s, 2H), 3.46-3.09 (m, 3H), 2.85 (s, 2H), 1.93 (s, 2H), 1.67 (d, J=36.3 Hz, 4H), 1.49 (s, 2H).

Example 23 6-[(E)-2-(aminomethyl)-3-fluoro-allyloxy]-2-(p-methylphenyl)-3,4-dihydroiso quinolin-1-one hydrochloride 24

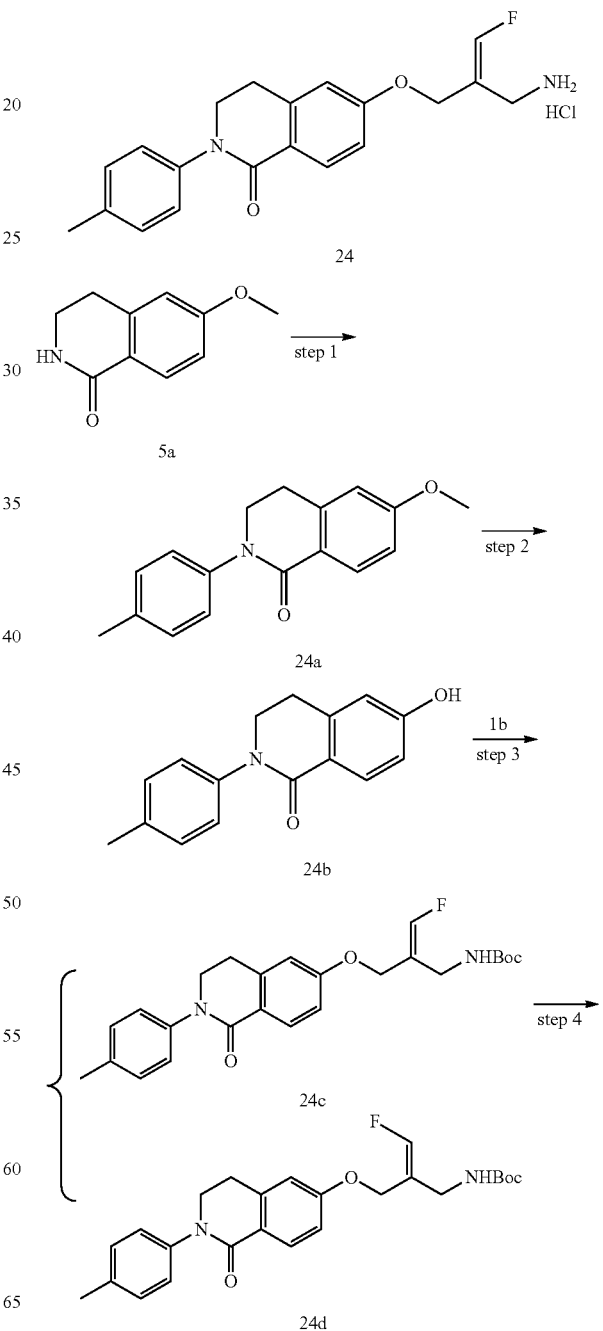

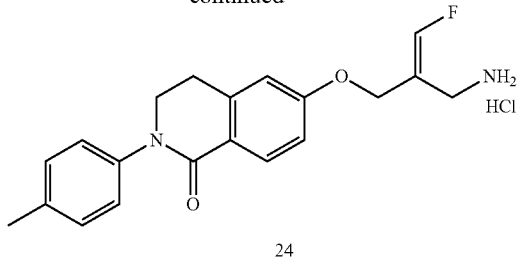

24

Step 1 2-(4-p-methylphenyl)-6-methoxy-3,4-dihydroisoquinolin-1-one 24a 6-(Methoxy)-3,4-dihydro-1(2H)-isoquinolinone 5a (2.00 g, 11.30 mmol) was dissolved in N,N-dimethylformamide (20 mL), and then 4-methyliodobenzene (5.00 g, 22.90 mmol), cuprous iodide (0.40 g, 2.10 mmol) and potassium carbonate (3.20 g, 22.90 mmol) were added, the resulting mixture was refluxed at 150° C. for 72 hours. After the mixture was cooled drown, the reaction was quenched with water (20 mL). The resulting mixture was extracted with ethyl acetate (100 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 24a (1.60 g, yield: 53%) as a white solid.

MS (ESI, pos. ion) m/z: 268.1 [M+H]$^+$.

Step 2 6-hydroxy-2-(p-methylphenyl)-3,4-dihydroisoquinolin-1-one 24b 2-(4-p-Methylphenyl)-6-methoxy-3,4-dihydroisoquinolin-1-one 24a (0.60 g, 2.20 mmol) was dissolved in dichloromethane (20 mL), and then boron tribromide (1.00 mL, 10.55 mmol) was added dropwise at −60° C., the resulting mixture was stirred at −20° C. for 5 hours. The reaction mixture was poured into ice-water (10 mL) to quench the reaction, when the ice melt, a lot of solid precipitated out. The mixture was filtered by suction filtration, the filter cake was purified by silica gel column chromatography (petroleum ether/ethyl acetate (v/v)=1/1) to give the title compound 24b (0.05 g, yield: 9%) as a white solid.

MS (ESI, pos. ion) m/z: 254.1 [M+H]$^+$.

Step 3 t-butyl N—[(E)-3-fluoro-2-[(1-oxo-2-(p-methylphenyl)-3,4-dihydroisoquinolin-6-yl) oxymethyl]allyl]carbamate 24c and t-butyl N—[(Z)-3-fluoro-2-[(1-oxo-2-(p-methylphenyl)-3,4-dihydroisoquinolin-6-yl)oxymethyl]allyl]carbamate 24d To a solution of 6-hydroxy-2-(p-methylphenyl)-3,4-dihydroisoquinolin-1-one 24b (50 mg, 0.20 mmol) in N,N-dimethyl formamide (5 mL) were added t-butyl N-[2-(bromomethyl)-3-fluoro-allyl]carbamate (60 mg, 0.22 mmol) and cesium carbonate (200 mg, 0.61 mmol), the resulting mixture was stirred at rt for 1 hour. The reaction was quenched with water (5 mL). The resulting mixture was extracted with ethyl acetate (10 mL). The organic phase was washed with saturated sodium chloride solution (10 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 24c (20 mg, yield: 23%) and 24d (11 mg, yield: 12%), both are colorless oil.

MS (ESI, pos. ion) m/z: 441.2 [M+H]$^+$.

Step 4 6-[(E)-2-(aminomethyl)-3-fluoro-allyloxy]-2-(p-methylphenyl)-3,4-dihydroisoquinolin-1-one hydrochloride 24 t-Butyl N—[(E)-3-fluoro-2-[(1-oxo-2-(p-methylphenyl)-3,4-dihydroisoquinolin-6-yl) oxymethyl]allyl]carbamate 24c (20 mg, 0.05 mmol) was dissolved in ethyl acetate (2 mL), and then hydrogen chloride-ethyl acetate solution (2 mL, 4 mol/L) was added, the mixture was stirred at rt for 1 hour. The mixture was concentrated to give the title compound 24 (15 mg, yield: 88%, HPLC: 95.09%) as a white solid.

MS (ESI, pos. ion) m/z: 341.2 [M−Cl]$^+$;

$^1$H NMR (400 MHz, DMSO-d$_6$) δ (ppm) 8.18 (s, 3H), 7.89 (d, J=8.3 Hz, 1H), 7.36 (d, J=82.1 Hz, 1H), 7.27 (d, J=8.4 Hz, 2H), 7.21 (d, J=8.3 Hz, 2H), 7.00 (d, J=8.3 Hz, 1H), 6.99 (s, 1H), 4.71 (s, 2H), 3.90 (t, J=6.4 Hz, 2H), 3.63 (d, J=4.6 Hz, 2H), 3.10 (t, J=6.3 Hz, 2H), 2.32 (s, 3H).

Example 24 6-[(Z)-2-(aminomethyl)-3-fluoro-allyloxy]-2-(p-methylphenyl)-3,4-dihydroiso quinolin-1-one hydrochloride 25

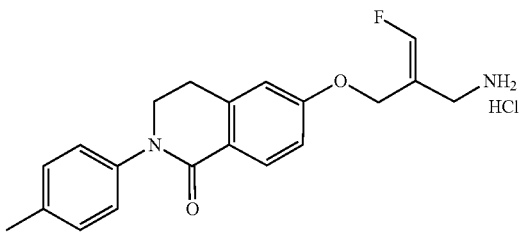

25

The title compound 25 (9 mg, yield: 95%, HPLC: 99.33%) as a white solid was obtained according to the method described in step 4 of example 23 by using t-butyl N—[(Z)-3-fluoro-2-[(1-oxo-2-(p-methylphenyl)-3,4-dihydroisoquinolin-6-yl)oxymethyl]allyl]carbamate 24d (11 mg, 0.02 mmol) instead of compound 24c.

MS (ESI, pos. ion) m/z: 341.1 [M−Cl]$^+$;

$^1$H NMR (400 MHz, DMSO-d$_6$) δ (ppm) 8.07 (s, 3H), 7.89 (d, J=9.1 Hz, 1H), 7.27 (d, J=8.3 Hz, 2H), 7.25 (d, J=82.1 Hz, 1H), 7.21 (d, J=8.3 Hz, 2H), 7.02 (s, 1H), 7.00 (s, 1H), 4.81 (s, 2H), 3.90 (t, J=6.3 Hz, 2H), 3.57 (s, 2H), 3.10 (t, J=6.5 Hz, 2H), 2.32 (s, 3H).

Example 25 6-[(E)-2-(aminomethyl)-3-fluoro-allyloxy]-2-(4-fluorophenyl)-3,4-dihydroiso quinolin-1-one hydrochloride 26

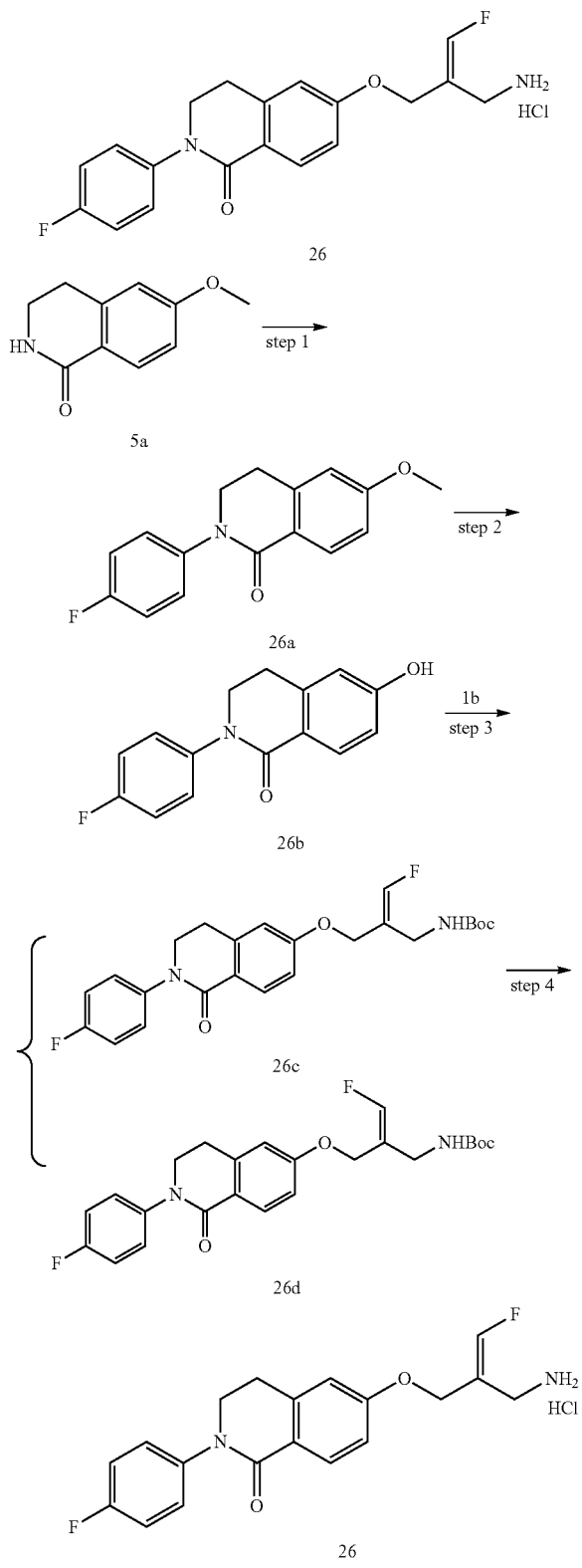

Step 1 2-(4-fluorophenyl)-6-methoxy-3,4-dihydroisoquinolin-1-one 26a 6-(Methoxy)-3,4-dihydro-1(2H)-isoquinolinone 5a (1.00 g, 5.64 mmol) was dissolved in N,N-dimethylformamide (20 mL), and then 4-fluoroiodobenzene (2.50 g, 11.30 mmol), cuprous iodide (0.40 g, 2.10 mmol) and potassium carbonate (1.60 g, 11.50 mmol) were added, the resulting mixture was refluxed at 150° C. for 23 hours. The mixture was cooled down; the reaction was quenched with water (20 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 26a (0.30 g, yield: 20%) as a white solid.

MS (ESI, pos. ion) m/z: 272.2 [M+H]$^+$.

Step 2 2-(4-fluorophenyl)-6-hydroxy-3,4-dihydroisoquinolin-1-one 26b 2-(4-Fluorophenyl)-6-methoxy-3,4-dihydroisoquinolin-1-one 26a (0.30 g, 1.10 mmol) was dissolved in dichloromethane (20 mL), and then boron tribromide (0.50 mL, 1.70 mmol) was added dropwise at 0° C., the resulting mixture was stirred for 1 hour. The reaction mixture was poured into trash ice to quench the reaction, when the ice melt, a lot of solid precipitated out. The mixture was filtered by suction filtration to give the title compound 26b (0.25 g, yield: 88%) as a white solid.

MS (ESI, pos. ion) m/z: 258.2 [M+H]$^+$.

Step 3 t-butyl N—[(E)-3-fluoro-2-[(1-oxo-2-(4-fluorophenyl)-3,4-dihydroisoquinolin-6-yl) oxymethyl]allyl]carbamate 26c and t-butyl N—[(Z)-3-fluoro-2-[(1-oxo-2-(4-fluorophenyl)-3,4-dihydroisoquinolin-6-yl)oxymethyl]allyl]carbamate 26d To a solution of 2-(4-fluorophenyl)-6-hydroxy-3,4-dihydroisoquinolin-1-one 26b (250 mg, 0.97 mmol) in N,N-dimethyl formamide (10 mL) were added t-butyl N-[2-(bromomethyl)-3-fluoro-allyl]carbamate 1b (270 mg, 1.00 mmol) and cesium carbonate (600 mg, 1.80 mmol), the resulting mixture was stirred at rt for 3 hours. The reaction was quenched with water (20 mL). The resulting mixture was extracted with ethyl acetate (30 mL). The organic phase was washed with saturated sodium chloride solution (30 mL×2), dried over anhydrous sodium sulfate, filtered by suction filtration. The filtrate was concentrated. The residue was purified by silica gel column chromatography (petroleum ether/ethyl acetate (v/v)=1/1) to give the title compound 26c (25 mg, yield: 5.8%) and 26d (43 mg, yield: 10%), both are colorless oil.

MS (ESI, pos. ion) m/z: 445.3 [M+H]$^+$.

Step 4 6-[(E)-2-(aminomethyl)-3-fluoro-allyloxy]-2-(4-fluorophenyl)-3,4-dihydroisoquinolin-1-one hydrochloride 26 t-Butyl N—[(E)-3-fluoro-2-[(1-oxo-2-(4-fluorophenyl)-3,4-dihydroisoquinolin-6-yl) oxymethyl]allyl]carbamate 26c (25 mg, 0.06 mmol) was dissolved in ethyl acetate (2 mL), and then hydrogen chloride-ethyl acetate solution (2 mL, 4 mol/L) was added, the mixture was stirred at rt for 1 hour. The mixture was concentrated to give the title compound 26 (20 mg, yield: 93%, HPLC: 98.55%) as colorless oil.

MS (ESI, pos. ion) m/z: 345.1 [M–Cl]+;

¹H NMR (400 MHz, DMSO-d₆) δ (ppm) 8.40-7.94 (s, 3H), 7.89 (m, 2H), 7.43 (m, 2H), 7.25 (m, 2H), 6.99 (m, 2H), 4.69 (s, 2H), 3.92 (m, 2H), 3.71 (m, 2H), 3.11 (m, 2H).

Example 26 6-[(Z)-2-(aminomethyl)-3-fluoro-allyloxy]-2-(4-fluorophenyl)-3,4-dihydro isoquinolin-1-one hydrochloride 27

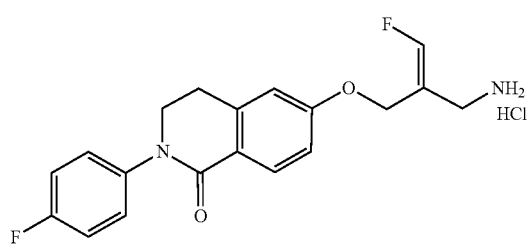

27

The title compound 27 (35 mg, yield: 95%, HPLC: 92.05%) as colorless oil was obtained according to the method described in step 4 of example 25 by using t-butyl N—[(Z)-3-fluoro-2-[(1-oxo-2-(4-fluorophenyl)-3,4-dihydroisoquinolin-6-yl)oxymethyl]allyl]carbamate 26d (43 mg, 0.10 mmol) instead of compound 26c.

MS (ESI, pos. ion) m/z: 345.1 [M–Cl]+;

¹H NMR (400 MHz, DMSO-d₆) δ (ppm) 8.03 (s, 3H), 7.89 (d, J=9.3 Hz, 2H), 7.43 (dd, J=8.8, 5.1 Hz, 2H), 7.26 (dd, J=19.0, 10.2 Hz, 2H), 7.11-6.94 (m, 2H), 4.79 (s, 2H), 3.92 (t, J=6.4 Hz, 2H), 3.53 (d, J=2.3 Hz, 2H), 3.11 (t, J=6.3 Hz, 2H).

Example 27 6-[(E)-2-(aminomethyl)-3-fluoro-allyloxy]-2-(2-pyridyl)-3,4-dihydroiso quinolin-1-one hydrochloride 28

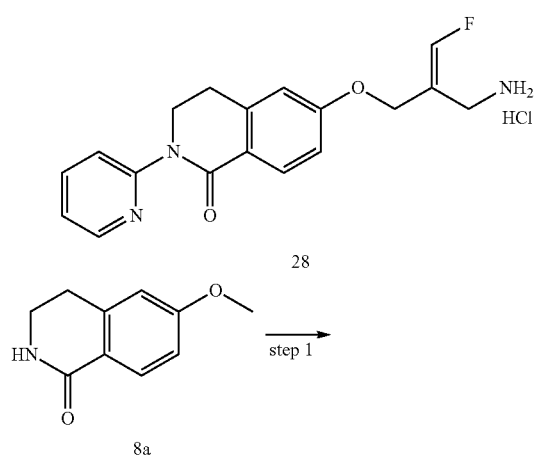

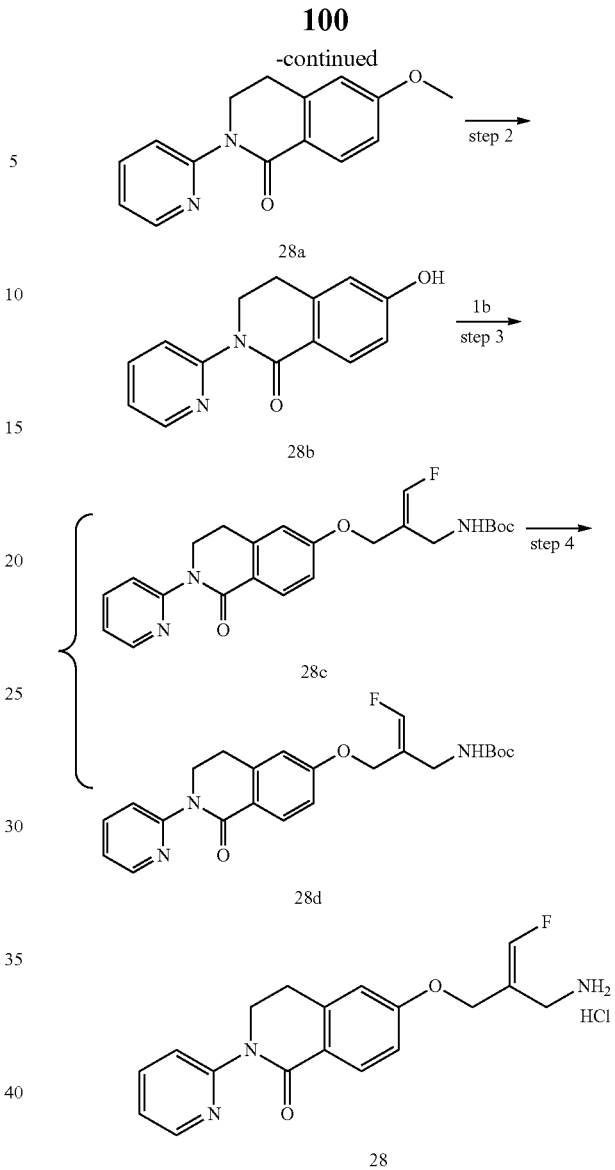

Step 1 6-methoxy-2-(2-pyridyl)-3,4-dihydroisoquinolin-1-one 28a 6-(Methoxy)-3,4-dihydro-2H-isoquinolin-1-one 5a (1.00 g, 5.64 mmol) was dissolved in N,N-dimethylformamide (20 mL), and then 2-iodopyridine (2.00 g, 5.64 mmol), cuprous iodide (0.20 g, 1.10 mmol) and potassium carbonate (0.90 g, 6.40 mmol) were added, the resulting mixture was refluxed at 150° C. for 6 hours. The mixture was cooled down, the reaction was quenched with water (20 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 28a (1.00 g, yield: 70%) as a white solid.

MS (ESI, pos. ion) m/z: 255.3 [M+H]+.

Step 2 6-hydroxy-2-(2-pyridyl)-3,4-dihydroisoquinolin-1-one 28b

6-Methoxy-2-(2-pyridyl)-3,4-dihydroisoquinolin-1-one 28a (0.50 g, 2.00 mmol) was dissolved in dichloromethane (15 mL), boron tribromide (1.00 mL, 10.40 mmol) was added dropwise at 0° C., the resulting mixture was stirred at rt for 5.5 hours. The reaction mixture was poured into ice-water (15 mL) to quench the reaction, the mixture was filtered by suction filtration to give the title compound 28b (0.40 g, yield: 85%) as a white solid.

MS (ESI, pos. ion) m/z: 241.1 [M+H]$^+$.

Step 3 t-butyl N—[(E)-3-fluoro-2-[(1-oxo-2-(2-pyridyl)-3,4-dihydroisoquinolin-6-yl)oxymethyl]allyl]carbamate 28c and t-butyl N—[(Z)-3-fluoro-2-[(1-oxo-2-(2-pyridyl)-3,4-dihydroiso quinolin-6-yl)oxymethyl]allyl]carbamate 28d To a solution of 6-hydroxy-2-(2-pyridyl)-3,4-dihydroisoquinolin-1-one 28b (400 mg, 1.70 mmol) in N,N-dimethyl formamide (10 mL) were added t-butyl N-[2-(bromomethyl)-3-fluoro-allyl]carbamate 1b (500 mg, 1.90 mmol) and cesium carbonate (1.00 g, 3.07 mmol), the resulting mixture was stirred at rt for 2 hours. The reaction was quenched with water (20 mL). The resulting mixture was extracted with ethyl acetate (30 mL). The organic phase was washed with saturated sodium chloride solution (30 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 28c (53 mg, yield: 7.3%) and 28d (85 mg, yield: 12%), both are colorless oil.

MS (ESI, pos. ion) m/z: 428.2 [M+H]$^+$.

Step 4 6-[(E)-2-(aminomethyl)-3-fluoro-allyloxy]-2-(2-pyridyl)-3,4-dihydroisoquinolin-1-one hydrochloride 28 t-Butyl N—[(E)-3-fluoro-2-[(1-oxo-2-(2-pyridyl)-3,4-dihydroisoquinolin-6-yl)oxymethyl]allyl]carbamate 28c (53 mg, 0.12 mmol) was dissolved in ethyl acetate (2 mL), and then hydrogen chloride-ethyl acetate solution (2 mL, 4 mol/L) was added, the mixture was stirred at rt for 1 hour. The mixture was concentrated to give the title compound 28 (45 mg, yield: 99%, HPLC: 99.36%) as colorless oil.

MS (ESI, pos. ion) m/z: 328.2 [M−Cl]$^+$;
$^1$H NMR (400 MHz, DMSO-d$_6$) δ (ppm) 8.48 (d, J=4.7 Hz, 1H), 8.46 (s, 3H), 7.97 (d, J=9.0 Hz, 1H), 7.93-7.82 (m, 2H), 7.35 (d, J=82.1 Hz, 1H), 7.24 (dd, J=8.3, 3.3 Hz, 1H), 7.04 (d, J=7.5 Hz, 2H), 4.81-4.72 (m, 2H), 4.18 (t, J=6.3 Hz, 2H), 3.55 (s, 2H), 3.09 (t, J=6.3 Hz, 2H).

Example 28 6-[(Z)-2-(aminomethyl)-3-fluoro-allyloxy]-2-(4-fluorophenyl)-3,4-dihydro isoquinolin-1-one hydrochloride 29

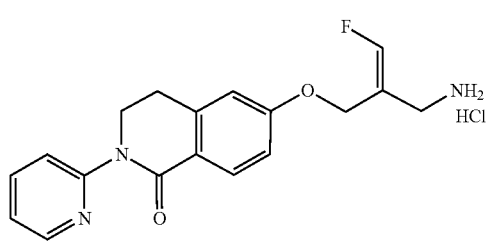

29

The title compound 29 (70 mg, yield: 97%, HPLC: 91.81%) as colorless oil was obtained according to the method described in step 4 of example 27 by using t-butyl N—[(Z)-3-fluoro-2-[(1-oxo-2-(2-pyridyl)-3,4-dihydroisoquinolin-6-yl)oxymethyl]allyl]carbamate 28d (85 mg, 0.20 mmol) instead of compound 28c.

MS (ESI, pos. ion) m/z: 328.3 [M−Cl]$^+$;
$^1$H NMR (400 MHz, DMSO-d$_6$) δ (ppm) 8.47 (d, J=4.7 Hz, 1H), 8.33 (s, 3H), 7.97 (d, J=9.0 Hz, 1H), 7.93-7.82 (m, 2H), 7.27 (d, J=82.1 Hz, 1H), 7.24 (dd, J=8.3, 3.3 Hz, 1H), 7.04 (d, J=7.5 Hz, 2H), 4.81-4.72 (m, 2H), 4.18 (t, J=6.3 Hz, 2H), 3.55 (s, 2H), 3.09 (t, J=6.3 Hz, 2H).

Example 29 7-[(E)-2-(aminomethyl)-3-fluoro-allyloxy]-1H-quinazolin-4-one hydrochloride 30

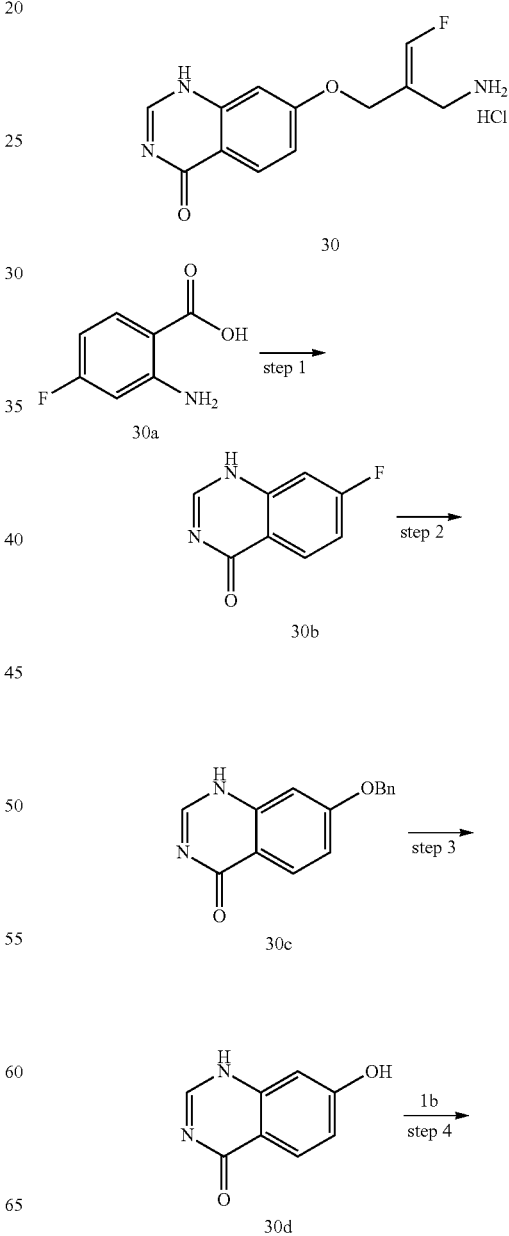

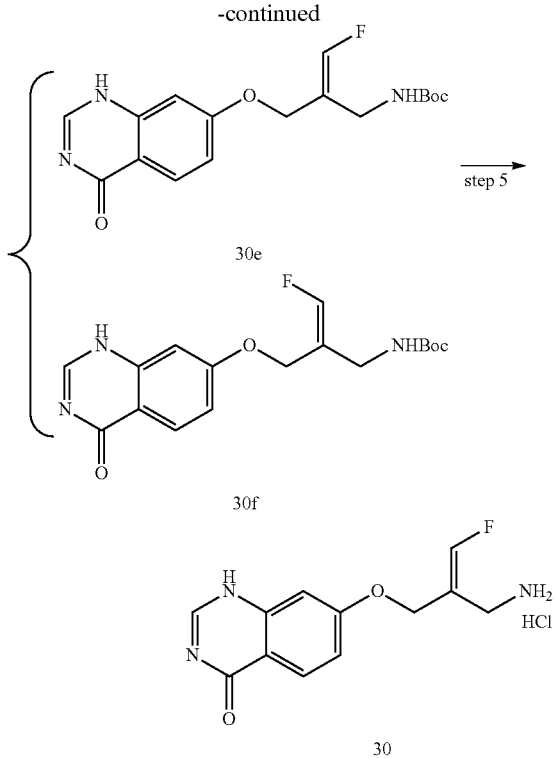

Step 1 7-fluoro-1H-quinazolin-4-one 30b

2-Amino-4-fluoro-benzoic acid 30a (2.00 g, 12.9 mmol) and formamidine acetate (2.70 g, 25.9 mmol) were dissolved in ethanol (20 mL), the resulting mixture was heated to 85° C. and refluxed for 25 hours. The mixture was concentrated. The residue was purified by silica gel column chromatography (petroleum ether/ethyl acetate (v/v)=1/1) to give the title compound 30b (1.53 g, yield: 72%) as a white solid.

MS (ESI, pos. ion) m/z: 165.3 [M−Cl]$^+$.

Step 2 7-benzyloxy-1H-quinazolin-4-one 30c

Benzyl alcohol (179 mg, 1.66 mmol) was dissolved in N,N-dimethylformamide (2.0 mL); at 0° C. and under $N_2$, sodium hydride (68 mg, 1.7 mmol, 60 wt %) was added, the resulting mixture was warmed to rt and stirred for 30 min; then a solution of 7-fluoro-1H-quinazolin-4-one 30b (64 mg, 0.39 mmol) in N,N-dimethylformamide (2.0 mL) was added at 0° C., the mixture was warmed to 95° C. and stirred for 16 hours. The mixture was cooled to rt, the reaction was quenched with water (8 mL). The resulting mixture was extracted with ethyl acetate (10×3 mL). The combined organic phases were washed with saturated sodium chloride solution (10 mL), dried over anhydrous sodium sulfate, filtered by suction filtration. The filtrate was concentrated. The residue was purified by silica gel column chromatography (ethyl acetate/petroleum ether (v/v)=2/1) to give the title compound 30c (87 mg, yield: 88%) as a white power solid.

MS (ESI, pos. ion) m/z: 253.2 [M+H]$^+$;

$^1$H NMR (400 MHz, DMSO-d$_6$) δ (ppm) 12.11 (s, 1H), 8.06-8.01 (m, 2H), 7.49 (d, J=7.1 Hz, 2H), 7.42 (t, J=7.3 Hz, 2H), 7.35 (t, J=7.2 Hz, 1H), 7.21-7.15 (m, 2H), 5.27 (s, 2H).

Step 3 7-hydroxy-1H-quinazolin-4-one 30d

7-Benzyloxy-1H-quinazolin-4-one 30c (47 mg, 0.19 mmol) was dissolved in N,N-dimethylformamide (2.0 mL), and a mixture of 10% Pd—C (18 mg) and ammonium formate (117 mg, 1.86 mmol) in water (2 mL) was added, the resulting mixture was stirred under $N_2$ for 21 hours. The mixture was filtered by suction filtration. The filtrate was diluted with water (2 mL), and the mixture was extracted with ethyl acetate (10 mL×2). The combined organic layers were washed with saturated sodium chloride solution (10 mL), dried over anhydrous sodium sulfate, and filtered by suction filtration. The filtrate was concentrated to give the title compound 30d (30 mg, yield: 99%).

MS (ESI, pos. ion) m/z: 163.2 [M+H]$^+$.

Step 4 t-butyl N—[(E)-3-fluoro-2-[(4-oxo-1H-quinazolin-7-yl)oxymethyl]allyl]carbamate 30e and t-butyl N—[(Z)-3-fluoro-2-[(4-oxo-1H-quinazolin-7-yl)oxymethyl]allyl]carbamate 30f 7-Hydroxy-1H-quinazolin-4-one 30d (200 mg, 1.23 mmol) was dissolved in dimethylsulfoxide (40 mL), potassium carbonate (232 mg, 1.66 mmol) was added at 0° C. and under $N_2$, the mixture was stirred for 10 min and t-butyl N-[2-(bromomethyl)-3-fluoro-allyl]carbamate 1b (200 mg, 0.746 mmol) was added, the resulting mixture was stirred at rt for 24 hours. To the reaction mixture was added water (40 mL) to quench the reaction. The resulting mixture was extracted with ethyl acetate (20 mL×3). The combined organic phases were washed with saturated sodium chloride solution (20 mL×2), dried over anhydrous sodium sulfate, filtered by suction filtration. The filtrate was concentrated. The residue was purified by silica gel column chromatography (ethyl acetate/petroleum ether (v/v)=2/3) to give the title compound 30e (68 mg, yield: 16%) and 30f (15 mg, yield: 3.5%), both are white solid.

Step 5 7-[(E)-2-(aminomethyl)-3-fluoro-allyloxy]-1H-quinazolin-4-one hydrochloride 30 t-Butyl N—[(E)-3-fluoro-2-[(4-oxo-1H-quinazolin-7-yl)oxymethyl]allyl]carbamate 30e (68 mg, 0.19 mmol) was dissolved in ethyl acetate (5 mL), and then hydrogen chloride-ethyl acetate solution (3 mL, 4 mol/L) was added dropwise at 0° C. and under $N_2$, the mixture was stirred at rt for 15 hours, and then the mixture was concentrated to give the title compound 30 (55 mg, yield: 99%, HPLC: 100%) as a white solid.

MS (ESI, pos. ion) m/z: 250.2 [M+H]$^+$;

$^1$H NMR (400 MHz, DMSO-d$_6$) δ (ppm) 11.03 (s, 1H), 8.91 (s, 1H), 8.38 (s, 3H), 8.11-7.88 (m, 1H), 7.31 (d, J=81.8 Hz, 1H), 7.09 (dd, J=4.3, 2.3 Hz, 2H), 4.74 (s, 2H), 3.50 (d, J=4.7 Hz, 2H).

Example 30 7-[(Z)-2-(aminomethyl)-3-fluoro-allyloxy]-1H-quinazolin-4-one hydrochloride 31

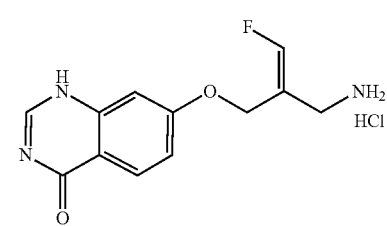

The title compound 31 (12 mg, yield: 97%, HPLC: 99.8%) as a white solid was obtained according to the method described in step 5 of example 29 by using t-butyl N—[(Z)-3-fluoro-2-[(4-oxo-1H-quinazolin-7-yl)oxymethyl]allyl]carbamate 30f (15 mg, 0.043 mmol) instead of compound 30e.

MS (ESI, pos. ion) m/z: 250.2 [M+H]⁺;

¹H NMR (400 MHz, DMSO-d₆) δ (ppm) 10.81 (s, 1H), 8.56 (s, 1H), 8.24 (s, 3H), 8.01 (d, J=8.7 Hz, 1H), 7.09 (dd, J=48.3, 41.7 Hz, 1H), 7.05 (s, 1H), 7.00 (d, J=2.0 Hz, 1H), 4.76 (s, 2H), 3.48 (s, 2H).

Example 31 (E)-2-[(1,1-dioxo-3,4-dihydro-2H-benzo[e][1,2]thiazin-6-yl)oxymethyl]-3-fluoro-prop-2-enyl-1-amine hydrochloride 32

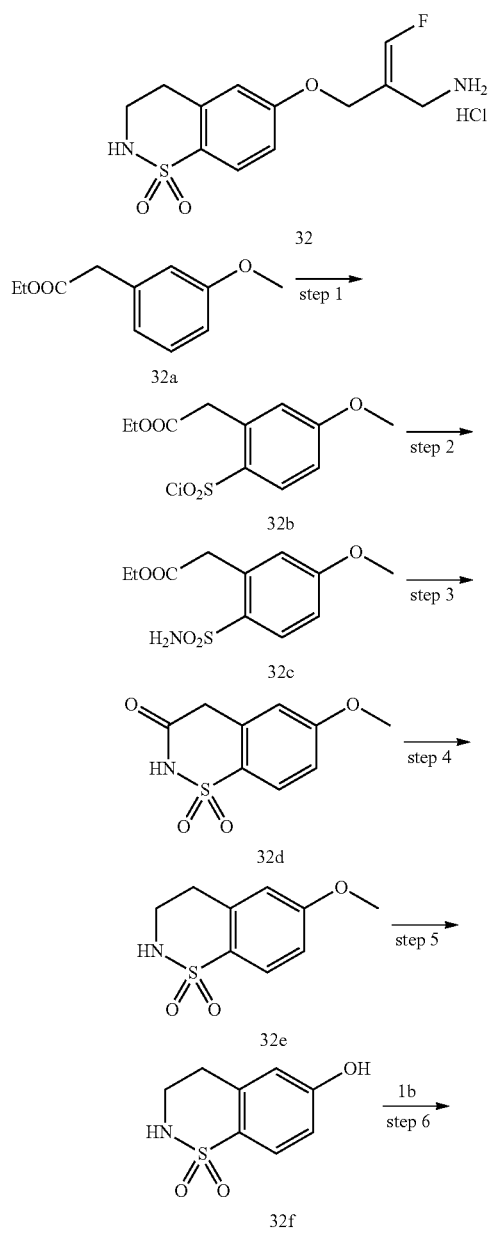

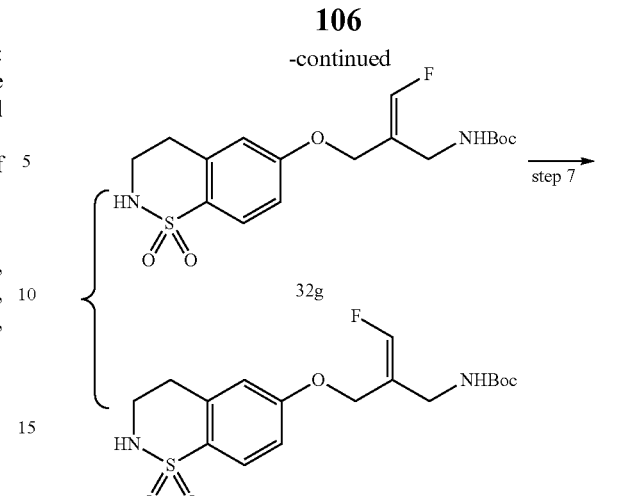

Step 1 ethyl 2-(2-chlorosulfonyl-5-methoxy-phenyl)acetate 32b

At 0° C., a solution of chlorosulfonic acid (5.5 mL, 79 mmol) in dichloromethane (10 mL) was added dropwise into a solution of ethyl 2-(3-methoxyphenyl)acetate 32a (5.02 g, 25.8 mmol) in dichloromethane (20 mL), the mixture was stirred for 10 min, and then moved to rt and stirred for 1 hour. The reaction mixture was poured into ice-water (10 mL), the organic layer was washed with water (10 mL), saturated sodium carbonate solution (10 mL) and saturated sodium chloride (10 mL) in turn, dried over anhydrous sodium sulfate. The mixture was filtered by suction filtration. The filtrate was concentrated to give the title compound 32b (2.39 g, yield: 32%) as a white solid.

¹H NMR (400 MHz, DMSO-d₆) δ (ppm) 7.66 (d, J=8.3 Hz, 1H), 6.80-6.71 (m, 2H), 4.07-3.96 (m, 4H), 3.74 (s, 3H), 1.17 (t, J=7.1 Hz, 3H).

Step 2 ethyl 2-(5-methoxy-2-sulfonylamino-phenyl)acetate 32c

At 0° C., an ammonia/methanol solution (1.5 mL, 17.9 mmol, 7 mol/L) was added into a solution of ethyl 2-(2-chlorosulfonyl-5-methoxy-phenyl)acetate 32b (1.04 g, 3.55 mmol) in tetrahydrofuran (15 mL), and then triethylamine (1.2 mL, 8.5 mmol) was added, and the reaction mixture was moved to rt and stirred for 3 hours. The stirrer was stopped, the mixture was filtered by suction filtration. The filtrate was concentrated to give the title compound 32c (0.93 g, yield: 98%) as light yellow liquid.

MS (ESI, neg. ion) m/z: 272.2 [M−H]⁻.

Step 3 6-methoxy-1,1-dioxo-4H-benzo[e][1,2]thiazin-3-one 32d

Potassium hydroxide (0.40 g, 7.1 mmol) was added into a solution of ethyl 2-(5-methoxy-2-sulfonylamino-phenyl)

acetate 32c (0.93 g, 3.4 mmol) in ethanol (10 mL), the resulting mixture was stirred at rt for 2 hours. The mixture was concentrated, the residue was dissolved in water (5 mL), the mixture was adjusted with hydrochloric acid (1 mol/L) to pH 1 and filtered by suction filtration to give the title compound 32d (0.60 g, yield: 78%) as a yellow solid.

MS (ESI, pos. ion) m/z: 228.0 [M+H]$^+$;

$^1$H NMR (400 MHz, DMSO-d$_6$) δ (ppm) 7.80 (d, J=8.7 Hz, 1H), 7.18 (d, J=2.1 Hz, 1H), 7.08 (dd, J=8.7, 2.4 Hz, 1H), 4.02 (s, 2H), 3.85 (s, 3H), 3.44 (s, 1H).

Step 4 6-methoxy-3,4-dihydro-2H-1,2-benzothiazinyl-1,1-dioxide 32e

A borane-tetrahydrofuran solution (4.5 mL, 4.5 mmol, 1.0 mol/L) was added dropwise into a solution of 6-methoxy-1,1-dioxo-4H-benzo[e][1,2]thiazin-3-one 32d (0.38 g, 1.7 mmol) in tetrahydrofuran (8 mL), the reaction was heated to 70° C. and refluxed for 3 hours. After the mixture was cooled to rt, the reaction was quenched by adding methanol (2 mL) dropwise and the mixture was concentrated, and the obtained residue was diluted with ethyl acetate (20 mL), and the resulting mixture was washed with water (10 mL) and saturated sodium chloride solution (10 mL) in turn, dried over anhydrous sodium sulfate, and filtered by suction filtration. The filtrate was concentrated to give the title compound 32e (0.33 g, yield: 93%) as colorless liquid.

MS (ESI, neg. ion) m/z: 212.1 [M−H]$^-$;

$^1$H NMR (400 MHz, CDCl$_3$) δ (ppm) 7.69 (d, J=8.8 Hz, 1H), 6.84 (dd, J=8.8, 2.4 Hz, 1H), 6.65 (d, J=2.2 Hz, 1H), 4.72 (t, J=7.5 Hz, 1H), 3.81 (s, 3H), 3.72 (q, 2H), 2.91 (t, J=6.0 Hz, 2H).

Step 5 1,1-dioxo-3,4-dihydro-2H-benzo[e][1,2]thiazin-6-ol 32f

At 0° C., a solution of boron tribromide (0.30 mL, 3.1 mmol) in dichloromethane (5 mL) was added dropwise into a solution of 6-methoxy-3,4-dihydro-2H-benzo[e][1,2]thiazin-1,1-dioxide 32e (0.33 g, 1.5 mmol) in dichloromethane (5 mL), the mixture was stirred at rt for 1.5 hours. After the mixture was cooled to 0° C., methanol (6 mL) was added dropwise, and the mixture was stirred for 10 min and concentrated, and the obtained residue was diluted with ethyl acetate (20 mL), and the resulting mixture was washed with water (10 mL) and saturated sodium chloride solution (10 mL) in turn, dried over anhydrous sodium sulfate, and filtered by suction filtration. The filtrate was concentrated to give the title compound 32f (0.30 g, yield: 97%) as light yellow liquid.

MS (ESI, pos. ion) m/z: 200.2 [M+H]$^+$.

Step 6 tert-butyl (E)-N-[2-[(1,1-dioxo-3,4-dihydro-2H-benzo[e][1,2]thiazin-6-yl)oxymethyl]-3-fluoro-allyl]formate 32 g and tert-butyl (Z)—N-[2-[(1,1-dioxo-3,4-dihydro-2H-benzo[e][1,2]thiazin-6-yl)oxymethyl]-3-fluoro-allyl]formate 32h To a solution of 1,1-dioxo-3,4-dihydro-2H-benzo[e][1,2]thiazin-6-ol 32f (0.56 g, 2.8 mmol) and t-butyl N-[2-(bromomethyl)-3-fluoro-allyl]carbamate 1b (0.83 g, 3.1 mmol) in N,N-dimethylformamide (10 mL) was added potassium carbonate (0.79 g, 5.6 mmol). The mixture was stirred at 60° C. for 14 hours. To the mixture was added water (20 mL) and ethyl acetate (20 mL), and the mixture was stirred for 10 min, and the water phase was extracted with ethyl acetate (10 mL×2), and the combined organic layers were washed with water (10 mL) and saturated sodium chloride solution (10 mL), dried over anhydrous sodium sulfate. The mixture was filtered by suction filtration, the filtrate was concentrated. The residue was purified by silica gel column chromatography (petroleum ether/ethyl acetate (v/v)=3/2) to give the title compound 32g (0.17 g, yield: 16%) and 32h (0.24 g, yield: 22%), both are colorless liquid.

MS (ESI, neg. ion) m/z: 385.0 [M−H]$^-$;

Compound 32g:

$^1$H NMR (400 MHz, CDCl$_3$) δ (ppm) 7.60 (d, J=8.7 Hz, 1H), 6.81 (dd, J=9.0, 2.4 Hz, 1H), 6.72 (d, J=81.2 Hz, 1H), 6.67 (d, J=1.8 Hz, 1H), 5.28 (t, J=7.5 Hz, 1H), 4.97 (t, J=6.1 Hz, 1H), 4.42 (d, J=2.6 Hz, 2H), 3.92 (d, J=3.2 Hz, 2H), 3.66 (q, 2H), 2.87 (t, J=5.9 Hz, 2H), 1.37 (s, 9H);

Compound 32h:

$^1$H NMR (400 MHz, CDCl$_3$) δ (ppm) 7.74 (d, J=8.7 Hz, 1H), 6.90 (dd, J=8.7, 1.9 Hz, 1H), 6.73 (d, J=1.6 Hz, 1H), 6.72 (d, J=82.4 Hz, 1H), 4.71 (overlap, 3H), 4.59-4.48 (m, 1H), 3.84-3.65 (m, 4H), 2.94 (t, J=6.0 Hz, 2H), 1.41 (s, 9H).

Step 7 (E)-2-[(1,1-dioxo-3,4-dihydro-2H-benzo[e][1,2]thiazin-6-yl)oxymethyl]-3-fluoro-prop-2-enyl-1-amine hydrochloride 32

A hydrogen chloride-ethyl acetate solution (5 mL, 4 mol/L) was added to a solution of tert-butyl (E)-N-[2-[(1,1-dioxo-3,4-dihydro-2H-benzo[e][1,2]thiazin-6-yl)oxymethyl]-3-fluoro-allyl]formate 32 g (0.12 g, 0.31 mmol) in dichloromethane (2 mL), the mixture was stirred at rt for 40 min. The mixture was concentrated to give the title compound 32 (0.10 g, yield: 99%, HPLC: 90.09%) as a white solid.

MS (ESI, pos. ion) m/z: 287.0 [M−Cl]$^+$;

$^1$H NMR (400 MHz, CD$_3$OD) δ (ppm) 7.71 (d, J=8.7 Hz, 1H), 7.25 (d, J=81.0 Hz, 1H), 7.06 (dd, J=8.7, 2.4 Hz, 1H), 6.97 (d, J=2.2 Hz, 1H), 4.69 (d, J=3.3 Hz, 2H), 3.84 (s, 2H), 3.68 (t, J=6.0 Hz, 2H), 2.99 (t, J=6.0 Hz, 2H);

$^{19}$F NMR (376 MHz, CD$_3$OD) δ (ppm) −122.57.

Example 32 (E)-2-[(1,1-dioxo-3,4-dihydro-2H-benzo[e][1,2]thiazin-6-yl)oxymethyl]-3-fluoro-prop-2-enyl-1-amine hydrochloride 33

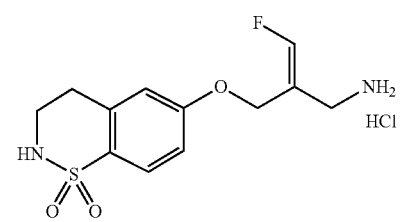

The title compound 33 (0.20 g, yield: 99%, HPLC: 84.09%) as a white solid was obtained according to the method described in step 7 of example 31 by using tert-butyl (Z)—N-[2-[(1,1-dioxo-3,4-dihydro-2H-benzo[e][1,2]thiazin-6-yl)oxymethyl]-3-fluoro-allyl]formate 32h (0.24 g, 0.62 mmol) instead of compound 32g.

MS (ESI, pos. ion) m/z: 287.1 [M−Cl]+;

$^1$H NMR (400 MHz, CD$_3$OD) δ (ppm) 7.72 (dd, J=8.7, 2.5 Hz, 1H), 7.14 (d, J=80.4 Hz, 1H), 7.08 (dd, J=8.7, 2.4 Hz, 1H), 7.04 (s, 1H), 6.98 (s, 1H), 4.61 (s, 2H), 3.71-3.61 (m, 4H), 2.99 (t, J=6.0 Hz, 2H);

$^{19}$F NMR (376 MHz, CD$_3$OD) δ (ppm) −121.02.

Example 33 6-[(E)-2-(aminomethyl)-3-fluoro-allyloxy]-2-(2-fluorophenyl)-3,4-dihydro isoquinolin-1-one hydrochloride 34 and 6-[(Z)-2-(aminomethyl)-3-fluoro-allyloxy]-2-(2-fluorophenyl)-3,4-dihydroisoquinolin-1-one hydrochloride 35

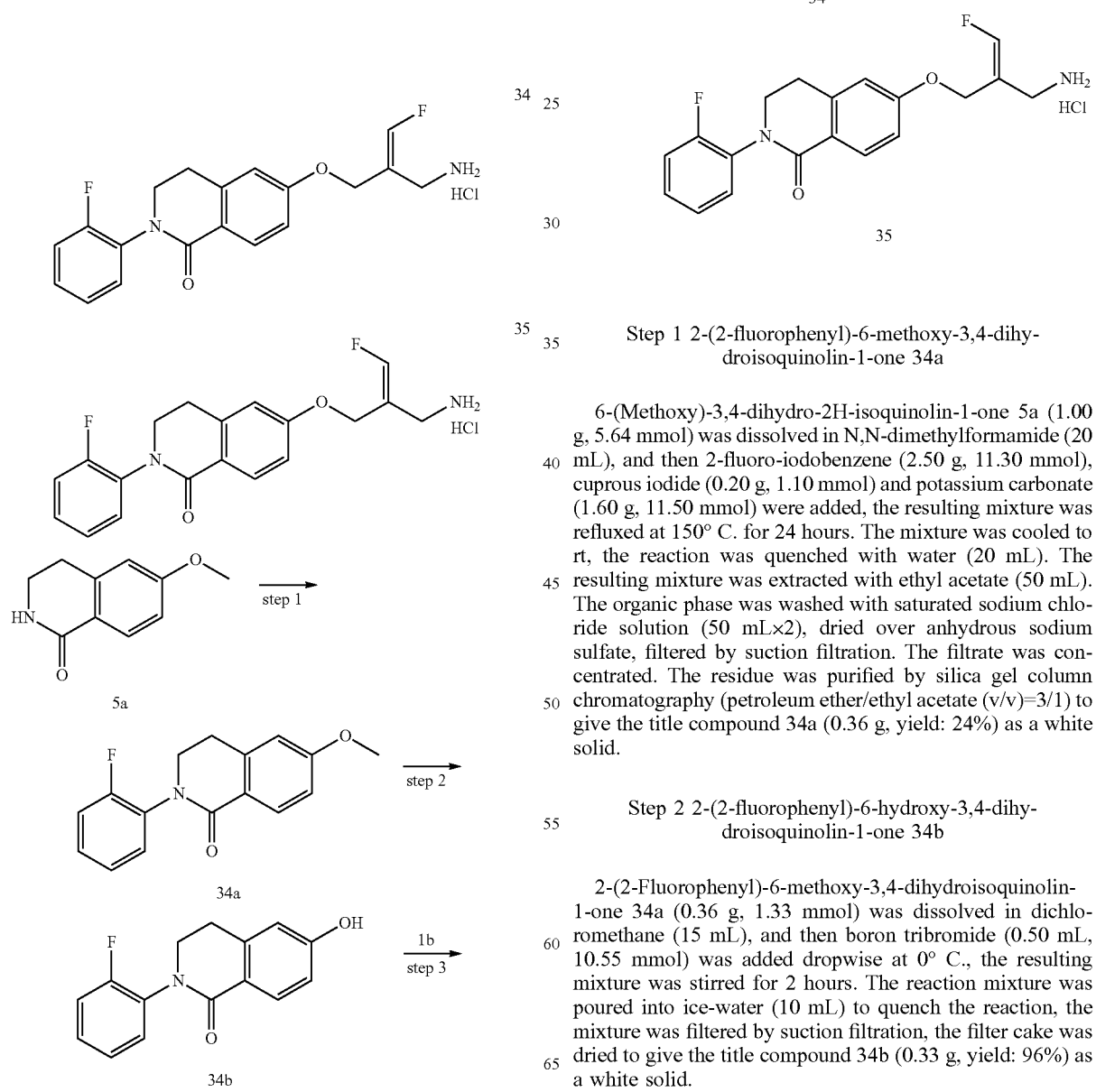

Step 1 2-(2-fluorophenyl)-6-methoxy-3,4-dihydroisoquinolin-1-one 34a 6-(Methoxy)-3,4-dihydro-2H-isoquinolin-1-one 5a (1.00 g, 5.64 mmol) was dissolved in N,N-dimethylformamide (20 mL), and then 2-fluoro-iodobenzene (2.50 g, 11.30 mmol), cuprous iodide (0.20 g, 1.10 mmol) and potassium carbonate (1.60 g, 11.50 mmol) were added, the resulting mixture was refluxed at 150° C. for 24 hours. The mixture was cooled to rt, the reaction was quenched with water (20 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 34a (0.36 g, yield: 24%) as a white solid.

Step 2 2-(2-fluorophenyl)-6-hydroxy-3,4-dihydroisoquinolin-1-one 34b 2-(2-Fluorophenyl)-6-methoxy-3,4-dihydroisoquinolin-1-one 34a (0.36 g, 1.33 mmol) was dissolved in dichloromethane (15 mL), and then boron tribromide (0.50 mL, 10.55 mmol) was added dropwise at 0° C., the resulting mixture was stirred for 2 hours. The reaction mixture was poured into ice-water (10 mL) to quench the reaction, the mixture was filtered by suction filtration, the filter cake was dried to give the title compound 34b (0.33 g, yield: 96%) as a white solid.

MS (ESI, pos. ion) m/z: 258.1 [M+H]+.

Step 3 t-butyl N-[2-fluoro-2-[(1-oxo-2-(2-fluorophenyl)-3,4-dihydroisoquinolin-6-yl)oxymethyl]allyl]carbamate 34c To a solution of 2-(2-fluorophenyl)-6-hydroxy-3,4-dihydroisoquinolin-1-one 34b (0.33 g, 1.30 mmol) in N,N-dimethyl formamide (10 mL) were added t-butyl N-[2-(bromomethyl)-3-fluoro-allyl]carbamate 1b (0.35 g, 1.31 mmol) and cesium carbonate (0.80 g, 2.50 mmol), the resulting mixture was stirred at rt for 1 hour. The reaction was quenched with water (10 mL). The resulting mixture was extracted with ethyl acetate (20 mL). The organic phase was washed with saturated sodium chloride solution (20 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 34c (0.34 g, yield: 60%) as colorless oil.

MS (ESI, pos. ion) m/z: 445.1 [M+H]$^+$.

Step 4 6-[(E)-2-(aminomethyl)-3-fluoro-allyloxy]-2-(2-fluorophenyl)-3,4-dihydroisoquinolin-1-one hydrochloride 34 and 6-[(Z)-2-(aminomethyl)-3-fluoro-allyloxy]-2-(2-fluorophenyl)-3,4-dihydroisoquinolin-1-one hydrochloride 35 t-Butyl N-[2-fluoro-2-[(1-oxo-2-(2-fluorophenyl)-3,4-dihydro isoquinolin-6-yl)oxymethyl]allyl]carbamate 34c (0.34 g, 0.76 mmol) was dissolved in ethyl acetate (10 mL), and then a hydrogen chloride-ethyl acetate solution (10 mL, 2 mol/L) was added, the mixture was stirred at rt for 4 hours. The reaction mixture was concentrated, the residue was purified, and reacted with hydrogen chloride-ethyl acetate solution to give the title compound 34 (0.13 g, yield: 38%, HPLC: 90.48%) and 35 (0.15 g, yield: 44%, HPLC: 99.29%), both are white solid.

Compound 34:
MS (ESI, pos. ion) m/z: 345.1 [M−Cl]$^+$;
$^1$H NMR (400 MHz, DMSO-d$_6$) δ (ppm) 8.32 (s, 3H), 7.89 (d, J=9.2 Hz, 1H), 7.49 (d, J=7.8 Hz, 1H), 7.36 (d, J=80 Hz, 1H), 7.38-7.19 (m, 3H), 7.01 (s, 2H), 4.74 (s, 2H), 3.87 (t, J=6.2 Hz, 2H), 3.63 (d, J=4.3 Hz, 2H), 3.13 (t, J=6.1 Hz, 2H);

Compound 35:
MS (ESI, pos. ion) m/z: 345.1 [M−Cl]$^+$;
$^1$H NMR (400 MHz, DMSO-d$_6$) δ (ppm) 8.31 (s, 3H), 7.89 (d, J=9.3 Hz, 1H), 7.48 (t, J=7.7 Hz, 1H), 7.41-7.27 (m, 3H), 7.24 (d, J=80 Hz, 1H), 7.02 (d, J=5.7 Hz, 2H), 4.84 (s, 2H), 3.89-3.85 (m, 2H), 3.56 (s, 2H), 3.12 (t, J=6.2 Hz, 2H).

Example 34 6-[(E)-2-(aminomethyl)-3-fluoro-allyloxy]-2-(3-fluorophenyl)-3,4-dihydro isoquinolin-1-one hydrochloride 36 and 6-[(Z)-2-(aminomethyl)-3-fluoro-allyloxy]-2-(3-fluorophenyl)-3,4-dihydroisoquinolin-1-one hydrochloride 37

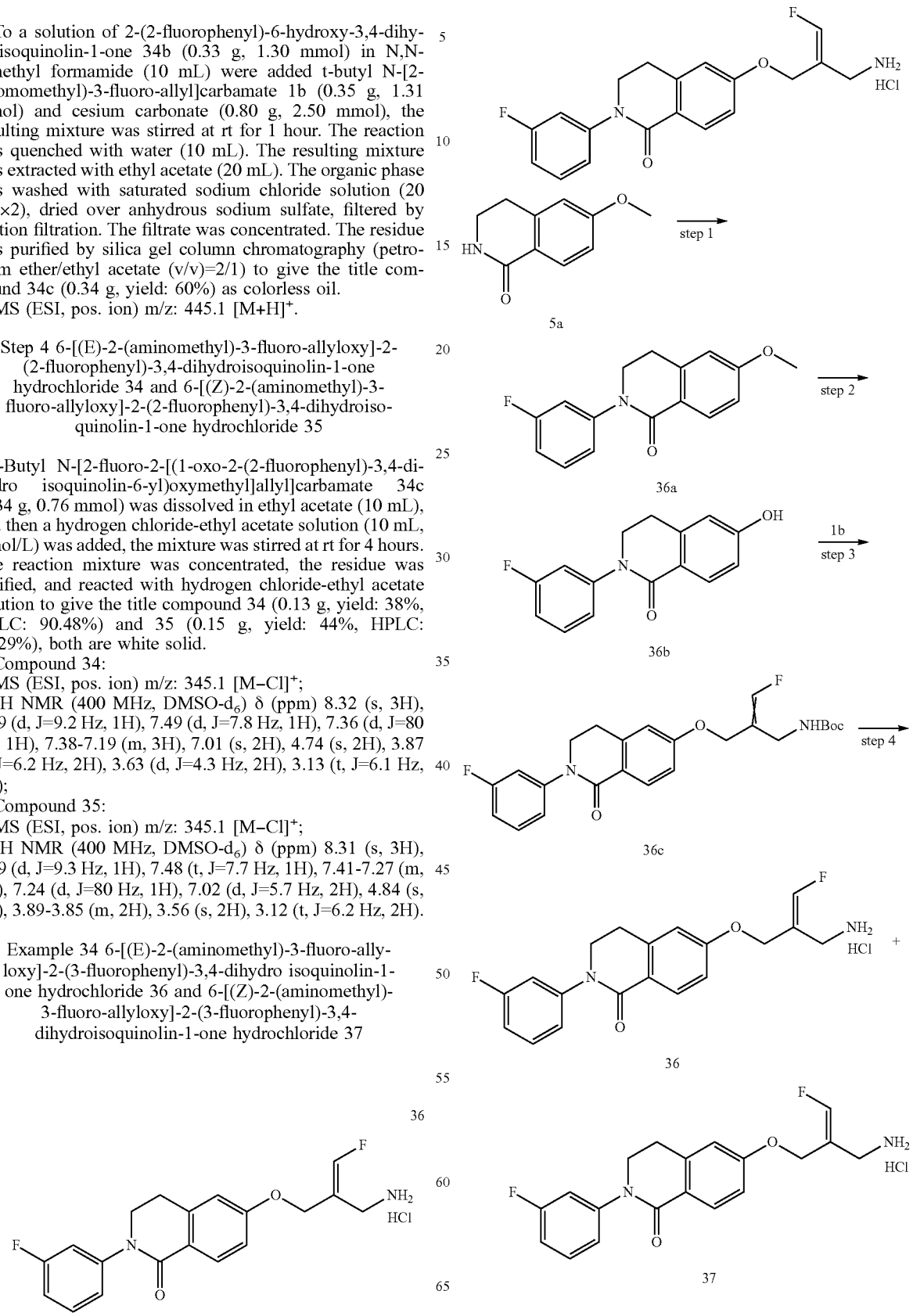

Step 1 2-(3-fluorophenyl)-6-methoxy-3,4-dihydroisoquinolin-1-one 36a 6-(Methoxy)-3,4-dihydro-2H-isoquinolin-1-one 5a (1.00 g, 5.64 mmol) was dissolved in N,N-dimethylformamide (20 mL), and then m-fluoro iodobenzene (2.50 g, 11.30 mmol), cuprous iodide (0.20 g, 1.10 mmol) and potassium carbonate (1.60 g, 11.50 mmol) were added, the resulting mixture was refluxed at 150° C. for 24 hours. The mixture was cooled to rt, the reaction was quenched with water (20 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 36a (0.36 g, yield: 24%) as a white solid.

Step 2 2-(3-fluorophenyl)-6-hydroxy-3,4-dihydroisoquinolin-1-one 36b 2-(3-Fluorophenyl)-6-methoxy-3,4-dihydroisoquinolin-1-one 36a (0.36 g, 1.33 mmol) was dissolved in dichloromethane (15 mL), and then boron tribromide (0.50 mL, 5.10 mmol) was added dropwise at 0° C., the resulting mixture was stirred for 2 hours. The reaction mixture was poured into ice-water (10 mL) to quench the reaction, the mixture was filtered, the filter cake was collected to give the title compound 36b (0.33 g, yield: 96%) as a white solid.

MS (ESI, pos. ion) m/z: 258.1 [M+H]$^+$.

Step 3 t-butyl N-[2-fluoro-2-[[2-(3-fluorophenyl)-1-oxo-3,4-dihydroisoquinolin-6-yl]oxymethyl]allyl]carbamate 36c To a solution of 2-(3-fluorophenyl)-6-hydroxy-3,4-dihydroisoquinolin-1-one 36b (0.33 g, 1.30 mmol) in N,N-dimethyl formamide (10 mL) were added t-butyl N-[2-(bromomethyl)-3-fluoro-allyl]carbamate 1b (0.35 g, 1.31 mmol) and cesium carbonate (0.80 g, 2.50 mmol), the resulting mixture was stirred at rt for 1 hour. The reaction was quenched with water (10 mL). The resulting mixture was extracted with ethyl acetate (20 mL). The organic phase was washed with saturated sodium chloride solution (20 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 36c (0.34 g, yield: 60%) as colorless oil.

MS (ESI, pos. ion) m/z: 445.1 [M+H]$^+$.

Step 4 6-[(E)-2-(aminomethyl)-3-fluoro-allyloxy]-2-(3-fluorophenyl)-3,4-dihydroisoquinolin-1-one hydrochloride 36 and 6-[(Z)-2-(aminomethyl)-3-fluoro-allyloxy]-2-(3-fluorophenyl)-3,4-dihydroisoquinolin-1-one hydrochloride 37 t-Butyl N-[2-fluoro-2-[[2-(3-fluorophenyl)-1-oxo-3,4-dihydroisoquinolin-6-yl]oxymethyl]allyl]carbamate 36c (0.34 g, 0.76 mmol) was dissolved in ethyl acetate (10 mL), and then a hydrogen chloride-ethyl acetate solution (10 mL, 2 mol/L) was added, the mixture was stirred at rt for 2 hours. The reaction mixture was concentrated, the residue was purified, and reacted with a hydrogen chloride-ethyl acetate solution to give the title compound 36 (0.13 g, yield: 38%, HPLC: 90.48%) and 37 (0.15 g, yield: 44%, HPLC: 99.29%), both are white solid.

Compound 36:

MS (ESI, pos. ion) m/z: 345.1 [M−Cl]$^+$;

$^1$H NMR (400 MHz, DMSO-d$_6$) δ (ppm) 8.32 (s, 3H), 7.89 (d, J=9.2 Hz, 1H), 7.49 (d, J=7.8 Hz, 1H), 7.36 (d, J=80 Hz, 1H), 7.38-7.19 (m, 3H), 7.01 (s, 2H), 4.74 (s, 2H), 3.87 (t, J=6.2 Hz, 2H), 3.63 (d, J=4.3 Hz, 2H), 3.13 (t, J=6.1 Hz, 2H);

Compound 37:

MS (ESI, pos. ion) m/z: 345.1 [M−Cl]$^+$;

HPLC: 99.29%; $^1$H NMR (400 MHz, DMSO-d$_6$) δ (ppm) 8.31 (s, 3H), 7.89 (d, J=9.3 Hz, 1H), 7.48 (t, J=7.7 Hz, 1H), 7.41-7.27 (m, 3H), 7.24 (d, J=80 Hz, 1H), 7.02 (d, J=5.7 Hz, 2H), 4.84 (s, 2H), 3.89-3.85 (m, 2H), 3.56 (s, 2H), 3.12 (t, J=6.2 Hz, 2H).

Example 35

4-[6-[(E)-2-(aminomethyl)-3-fluoro-allyloxy]-1-oxo-3,4-dihydroisoquinolin-2-yl]benzonitrile hydrochloride 38

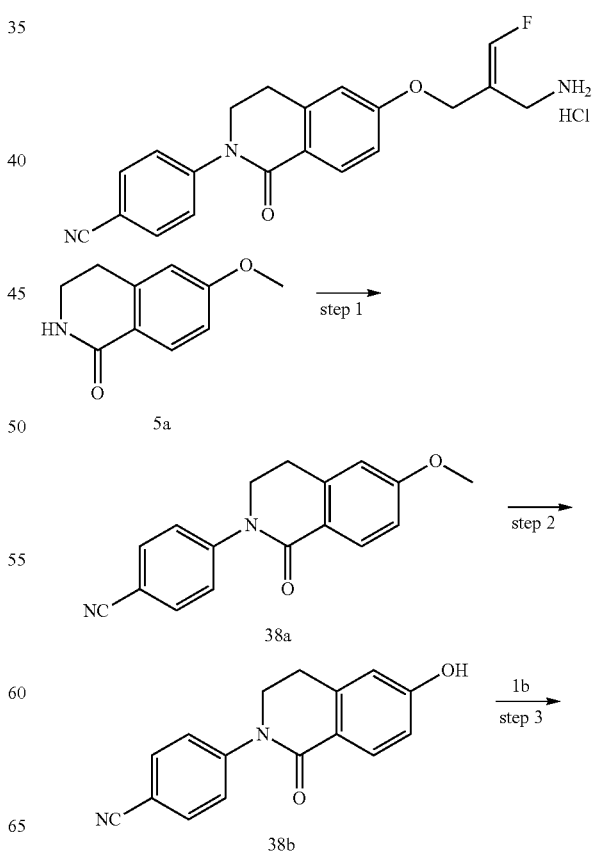

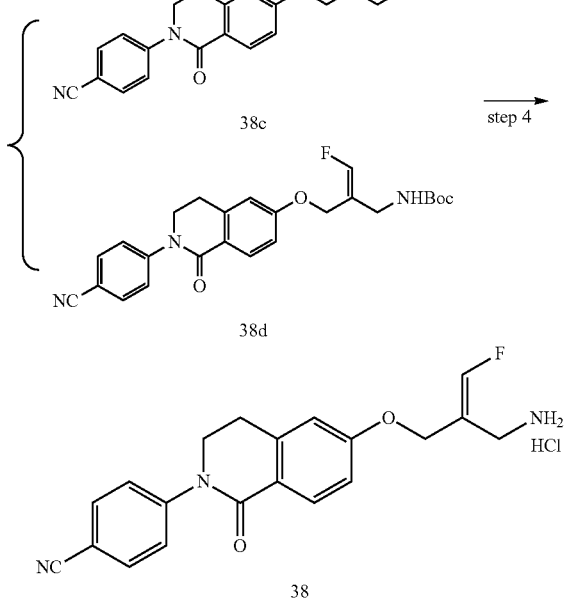

Step 1 4-(6-methoxy-1-oxo-3,4-dihydroisoquinolin-2-yl)benzonitrile 38a 6-(Methoxy)-3,4-dihydro-2H-isoquinolin-1-one 5a (2.0 g, 11.3 mmol) was dissolved in N,N-dimethylformamide (20 mL), and then 4-iodobenzonitrile (3.1 g, 13.0 mmol), cuprous iodide (0.22 g, 1.13 mmol), trans-1,2-cyclohexanediamine (0.66 g, 5.64 mmol) and anhydrous potassium carbonate (4.9 g, 22.0 mmol) were added, the resulting mixture was refluxed at 160° C. for 24 hours. The mixture was cooled to rt and filtered. The filtrate was diluted with water (50 mL), and the mixture was extracted with ethyl acetate (100 mL×3). The combined organic layers were washed with saturated sodium chloride solution (100 mL×3), dried over anhydrous sodium sulfate, and filtered by suction filtration. The filtrate was concentrated to remove the most of the solvent, and then the residue was cooled to 0° C. and stirred for 30 min, the obtained mixture was filtered by suction filtration, the filter cake was dried to give the title compound 38a (1.7 g, yield: 54%) as a brown solid.

MS (ESI, pos. ion) m/z: 279.2[M+H]+;

$^1$H NMR (400 MHz, DMSO-d$_6$) δ (ppm) 7.89 (dd, J=12.1, 9.0 Hz, 3H), 7.63 (d, J=8.6 Hz, 2H), 7.01-6.88 (m, 2H), 4.01 (t, J=6.4 Hz, 2H), 3.85 (s, 3H), 3.11 (t, J=6.3 Hz, 2H).

Step 2 4-(6-hydroxy-1-oxo-3,4-dihydroisoquinolin-2-yl)benzonitrile 38b 4-(6-Methoxy-1-oxo-3,4-dihydroisoquinolin-2-yl)benzonitrile 38a (0.50 g, 1.80 mmol) was dissolved in dichloromethane (10 mL), and then boron tribromide (0.7 mL, 7.0 mmol) was added dropwise at 0° C., the resulting mixture was stirred for 24 hours. The reaction mixture was poured into ice-water (10 mL) to quench the reaction, and the mixture was extracted with ethyl acetate (50 mL×3). The combined organic layers were washed with saturated sodium chloride solution (30 mL×3), dried over anhydrous sodium sulfate, and filtered by suction filtration. The filtrate was concentrated to give the title compound 38b (0.47 g, yield: 99%) as a brown solid.

MS (ESI, pos. ion) m/z: 265.1 [M+H]+.

Step 3 t-butyl N—[(E)-2-[[2-(4-cyanophenyl)-1-oxo-3,4-dihydroisoquinolin-6-yl]oxymethyl]-3-fluoro-allyl]carbamate 38c and t-butyl N—[(Z)-2-[[2-(4-cyanophenyl)-1-oxo-3,4-dihydroisoquinolin-6-yl]oxymethyl]-3-fluoro-allyl]carbamate 38d To a solution of 4-(6-hydroxy-1-oxo-3,4-dihydroisoquinolin-2-yl)benzonitrile 38b (0.47 g, 1.79 mmol) and t-butyl N-[2-(bromomethyl)-3-fluoro-allyl]carbamate 1b (0.48 g, 1.79 mmol) in N,N-dimethylformamide (10 mL) was added cesium carbonate (1.17 g, 3.57 mmol), the mixture was stirred at rt for 24 hours. To the reaction was added water (20 mL). The resulting mixture was extracted with ethyl acetate (50 mL×2). The combined organic phases were washed with saturated sodium chloride solution (30 mL×3), dried over anhydrous sodium sulfate, filtered by suction filtration. The filtrate was concentrated. The residue was purified by silica gel column chromatography (ethyl acetate/petroleum ether (v/v)=1/4) to give the title compound 38c (0.29 g, yield: 35%) and 38d (0.48 g, yield: 59%), both are white solid.

MS (ESI, pos. ion) m/z: 474.3 [M+Na]+.

Step 4 4-[6-[(E)-2-(aminomethyl)-3-fluoro-allyloxy]-1-oxo-3,4-dihydroisoquinolin-2-yl]benzonitrile hydrochloride 38 t-Butyl N—[(E)-2-[[2-(4-cyanophenyl)-1-oxo-3,4-dihydroisoquinolin-6-yl]oxymethyl]-3-fluoro-allyl]carbamate 38c (0.29 g, 0.64 mmol) was dissolved in ethyl acetate (4 mL), and then a hydrogen chloride-methanol solution (6 mL, 4.0 mol/L) was added, the mixture was stirred at rt for 1 hour. The mixture was concentrated to give the title compound 38 (0.25 g, yield: 99%, HPLC: 99.41%) as a white solid.

MS (ESI, pos. ion) m/z: 352.1[M−Cl]+;

$^1$H NMR (400 MHz, DMSO-d$_6$) δ (ppm) 8.43 (s, 3H), 7.89 (dd, J=14.5, 8.7 Hz, 3H), 7.63 (d, J=8.1 Hz, 2H), 7.35 (d, J=81.9 Hz, 1H), 7.02 (s, 2H), 4.76 (s, 2H), 4.01 (s, 2H), 3.59 (s, 2H), 3.11 (s, 2H).

Example 36

4-[6-[(Z)-2-(aminomethyl)-3-fluoro-allyloxy]-1-oxo-3,4-dihydroisoquinolin-2-yl]benzonitrile hydrochloride 39

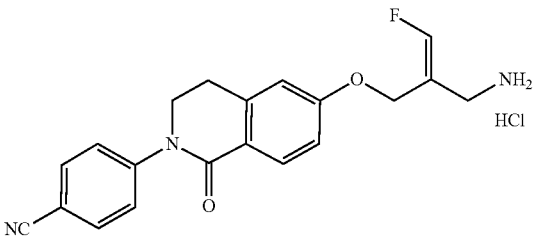

The title compound 39 (0.41 g, yield: 99%, HPLC: 96.82%) as a white solid was obtained according to the method described in step 4 of example 35 by using t-butyl N—[(Z)-2-[[2-(4-cyanophenyl)-1-oxo-3,4-dihydroisoquinolin-6-yl]oxymethyl]-3-fluoro-allyl]carbamate 38d (0.48 g, 1.06 mmol) instead of compound 38c.

MS (ESI, pos. ion) m/z: 352.1[M–Cl]+;

$^1$H NMR (400 MHz, DMSO-d$_6$) δ (ppm) 8.43 (s, 3H), 7.98-7.81 (m, 3H), 7.62 (d, J=6.7 Hz, 2H), 7.26 (d, J=81.9 Hz, 1H), 7.02 (s, 2H), 4.85 (s, 2H), 4.00 (s, 2H), 3.56 (s, 2H), 3.10 (s, 2H).

Example 37 6-[(E)-2-(aminomethyl)-3-fluoro-allyloxy]-2-thiazol-2-yl-3,4-dihydro isoquinolin-1-one hydrochloride 40 and 6-[(Z)-2-(aminomethyl)-3-fluoro-allyloxy]-2-thiazol-2-yl-3,4-dihydroisoindolin-1-one hydrochloride 41

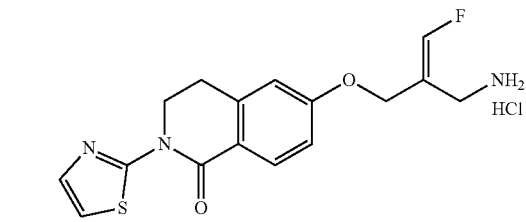

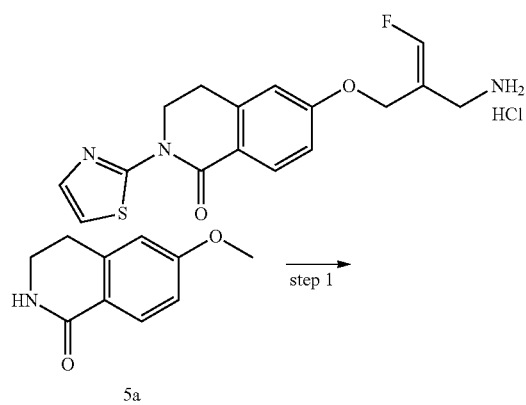

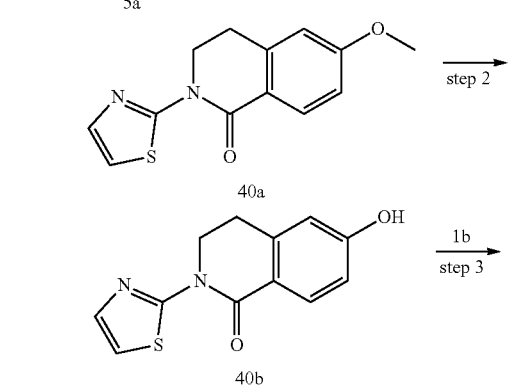

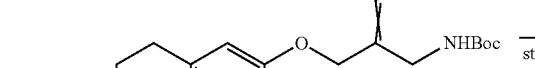

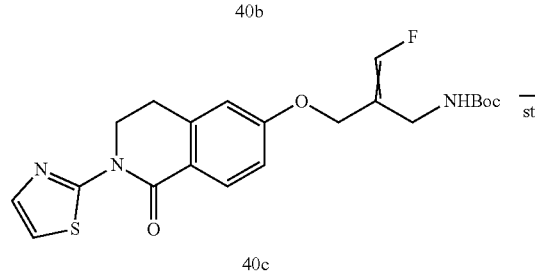

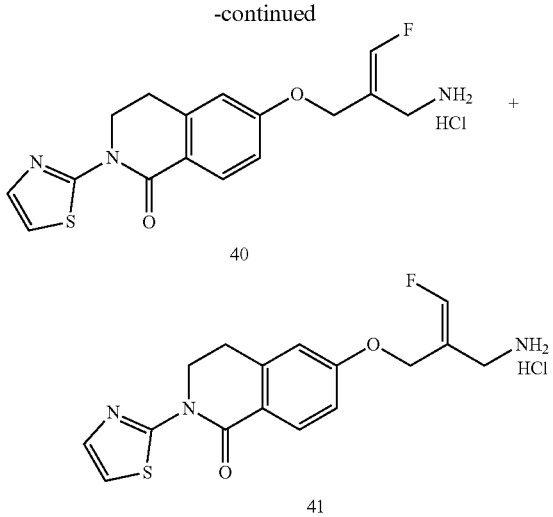

Step 1 6-methoxy-2-thiazol-2-yl-3,4-dihydroisoquinolin-1-one 40a 6-(Methoxy)-3,4-dihydro-2H-isoquinolin-1-one 5a (1.00 g, 5.64 mmol) was dissolved in N,N-dimethylformamide (20 mL), and then 2-bromothiazole (2.00 g, 12.20 mmol), cuprous iodide (0.30 g, 1.60 mmol) and potassium carbonate (1.50 g, 10.90 mmol) were added, the resulting mixture was stirred at 150° C. for 18 hours. The mixture was cooled to rt, the reaction was quenched with water (20 mL). The resulting mixture was extracted with ethyl acetate (50 mL). The organic phase was washed with saturated sodium chloride solution (50 mL×2), dried over anhydrous sodium sulfate, filtered by suction filtration. The filtrate was concentrated. The residue was purified by silica gel column chromatography (petroleum ether/ethyl acetate (v/v)=3/1) to give the title compound 40a (0.69 g, yield: 47%) as a white solid.

Step 2 6-hydroxy-2-thiazol-2-yl-3,4-dihydroisoquinolin-1-one 40b

6-Methoxy-2-thiazol-2-yl-3,4-dihydroisoquinolin-1-one 40a (0.69 g, 2.65 mmol) was dissolved in dichloromethane (15 mL), and then boron tribromide (1.00 mL, 10.30 mmol) was added dropwise at 0° C., the resulting mixture was stirred at rt for 16 hours. The reaction mixture was poured into ice-water (10 mL) to quench the reaction, the mixture was filtered by suction filtration, the filter cake was dried to give the title compound 40b (0.60 g, yield: 92%) as a white solid.

MS (ESI, pos. ion) m/z: 247.2 [M+H]+.

Step 3 t-butyl N-[3-fluoro-2-[(1-oxo-2-thiazol-2-yl-3,4-dihydroisoquinolin-6-yl)oxymethyl]allyl]carbamate 40c To a solution of 6-hydroxy-2-thiazol-2-yl-3,4-dihydroisoquinolin-1-one 40b (0.60 g, 2.40 mmol) in N,N-dimethyl formamide (20 mL) were added t-butyl N-[2-(bromomethyl)-3-fluoro-allyl]carbamate 1b (0.70 g, 2.60 mmol) and cesium carbonate (1.50 g, 4.60 mmol), the resulting mixture was stirred at rt for 2 hours. The reaction was quenched with water (20 mL). The resulting mixture was extracted with ethyl acetate (30 mL). The organic phase was washed with saturated sodium chloride solution (30 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 40c (0.87 g, yield: 82%) as colorless oil.

MS (ESI, pos. ion) m/z: 457.2 [M+Na]$^+$.

Step 4 6-[(E)-2-(aminomethyl)-3-fluoro-allyloxy]-2-thiazol-2-yl-3,4-dihydroisoquinolin-1-one hydrochloride 40 and 6-[(Z)-2-(aminomethyl)-3-fluoro-allyloxy]-2-thiazol-2-yl-3,4-dihydroisoquinolin-1-one hydrochloride 41 t-Butyl N-[3-fluoro-2-[(1-oxo-2-thiazol-2-yl-3,4-dihydroisoquinolin-6-yl)oxymethyl]allyl]carbamate 40c (0.87 g, 2.00 mmol) was dissolved in ethyl acetate (10 mL), and then a hydrogen chloride-ethyl acetate solution (10 mL, 2 mol/L) was added, the mixture was stirred at rt for 2 hours. The reaction mixture was concentrated, the residue was purified, and reacted with a hydrogen chloride-ethyl acetate solution to give the title compound 40 (0.22 g, yield: 30%, HPLC: 98.84%) and 41 (0.20 g, yield: 27%, HPLC: 99.16%), both are white solid.

Compound 40:
MS (ESI, pos. ion) m/z: 334.1 [M−Cl]$^+$;
$^1$H NMR (400 MHz, DMSO-d$_6$) δ (ppm) 8.01 (s, 3H), 7.99 (s, 1H), 7.59 (d, J=3.5 Hz, 1H), 7.35 (s, 1H), 7.12 (d, J=20 Hz, 1H), 7.08 (d, J=8.5 Hz, 2H), 4.82 (s, 2H), 4.51 (t, J=6.5 Hz, 2H), 3.59 (s, 2H), 3.17 (t, J=6.4 Hz, 2H);

Compound 41:
MS (ESI, pos. ion) m/z: 334.2 [M−Cl]$^+$;
$^1$H NMR (400 MHz, DMSO-d$_6$) δ (ppm) 8.11 (s, 3H), 8.00 (d, J=8.5 Hz, 1H), 7.58 (d, J=3.6 Hz, 1H), 7.38 (d, J=82 Hz, 1H), 7.34 (d, J=3.6 Hz, 1H), 7.07 (dd, J=11.5, 2.8 Hz, 2H), 4.71 (d, J=2.8 Hz, 2H), 4.51 (t, J=6.5 Hz, 2H), 3.66 (d, J=4.6 Hz, 2H), 3.17 (t, J=6.5 Hz, 2H).

Example 38 6-[(E)-2-(aminomethyl)-3-fluoro-allyloxy]-2-(isoxazol-3-yl-methyl)-3,4-dihydroisoquinolin-1-one hydrochloride 42 and 6-[(Z)-2-(aminomethyl)-3-fluoro-allyloxy]-2-(isoxazol-3-yl-methyl)-3,4-dihydroisoquinolin-1-one hydrochloride 43

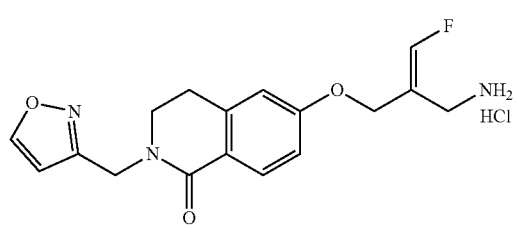

42

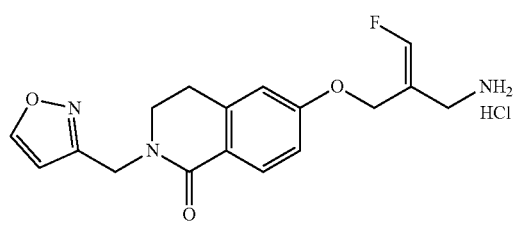

43

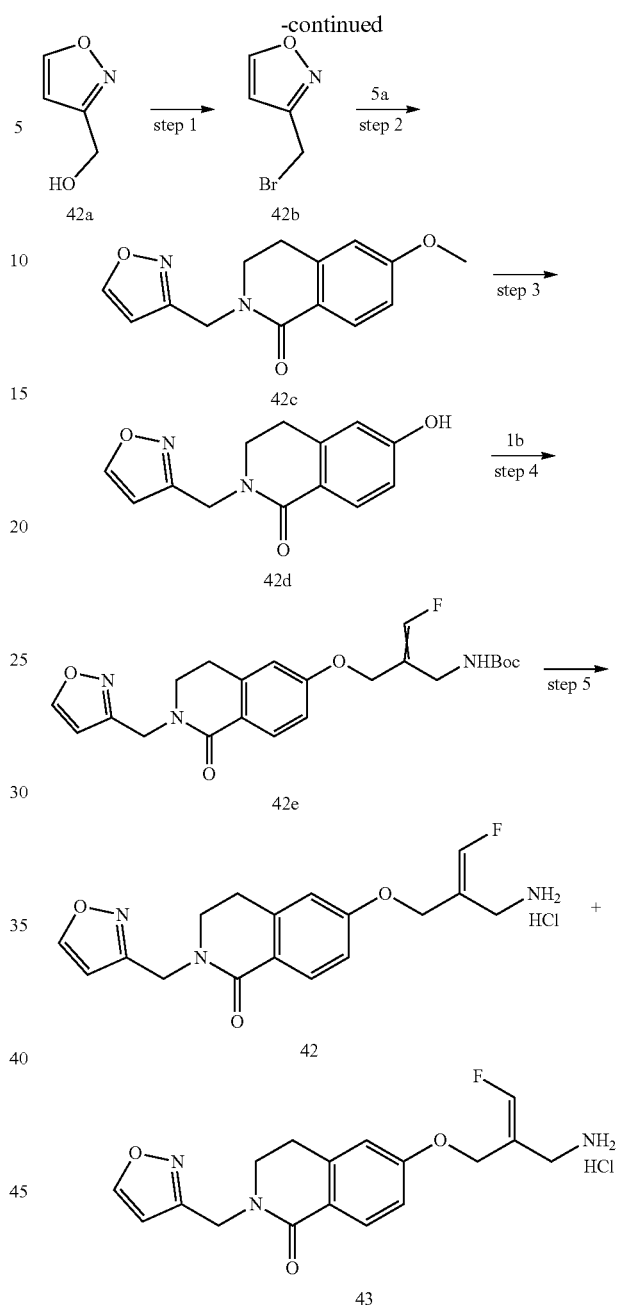

Step 1 3-(bromomethyl)isoxazole 42b

Isoxazole-3-methanol 42a (2.00 g, 20.2 mmol) was dissolved in dichloromethane (50 mL), carbontetrabromide (10.0 g, 29.6 mmol) and triphenylphosphine (8.00 g, 29.9 mmol) were added at 0° C., the mixture was stirred at rt for 2 hours. The mixture was concentrated. The residue was purified by silica gel column chromatography (petroleum ether/ethyl acetate (v/v)=5/1) to give the title compound 42b (0.90 g, yield: 28%) as orange oil.

MS (ESI, pos. ion) m/z: 162.1 [M+H]$^+$.

Step 2 2-(isoxazol-3-yl-methyl)-6-methoxy-3,4-dihydro isoquinolin-1-one 42c

6-Methoxy-3,4-dihydro-2H-isoquinolin-1-one 5a (1.00 g, 5.64 mmol) was dissolved in tetrahydrofuran (20 mL), sodium hydride (0.50 g, 13.00 mmol, 60% wt) was added at 0° C., After stirring for 0.5 hour, 3-(bromomethyl)isoxazole 42b (0.90 g, 5.60 mmol) was added, and the mixture was stirred at 50° C. for 5.5 hours. The mixture was quenched by adding water (10 mL), the organic layer was dried over anhydrous sodium sulfate, filtered by suction filtration. The filtrate was concentrated. The residue was purified by silica gel column chromatography (petroleum ether/ethyl acetate (v/v)=3/1) to give the title compound 42c (0.74 g, yield: 51%) as a white solid.

MS (ESI, pos. ion) m/z: 259.2 [M+H]$^+$.

Step 3 6-hydroxy-2-(isoxazol-3-yl-methyl)-3,4-dihydroisoquinolin-1-one 42d 2-(Isoxazol-3-yl-methyl)-6-methoxy-3,4-dihydroisoquinolin-1-one 42c (0.74 g, 2.90 mmol) was dissolved in dichloromethane (15 mL), and then boron tribromide (1.0 mL, 10.4 mmol) was added dropwise at 0° C., the resulting mixture was stirred at rt for 1 hour. The reaction mixture was poured into ice-water (10 mL) to quench the reaction, the mixture was filtered by suction filtration, the filter cake was dried to give the title compound 42d (0.40 g, yield: 57%) as a white solid.

MS (ESI, neg. ion) m/z: 243.8 [M–H]$^-$;

Step 4 t-butyl N-[3-fluoro-2-[[2-(isoxazol-3-yl-methyl)-1-oxo-3,4-dihydroisoquinolin-6-yl]oxymethyl]allyl]carbamate 42e To a solution of 6-hydroxy-2-(isoxazol-3-yl-methyl)-3,4-dihydroisoquinolin-1-one 42d (0.42 g, 1.72 mmol) in N,N-dimethyl formamide (10 mL) were added t-butyl N-[2-(bromomethyl)-3-fluoro-allyl]carbamate 1b (0.50 g, 1.86 mmol) and cesium carbonate (1.00 g, 3.07 mmol), the resulting mixture was stirred at rt for 1.5 hours. The reaction was quenched with water (10 mL). The resulting mixture was extracted with ethyl acetate (20 mL). The organic phase was washed with saturated sodium chloride solution (20 mL×2), dried over anhydrous sodium sulfate, filtered by suction filtration. The filtrate was concentrated. The residue was purified by silica gel column chromatography (petroleum ether/ethyl acetate (v/v)=2/1) to give the title compound 42e (0.27 g, yield: 36%) as colorless oil.

MS (ESI, pos. ion) m/z: 454.1 [M+Na]$^+$.

Step 5 6-[(E)-2-(aminomethyl)-3-fluoro-allyloxy]-2-(isoxazol-3-yl-methyl)-3,4-dihydroiso quinolin-1-one hydrochloride 42 and 6-[(Z)-2-(aminomethyl)-3-fluoro-allyloxy]-2-(isoxazol-3-yl-methyl)-3,4-dihydroisoquinolin-1-one hydrochloride 43 t-Butyl N-[3-fluoro-2-[[2-(isoxazol-3-yl-methyl)-1-oxo-3,4-dihydroisoquinolin-6-yl]oxymethyl]allyl]carbamate 42e (0.16 g, 0.37 mmol) was dissolved in ethyl acetate (5 mL), and then a hydrogen chloride-ethyl acetate solution (15 mL, 2 mol/L) was added, the mixture was stirred at rt for 16 hours. The reaction mixture was concentrated, the residue was purified, and reacted with hydrogen chloride-ethyl acetate solution to give the title compound 42 (37 mg, yield: 28%, HPLC: 87.08%) and 43 (55 mg, yield: 41%, HPLC: 99.55%), both are white solid.

Compound 42:

MS (ESI, pos. ion) m/z: 332.3 [M–Cl]$^+$;

$^1$H NMR (400 MHz, DMSO-d$_6$) δ (ppm) 8.88 (s, 1H), 8.25 (s, 3H), 7.86 (d, J=8.6 Hz, 1H), 7.34 (d, J=80, 1H), 6.98 (dd, J=8.6, 2.1 Hz, 1H), 6.93 (s, 1H), 6.52 (d, J=1.2 Hz, 1H), 4.77 (s, 2H), 4.70 (s, 2H), 3.67-3.56 (m, 4H), 2.97 (s, 2H).

Compound 43:

MS (ESI, pos. ion) m/z: 332.1 [M–Cl]$^+$;

$^1$H NMR (400 MHz, DMSO-d$_6$) δ (ppm) 8.88 (s, 1H), 8.32 (s, 3H), 7.86 (d, J=8.6 Hz, 1H), 7.24 (d, J=80 Hz, 1H), 6.98 (d, J=8.6 Hz, 1H), 6.94 (s, 1H), 6.52 (s, 1H), 4.80 (s, 2H), 4.77 (s, 2H), 3.55 (s, 4H), 2.97 (t, J=6.3 Hz, 2H).

Example 39 6-[(E)-2-(aminomethyl)-3-fluoro-allyloxy]-8-fluoro-3,4-dihydro-2H-isoquinolin-1-one hydrochloride 44

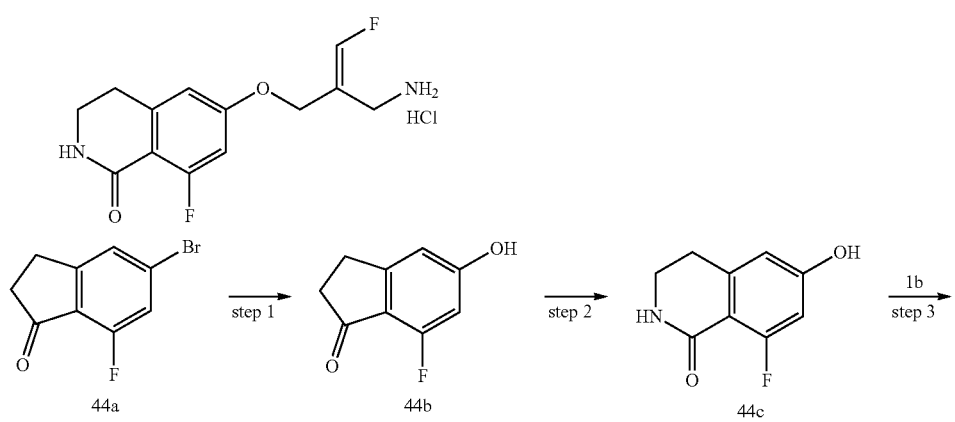

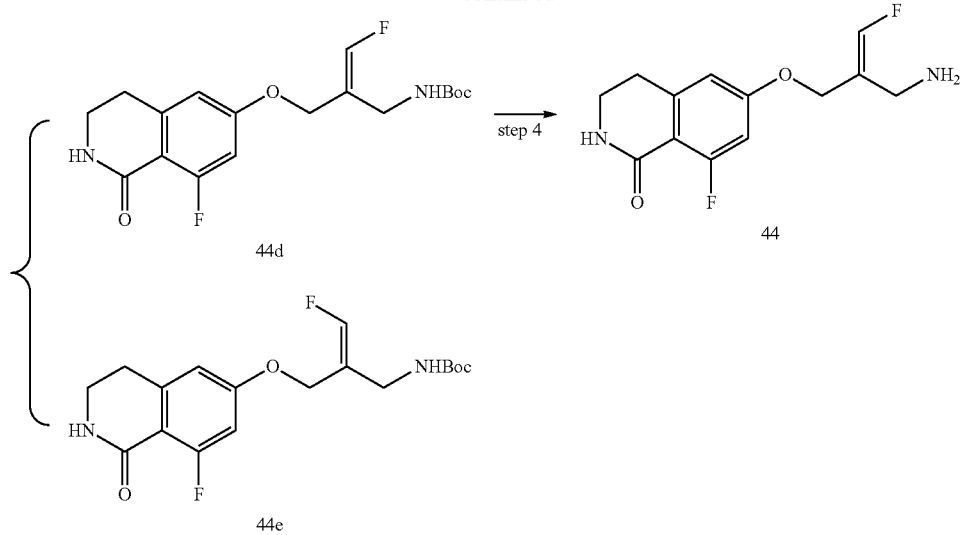

Step 1 7-fluoro-5-hydroxy-indan-1-one 44b

5-Bromo-7-fluoro-indan-1-one 44a (2.0 g, 8.7 mmol) was dissolved in a mixture of 1,4-dioxane (5 mL) and water (5 mL), then tris(dibenzylideneacetone)dipalladium (0.32 g, 0.34 mmol), 2-di-t-butylphosphino-2',4',6'-triisopropylbiphenyl (0.30 g, 0.69 mmol) and potassium hydroxide (1.0 g, 18 mmol) were added. The atmosphere in the flask was flushed with nitrogen, the mixture was stirred at 80° C. for 18 hours. The mixture was cooled to rt, the mixture was adjusted with concentrated hydrochloric acid to pH 1 and filtered by suction filtration, the filtrate was extracted with ethyl acetate (30 mL). The organic phase was washed with water (10 mL) and saturated sodium chloride solution (10 mL), dried over anhydrous sodium sulfate, filtered by suction filtration. The filtrate was concentrated. The residue was purified by silica gel column chromatography (petroleum ether/ethyl acetate (v/v)=2/1) to give the title compound 44b (1.0 g, yield: 69%) as a yellow solid.

MS (ESI, neg. ion) m/z: 165.1 [M–H]$^-$;

$^1$H NMR (400 MHz, CD$_3$OD) δ (ppm) 6.70 (s, 1H), 6.45 (d, J=11.3 Hz, 1H), 3.09 (t, 2H), 2.64 (t, 2H).

Step 2 8-fluoro-6-hydroxy-3,4-dihydro-2H-isoquinolin-1-one 44c

7-Fluoro-5-hydroxy-indan-1-one 44b (0.60 g, 3.6 mmol) was dissolved in dichloromethane (20 mL), and methanesulfonic acid (5 mL, 75.5 mmol) was added, then sodium azide (0.59 g, 9.0 mmol) was added at 0° C., the mixture was stirred at rt for 2 hours. The mixture was poured into ice-water (20 mL) to quench the reaction, the resulting mixture was adjusted with sodium bicarbonate to pH=7 and concentrated, the residue was triturated with ethanol (30 mL) and ethyl acetate (30 mL) then filtered by suction filtration. The filtrate was concentrated. The residue was purified by silica gel column chromatography (dichloromethane/methanol (v/v)=9/1) to give the title compound 44c (0.54 g, yield: 83%) as a yellow solid.

MS (ESI, pos. ion) m/z: 182.2 [M+H]$^+$;

$^1$H NMR (400 MHz, CD$_3$OD) δ (ppm) 6.55 (s, 1H), 6.47 (dd, J=13.2, 2.2 Hz, 1H), 3.42 (t, J=6.5 Hz, 2H), 2.90 (t, J=6.5 Hz, 2H).

Step 3 tert-butyl N—[(E)-3-fluoro-2-[(8-fluoro-1-oxo-3,4-dihydro-2H-isoquinolin-6-yl)oxymethyl]allyl]formate 44d and tert-butyl N—[(Z)-3-fluoro-2-[(8-fluoro-1-oxo-3,4-dihydro-2H-isoquinolin-6-yl)oxymethyl]allyl]formate 44e To a solution of 8-fluoro-6-hydroxy-3,4-dihydro-2H-isoquinolin-1-one 44c (0.54 g, 3.0 mmol) and t-butyl N-[2-(bromomethyl)-3-fluoro-allyl]carbamate 1b (1.0 g, 3.7 mmol) in N,N-dimethylformamide (10 mL) was added potassium carbonate (0.87 g, 6.2 mmol), the mixture was stirred at rt for 16 hours. The reaction was quenched with water (20 mL). The resulting mixture was extracted with ethyl acetate (20 mL). The organic phase was washed with water (10 mL) and saturated sodium chloride solution (10 mL), dried over anhydrous sodium sulfate, filtered by suction filtration. The filtrate was concentrated. The residue was purified by preparative chromatography to give the title compound 44d (0.16 g, yield: 15%) and 44e (0.24 g, yield: 22%), both are white solid.

MS(ESI, pos. ion) m/z: 369.1 [M+H]$^+$;

Compound 44d:

$^1$H NMR (400 MHz, CDCl$_3$) δ (ppm) 6.75 (d, J=81.7 Hz, 1H), 6.67-6.55 (m, 2H), 6.12 (s, 1H), 4.76 (s, 1H), 4.45 (s, 2H), 3.99 (d, J=4.9 Hz, 2H), 3.48 (td, J=6.4, 3.1 Hz, 2H), 2.92 (t, J=6.4 Hz, 2H), 1.41 (s, 9H);

Compound 44e:

$^1$H NMR (400 MHz, CDCl$_3$) δ (ppm) 6.74 (d, J=82.6 Hz, 1H), 6.62-6.53 (m, 2H), 6.07 (s, 1H), 4.74 (s, 1H), 4.70 (d, J=1.9 Hz, 2H), 3.76 (s, 2H), 3.48 (td, J=6.4, 3.1 Hz, 2H), 2.93 (t, J=6.4 Hz, 2H), 1.41 (s, 9H).

Step 4 6-[(E)-2-(aminomethyl)-3-fluoro-allyloxy]-8-fluoro-3,4-dihydro-2H-isoquinolin-1-one hydrochloride 44 tert-Butyl N—[(E)-3-fluoro-2-[(8-fluoro-1-oxo-3,4-dihydro-2H-isoquinolin-6-yl)oxymethyl]allyl]formate 44d (0.16 g, 0.43 mmol) was dissolved in a hydrogen chloride-ethyl acetate solution (10 mL, 2 mol/L), the mixture was stirred at rt for 3 hours, and then the mixture was concen trated to give the title compound 44 (0.13 g, yield: 99%, HPLC: 96.56%) as a white solid.

MS(ESI, pos. ion) m/z: 269.1 [M−Cl]⁻;

$^{1}$H NMR (400 MHz, CD$_3$OD) δ (ppm) 7.26 (d, J=80.9 Hz, 1H), 6.81 (s, 1H), 6.77 (dd, J=12.9, 2.1 Hz, 1H), 4.70 (d, J=3.2 Hz, 2H), 3.84 (s, 2H), 3.45 (t, J=6.5 Hz, 2H), 2.97 (t, J=6.4 Hz, 2H);

$^{19}$F NMR (376 MHz, CD$_3$OD) δ (ppm) −110.63, −122.06.

Example 40 6-[(Z)-2-(aminomethyl)-3-fluoro-allyloxy]-8-fluoro-3,4-dihydro-2H-isoquinolin-1-one hydrochloride 45

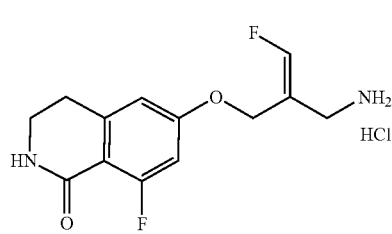

The title compound 45 (0.20 g, yield: 99%, HPLC: 99.03%) as a white solid was obtained according to the method described in step 4 of example 39 by using tert-butyl N—[(Z)-3-fluoro-2-[(8-fluoro-1-oxo-3,4-dihydro-2H-isoquinolin-6-yl)oxymethyl]allyl]formate 44e (0.48 g, 1.06 mmol) instead of compound 44d.

MS(ESI, pos. ion) m/z: 269.1 [M−Cl]⁻;

$^{1}$H NMR (400 MHz, CD$_3$OD) δ (ppm) 7.16 (d, J=80.7 Hz, 1H), 6.82 (s, 1H), 6.78 (dd, J=12.9, 1.9 Hz, 1H), 4.84 (s, 2H), 3.72 (s, 2H), 3.45 (t, J=6.5 Hz, 2H), 2.97 (t, J=6.4 Hz, 2H);

$^{19}$F NMR (376 MHz, CD$_3$OD) δ (ppm) −110.64, −120.64.

Example 41 6-[(E)-2-(aminomethyl)-3-fluoro-allyloxy]-2-o-methylphenyl-3,4-dihydroiso quinolin-1-one hydrochloride 46

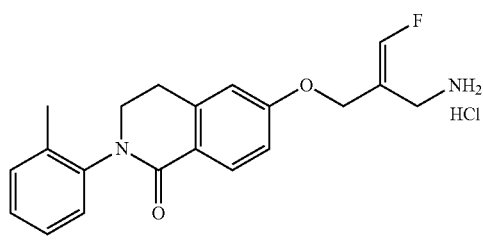

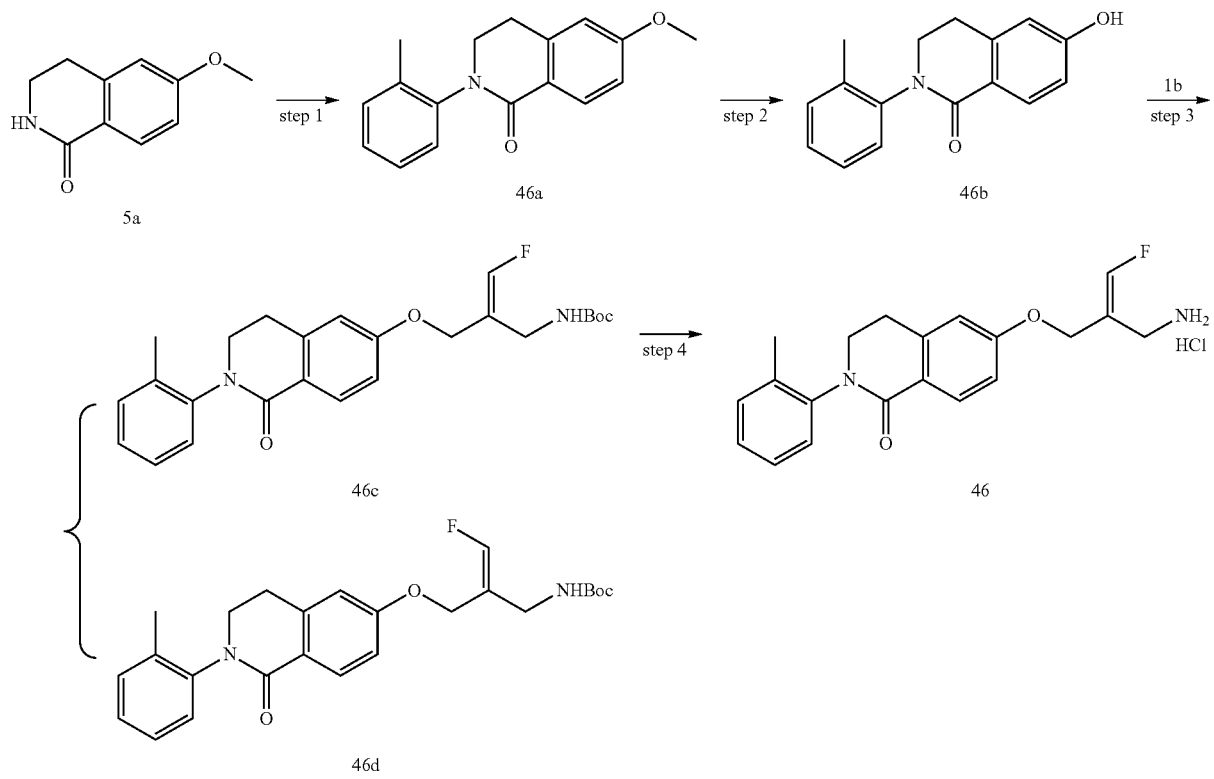

Step 1 6-methoxy-2-o-methylphenyl-3,4-dihydroisoquinolin-1-one 46a 6-methoxy-3,4-dihydro-2H-isoquinolin-1-one 5a (2.0 g, 11 mmol), 1-iodo-2-methyl-benzene (3.0 g, 14 mmol), cuprous iodide (0.30 g, 1.6 mmol), potassiumphosphate (4.9 g, 23 mmol), 1,2-diaminocyclohexane (0.70 g, 6.1 mmol) were dissolved in N,N-dimethylformamide (20 mL), the flask was fully replaced by nitrogen, the mixture was stirred at 160° C. for 48 hours. The mixture was cooled to rt, and diluted with ethyl acetate (20 mL) and filtered. The filtrate was washed with water (10 mL) and saturated sodium chloride solution (10 mL), dried over anhydrous sodium sulfate, filtered by suction filtration. The filtrate was concentrated. The residue was purified by silica gel column chromatography (petroleum ether/ethyl acetate (v/v)=4/1) to give the title compound 46a (2.1 g, yield: 69%) as a brown solid.

MS (ESI, pos. ion) m/z: 268.1 [M+H]$^+$;
$^1$H NMR (400 MHz, CDCl$_3$) δ (ppm) 8.00 (d, J=8.6 Hz, 1H), 7.20-7.08 (m, 4H), 6.78 (dd, J=8.6, 2.2 Hz, 1H), 6.64 (d, J=1.6 Hz, 1H), 3.89-3.79 (m, 1H), 3.76 (s, 3H), 3.65-3.56 (m, 1H), 3.14-3.05 (m, 1H), 2.96-2.90 (m, 1H), 2.19 (s, 3H).

Step 2 6-hydroxy-2-o-methylphenyl-3,4-dihydroisoquinolin-1-one 46b

6-Methoxy-2-o-methylphenyl-3,4-dihydroisoquinolin-1-one 46a (1.0 g, 3.7 mmol) was dissolved in dichloromethane (20 mL), the flask was fully replaced by nitrogen, and then boron tribromide (0.70 mL, 7.3 mmol) was added at 0° C., the resulting mixture was stirred at rt for 16 hours. The reaction mixture was quenched with water (15 mL) at 0° C., and the organic layer was washed with saturated sodium bicarbonate solution (10 mL) and saturated sodium chloride solution (10 mL), dried over anhydrous sodium sulfate, and filtered by suction filtration. The filtrate was concentrated to give the title compound 46b (0.95 g, yield: 99%) as a yellow solid.

MS (ESI, pos. ion) m/z: 254.4 [M+H]$^+$.

Step 3 tert-butyl N—[(E)-3-fluoro-2-[(2-o-methylphenyl-1-oxo-3,4-dihydroisoquinolin-6-yl) oxymethyl]allyl]formate 46c and tert-butyl N—[(Z)-3-fluoro-2-[(2-o-methylphenyl-1-oxo-3,4-dihydroisoquinolin-6-yl)oxymethyl]allyl]formate 46d To a solution of 6-hydroxy-2-o-methylphenyl-3,4-dihydroisoquinolin-1-one 46b (1.78 g, 7.0 mmol) and t-butyl N-[2-(bromomethyl)-3-fluoro-allyl]carbamate 1b (2.1 g, 7.8 mmol) in N,N-dimethylformamide (10 mL) was added potassium carbonate (2.0 g, 14.5 mmol), the mixture was stirred at rt for 6 hours. The reaction was quenched with water (20 mL). The resulting mixture was extracted with ethyl acetate (20 mL). The organic phase was washed with saturated sodium chloride solution (10 mL), dried over anhydrous sodium sulfate, filtered by suction filtration. The filtrate was concentrated. The residue was purified by preparative chromatography to give the title compound 46c (0.61 g, yield: 20%) and 46d (1.12 g, yield: 36%), both are white solid.

MS (ESI, pos. ion) m/z: 441.2 [M+H]$^+$

Compound 46c: $^1$H NMR (400 MHz, CDCl$_3$) δ (ppm) 8.12 (d, J=8.6 Hz, 1H), 7.37-7.19 (m, 5H), 6.91 (overlap, 1H), 6.79 (d, J=8.6 Hz, 1H), 6.78 (s, 1H), 4.81 (s, 1H), 4.53 (d, J=2.9 Hz, 2H), 4.03 (d, J=4.7 Hz, 2H), 4.01-3.92 (m, 1H), 3.78-3.68 (m, 1H), 3.22 (ddd, J=15.4, 10.1, 5.1 Hz, 1H), 3.05 (dt, J=15.8, 5.2 Hz, 1H), 2.30 (s, 3H), 1.45 (s, 9H);

Compound 46d: $^1$H NMR (400 MHz, CDCl$_3$) δ (ppm) 8.12 (d, J=8.6 Hz, 1H), 7.33-7.22 (m, 4H), 6.93 (dd, J=8.6, 2.3 Hz, 1H), 6.80 (s, 1H), 6.76 (d, J=82.8 Hz, 1H), 4.78 (overlap, 3H), 3.97 (td, J=12.1, 4.6 Hz, 1H), 3.80 (s, 2H), 3.78-3.70 (m, 1H), 3.22 (ddd, J=15.4, 10.1, 5.1 Hz, 1H), 3.05 (dt, J=10.3, 4.8 Hz, 1H), 2.30 (s, 3H), 1.45 (s, 9H).

Step 4 6-[(E)-2-(aminomethyl)-3-fluoro-allyloxy]-2-o-methylphenyl-3,4-dihydroisoquinolin-1-one hydrochloride 46 tert-Butyl N—[(E)-3-fluoro-2-[(2-o-methylphenyl-1-oxo-3,4-dihydroisoquinolin-6-yl)oxymethyl]allyl]formate 46c (0.61 g, 1.4 mmol) was dissolved in a hydrogen chloride-ethyl acetate solution (20 mL, 2 mol/L), the mixture was stirred at rt for 1 hour, and then the mixture was concentrated to give the title compound 46 (0.52 g, yield: 99%, HPLC: 97.95%) as a white solid.

MS (ESI, pos. ion) m/z: 341.2 [M−Cl]$^+$;
$^1$H NMR (400 MHz, CD$_3$OD) δ (ppm) 7.98 (d, J=8.6 Hz, 1H), 7.40-7.14 (m, 5H), 7.04 (dd, J=8.7, 2.1 Hz, 1H), 7.01 (s, 1H), 4.73 (d, J=3.3 Hz, 2H), 4.03-3.91 (m, 1H), 3.86 (s, 2H), 3.76 (dd, J=12.4, 6.0 Hz, 1H), 3.30-3.11 (m, 2H), 2.28 (s, 3H);
$^{19}$F NMR (376 MHz, CD$_3$OD) δ (ppm) −122.82.

Example 42 6-[(Z)-2-(aminomethyl)-3-fluoro-allyloxy]-2-o-methylphenyl-3,4-dihydroiso quinolin-1-one hydrochloride 47

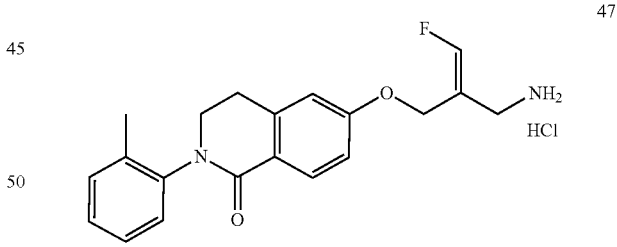

The title compound 47 (0.95 g, yield: 99%, HPLC: 96.05%) as a white solid was obtained according to the method described in step 4 of example 41 by using tert-butyl N—[(Z)-3-fluoro-2-[(2-o-methylphenyl-1-oxo-3,4-dihydroisoquinolin-6-yl)oxymethyl]allyl]formate 46d (1.12 g, 2.54 mmol) instead of compound 46c.

MS (ESI, pos. ion) m/z: 341.2 [M−Cl]$^+$;
$^1$H NMR (400 MHz, CD$_3$OD) δ (ppm) 7.99 (d, J=8.6 Hz, 1H), 7.42-7.23 (m, 4H), 7.10-6.97 (m, 2H), 4.93 (d, J=2.4 Hz, 2H), 3.98 (ddd, J=12.7, 9.6, 5.0 Hz, 1H), 3.78 (dd, J=12.3, 6.4 Hz, 1H), 3.73 (s, 2H), 2.30-2.13 (m, 2H), 2.28 (s, 3H);
$^{19}$F NMR (376 MHz, CD$_3$OD) δ (ppm) −121.17.

Example 43 6-[(E)-2-(aminomethyl)-3-fluoro-allyloxy]-2-[2,6-dimethylphenyl]-3,4-dihydro-isoquinolin-1-one hydrochloride 48
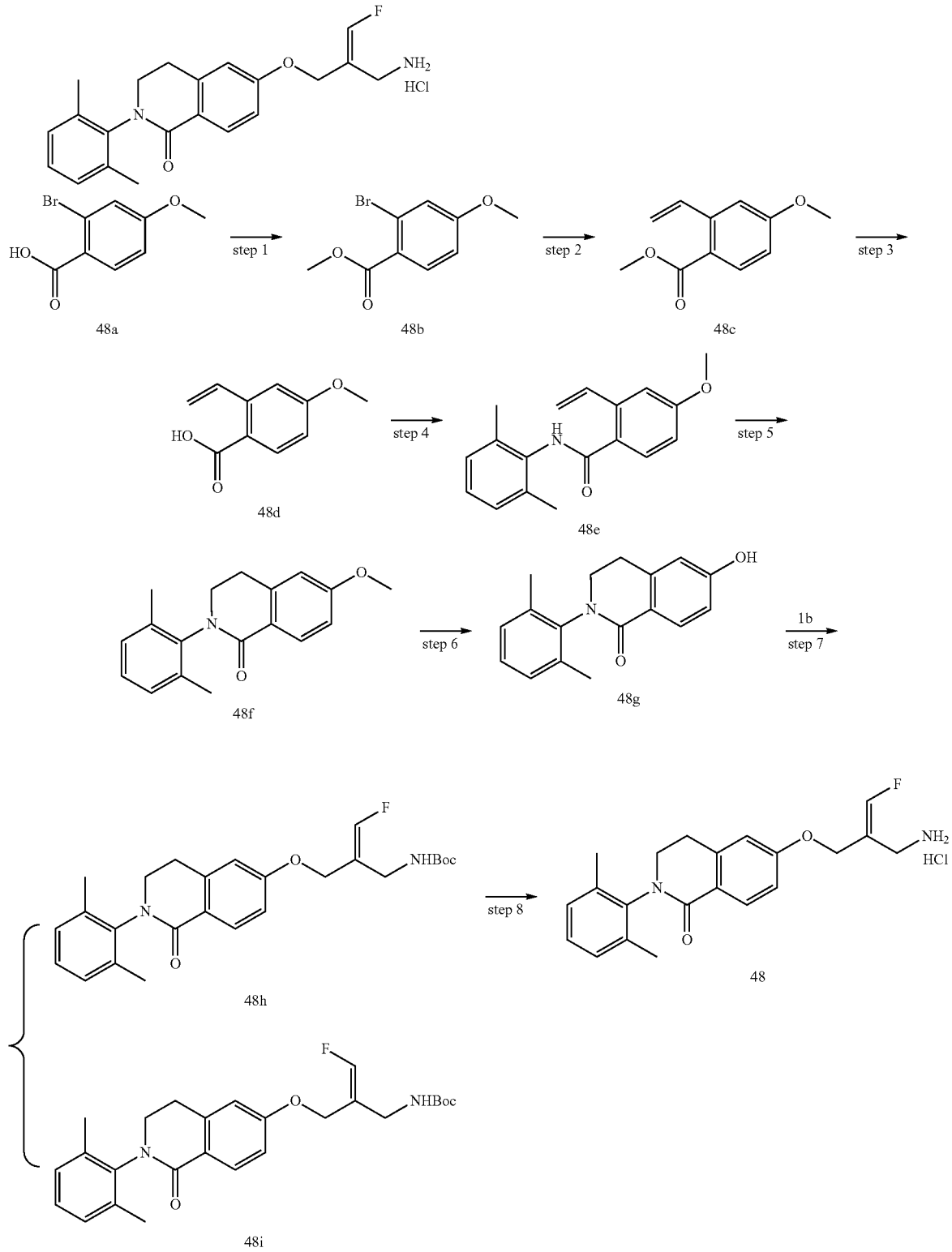

Step 1 methyl 2-bromo-4-methoxy-benzoate 48b

2-Bromo-4-methoxy-benzoic acid 48a (10.0 g, 43.3 mmol) was dissolved in methanol (80 mL), and concentrated sulfuric acid (2 mL) was added, the mixture was refluxed at 75° C. for 22 hours. The mixture was concentrated, and the residue was dissolved in ethyl acetate (30 mL), and the resulting mixture was washed with water (10 mL) and saturated sodium carbonate solution (10 mL), dried over anhydrous sodium sulfate, and filtered by suction filtration. The filtrate was concentrated to give the title compound 48b (10.0 g, yield: 94%) as yellow liquid.

MS (ESI, pos. ion) m/z: 246.1 $[M+H]^+$.

Step 2 methyl 4-methoxy-2-vinyl-benzoate 48c

Methyl 2-bromo-4-methoxy-benzoate 48b (2.0 g, 8.2 mmol), potassium vinyltrifluoroborate (1.2 g, 8.8 mmol), palladium chloride (59 mg, 0.33 mmol) and triphenylphosphine (0.26 g, 0.98 mmol) were dissolved in tetrahydrofuran (20 mL) and water (2 mL), the flask was fully replaced by nitrogen, the mixture was stirred at 75° C. for 17 hours. The mixture was cooled to rt, to the mixture was added water (20 mL). The resulting mixture was extracted with dichloromethane (10 mL×3). The combined organic phases were washed with saturated sodium chloride solution (20 mL), dried over anhydrous sodium sulfate, filtered by suction filtration. The filtrate was concentrated. The residue was purified by silica gel column chromatography (petroleum ether/ethyl acetate (v/v)=8/1) to give the title compound 48c (1.12 g, yield: 71%) as yellow liquid.

MS(ESI, pos. ion) m/z: 193.1 $[M+H]^+$;
$^1$H NMR (400 MHz, CDCl$_3$) δ (ppm) 7.91 (d, J=8.7 Hz, 1H), 7.55 (dd, J=17.4, 10.9 Hz, 1H), 7.04 (d, J=2.5 Hz, 1H), 6.82 (dd, J=8.7, 2.5 Hz, 1H), 5.61 (d, J=17.4 Hz, 1H), 5.34 (d, J=10.9 Hz, 1H), 3.86 (s, 6H).

Step 3 4-methoxy-2-vinyl-benzoic acid 48d

Potassium hydroxide (0.89 g, 16 mmol) was added to a solution of methyl 4-methoxy-2-vinyl-benzoate 48c (1.12 g, 5.83 mmol) in a mixed solution of tetrahydrofuran (20 mL), methanol (5 mL) and water (5 mL), the mixture was stirred at 70° C. for 2 hours. The reaction mixture was concentrated, the residue was diluted with water (20 mL), and the resulting mixture was adjusted to pH 1 and extracted with ethyl acetate (20 mL×3). The combined organic layers were washed with saturated sodium chloride solution (20 mL), dried over anhydrous sodium sulfate, and filtered by suction filtration. The filtrate was concentrated to give the title compound 48d (0.95 g, yield: 92%) as an off-white solid.

MS (ESI, neg. ion) m/z: 177.1 $[M-H]^-$.

Step 4 2-(2,6-dimethylphenyl)-4-methoxy-2-vinyl-benzamide 48e

Oxalyl chloride (0.20 mL, 2.3 mmol) was added to a solution of 4-methoxy-2-vinyl-benzoic acid 48d (0.20 g, 1.1 mmol) in dichloromethane (10 mL), and then N,N-dimethylformamide (0.05 mL) was added dropwise slowly, the mixture was stirred at 50° C. and refluxed for 2 hours. The reaction was concentrated to obtain a yellow solid, which was dissolved in dichloromethane (5 mL), a solution of 2,6-dimethylaniline (0.15 g, 1.2 mmol) and triethylamine (0.30 mL, 2.1 mmol) in dichloromethane (5 mL) was added at 0° C., then the mixture was stirred at rt for 1.5 hours. The mixture was concentrated. The residue was purified by silica gel column chromatography (petroleum ether/ethyl acetate (v/v)=2/1) to give the title compound 48e (0.27 g, yield: 85%) as an off-white solid.

MS (ESI, pos. ion) m/z: 282.2 $[M+H]^+$;
$^1$H NMR (400 MHz, CDCl$_3$) δ (ppm) 7.66 (d, J=8.5 Hz, 1H), 7.34-7.25 (dd, J=17.6, 11.2, Hz, 1H), 7.18-7.09 (m, 4H), 7.03 (s, 1H), 6.90 (dd, J=8.5, 2.4 Hz, 1H), 5.75 (d, J=17.4 Hz, 1H), 5.40 (d, J=11.0 Hz, 1H), 3.88 (s, 3H), 2.32 (s, 6H).

Step 5 2-(2,6-dimethylphenyl)-6-methoxy-3,4-dihydroisoquinolin-1-one 48f

Potassium tert-butoxide (24 mg, 0.21 mmol) was added to a solution of 2-(2,6-dimethylphenyl)-4-methoxy-2-vinyl-benzamide 48e (0.20 g, 0.71 mmol) in N,N-dimethylformamide (7 mL), the flask was fully replaced by nitrogen, the mixture was stirred at 120° C. for 2 hours. The mixture was cooled to rt, to the mixture was added water (10 mL). The resulting mixture was extracted with ethyl acetate (10 mL×3). The combined organic phases were washed with saturated sodium chloride solution (10 mL), dried over anhydrous sodium sulfate, filtered by suction filtration. The filtrate was concentrated. The residue was purified by silica gel column chromatography (petroleum ether/ethyl acetate (v/v)=2/1) to give the title compound 48f (0.19 g, yield: 99%) as a yellow solid.

$^1$H NMR (400 MHz, CDCl$_3$) δ (ppm) 8.09 (d, J=8.6 Hz, 1H), 7.15-7.08 (m, 3H), 6.87 (dd, J=8.6, 2.4 Hz, 1H), 6.74 (d, J=2.1 Hz, 1H), 3.84 (s, 3H), 3.70 (t, J=6.6 Hz, 2H), 3.13 (t, J=6.5 Hz, 2H), 2.24 (s, 6H).

Step 6 2-(2,6-dimethylphenyl)-6-hydroxy-3,4-dihydroisoquinolin-1-one 48 g

At 0° C., boron tribromide (0.10 mL, 1.0 mmol) was added to a solution of 2-(2,6-dimethylphenyl)-6-methoxy-3,4-dihydroisoquinolin-1-one 48f (0.12 g, 0.43 mmol) in dichloromethane (5 mL), the mixture was stirred at rt for 2 hours. The reaction mixture was poured into ice-water (10 mL), and the mixture was extracted with ethyl acetate (30 mL), the organic layer was washed with saturated sodium bicarbonate solution (10 mL) and saturated sodium chloride solution (10 mL), dried over anhydrous sodium sulfate, and filtered by suction filtration. The filtrate was concentrated to give the title compound 48g (0.11 g, yield: 97%) as a light yellow solid.

MS(ESI, pos. ion) m/z: 268.1 $[M+H]^+$.

Step 7 tert-butyl N—[(E)-2-[[2-(2,6-dimethylphenyl)-1-oxo-3,4-dihydroisoquinolin-6-yl]oxymethyl]-3-fluoro-allyl]formate 48h and tert-butyl N—[(Z)-2-[[2-(2,6-dimethylphenyl)-1-oxo-3,4-dihydroisoquinolin-6-yl]oxymethyl]-3-fluoro-allyl]formate 48i To a solution of 2-(2,6-dimethylphenyl)-6-hydroxy-3,4-dihydroisoquinolin-1-one 48 g (0.11 g, 0.41 mmol) and t-butyl N-[2-(bromomethyl)-3-fluoro-allyl]carbamate 1b (0.12 g, 0.45 mmol) in N,N-dimethylformamide (4 mL) was added potassium carbonate (0.12 g, 0.86 mmol), the mixture was stirred at rt for 16 hours. Water (10 mL) was added to the reaction to quench the reaction. The resulting mixture was extracted with ethyl acetate (10 mL×3). The combined organic phases were washed with saturated sodium chloride solution (10 mL), dried over anhydrous sodium sulfate, filtered by suction filtration. The filtrate was concentrated. The residue was purified by silica gel column chromatography (petroleum ether/ethyl acetate (v/v)=2/1) to give the title compound 48h (55 mg, yield: 29%) and 48i (95 mg, yield: 50%), both are white solid.

MS (ESI, pos. ion) m/z: 455.2 [M+H]$^+$;

Compound 48h: $^1$H NMR (400 MHz, CDCl$_3$) δ (ppm) 8.10 (d, J=8.6 Hz, 1H), 7.19-7.07 (m, 3H), 6.92-6.83 (overlap, 1H), 6.78 (J=80.8 Hz, 1H), 6.77 (s, 1H), 4.78 (br, 1H), 4.51 (d, J=3.0 Hz, 2H), 4.01 (d, J=4.7 Hz, 2H), 3.73 (t, J=6.5 Hz, 2H), 3.13 (t, J=6.5 Hz, 2H), 2.25 (s, 6H), 1.42 (s, 9H);

$^{19}$F NMR (376 MHz, CDCl$_3$) δ (ppm) −128.44;

Compound 48i: $^1$H NMR (400 MHz, CDCl$_3$) δ (ppm) 8.10 (d, J=8.6 Hz, 1H), 7.20-7.08 (m, 3H), 6.91 (dd, J=8.6, 2.3 Hz, 1H), 6.78 (d, J=1.7 Hz, 1H), 6.75 (s, J=82.8 Hz, 1H), 4.76 (d, J=1.8 Hz, 3H), 3.78 (s, 2H), 3.73 (t, J=6.5 Hz, 2H), 3.14 (t, J=6.5 Hz, 2H), 2.25 (s, 6H), 1.42 (s, 9H);

$^{19}$F NMR (376 MHz, CDCl$_3$) δ (ppm) −127.64.

Step 8 6-[(E)-2-(aminomethyl)-3-fluoro-allyloxy]-2-(2,6-dimethylphenyl)-3,4-dihydroiso quinolin-1-one hydrochloride 48 tert-Butyl N—[(E)-2-[[2-(2,6-dimethylphenyl)-1-oxo-3,4-dihydroisoquinolin-6-yl]oxymethyl]-3-fluoro-allyl]formate 48h (0.18 g, 0.40 mmol) was dissolved in a hydrogen chloride-ethyl acetate solution (5 mL, 2 mol/L), the mixture was stirred at rt for 2 hours. The mixture was concentrated to give the title compound 48 (0.15 g, yield: 99%, HPLC: 96.62%) as a yellow solid.

MS (ESI, pos. ion) m/z: 355.1 [M−Cl]$^+$;

$^1$H NMR (400 MHz, CD$_3$OD) δ (ppm) 7.98 (d, J=8.4 Hz, 1H), 7.27 (d, J=76.4 Hz, 1H), 7.22 (overlap, 3H), 7.04 (d, J=8.4 Hz, 2H), 4.74 (d, J=2.9 Hz, 2H), 3.86 (s, 2H), 3.78 (t, J=6.5 Hz, 2H), 3.23 (t, J=6.4 Hz, 2H), 2.25 (s, 6H);

$^{19}$F NMR (376 MHz, CD$_3$OD) δ (ppm) −122.80.

Example 44 6-[(Z)-2-(aminomethyl)-3-fluoro-allyloxy]-2-[2,6-dimethylphenyl]-3,4-dihydro-isoquinolin-1-one hydrochloride 49

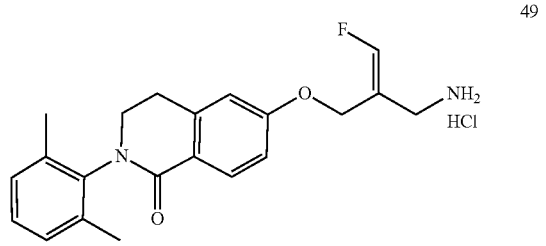 [SMILES: Cc1cccc(C)c1N1CCc2cc(OC/C(=C\F)CN)ccc2C1=O ; Cl]

49

The title compound 49 (0.27 g, yield: 99%, HPLC: 98.75%) as a light yellow solid was obtained according to the method described in step 8 of example 43 by using tert-butyl N—[(Z)-2-[[2-(2,6-dimethylphenyl)-1-oxo-3,4-dihydro isoquinolin-6-yl]oxymethyl]-3-fluoro-allyl]formate 48i (0.31 g, 0.68 mmol) instead of compound 48g.

MS (ESI, pos. ion) m/z: 355.1 [M−Cl]$^+$;

$^1$H NMR (400 MHz, CD$_3$OD) δ (ppm) 7.99 (d, J=8.5 Hz, 1H), 7.26 (s, 1H), 7.19 (s, 3H), 7.10-7.00 (overlap, 2H), 4.93 (d, J=1.9 Hz, 2H), 3.79 (t, J=6.6 Hz, 2H), 3.73 (s, 2H), 3.24 (t, J=6.5 Hz, 2H), 2.26 (s, 6H);

$^{19}$F NMR (376 MHz, CD$_3$OD) δ (ppm) −121.16.

Example 45 8-[(E)-2-(aminomethyl)-3-fluoro-allyloxy]-6-fluoro-3,4-dihydro-2H-isoquinolin-1-one hydrochloride 50

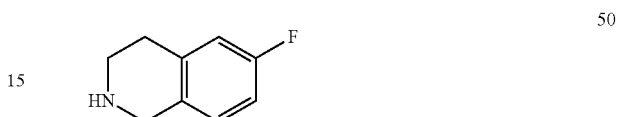

50

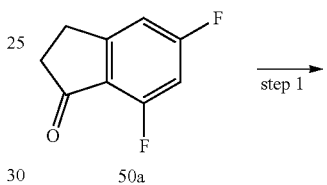

50a

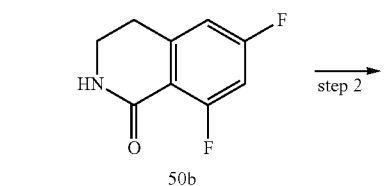

50b

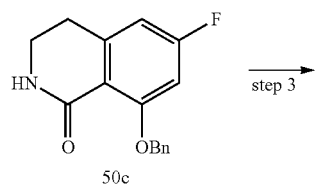

50c

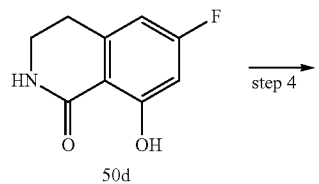

50d

-continued

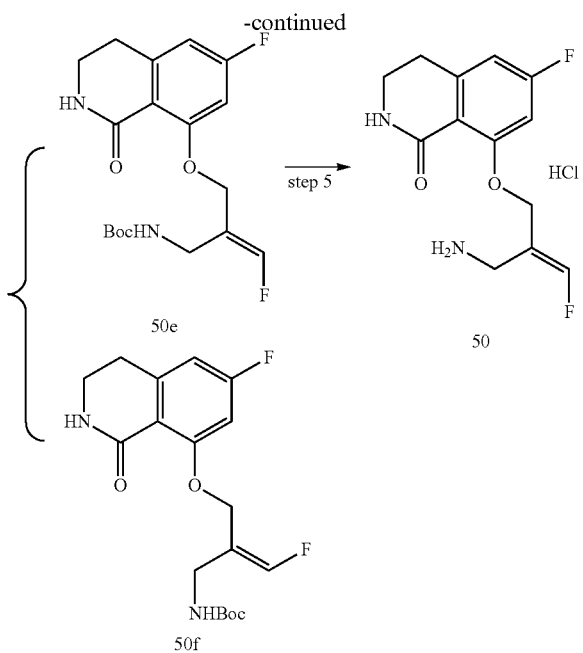

Step 1 6,8-difluoro-3,4-dihydro-2H-isoquinolin-1-one 50b 5,7-Difluoro-1-indanone 50a (0.17 g, 1.0 mmol) was dissolved in methanesulfonic acid (2 mL), and sodium azide (80 mg, 1.22 mmol) was added at 0° C., the mixture was stirred at rt for 2 hours. The mixture was poured into ice-water to quench the reaction, and adjusted with sodium hydroxide aqueous solution (1 mol/L) to pH 10. The resulting mixture was extracted with ethyl acetate (10 mL×3). The combined organic phases were washed with saturated sodium chloride solution (15 mL), dried over anhydrous sodium sulfate, filtered by suction filtration. The filtrate was concentrated. The residue was purified by silica gel column chromatography (petroleum ether/ethyl acetate (v/v)=1/1) to give the title compound 50b (0.089 g, yield: 48%) as a white solid.

MS (ESI, pos. ion) m/z: 184.1 [M+H]$^+$.

Step 2 8-benzyloxy-6-fluoro-3,4-dihydro-2H-isoquinolin-1-one 50c

Benzyl alcohol (0.32 g, 3.0 mmol) was added to a mixture of sodium hydride (0.16 g, 4.1 mmol, 60% wt) in 1,4-dioxane (5 mL), the mixture was stirred at rt for 5 min, then 6,8-difluoro-3,4-dihydro-2H-isoquinolin-1-one 50b (0.50 g, 2.7 mmol) was added, the resulting mixture was heated to 90° C. and stirred for 16 hours. The mixture was cooled to rt, the reaction was quenched with water (15 mL). The resulting mixture was extracted with ethyl acetate (20 mL×3). The organic phase was washed with saturated sodium chloride solution (15 mL), dried over anhydrous sodium sulfate, filtered by suction filtration. The filtrate was concentrated. The residue was purified by silica gel column chromatography (100% ethyl acetate) to give the title compound 50c (0.34 g, yield: 46%) as a white solid.

MS (ESI, pos. ion) m/z: 184.1 [M+H]$^+$;
$^1$H NMR (400 MHz, DMSO-d$_6$) δ (ppm) 7.70 (s, 1H), 7.57 (d, J=7.5 Hz, 2H), 7.38 (t, J=7.4 Hz, 2H), 7.30 (t, J=7.3 Hz, 1H), 6.94 (dd, J=11.7, 2.1 Hz, 1H), 6.75 (dd, J=8.7, 1.9 Hz, 1H), 5.18 (s, 2H), 3.25 (dd, J=9.5, 6.0 Hz, 2H), 2.83 (t, J=6.1 Hz, 2H);
19F NMR (376 MHz, DMSO-d$_6$) δ (ppm) −106.56 (s).

Step 3 6-fluoro-8-hydroxy-3,4-dihydro-2H-isoquinolin-1-one 50d

8-Benzyloxy-6-fluoro-3,4-dihydro-2H-isoquinolin-1-one 50c (2.60 g, 9.58 mmol) was dissolved in methanol (20 mL), and 10% Pd/C (0.26 g) was added, the flask was fully replaced by hydrogen, the mixture was hydrogenated (4 MPa) for 5 hours. The mixture was filtered by suction filtration, the filtrate was concentrated. The residue was purified by silica gel column chromatography [ethyl acetate/petroleum ether (v/v)=1/3], and the obtained solid was recrystallized [ethyl acetate/petroleum ether (v/v)=1/2, 15 mL] to give the title compound 50d (1.36 g, yield: 78%) as a white solid.

Step 4 t-butyl N—[(E)-3-fluoro-2-[(6-fluoro-1-oxo-3,4-dihydro-2H-isoquinolin-8-yl)oxymethyl]allyl]carbamate 50e and t-butyl N—[(Z)-3-fluoro-2-[(6-fluoro-1-oxo-3,4-dihydro-2H-isoquinolin-8-yl)oxymethyl]allyl]carbamate 50f To a solution of 6-fluoro-8-hydroxy-3,4-dihydro-2H-isoquinolin-1-one 50d (0.50 g, 2.8 mmol) in N,N-dimethyl formamide (10 mL) were added t-butyl N-[2-(bromomethyl)-3-fluoro-allyl]carbamate 1b (1.1 g, 4.1 mmol) and potassium carbonate (0.79 g, 5.7 mmol), the resulting mixture was stirred at rt for 16 hours. Water (20 mL) was added to the reaction to quench the reaction. The resulting mixture was extracted with ethyl acetate (20 mL×3). The combined organic phases were washed with water (20 mL) and saturated sodium chloride solution (20 mL), dried over anhydrous sodium sulfate, filtered by suction filtration. The filtrate was concentrated. The residue was purified by silica gel column chromatography (petroleum ether/ethyl acetate (v/v)=1/1) to give the title compound 50e (90 mg, yield: 9.0%) and 50f (0.34 g, yield: 34%), both are white solid.

MS (ESI, pos. ion) m/z: 369.1 [M+H]$^+$;
Compound 50e: $^1$H NMR (400 MHz, CDCl$_3$) δ (ppm) 6.80 (d, J=81.6 Hz, 1H), 6.57 (overlap, 3H), 6.20 (br, 1H), 4.47 (s, 2H), 4.05 (d, J=3.1 Hz, 2H), 3.49-3.40 (m, 2H), 2.92 (t, J=6.2 Hz, 2H), 1.38 (s, 9H);
Compound 50f: $^1$H NMR (400 MHz, CDCl$_3$) δ (ppm) 7.15 (br, 1H), 6.82 (d, J=83.1 Hz, 1H), 6.63 (d, J=11.1 Hz, 1H), 6.56 (d, J=8.2 Hz, 1H), 6.06 (br, 1H), 4.79 (s, 2H), 3.77 (s, 2H), 3.48-3.44 (m, 2H), 2.92 (t, J=6.2 Hz, 2H), 1.39 (s, 9H).

Step 5 8-[(E)-2-(aminomethyl)-3-fluoro-allyloxy]-6-fluoro-3,4-dihydro-2H-isoquinolin-1-one hydrochloride 50 t-Butyl N—[(E)-3-fluoro-2-[(6-fluoro-1-oxo-3,4-dihydro-2H-isoquinolin-8-yl)oxymethyl]allyl]carbamate 50e (90 mg, 0.25 mmol) was dissolved in a hydrogen chloride-ethyl acetate solution (5 mL, 2 mol/L). The mixture was stirred at rt for 2 hours. The mixture was concentrated to give the title compound 50 (75 mg, yield: 99%, HPLC: 96.90%) as a white solid.

MS (ESI, pos. ion) m/z: 269.0 [M−Cl]$^+$;
$^1$H NMR (400 MHz, CD$_3$OD) δ (ppm) 7.26 (d, J=80.9 Hz, 1H), 6.90 (dd, J=11.1, 2.1 Hz, 1H), 6.78 (dd, J=8.5, 1.9 Hz, 1H), 4.72 (d, J=2.8 Hz, 2H), 3.86 (s, 2H), 3.42 (t, J=6.5 Hz, 2H), 2.97 (t, J=6.5 Hz, 2H);

$^{19}$F NMR (376 MHz, CD$_3$OD) δ (ppm) −105.39, −123.37.

Example 46 8-[(Z)-2-(aminomethyl)-3-fluoro-allyloxy]-6-fluoro-3,4-dihydro-2H-isoquinolin-1-one hydrochloride 50

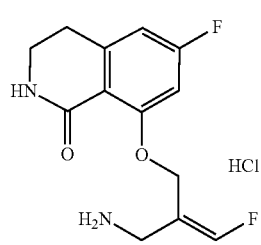

51

The title compound 51 (0.29 g, yield: 99%, HPLC: 95.35%) as a white solid was obtained according to the method described in step 5 of example 45 by using t-butyl N—[(Z)-3-fluoro-2-[(6-fluoro-1-oxo-3,4-dihydro-2H-isoquinolin-8-yl)oxymethyl]allyl]carbamate 50f (0.36 g, 0.96 mmol) instead of compound 50e.

MS (ESI, pos. ion) m/z: 269.0 [M−Cl]$^+$;

$^1$H NMR (400 MHz, CD$_3$OD) δ (ppm) 7.11 (d, J=80.4 Hz, 1H), 6.96 (dd, J=11.1, 2.1 Hz, 1H), 6.79 (dd, J=8.4, 1.9 Hz, 1H), 4.85 (s, 2H), 3.73 (d, J=1.6 Hz, 2H), 3.43 (t, J=6.5 Hz, 2H), 2.97 (t, J=6.5 Hz, 2H);

$^{19}$F NMR (376 MHz, CD$_3$OD) δ (ppm) −105.18, −120.45.

Example 47 (E)-3-fluoro-2-[(2-phenyl-3,4-dihydro-1H-isoquinolin-6-yl)oxymethyl]prop-2-enyl-1-amine hydrochloride 52

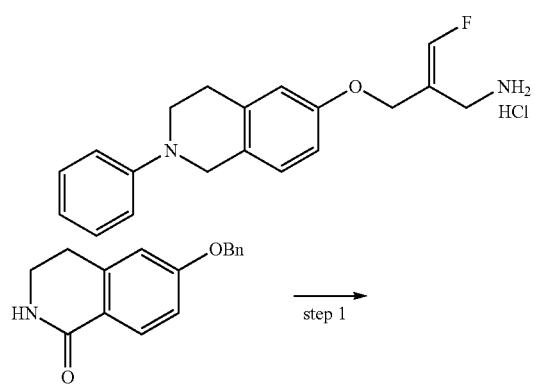

52

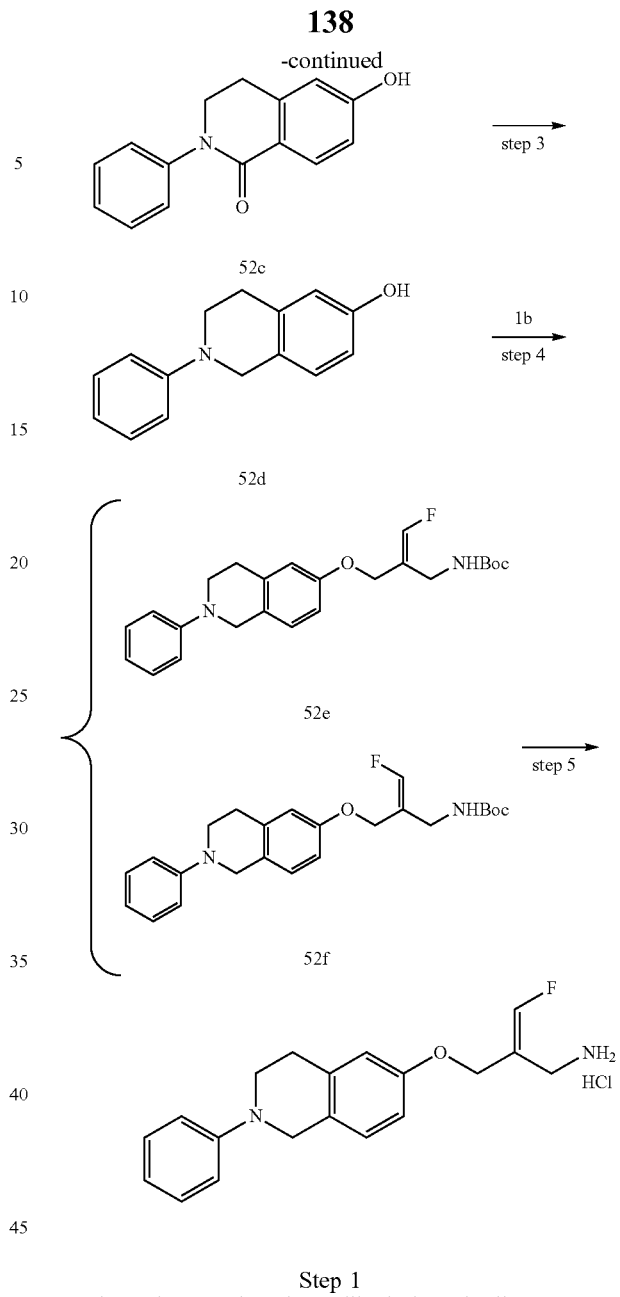

Step 1
6-benzyloxy-2-phenyl-3,4-dihydroisoquinolin-1-one 52b

6-Benzyloxy-3,4-dihydro-2H-isoquinolin-1-one 52a (658 mg, 2.60 mmol) was dissolved in N,N-dimethylformamide (10 mL), and then potassium carbonate (440 mg, 3.15 mmol), iodobenzene (0.58 mL, 5.20 mmol) and cuprous iodide (200 mg, 1.05 mmol) were added, the resulting mixture was refluxed at 150° C. for 36 hours. To the mixture was added saturated sodium chloride solution (20 mL) to quench the reaction. The resulting mixture was extracted with ethyl acetate (25 mL×3). The combined organic phases were washed with saturated sodium chloride solution (15 mL×3), dried over anhydrous sodium sulfate, filtered. The filtrate was concentrated. The residue was purified by silica gel column chromatography (petroleum ether/ethyl acetate (v/v)=1/1) to give the title compound 52b (388 mg, yield: 45%) as a white solid.

$^1$H NMR (400 MHz, DMSO-d$_6$) δ (ppm) 7.92-7.84 (m, 1H), 7.47 (d, J=7.0 Hz, 2H), 7.44-7.31 (m, 6H), 7.28-7.20

(m, 1H), 7.01 (d, J=6.8 Hz, 2H), 5.19 (s, 2H), 3.93 (t, J=6.4 Hz, 2H), 3.09 (t, J=6.4 Hz, 2H).

Step 2
6-hydroxy-2-phenyl-3,4-dihydroisoquinolin-1-one 52c

6-Benzyloxy-2-phenyl-3,4-dihydroisoquinolin-1-one 52b (274 mg, 0.83 mmol) was dissolved in methanol (5.0 mL), and 10% Pd/C (10 mg) was added, the flask was fully replaced by hydrogen, the mixture was hydrogenated (4 MPa) at rt for 12 hours. The mixture was filtered. The filtrate was concentrated to give the title compound 52c (195 mg, yield: 98%) as a white solid.

Step 3 2-phenyl-3,4-dihydro-1H-isoquinolin-6-ol 52d

6-Hydroxy-2-phenyl-3,4-dihydroisoquinolin-1-one 52c (195 mg, 0.81 mmol) was dissolved in tetrahydrofuran (10 mL), and lithium aluminium hydride (95 mg, 2.4 mmol) was added slowly, then the mixture was stirred at 50° C. for 4 hours. Ethyl acetate (15 mL) was added to the mixture to cause precipitation, the resulting mixture was filtered. The filtrate was concentrated. The residue was purified by silica gel column chromatography (petroleum ether/ethyl acetate (v/v)=3/1) to give the title compound 52d (164 mg, yield: 89%) as yellow oil.
$^1$H NMR (400 MHz, DMSO-d$_6$) δ (ppm) 9.17 (s, 1H), 7.21 (t, J=7.9 Hz, 2H), 6.98 (dd, J=18.7, 8.1 Hz, 3H), 6.72 (t, J=7.2 Hz, 1H), 6.65-6.52 (m, 2H), 4.25 (s, 2H), 3.47 (t, J=5.9 Hz, 2H), 2.81 (t, J=5.8 Hz, 2H).

Step 4 tert-butyl N—[(E)-3-fluoro-2-[(2-phenyl-3,4-dihydro-1H-isoquinolin-6-yl)oxymethyl]carbonate 52e and tert-butyl-fluoro-2-[(2-phenyl-3,4-dihydro-1H-isoquinol-6-yl) oxymethyl]allyl]carbonate 52f To a solution of 2-phenyl-3,4-dihydro-1H-isoquinolin-6-ol 52d (164 mg, 0.73 mmol) and t-butyl N-[2-(bromomethyl)-3-fluoro-allyl]carbamate (233 mg, 0.87 mmol) in N,N-dimethylformamide (15 mL) was added cesium carbonate (710 mg, 2.2 mmol), the mixture was stirred for 16 hours. To the mixture was added saturated sodium chloride solution (15 mL), and the resulting mixture was extracted with ethyl acetate (15 mL×3), the combined organic layers were dried over anhydrous sodium sulfate, filtered by suction filtration. The filtrate was concentrated. The residue was purified by silica gel column chromatography (petroleum ether/ethyl acetate (v/v)=5/1) to give the title compound 52e (60 mg, yield: 20%) and 52f (30 mg, yield: 10%), both are yellow solid.

Step 5 (E)-3-fluoro-2-[(2-phenyl-3,4-dihydro-1H-isoquinolin-6-yl)oxymethyl]prop-2-enyl-1-amine hydrochloride 52

Hydrogen chloride-methanol solution (2 mL, 5 mol/L) was added into a solution of tert-butyl N—[(E)-3-fluoro-2-[(2-phenyl-3,4-dihydro-1H-isoquinolin-6-yl)oxymethyl]allyl]carbonate 52e (30 mg, 0.07 mmol) in ethyl acetate (3 mL), the mixture was stirred at rt for 1 hour and concentrated to give the title compound 52 (15 mg, yield: 59%, HPLC: 86.64%) as a light yellow solid.
MS (ESI, pos. ion) m/z: 313.2 [M−Cl]$^+$;
$^1$H NMR (400 MHz, DMSO-d$_6$) δ (ppm) 8.25 (s, 3H), 7.41-7.15 (m, 6H), 6.97 (s, 1H), 6.87 (d, J=7.8 Hz, 2H), 4.62 (d, J=2.8 Hz, 2H), 4.43 (s, 2H), 3.65-3.60 (m, 4H), 3.00 (s, 2H).

Example 48 (Z)-3-fluoro-2-[(2-phenyl-3,4-dihydro-1H-isoquinolin-6-yl)oxymethyl]prop-2-enyl-1-amine hydrochloride 53

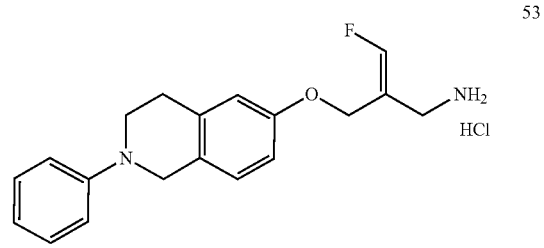 [SMILES: NC/C(=C/F)COc1ccc2c(c1)CCN(c1ccccc1)C2 ; Cl]

The title compound 53 (40 mg, yield: 79%, HPLC: 91.10%) as a light yellow solid was obtained according to the method described in step 5 of example 47 by using tert-butyl N—[(Z)-3-fluoro-2-[(2-phenyl-3,4-dihydro-1H-isoquinolin-6-yl)oxymethyl]allyl]carbonate 52f (60 mg, 0.14 mmol) instead of compound 52e.
MS (ESI, pos. ion) m/z: 313.2 [M−Cl]$^+$;
$^1$H NMR (400 MHz, DMSO-d$_6$) δ (ppm) 8.24 (s, 3H), 7.32 (t, J=14.6 Hz, 4H), 7.21-7.08 (m, 2H), 7.00 (s, 1H), 6.88 (d, J=6.8 Hz, 2H), 4.74 (s, 2H), 4.44 (s, 2H), 3.65 (s, 2H), 3.52 (s, 2H), 3.02 (s, 2H).
$^{19}$F NMR (376 MHz, CD$_3$OD) δ (ppm) −105.18, −120.45.

Example 49 6-[(E)-2-[(aminomethyl)-3-fluoro-allyloxy]-2-(2-methoxypyrimidin-5-yl)-3,4-dihydroisoquinolin-1-one hydrochloride 54

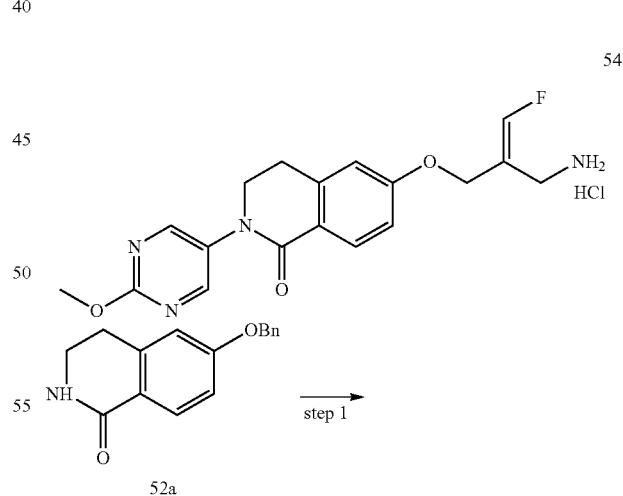

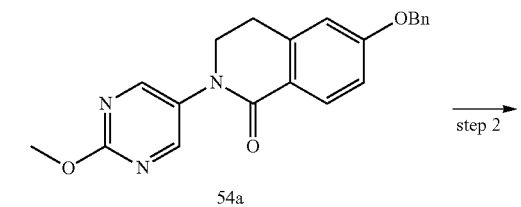

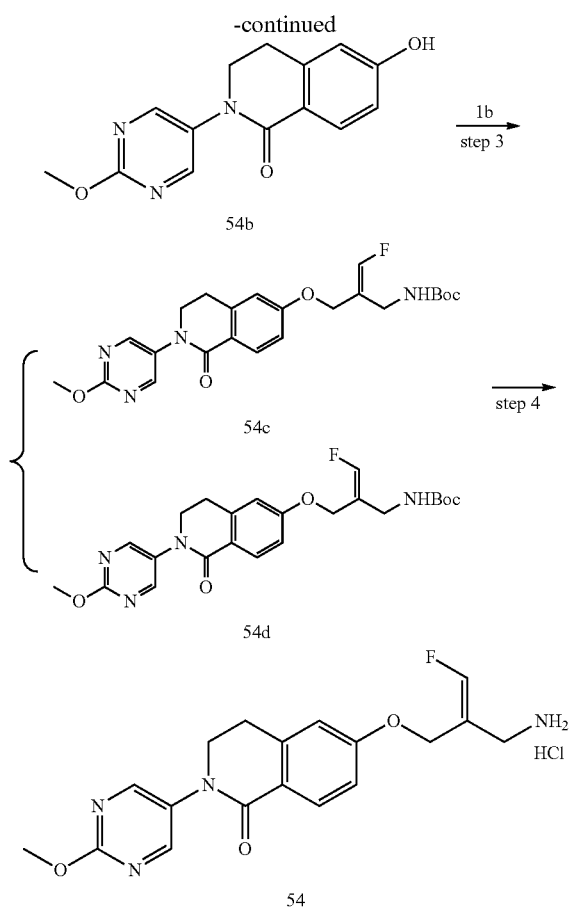

Step 1 6-benzyloxy-2-(2-methoxypyrimidin-5-yl)-3,4-dihydroisoquinolin-1-one 54a 6-Benzyloxy-3,4-dihydro-2H-isoquinolin-1-one 52a (0.24 g, 0.95 mmol) was dissolved in 1,4-dioxane (10 mL), and cesium carbonate (0.44 g, 3.15 mmol), 5-bromo-2-methoxypyrimidine (0.27 g, 1.4 mmol), 4,5-bis(diphenylphosphino)-9,9-dimethylxanthene (67 mg, 0.11 mmol) and tris(dibenzylideneacetone)dipalladium (54 mg, 0.57 mmol) were added, the mixture was stirred at 100° C. for 24 hours. The mixture was concentrated. The residue was purified by silica gel column chromatography (petroleum ether/ethyl acetate (v/v)=1/1) to give the title compound 54a (0.21 g, yield: 61%) as a white solid.

MS (ESI, pos. ion) m/z: 362.3 [M+H]$^+$;

$^1$H NMR (400 MHz, DMSO-d$_6$) δ (ppm) 8.69 (s, 2H), 7.88 (d, J=9.1 Hz, 1H), 7.51-7.32 (m, 5H), 7.06-6.98 (m, 2H), 5.20 (s, 2H), 3.99-3.93 (m, 5H), 3.12 (t, J=6.4 Hz, 2H).

Step 2 6-hydroxy-2-(2-methoxypyrimidin-5-yl)-3,4-dihydroisoquinolin-1-one 54b 6-Benzyloxy-2-(2-methoxypyrimidin-5-yl)-3,4-dihydroisoquinolin-1-one 54a (0.21 g, 0.58 mmol) was dissolved in a mixed solution of tetrahydrofuran/methanol (v/v=2/1, 6 mL), and 10% Pd/C (21 mg) was added, the flask was fully replaced by hydrogen, the mixture was hydrogenated (4 MPa) at rt for 2.5 hours. The mixture was filtered, the filtrate was concentrated to give the title compound 54b (0.15 g, yield: 89%, HPLC: 95%) as colorless oil.

MS (ESI, pos. ion) m/z: 272.0 [M+H]$^+$.

Step 3 tert-butyl N—[(E)-3-fluoro-2-[[(2-(2-methoxypyrimidin-5-yl)-1-oxo-3,4-dihydro-1H-isoquinolin-6-yl)oxymethyl]allyl]formate 54c and tert-butyl N—[(Z)-3-fluoro-2-[[(2-(2-methoxypyrimidin-5-yl)-1-oxo-3,4-dihydro-1H-isoquinolin-6-yl)oxymethyl]allyl]formate 54d To a solution of 6-hydroxy-2-(2-methoxypyrimidin-5-yl)-3,4-dihydroisoquinolin-1-one 54b (0.15 g, 0.55 mmol) and t-butyl N-[2-(bromomethyl)-3-fluoro-allyl]carbamate 1b (0.18 g, 0.67 mmol) in N,N-dimethylformamide (5 mL) was added potassium carbonate (0.12 g, 0.86 mmol), the mixture was stirred at rt for 18 hours. The reaction was quenched by adding water (15 mL). The resulting mixture was extracted with ethyl acetate (20 mL×2). The combined organic phases were washed with saturated sodium chloride solution (30 mL), dried over anhydrous sodium sulfate, filtered by suction filtration. The filtrate was concentrated. The residue was purified by preparative chromatography to give the title compound 54c (35 mg, yield: 14%) and 54d (81 mg, yield: 32%), both are white solid.

MS (ESI, pos. ion) m/z: 459.3 [M+H]$^+$.

Step 4 6-[(E)-2-[(aminomethyl)-3-fluoro-allyloxy]-2-(2-methoxypyrimidin-5-yl)-3,4-dihydroiso quinolin-1-one 54 tert-Butyl N—[(E)-3-fluoro-2-[[(2-(2-methoxypyrimidin-5-yl)-1-oxo-3,4-dihydro-1H-isoquinol-6-yl)oxymethyl]allyl]formate 54c (35 mg, 0.07 mmol) was dissolved in ethyl acetate (3 mL), and then a hydrogen chloride-methanol solution (5 mL, 4 mol/L) was added, the mixture was stirred at rt for 3 hours. The mixture was concentrated to give the title compound 54 (23 mg, yield: 69%, HPLC: 90.68%) as a light yellow solid.

MS (ESI, pos. ion) m/z: 359.3 [M−Cl]$^+$;

$^1$H NMR (400 MHz, DMSO-d$_6$) δ (ppm) 8.70 (s, 2H), 8.26 (s, 3H), 7.91 (d, J=9.3 Hz, 1H), 7.37 (d, J=82.0 Hz, 1H), 7.02 (d, J=6.4 Hz, 2H), 4.73 (s, 2H), 4.08-3.85 (m, 5H), 3.62 (s, 2H), 3.13 (d, J=6.2 Hz, 2H).

Example 50 6-[(Z)-2-[(aminomethyl)-3-fluoro-allyloxy]-2-(2-methoxypyrimidin-5-yl)-3,4-dihydroisoquinolin-1-one hydrochloride 55

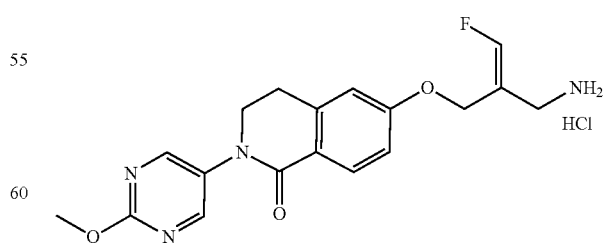

The title compound 55 (65 mg, yield: 87%, HPLC: 93.28%) as a light yellow solid was obtained according to the method described in step 4 of example 49 by using tert-butyl N—[(Z)-3-fluoro-2-[[(2-(2-methoxypyrimidin-5- yl)-1-oxo-3,4-dihydro-1H-isoquinolin-6-yl)oxymethyl]al-lyl]formate 54d (81 mg, 0.18 mmol) instead of compound 54c.

MS (ESI, pos. ion) m/z: 359.3 [M−Cl]+;

$^1$H NMR (400 MHz, DMSO-$d_6$) δ (ppm) 8.70 (s, 2H), 8.27 (s, 3H), 7.95-7.86 (m, 1H), 7.26 (d, J=82.0 Hz, 1H), 7.03 (s, 2H), 4.83 (s, 2H), 4.11-3.77 (m, 5H), 3.56 (s, 2H), 3.13 (t, J=6.3 Hz, 2H).

Example 51 methyl 3-[6-[(E)-2-(aminomethyl)-3-fluoro-allyloxy]-1-oxo-3,4-dihydro isoquinolin-2-yl] propionate hydrochloride 56

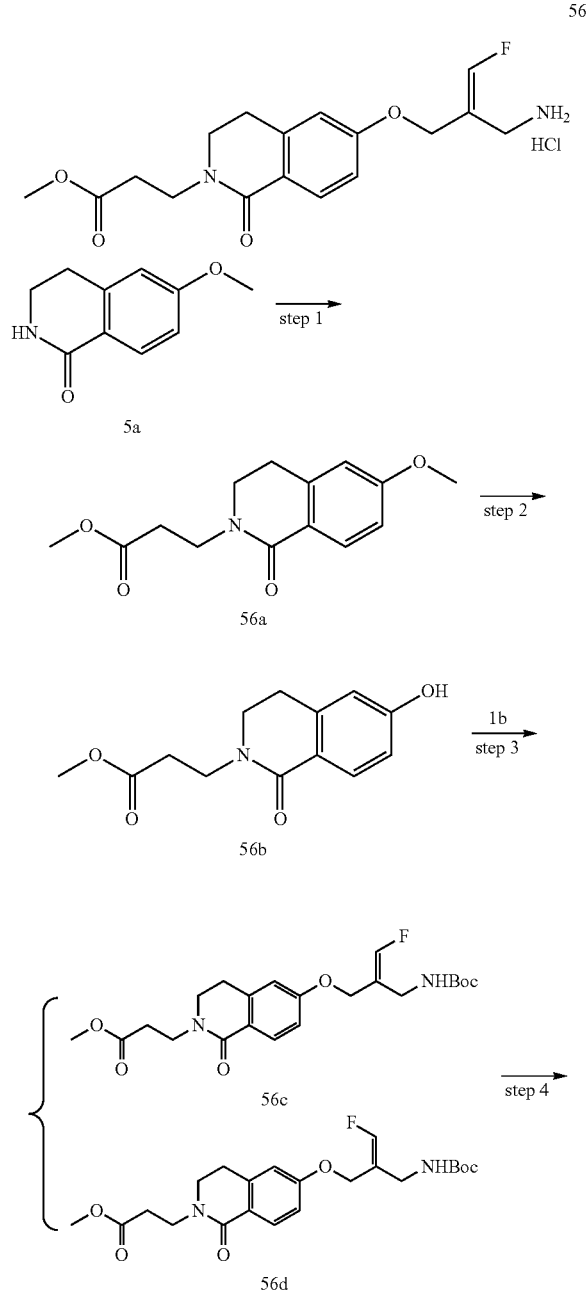

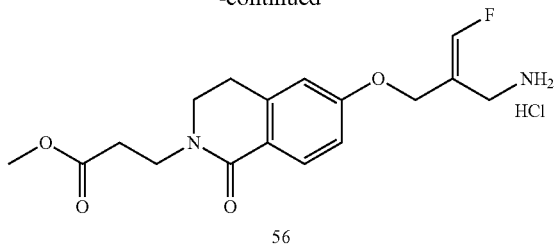

Step 1 methyl 3-(6-methoxy-1-oxo-3,4-dihydroiso-quinolin-2-yl)propionate 56a

At 0° C., 6-methoxy-3,4-dihydro-2H-isoquinolin-1-one 5a (2.00 g, 11.1 mmol) was added to a mixture of sodium hydride (0.58 g, 15 mmol, 60% wt) in anhydrous tetrahydrofuran (30 mL), the mixture was stirred at rt for 30 min, methyl 3-bromopropionate (1.4 mL, 14 mmol) and tetrabutylammonium bromide (0.20 g, 0.62 mol) were added dropwise, the resulting mixture was stirred at rt for 18 hours. The mixture was poured into ice-water (20 mL) to quench the reaction. The resulting mixture was extracted with ethyl acetate (30 mL×2). The combined organic phases were washed with saturated sodium chloride solution (50 mL), dried over anhydrous sodium sulfate, filtered by suction filtration. The filtrate was concentrated. The residue was purified by silica gel column chromatography (petroleum ether/ethyl acetate (v/v)=1/1) to give the title compound 56a (1.65 g, yield: 57%) as colorless oil.

$^1$H NMR (600 MHz, CDCl$_3$) δ (ppm) 8.01 (d, J=8.6 Hz, 1H), 6.85 (dd, J=8.6, 2.5 Hz, 1H), 6.67 (d, J=2.4 Hz, 1H), 3.85 (s, 3H), 3.81 (t, J=6.7 Hz, 2H), 3.70 (s, 3H), 3.65-3.61 (m, 2H), 2.95 (t, J=6.6 Hz, 2H), 2.73 (t, J=6.7 Hz, 2H).

Step 2 methyl 3-(6-hydroxy-1-oxo-3,4-dihydroiso-quinolin-2-yl)propionate 56b

Methyl 3-(6-methoxy-1-oxo-3,4-dihydroisoquinolin-2-yl)propionate 56a (1.60 g, 6.08 mmol) was dissolved in dichloromethane (20 mL), and then boron tribromide (15.2 mL, 15.2 mmol) was added dropwise at −5° C., the resulting mixture was stirred at rt for 7 hours. The reaction was quenched with ethanol (5 mL) at 0° C. The mixture was poured into ice-water (30 mL). The resulting mixture was extracted with ethyl acetate (50 mL). The organic phase was washed with saturated sodium chloride solution (30 mL), dried over anhydrous sodium sulfate, filtered by suction filtration. The filtrate was concentrated. The residue was purified by silica gel column chromatography (petroleum ether/ethyl acetate (v/v)=1/1) to give the title compound 56b (0.37 g, yield: 24%) as a white solid.

$^1$H NMR (600 MHz, DMSO-$d_6$) δ (ppm) 10.02 (s, 1H), 7.68 (d, J=8.5 Hz, 1H), 6.69 (dd, J=8.5, 2.4 Hz, 1H), 6.60 (d, J=2.3 Hz, 1H), 3.65 (t, J=7.1 Hz, 2H), 3.60 (s, 3H), 3.51 (t, J=6.6 Hz, 2H), 2.84 (t, J=6.6 Hz, 2H), 2.60 (t, J=7.1 Hz, 2H).

Step 3 methyl 3-[6-[(E)-2-[(t-butoxycarbonylamino) methyl]-3-fluoro-allyloxy]-1-oxo-3,4-dihydroisoqui-nolin-2-yl]propionate 56c and methyl 3-[6-[(Z)-2-[(t-butoxycarbonylamino)methyl]-3-fluoro-allyloxy]-1-oxo-3,4-dihydroisoquinolin-2-yl] propionate 56d To a solution of methyl 3-(6-hydroxy-1-oxo-3,4-dihy-droisoquinolin-2-yl)propionate 56b (0.27 g, 1.08 mmol) in N,N-dimethyl formamide (10 mL) were added t-butyl N-[2-(bromomethyl)-3-fluoro-allyl]carbamate 1b (0.35 g, 1.30 mmol) and potassium carbonate (0.20 g, 1.41 mmol), the resulting mixture was stirred at rt for 16 hours. The reaction was quenched with water (15 mL). The resulting mixture was extracted with ethyl acetate (30 mL×2). The organic phase was washed with saturated sodium chloride solution (30 mL), dried over anhydrous sodium sulfate, filtered by suction filtration. The filtrate was concentrated. The residue was purified by silica gel column chromatography (petroleum ether/ethyl acetate (v/v)=2/1) to give the title compound 56c (55 mg, yield: 12%) and 56d (0.10 g, yield: 21%), both are colorless oil.

MS (ESI, pos. ion) m/z: 437.1 [M+H]$^+$.

Step 4 methyl 3-[6-[(E)-2-(aminomethyl)-3-fluoro-allyloxy]-1-oxo-3,4-dihydroisoquinolin-2-yl]propionate hydrochloride 56

Methyl 3-[6-[(E)-2-[(t-butoxycarbonylamino)methyl]-3-fluoro-allyloxy]-1-oxo-3,4-dihydroisoquinolin-2-yl]propionate 56c (20 mg, 0.05 mmol) was dissolved in ethyl acetate (2 mL), and then a hydrogen chloride-ethyl acetate solution (6 mL, 2 mol/L) was added, the mixture was stirred at rt for 1 hour. The mixture was concentrated to give the title compound 56 (44 mg, yield: 95%, HPLC: 85.83%) as light yellow thick oil.

MS (ESI, pos. ion) m/z: 337.1 [M−Cl]$^+$;

$^1$H NMR (400 MHz, DMSO-d$_6$) δ (ppm) 8.27 (s, 3H), 7.80 (d, J=8.6 Hz, 1H), 7.23 (d, J=82.1 Hz, 1H), 6.99-6.87 (m, 2H), 4.79 (s, 2H), 3.67 (t, J=7.0 Hz, 2H), 3.60 (s, 3H), 3.55 (dd, J=11.7, 5.1 Hz, 4H), 2.91 (t, J=6.4 Hz, 2H), 2.62 (t, J=7.1 Hz, 2H).

Example 52 methyl 3-[6-[(Z)-2-(aminomethyl)-3-fluoro-allyloxy]-1-oxo-3,4-dihydro isoquinolin-2-yl]propionate hydrochloride 56

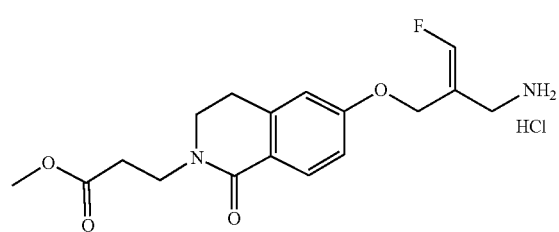

The title compound 57 (38 mg, yield: 44%, HPLC: 86.05%) as light yellow thick oil was obtained according to the method described in step 4 of example 51 by using methyl 3-[6-[(E)-2-[(t-butoxycarbonylamino)methyl]-3-fluoro-allyloxy]-1-oxo-3,4-dihydroisoquinolin-2-yl]propionate 56d (0.10 g, 0.23 mmol) instead of compound 56c.

MS (ESI, pos. ion) m/z: 337.1 [M−Cl]$^+$;

$^1$H NMR (400 MHz, DMSO-d$_6$) δ (ppm) 8.27 (s, 3H), 7.80 (d, J=8.6 Hz, 1H), 7.23 (d, J=82.1 Hz, 1H), 6.99-6.87 (m, 2H), 4.79 (s, 2H), 3.67 (t, J=7.0 Hz, 2H), 3.60 (s, 3H), 3.55 (dd, J=11.7, 5.1 Hz, 4H), 2.91 (t, J=6.4 Hz, 2H), 2.62 (t, J=7.1 Hz, 2H).

Example 53 methyl 2-[6-[(E)-2-(aminomethyl)-3-fluoro-allyloxy]-1-oxo-3,4-dihydro isoquinolin-2-yl] acetate hydrochloride 58

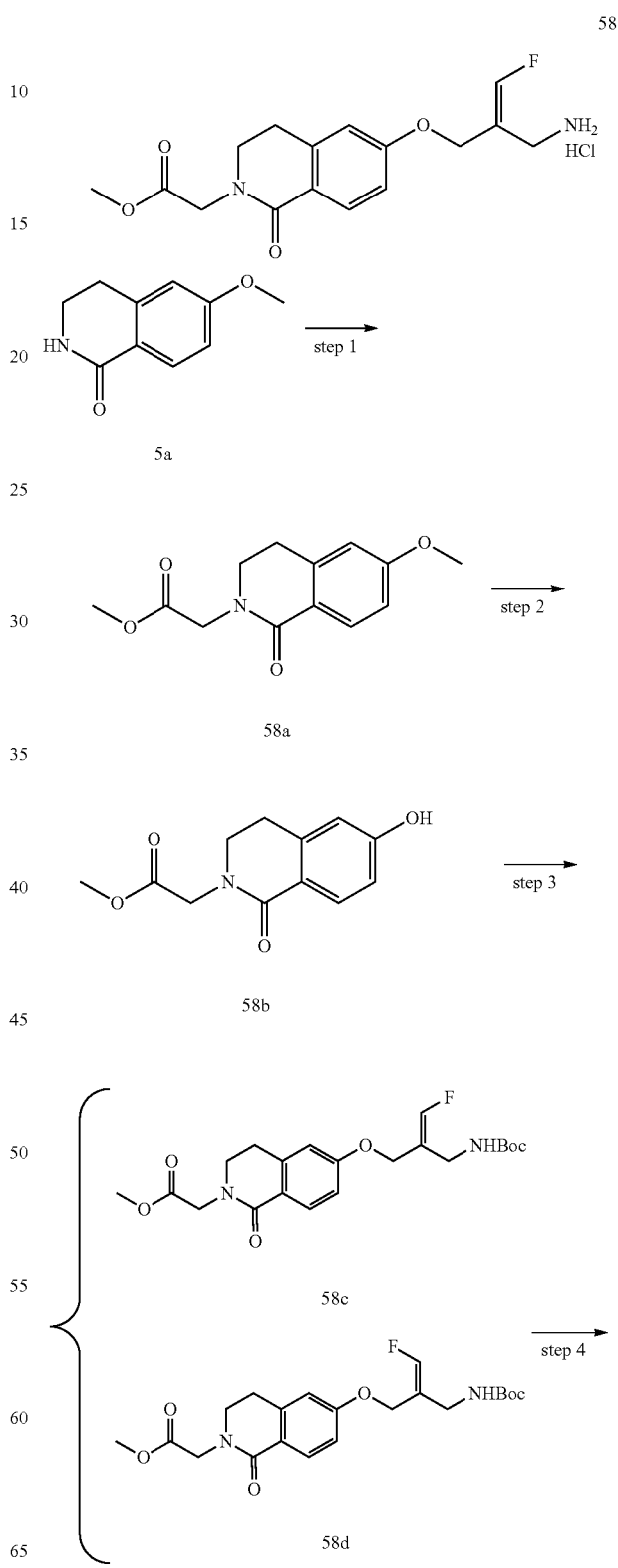

-continued

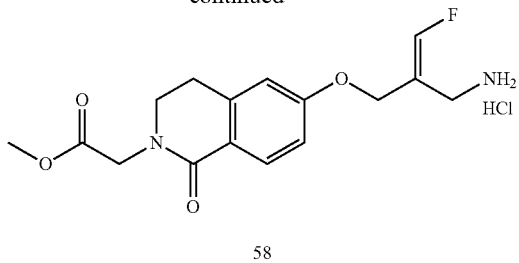

58

Step 1 methyl 2-(6-methoxy-1-oxo-3,4-dihydroisoquinolin-2-yl)acetate 58a

6-Methoxy-3,4-dihydro-2H-isoquinolin-1-one 5a (0.50 g, 2.82 mmol) was added to a mixture of sodium hydride (0.17 g, 4.25 mmol, 60% wt) in tetrahydrofuran (10 mL), the mixture was stirred at rt for 30 min, then methyl bromoacetate (0.4 mL, 4 mmol) was added dropwise, and then tetrabutylammonium bromide (92 mg, 0.28 mmol) was added, the resulting mixture was stirred at rt for 24 hours. The reaction was quenched with ice-water (15 mL). The resulting mixture was extracted with ethyl acetate (30 mL×3). The combined organic phases were washed with saturated sodium chloride solution (10 mL×2), dried over anhydrous sodium sulfate, filtered by suction filtration. The filtrate was concentrated. The residue was purified by silica gel column chromatography (ethyl acetate/petroleum ether (v/v)=1/2) to give the title compound 58a (0.59 g, yield: 84%) as colorless oil.

MS (ESI, pos. ion) m/z: 250.2 [M+H]$^+$.

Step 2 methyl 2-(6-hydroxy-1-oxo-3,4-dihydroisoquinolin-2-yl)acetate 58b

Methyl 2-(6-methoxy-1-oxo-3,4-dihydroisoquinolin-2-yl)acetate 58a (1.3 g, 5.2 mmol) was dissolved in dichloromethane (20 mL), and then boron tribromide-dichloromethane solution (26 mL, 26 mmol, 1.0 mol/L) was added dropwise at −10° C., the resulting mixture was stirred at rt for 6 hours. The reaction was quenched by adding methanol (4 mL) at 0° C. The resulting mixture was extracted with dichloromethane (100×3 mL). The combined organic phases were washed with saturated sodium chloride solution (80 mL×2), dried over anhydrous sodium sulfate, filtered by suction filtration. The filtrate was concentrated. The residue was purified by silica gel column chromatography (ethyl acetate/petroleum ether (v/v)=1/1) to give the title compound 58b (0.88 g, yield: 72%) as a white solid.

MS (ESI, pos. ion) m/z: 236.1 [M+H]$^+$.

Step 3 methyl 2-[6-[(E)-2-[(tert-butyloxycarbonylamino)methyl]-3-fluoro-allyloxy]-1-oxo-3,4-dihydroisoquinolin-2-yl]acetate 58c and methyl 2-[6-[(Z)-2-[(tert-butyloxycarbonylamino) methyl]-3-fluoro-allyloxy]-1-oxo-3,4-dihydroisoquinolin-2-yl]acetate 58d To a solution of methyl 2-(6-hydroxy-1-oxo-3,4-dihydroisoquinolin-2-yl)acetate 58b (1.23 g, 5.23 mmol) and t-butyl N-[2-(bromomethyl)-3-fluoro-allyl]carbamate (1.4 g, 5.2 mmol) in N,N-dimethylformamide (20 mL) was added cesium carbonate (2.61 g, 7.85 mmol), the mixture was stirred at 35° C. for 18 hours. The reaction was quenched with water (50 mL). The resulting mixture was extracted with ethyl acetate (60 mL×3). The combined organic phases were washed with saturated sodium chloride solution (30 mL×3), dried over anhydrous sodium sulfate, filtered by suction filtration. The filtrate was concentrated. The residue was purified by silica gel column chromatography (ethyl acetate/petroleum ether (v/v)=2/3) to give the title compound 58c (0.45 g, yield: 20%) and 58d (0.87 g, yield: 39%), both are colorless oil.

MS (ESI, pos. ion) m/z: 445.1 [M+Na]$^+$.

Step 4 methyl 2-[6-[(E)-2-(aminomethyl)-3-fluoro-allyloxy]-1-oxo-3,4-dihydroisoquinolin-2-yl]acetate hydrochloride 58

Methyl 2-[6-[(E)-2-[(tert-butyloxycarbonylamino)methyl]-fluoro-allyloxy]1-oxo-3,4-dihydroisoquinolin-2-yl]acetate 58c (0.10 g, 0.24 mmol) was dissolved in ethyl acetate (1 mL), and then a hydrogen chloride-ethyl acetate solution (4 mL, 2 mol/L) was added, the mixture was stirred at rt for 1 hour. The mixture was concentrated to give the title compound 58 (76 mg, yield: 90%, HPLC: 90.77%) as a white solid.

MS (ESI, pos. ion) m/z: 323.1[M−Cl]$^+$;

$^1$H NMR (600 MHz, DMSO-d$_6$) δ (ppm) 8.45 (s, 3H), 7.81 (d, J=8.5 Hz, 1H), 7.33 (d, J=81.8 Hz, 1H), 7.04-6.86 (m, 2H), 4.73 (s, 2H), 4.28 (s, 2H), 3.66 (s, 3H), 3.61 (dd, J=14.1, 7.6 Hz, 4H), 2.98 (t, J=5.8 Hz, 2H).

Example 54 methyl 2-[6-[(Z)-2-(aminomethyl)-3-fluoro-allyloxy]-1-oxo-3,4-dihydro isoquinolin-2-yl]acetate hydrochloride 59

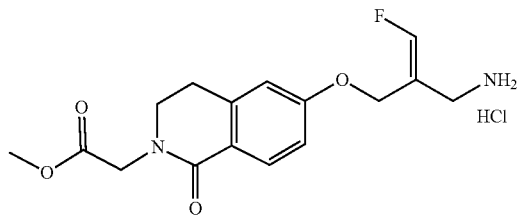

59

The title compound 59 (80 mg, yield: 94%, HPLC: 82.09%) as a white solid was obtained according to the method described in step 4 of example 53 by using methyl 2-[6-[(Z)-2-[(tert-butyloxycarbonylamino)methyl]-fluoro-allyloxy]-1-oxo-3,4-dihydroisoquinolin-2-yl]acetate 58d (0.10 g, 0.24 mmol) instead of compound 58c.

MS (ESI, pos. ion) m/z: 323.1 [M−Cl]$^+$;

$^1$H NMR (600 MHz, DMSO-d$_6$) δ (ppm) 8.46 (s, 3H), 7.81 (s, 1H), 7.26 (d, J=82.2 Hz, 1H), 6.96 (s, 2H), 4.83 (s, 2H), 4.29 (s, 2H), 3.66 (s, 3H), 3.53 (s, 4H), 2.98 (s, 2H).

Example 55 2-[6-[(E)-2-(aminomethyl)-3-fluoro-allyloxy]-1-oxo-3,4-dihydroisoquinolin-2-yl]acetic Acid hydrochloride 60

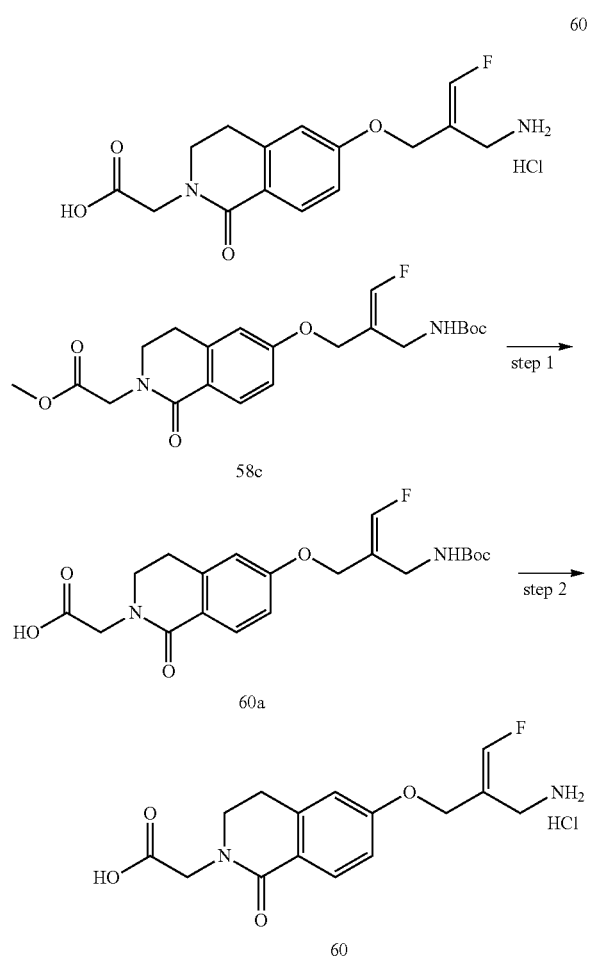

Step 1 2-[6-[(E)-2-[(tert-butyloxycarbonylamino)methyl]-3-fluoro-allyloxy]-1-oxo-3,4-dihydro isoquinolin-2-yl]acetic acid 60a Methyl 2-[6-[(E)-2-[(tert-butyloxycarbonylamino)methyl]-3-fluoro-allyloxy]-1-oxo-3,4-dihydroisoquinolin-2-yl]acetate 58c (0.15 g, 0.36 mmol) was dissolved in 1,4-dioxane (4 mL), and lithium hydroxide (0.15 g, 3.55 mmol) aqueous solution (4 mL) was added, the mixture was stirred at rt for 4 hours. To the reaction mixture was added water (5 mL), and the resulting mixture was adjusted to pH 4 with acetic acid and extracted with ethyl acetate (10 mL×3). The combined organic layers were washed with water (10 mL), dried over anhydrous sodium sulfate, and filtered by suction filtration. The filtrate was concentrated to give the title compound 60a (145 mg, yield: 100%) as a white solid.

MS (ESI, pos. ion) m/z: 431.2 [M+Na]$^+$.

Step 2 2-[6-[(E)-2-(aminomethyl)-3-fluoro-allyloxy]-1-oxo-3,4-dihydroisoquinolin-2-yl]acetic acid hydrochloride 60

2-[6-[(E)-2-[(tert-Butyloxycarbonylamino)methyl]-3-fluoro-allyloxy]-1-oxo-3,4-dihydroiso quinolin-2-yl]acetic acid 60a (145 mg, 0.36 mmol) was dissolved in ethyl acetate (1 mL), and then a hydrogen chloride-ethyl acetate solution (6 mL, 2 mol/L) was added, the mixture was stirred at rt for 1 hour. The mixture was concentrated to give the title compound 60 (116 mg, yield: 95%, HPLC: 93.69%) as a white solid.

MS (ESI, pos. ion) m/z: 309.1 [M−Cl]$^+$;

$^1$H NMR (400 MHz, DMSO-d$_6$) δ (ppm) 8.32 (s, 3H), 7.81 (d, J=8.2 Hz, 1H), 7.33 (d, J=81.8 Hz, 1H), 7.11-6.85 (m, 2H), 4.70 (s, 2H), 4.18 (s, 2H), 3.60 (s, 4H), 2.96 (s, 2H).

Example 56 2-[6-[(Z)-2-(aminomethyl)-3-fluoro-allyloxy]-1-oxo-3,4-dihydroisoquinolin-2-yl]acetic acid hydrochloride 61

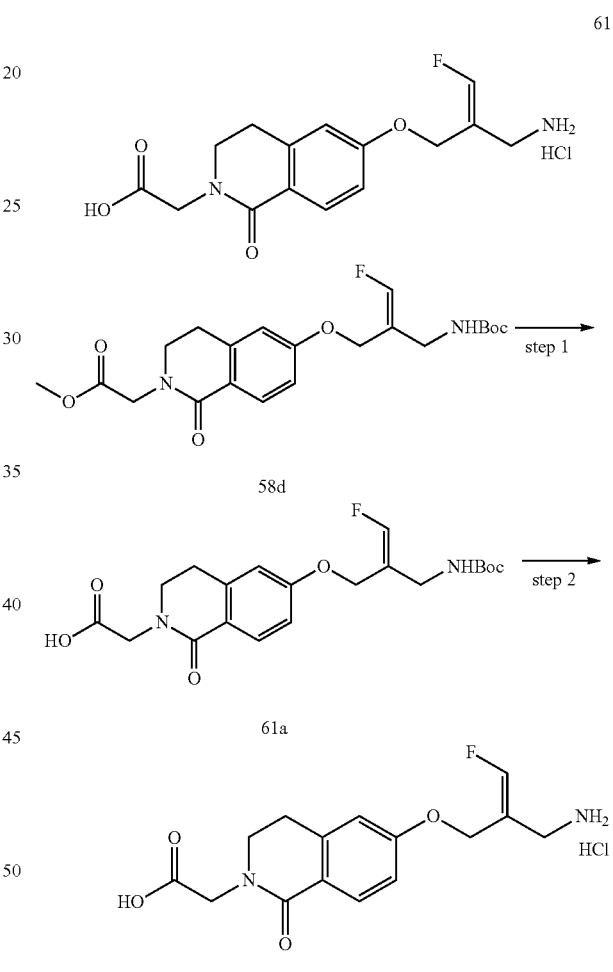

Step 1 2-[6-[(Z)-2-[(tert-butyloxycarbonylamino)methyl]-3-fluoro-allyloxy]-1-oxo-3,4-dihydro isoquinolin-2-yl]acetic acid 61a Methyl 2-[6-[(Z)-2-[(tert-butyloxycarbonylamino)methyl]-3-fluoro-allyloxy]-1-oxo-3,4-dihydroisoquinolin-2-yl]acetate 58d (0.15 g, 0.36 mmol) was dissolved in 1,4-dioxane (4 mL), and lithium hydroxide (0.15 g, 3.55 mmol) aqueous solution (4 mL) was added, the mixture was stirred at rt for 4 hours. To the reaction mixture was added water (5 mL), and the resulting mixture was adjusted to pH 4 with acetic acid and extracted with ethyl acetate (10 mL×3). The combined organic layers were washed with water (10 mL), dried over anhydrous sodium sulfate, and filtered by suction filtration. The filtrate was concentrated to give the title compound 61a (145 mg, yield: 100%) as a white solid.

MS (ESI, pos. ion) m/z: 431.1[M+Na]$^+$.

Step 2 2-[6-[(Z)-2-(aminomethyl)-3-fluoro-allyloxy]-1-oxo-3,4-dihydroisoquinolin-2-yl]acetic acid hydrochloride 61

2-[6-[(Z)-2-[(tert-Butyloxycarbonylamino)methyl]-3-fluoro-allyloxy]-1-oxo-3,4-dihydroiso quinolin-2-yl]acetic acid 61a (145 mg, 0.36 mmol) was dissolved in ethyl acetate (1 mL), and then a hydrogen chloride-ethyl acetate solution (6 mL, 2 mol/L) was added, the mixture was stirred at rt for 1 hour. The mixture was concentrated to give the title compound 61 (0.12 g, yield: 98%, HPLC: 85.75%) as a white solid.

MS (ESI, pos. ion) m/z: 309.1 [M−Cl]$^+$;

$^1$H NMR (400 MHz, DMSO-d$_6$) δ (ppm) 8.29 (s, 3H), 7.81 (d, J=8.4 Hz, 1H), 7.24 (d, J=82.0 Hz, 1H), 7.05-6.86 (m, 2H), 4.80 (s, 2H), 4.18 (s, 2H), 3.58 (dd, J=19.2, 12.9 Hz, 4H), 2.96 (s, 2H).

Example 57 2-[7-[(E)-2-(aminomethyl)-3-fluoro-allyloxy]-1-oxo-3,4-dihydroisoquinolin-2-yl] acetic acid hydrochloride 62

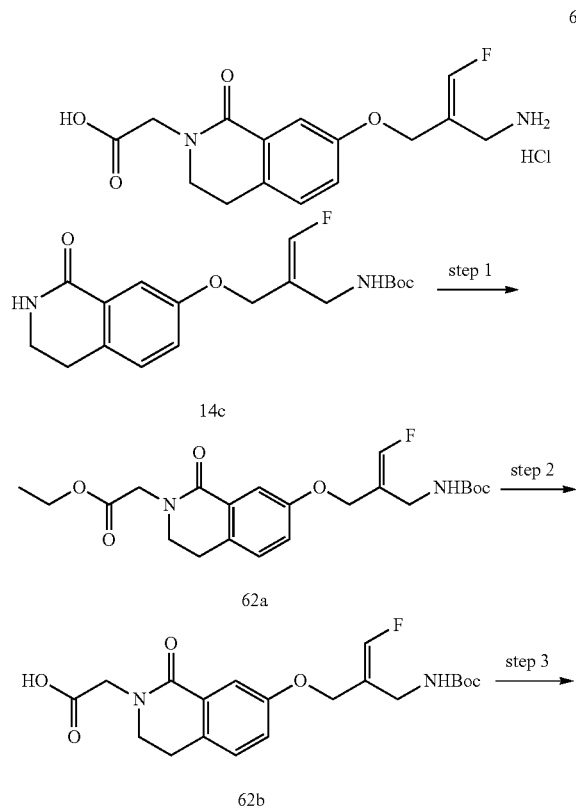

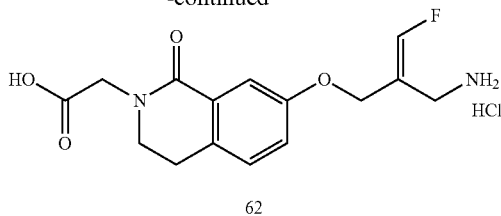

Step 1 ethyl 2-[7-[(E)-2-[(t-butoxycarbonylamino)methyl]-3-fluoro-allyloxy]-1-oxo-3,4-dihydroisoquinolin-2-yl]acetate 62a Sodium hydride (22 mg, 0.55 mmol, 60% wt) was added to tetrahydrofuran (2 mL), and a solution of tert-butyl N—[(E)-3-fluoro-2-[(1-oxo-3,4-dihydro-2H-isoquinolin-7-yl)oxymethyl]allyl]carbamate 14c (99 mg, 0.28 mmol) in tetrahydrofuran (5 mL) was added dropwise at rt, the mixture was stirred for 30 min, and ethyl bromoacetate (96 mg, 0.56 mmol) and tetrabutylammonium bromide (9 mg, 0.03 mmol) were added, the resulting mixture was further stirred for 24 hours. The mixture was poured into ice-water (8 mL) to quench the reaction. The resulting mixture was extracted with ethyl acetate (10 mL×3). The combined organic phases were washed with saturated sodium chloride solution (10 mL×3), dried over anhydrous sodium sulfate, filtered by suction filtration. The filtrate was concentrated. The residue was purified by silica gel column chromatography (ethyl acetate/petroleum ether (v/v)=1/2) to give the title compound 62a (105 mg, yield: 85%) as a white solid.

MS (ESI, pos. ion) m/z: 459.1[M+Na]$^+$.

Step 2 2-[7-[(E)-2-[(t-butoxycarbonylamino)methyl]-3-fluoro-allyloxy]-1-oxo-3,4-dihydroiso quinolin-2-yl]acetic acid 62b Ethyl 2-[7-[(E)-2-[(t-butoxycarbonylamino)methyl]-3-fluoro-allyloxy]-1-oxo-3,4-dihydro isoquinolin-2-yl]acetate 62a (105 mg, 0.24 mmol) was dissolved in 1,4-dioxane (6 mL), and lithium hydroxide (103 mg, 2.4 mmol) aqueous solution (6 mL) was added, the mixture was stirred at rt for 4 hours. To the reaction mixture was added water (10 mL), and the resulting mixture was adjusted to pH 4 with acetic acid and extracted with ethyl acetate (10 mL×3). The combined organic layers were washed with water (5 mL×3), dried over anhydrous sodium sulfate, and filtered by suction filtration. The filtrate was concentrated to give the title compound 62b (98 mg, yield: 99%) as colorless oil.

MS (ESI, pos. ion) m/z: 431.3[M+Na]$^+$.

Step 3 2-[7-[(E)-2-(aminomethyl)-3-fluoro-allyloxy]-1-oxo-3,4-dihydroisoquinolin-2-yl]acetic acid hydrochloride 62

2-[7-[(E)-2-[(tert-Butyloxycarbonylamino)methyl]-3-fluoro-allyloxy]-1-oxo-3,4-dihydroiso quinolin-2-yl]acetic acid 62b (98 mg, 0.24 mmol) was dissolved in ethyl acetate (1 mL), and then a hydrogen chloride-ethyl acetate solution (6 mL, 2 mol/L) was added, the mixture was stirred at rt for 1 hour. The mixture was concentrated to give the title compound 62 (82 mg, yield: 97%, HPLC: 93.23%) as a white solid.

MS (ESI, pos. ion) m/z: 309.2[M−Cl]$^+$;

¹H NMR (400 MHz, DMSO-d₆) δ (ppm) 8.19 (s, 3H), 7.47 (d, J=2.5 Hz, 1H), 7.29 (dd, J=45.2, 36.9 Hz, 2H), 7.14 (dd, J=8.3, 2.6 Hz, 1H), 4.65 (d, J=2.8 Hz, 2H), 4.21 (s, 2H), 3.63-3.58 (m, 4H), 2.93 (t, J=6.4 Hz, 2H).

Example 58 butyl 2-[6-[(E)-2-(aminomethyl)-3-fluoro-allyloxy]-1-oxo-3,4-dihydro isoquinolin-2-yl]acetate hydrochloride 63

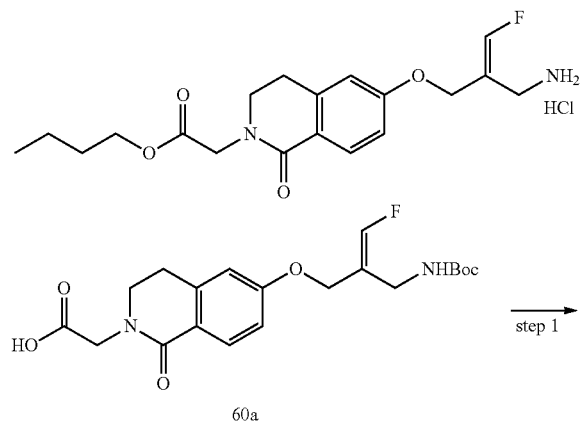

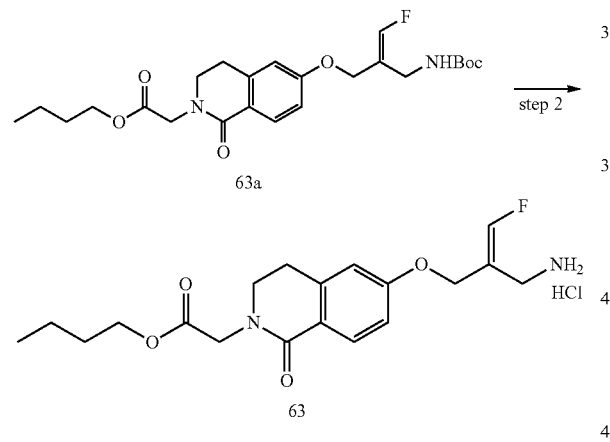

Step 1 butyl 2-[6-[(E)-2-[(t-butoxycarbonylamino)methyl]-3-fluoro-allyloxy]-1-oxo-3,4-dihydroisoquinolin-2-yl]acetate 63a 2-[6-[(E)-2-[(tert-Butyloxycarbonylamino)methyl]-3-fluoro-allyloxy]-1-oxo-3,4-dihydroiso quinolin-2-yl]acetic acid 60a (0.14 g, 0.34 mmol) was dissolved in n-butanol (6 mL), and then concentrated sulfuric acid (0.5 mL) was added dropwise, the mixture was stirred at 85° C. for 18 hours. The mixture was cooled to rt, and adding water (10 mL). The resulting mixture was adjusted with saturated sodium bicarbonate solution to pH 7 and extracted with ethyl acetate (20 mL×3). The combined organic phases were washed with saturated sodium chloride solution (20 mL×3), dried over anhydrous sodium sulfate, filtered by suction filtration. The filtrate was concentrated. The residue was purified by silica gel column chromatography (dichloromethane/methanol (v/v)=15/1) to give the title compound 63a (99 mg, yield: 79%) as colorless oil.

MS (ESI, pos. ion) m/z: 365.2[M+H]⁺.

Step 2 butyl 2-[6-[(E)-2-(aminomethyl)-3-fluoro-allyloxy]-1-oxo-3,4-dihydroisoquinolin-2-yl]acetate hydrochloride 63

Butyl 2-[6-[(E)-2-[(tert-butyloxycarbonylamino)methyl]-3-fluoro-allyloxy]-1-oxo-3,4-dihydroisoquinolin-2-yl]acetate 63a (99 mg, 0.2717 mmol) was dissolved in ethyl acetate (1 mL), and then a hydrogen chloride-1,4-dioxane solution (6 mL, 2 mol/L) was added, the mixture was stirred at rt for 1 hour. The mixture was concentrated to give the title compound 63 (98 mg, yield: 90%, HPLC: 95.26%) as a white solid.

MS (ESI, pos. ion) m/z: 365.3[M−Cl]⁺;

¹H NMR (400 MHz, DMSO-d₆) δ (ppm) 8.31 (s, 3H), 7.81 (d, J=8.5 Hz, 1H), 7.25 (d, J=82.1 Hz, 1H), 7.04-6.87 (m, 2H), 4.81 (s, 2H), 4.27 (s, 2H), 4.08 (t, J=6.5 Hz, 2H), 3.62 (t, J=6.4 Hz, 2H), 3.54 (s, 2H), 2.98 (t, J=6.3 Hz, 2H), 1.55 (dd, J=14.4, 6.7 Hz, 2H), 1.32 (dd, J=14.9, 7.4 Hz, 2H), 0.88 (t, J=7.4 Hz, 3H).

Example 59 6-[(E)-2-(aminomethyl)-3-fluoro-allyloxy]-2-(2-ethoxyethyl)-3,4-dihydro isoquinolin-1-one hydrochloride 64

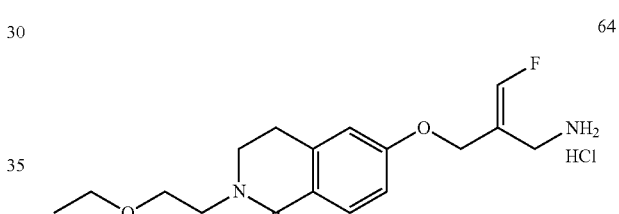

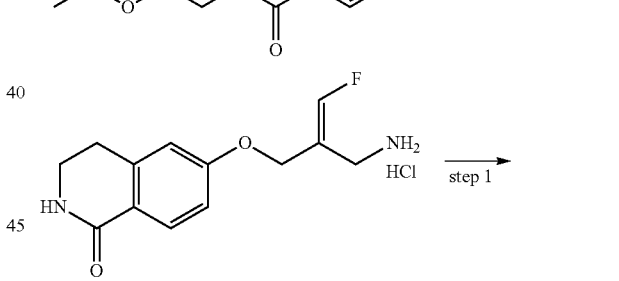

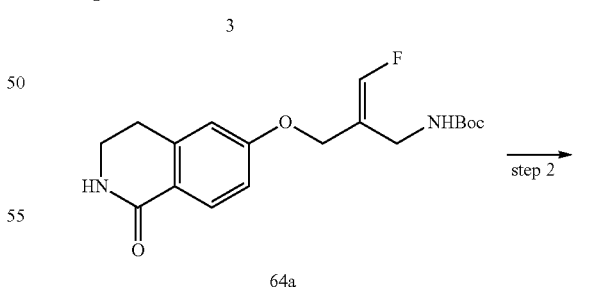

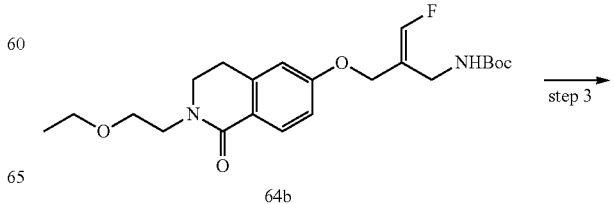

-continued

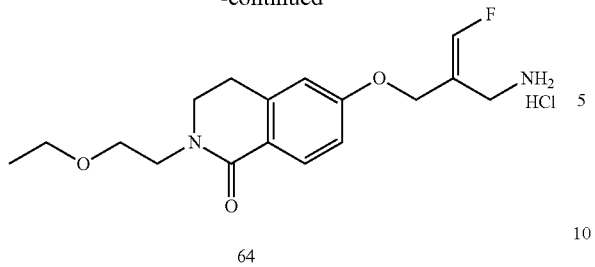

64

Step 1 t-butyl N-[3-fluoro-2-[(1-oxo-3,4-dihydro-2H-isoquinolin-6-yl)oxymethyl]allyl]carbamate 64a 6-[(E)-2-(Aminomethyl)-3-fluoro-allyloxy]-3,4-dihydro-2H-isoquinolin-1-one hydrochloride 3 (0.50 g, 1.7 mmol) was dissolved in methanol (8 mL), then triethylamine (0.61 mL, 4.4 mmol) was added, and then di-tert-butyl dicarbonate (0.45 mL, 1.9 mmol) was added dropwise, the mixture was stirred at rt for 30 min. The mixture was concentrated, the residue as a white solid was recrystallized (ethanol/ethyl acetate/petroleum ether (v/v/v)=1/10/9, 10 mL] to give the title compound 64a (0.49 g, yield: 80%) as a white solid.

Step 2 t-butyl N—[(E)-2-[[2-(2-ethoxyethyl)-1-oxo-3,4-dihydroisoquinolin-6-yl)oxymethyl]-3-fluoro-allyl]carbamate 64b At 0° C., a solution of t-butyl N-[3-fluoro-2-[(1-oxo-3,4-dihydro-2H-isoquinolin-6-yl)oxymethyl]allyl]carbamate 64a (100 mg, 0.28 mmol) in N,N-dimethylformamide (6 mL) was added to a solution of sodium hydride (15 mg, 0.37 mmol, 60% wt) in N,N-dimethylformamide (6 mL), the mixture was stirred at rt for 30 min, then 2-bromoethyl ethyl ether (0.036 mL, 0.31 mmol) was added, the reaction was allowed 11 hours. The mixture was poured into ice-water (10 mL) to quench the reaction. The resulting mixture was extracted with ethyl acetate (20 mL×2). The combined organic phases were washed with saturated sodium chloride solution (30 mL), dried over anhydrous sodium sulfate, filtered by suction filtration. The filtrate was concentrated. The residue was purified by silica gel column chromatography (ethyl acetate/petroleum ether (v/v)=4/3) to give the title compound 64b (71 mg, yield: 59%) as a white solid.
MS (ESI, pos. ion) m/z: 423.3 [M+H]+.

Step 3 6-[(E)-2-(aminomethyl)-3-fluoro-allyloxy]-2-(2-ethoxyethyl)-3,4-dihydroisoquinolin-1-one hydrochloride 64 t-Butyl N—[(E)-2-[[2-(2-ethoxyethyl)-1-oxo-3,4-dihydroisoquinolin-6-yl)oxymethyl]-3-fluoro-allyl]carbamate 64b (71 mg, 0.17 mmol) was dissolved in ethyl acetate (2 mL), and then a hydrogen chloride-ethyl acetate solution (3 mL, 2 mol/L) was added, the mixture was stirred at rt for 1 hour. The mixture was concentrated to give the title compound 64 (48 mg, yield: 80%, HPLC: 91.28%) as a white solid.
MS (ESI, pos. ion) m/z: 323.2 [M−Cl]+;
$^1$H NMR (400 MHz, DMSO-d$_6$) δ (ppm) 8.27 (s, 3H), 7.81 (d, J=8.4 Hz, 1H), 7.24 (d, J=82.1 Hz, 1H), 7.03-6.83 (m, 2H), 4.81 (s, 2H), 3.88 (m, 1H), 3.84 (t, J=11.2 Hz, 2H), 3.71 (t, J=8.0 Hz, 2H), 3.54 (s, 2H), 3.46 (q, J=11.8 Hz, 2H), 3.19-3.13 (m, 3H), 1.05 (t, J=11.8 Hz, 3H).

Example 60 benzyl 2-[6-[(E)-2-(aminomethyl)-3-fluoro-allyloxy]-1-oxo-3,4-dihydro isoquinolin-2-yl]acetate hydrochloride 65

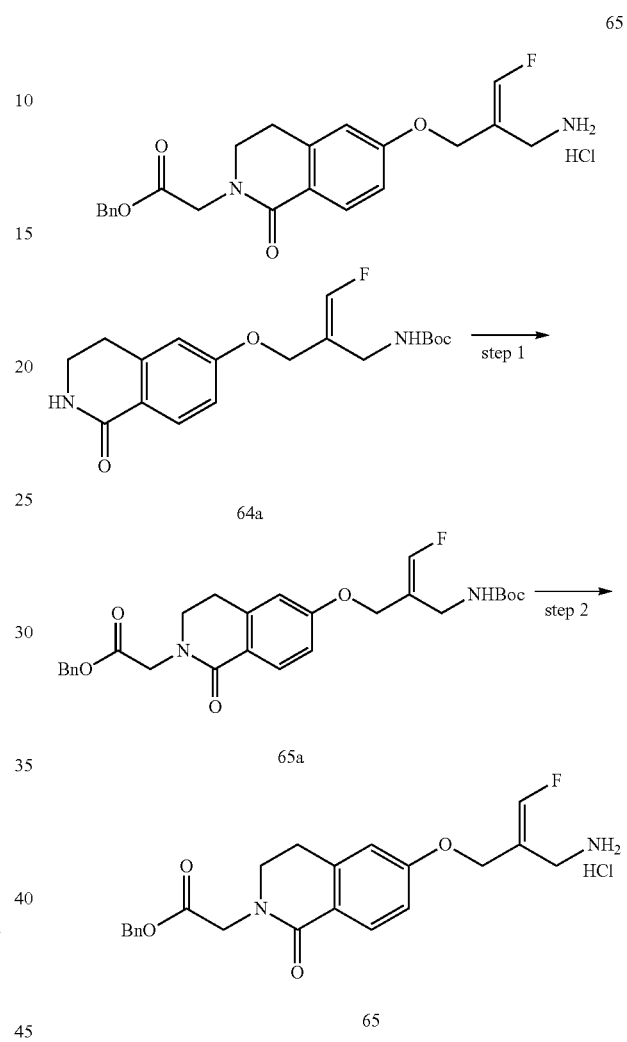

Step 1 benzyl 2-[6-[(E)-2-[(t-butoxycarbonylamino)methyl]-3-fluoro-allyloxy]-1-oxo-3,4-dihydroisoquinolin-2-yl]acetate 65a At 0° C., a solution of t-butyl N-[3-fluoro-2-[(1-oxo-3,4-dihydro-2H-isoquinolin-6-oxy)oxymethyl]allyl]carbamate 64a (100 mg, 0.28 mmol) in N,N-dimethylformamide (6 mL) was added into a solution of sodium hydride (15 mg, 0.37 mmol, 60% wt) in N,N-dimethylformamide (6 mL), the resulting mixture was stirred at rt for 30 min, and then benzyl 2-bromoacetate (0.052 mL, 0.32 mmol) was added, the resulting mixture was further stirred for 16 hours. The mixture was poured into ice-water (10 mL) to quench the reaction. The resulting mixture was extracted with ethyl acetate (20 mL×2). The combined organic phases were washed with saturated sodium chloride solution (30 mL), dried over anhydrous sodium sulfate, filtered by suction filtration. The filtrate was concentrated. The residue was purified by silica gel column chromatography (ethyl acetate/ petroleum ether (v/v)=2/1) to give the title compound 65a (54 mg, yield: 37%) as a white solid.

MS (ESI, pos. ion) m/z: 443.05 [M−55]+.

Step 2 benzyl 2-[6-[(E)-2-[(aminomethyl)-3-fluoro-allyloxy]-1-oxo-3,4-dihydroisoquinolin-1-one acetate 65

Benzyl 2-[6-[(E)-2-[(t-butoxycarbonylamino)methyl]-3-fluoro-allyloxy]-1-oxo-3,4-dihydro isoquinolin-2-yl]acetate 65a (52 mg, 0.10 mmol) was dissolved in ethyl acetate (2 mL), and then a hydrogen chloride-1,4-dioxane solution (3 mL, 2 mol/L) was added, the mixture was stirred at rt for 1 hour. The mixture was concentrated to give the title compound 65 (40 mg, yield: 88%, HPLC: 89.75%) as colorless thick oil.

MS (ESI, pos. ion) m/z: 399.1 [M−Cl]+;

$^1$H NMR (400 MHz, DMSO-$d_6$) δ (ppm) 8.25 (s, 3H), 7.82 (d, J=8.6 Hz, 1H), 7.44 (s, 1H), 7.41-7.30 (m, 5H), 7.23 (s, 1H), 7.01-6.89 (m, 2H), 5.16 (s, 2H), 4.69 (d, J=2.4 Hz, 2H), 4.34 (s, 2H), 3.69-3.56 (m, 4H), 2.98 (t, J=6.3 Hz, 2H).

Examples of Biological Assay

1. Determination of Inhibitory Activity of Human Recombinant SSAO/VAP-1

Test purpose: The following methods can be used to determine the inhibitory activity of the compounds described in the examples of the invention for human recombinant SSAO/VAP-1.

Test Materials:

Human recombinant SSAO/VAP-1 (VAP-1, human) purchased from Sigma, Cat. No. SRP6241;

Amplex® Red Monoamine Oxidase Assay Kit purchased from Invitrogen, Cat. No. A12214;

384-Well plate purchased from Corning, Cat. No. 6005174;

Amplex® Red Hydrogen PeroxidePeroxidase Assay Kit purchased from Invitrogen, Cat. No. A22188.

Benzylamine hydrochloride purchased from Sigma, Cat. No. B5136-25G;

DMSO (Dimethyl Sulfoxide) purchased from Sigma, Cat. No. D2650-100ML;

Test Method:

The test compound was dissolved in DMSO and diluted to 10 concentrations in 4-fold serial dilution. In 384 well plates, 25 μL of human recombinant SSAO/VAP-1 (1.6 μg/ml) was added to each well. 100 nL of test compounds with different concentrations were added to each well containing human recombinant SSAO/VAP-1 and incubated at room temperature for 30 min. After 30 min incubation, 25 μl of Amplex® red monoamine oxidase assay kit (containing a reaction mixture of 200 μm Amplex Red reagent, 1 U/ml HRP and 1 mm benzylamine hydrochloride) was added to the corresponding well, and incubated at room temperature and dark for 60 min. After 60 min, the relative fluorescence unit (RFU) was read by using PerkinElmer's Envision at 530-560 nm excitation and 590 nm emission. The curve was drawn by using the graph pad prism 5 software, and the $IC_{50}$ value was calculated. The results were shown in table 1, wherein the compound listed in table 1 is the compound in the preparation examples with the same compound number:

TABLE 1 the inhibitory activity of the compounds of the invention for human recombinant SSAO/VAP-1

| No. | SSAO/VAP-1(Human recombinant protein) $IC_{50}$/nM |
|---|---|
| 2 | 1.01 |
| 5 | 0.37 |
| 6 | 0.04 |
| 7 | 0.09 |
| 8 | 0.32 |
| 9 | 0.61 |
| 10 | 0.22 |
| 11 | 0.82 |
| 12 | 0.14 |
| 13 | 0.11 |
| 16 | 0.22 |
| 17 | 0.58 |
| 18 | 0.48 |
| 19 | 1.00 |
| 21 | 0.91 |
| 24 | 1.16 |
| 28 | 1.53 |
| 29 | 0.77 |
| 33 | 1.98 |
| 34 | 1.16 |
| 35 | 0.71 |
| 38 | 0.68 |
| 39 | 0.53 |
| 40 | 1.00 |
| 41 | 0.63 |
| 42 | 1.13 |
| 43 | 0.71 |
| 53 | 1.04 |
| 54 | 1.44 |
| 55 | 0.82 |
| 56 | 1.91 |
| 57 | 1.27 |
| 58 | 1.17 |
| 59 | 1.30 |

The test results shown that the $IC_{50}$ of the inhibition activity of human recombinant SSAO/VAP-1 of the compounds of the invention is less than 10 nm, and the $IC_{50}$ of the inhibition activity of human recombinant SSAO/VAP-1 of most compounds is less than 2 nM; and the $IC_{50}$ of the inhibition activity of human recombinant SSAO/VAP-1 of some compounds is less than 0.5 nm. It can be seen that the compound of the invention has obvious inhibitory effect on human recombinant SSAO/VAP-1.

2. Determination of Inhibitory Activity of Rat Adipose Tissue Homogenate SSAO/VAP-1

Test purpose: The following methods can be used to determine the inhibitory activity of the compounds of the invention for rat adipose tissue homogenate SSAO/VAP-1.

Test Materials

Sodium N-piperazine-N-ethanesulfonate (HEPES SODIUM SALT) purchased from AMRESCO, Cat. No. 0485-500G;

EDTA (Ethylenediaminetetraacetic acid) purchased from Sigma, Cat. No. EDS-100G;

Sucrose purchased from Sigma, Cat. No. V900116;

PMSF (Phenylmethanesulfonyl fluoride) purchased from Beyotime, Cat. No. ST506;

β-Glycerophosphate disodium salt hydrate purchased from Sigma, Cat. No. G5422-25G;

Pargyline hydrochloride purchased from Sigma, Cat. No. P8013-500MG;

DMSO (Dimethyl Sulfoxide) purchased from Sigma, Cat. No. D2650-100ML;

Benzylamine hydrochloride purchased from Sigma, Cat. No. B5136-25G;

96-Well plate purchased from COSTAR, Cat. No. 3631;

Amplex® Red Hydrogen PeroxidePeroxidase Assay Kit purchased from Invitrogen, Cat. No. A22188.

Test Method

The abdominal fat removed from Sprague Dawley rats was a tissue rich in SSAO/VAP-1. 5 mL Of HES buffer per gram of rat abdominal adipose tissue (20 mM Sodium N-piperazine-N-ethanesulfonate, 1 mm EDTA, 250 mM sucrose, 1×PMSF and 100 mM (3-glycerol phosphate disodium salt hydrate, pH 7.4) was added for homogenizing. The fat tissue was homogenized for 3 min by using Bertin precellys 24 multi-functional sample homogenizer of Bertin technologies, and the fat tissue homogenate was centrifuged for 10 min at 4° C. and 20000 g, and the middle transparent supernatant was taken. The supernatant was incubated with 0.5 mm Pargyline hydrochloride dissolved in HES buffer at 37° C. for 30 min. After 30 min incubation, 25 μl of fat tissue supernatant was added to the standard 96 well plate. The test compound was dissolved in DMSO and diluted to 6 concentrations. 25 μL Of the test compounds with different concentrations was added to each well containing the supernatant of fat tissue and incubated at 37° C. for 30 min. After incubation, 50 μL of the reaction mixture containing 80 μM benzylamine hydrochloride (containing 100 μM Amplex® red and 0.2 U/mL HRP, Amplex® Red Hydrogen peroxide-peroxidase assay kit) was added to the corresponding wells and incubated at 37° C. for 30 min. After 30 min, the relative fluorescence unit (RFU) was read by using PHERAstar FSX enzyme marker of BMG LABTECH at 540 nm excitation and 580 nm emission. The curve was drawn by using the graph pad prism 5 software, and the $IC_{50}$ value was calculated. The results were shown in table 2, wherein the compound listed in table 2 is the compound in the preparation examples with the same compound number: Table 2: inhibitory activity of the compound of examples of the invention for SSAO/VAP-1 of fat tissue homogenate

| No. | SSAO/VAP-1(adipose tissue homogenate) $IC_{50}$/nM |
|---|---|
| 1 | 10.09 |
| 2 | 11.64 |
| 5 | 4.875 |
| 7 | 8.977 |
| 8 | 8.835 |
| 9 | 8.050 |
| 10 | 9.536 |
| 11 | 11.70 |
| 12 | 10.05 |
| 13 | 8.032 |
| 16 | 6.014 |
| 17 | 5.034 |
| 18 | 6.131 |
| 19 | 5.701 |
| 32 | 6.218 |
| 33 | 4.882 |

The results shown that the compound of the invention has obvious inhibitory effect on adipose tissue homogenate SSAO/VAP-1.

3. Determination of Selective Inhibitory for DAO (Diamine Oxidase)

Test purpose: The following methods can be used to determine the selective inhibitory activity of the compounds of the invention for DAO.

Test Materials human recombinant DAO (Recombinant Human ABP-1/DAO) purchased from R&D, Cat. No. 8298-AO;

Amplex® Red Hydrogen PeroxidePeroxidase Assay Kit purchased from Invitrogen, Cat. No. A22188;

1,4-Diaminobutane dihydrochloride purchased from Aladdin, Cat. No. D106194-25G;

Test Method

The test compound was dissolved in DMSO and diluted to 6 concentrations in 5-fold serial dilution. In 384 well plates, 24 μL of human recombinant DAO (1 μg/mL) was added to each well. 1 μL Of test compounds with different concentrations were added to each well containing human recombinant DAO and incubated at 37° C. for 30 min. After 30 min incubation, 25 μL of Amplex® Red Hydrogen PeroxidePeroxidase Assay Kit (containing a reaction mixture of 100 μM Amplex® Red and 0.2 U/mL HRP) containing 1 M 1,4-Diaminobutane dihydrochloride was added to the corresponding well, and incubated at 37° C. and dark for 30 min. After 30 min, the relative fluorescence unit (RFU) was read by using PHERAstar FSX enzyme marker of BMG LABTECH at 540 nm excitation and 580 nm emission. The curve was drawn by using the graph pad prism 5 software, and the $IC_{50}$ value was calculated. The results were shown in table 3, wherein the compound listed in table 3 is the compound in the preparation examples with the same compound number:

TABLE 3

Inhibitory activity of the compound of the invention for DAO

| No. | DAO $IC_{50}$/μM |
|---|---|
| 3 | >0.1 |
| 12 | >0.1 |
| 14 | >1 |
| 24 | >0.1 |
| 46 | >0.1 |

The test results shown that the inhibition activity of the compound for DAO is far weaker than for SSAO/VAP-1 activity, indicating that the compound has high selectivity to SSAO/VAP-1.

4. Pharmacokinetic Activities of the Compounds of the Invention

Test purpose: The following methods were used to evaluate the pharmacokinetics of the compound of the invention.

Test Materials

Test reagents and test samples: propranolol (interior label), methanol, ammonium acetate, $K_2EDTA$ (dipotassium ethylenediamine tetraacetic acid), formic acid, acetonitrile, MTBE (methyl tert-butyl ether), KolliphorHS15 (polyethyleneglycol-12-hydroxy stearate) and DMSO (dimethyl sulfoxide) are commercially available;

SD rats: male, 180-220 g, 7-8 weeks old, purchased from Hunan SJA Laboratory Animal Co., Ltd.

Test Method

1). Preparation of Test Sample

Test compound was prepared by dissolving in a mixture of 5% DMSO+5% KolliphorHS15+90% Saline and adjusted according to the dissolution of each compound, so that the compound can be completely dissolved.

2). Animal Experiment Design

| Test substances | Compounds of the examples of the invention |
|---|---|
| Animals grouping | intravenous injection/I.V.: n = 3; blood collecting time (hours/h): 0.083, 0.25, 0.5, 1, 2, 5, 7, 24 oral administration/P.O.: n = 3; blood collecting time (hours/h): 0.083, 0.25, 0.5, 1, 2, 5, 7, 24 |
| drug-delivery way | Vein: administration through the crural vein of hind legs; oral: gavage. |

-continued

| Test substances | Compounds of the examples of the invention |
|---|---|
| blood collection methods | blood collection from tail veins |
| blood capacity taken | 200~400 μL/time point |
| anticoagulant | K₂EDTA |
| preparation of plasma | All samples within 60 min were centrifuged at 10000 rpm, 4° C. for 2 min to separate plasma. The sample was stored at −80° C. for testing. The backup samples shall be kept for 1 month after the analysis. |
| Fasting situation | Fasted for 15 h before administered, free drank. Eating after administration for 4 h. |
| stock solution vehicle | Test substances: 20% DMSO; interior label: Propranolol aqueous solution (100 ng/mL) |
| Data processing | Pharmacokinetic parameters were calculated using a noncompartmental method by WinNonLin 6.1 software. |

3). Animal Administration Dosage Scale

| Group | sex | Animal number | dosage of administration | dosage concentration | dosage volume |
|---|---|---|---|---|---|
| intravenous injection I.V. | male | 3 | 1 mg/kg | 1 mg/mL | 1 mL/kg |
| Oral P.O. | male | 3 | 5 mg/kg | 1 mg/mL | 5 mL/kg |

4). Preparation of Solution (1) Preparation of test sample stock solution: weighing accurately an appropriate amount of test sample, dissolving it with DMSO, diluting it with acetonitrile to 1 mg/mL, and shaking it well. Store at −20° C. prior to use.

(2) Preparation of internal standard solution: sucking accurately a certain amount of 1 mg/mL propranolol stock solution, and diluting to 100 ng/mL with water.

5). Analysis of the Sample

The samples were processed by liquid-liquid extraction, separated by chromatography, quantitatively analyzed by multiple reaction ion monitoring (MRM) on triple quadrupole tandem mass spectrometer, and the results were calculated by using quantitative software.

6). Pretreatment of Plasma Sample

Taking 30 μL of plasma sample precisely, adding 250 μL of internal standard, and vortex mixing uniformly. Extracting once with 1 mL MTBE, centrifugating at 13000 rpm and 4° C. for 2 min, taking 800 μL of supernatant, and evaporating it in a 96-well termovap sample concentrator, dissolving the residue with 150 μL methanol/water=50/50, vortex mixing, injecting 8 μL.

7). Preparation of Standard Sample

Taking accurately an appropriate amount of compound stock solution, adding acetonitrile to dilute to make standard series solution. Taking accurately 20 μL of each the above standard series of solution, adding 180 μL of blank plasma, vortex mixing, and preparing plasma samples at plasma concentrations of 3, 5, 10, 30, 100, 300, 1000, 3000, 5000 and 10000 ng/mL, all were operated according to the "pretreatment of plasma samples", two-sample analysis is conducted for each concentration to establish the standard curve.

8) Analysis Method:

Determining the content of different compounds in the plasma of rats after the administration by using LC/MS/MS method.

9). Data Processing

Pharmacokinetic parameters were calculated using a noncompartmental method by WinNonLin 6.1 software.

The pharmacokinetic data of the compounds of the invention were listed in table 4, wherein the compound listed in table 4 is the compound in the preparation examples with the same compound number:

TABLE 4

Pharmacokinetic activities of the compounds of the examples of the invention

| No. | administration on route | dosage mg/kg | $T_{max}$ h | $C_{max}$ ng/mL | $t_{1/2}$ h | $AUC_{last}$ hr * ng/mL | $AUC_{INF}$ hr * ng/mL | CL L/h/Kg | Vss L/Kg |
|---|---|---|---|---|---|---|---|---|---|
| 12 | I.V. | 1 | 0.25 | 946 | 0.936 | 837 | 843 | 19.8 | 1.07 |
|  | P.O. | 5 | 0.417 | 2190 | 0.959 | 2890 | 2900 | N/A | N/A |
| 24 | I.V. | 1 | 0.083 | 144 | 2.99 | 364 | 450 | 37 | 9.19 |
|  | P.O. | 5 | 2.5 | 569 | 3.45 | 5280 | 5320 | N/A | N/A |

The test results shown that the compound of the invention has excellent pharmacokinetic properties when administered intravenously or orally, for example, good absorption and high exposure. In particular, the compounds of the invention have high $C_{max}$, $AUC_{last}$ and $AUC_{inf}$ in SD rats, indicating that the compounds of the invention have high exposure and good absorption in rats.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, without any contradiction, those skilled in the art may combine different embodiments or examples and features of the different embodiments or examples described in this specification.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, a solvate, a pharmaceutically acceptable salt or a prodrug thereof,

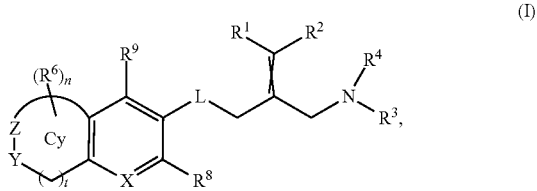

(I)

wherein
Y is —CH$_2$—, —S(=O)—, —S(=O)$_2$— or —C(=O)—;
Z is —N(R$^5$)— or —N=;
X is —N= or —C(R$^7$)—;
L is —O—, —S— or —NH—;
ring Cy is 5- to 8-membered heterocyclyl;
each R$^6$ is independently H;
R$^5$ is H, D, F, Cl, Br, I, CN, NO$_2$, =O, —C(=O)R$^a$, —C(=O)OR$^b$, —C(=O)NR$^c$R$^d$, —SR$^e$, —S(=O)$_2$R$^e$, —S(=O)R$^e$, —S(=O)$_2$NR$^c$R$^d$, —NR$^f$C(=O)R$^a$, —NR$^f$S(=O)$_2$R$^e$, —NR$^c$R$^d$, —OR$^b$, R$^b$O—C$_{1-4}$ alkylene, R$^b$O—C(=O)—C$_{1-4}$alkylene, R$^d$R$^c$N—C$_{1-4}$alkylene, C$_{1-6}$haloalkyl, C$_{1-6}$ alkyl, C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, 5- to 6-membered heteroaryl or (5- to 10-membered heteroaryl)-C$_{1-4}$ alkylene, wherein each of the C$_{2-6}$ alkenyl, C$_{2-6}$ alkynyl, C$_{3-8}$ cycloalkyl-C$_{1-4}$ alkylene, 3- to 8-membered heterocyclyl, (3- to 8-membered heterocyclyl)-C$_{1-4}$ alkylene, 5- to 6-membered heteroaryl and (5- to 10-membered heteroaryl)-C$_{1-4}$ alkylene is independently unsubstituted or substituted with 1, 2, 3 or 4 substituents, the substituent is independently selected from D, F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, C$_{6-10}$ aryl, 5- to 10-membered heteroaryl, C$_{1-6}$ haloalkyl, C$_{1-6}$ alkoxy, C$_{1-6}$ alkylamino or C$_{1-6}$ haloalkoxy; each of the C$_{1-6}$ alkyl is independently substituted with 1, 2, 3 or 4 substituents, the substituent is independently selected from F, Cl, Br, I, CN, NO$_2$, —OR$^b$, —NR$^c$R$^d$, —C(=O)OR$^b$, C$_{1-6}$ alkyl, C$_{3-8}$ cycloalkyl, 3- to 8-membered heterocyclyl, 5- to 10-membered heteroaryl, C$_{1-6}$ haloalkyl, C$_{1-6}$ alkoxy, C$_{1-6}$ alkylamino or C$_{1-6}$ haloalkoxy;
each of R$^8$ and R$^9$ is independently H, D, Br, I, CN, NO$_2$, —C(=O)R$^a$, —C(=O)OR$^b$, —C(=O)NR$^c$R$^d$, —OH, NH$_2$, R$^b$O—C$_{1-4}$ alkylene, R$^d$R$^c$N—C$_{1-4}$ alkylene, C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl or 5- to 8-membered heteroaryl, wherein each of the C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl and 5- to 8-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
R$^7$ is H, D, F, Cl, Br, I, CN, NO$_2$, —C(=O)R$^a$, —C(=O)OR$^b$, —C(=O)NR$^c$R$^d$, —OH, NH$_2$, R$^b$O—C$_{1-4}$ alkylene, R$^d$R$^c$N—C$_{1-4}$ alkylene, C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl or 5- to 8-membered heteroaryl, wherein each of the C$_{1-6}$ alkyl, C$_{1-6}$ haloalkyl, C$_{1-6}$ haloalkoxy, C$_{3-6}$ cycloalkyl, 3- to 8-membered heterocyclyl, C$_{6-10}$ aryl and 5- to 8-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
R$^1$ is H, D, F, Cl, Br, I, C$_{1-6}$ alkyl, —C(=O)OR$^b$, —C(=O)R$^a$, —OC(=O)R$^a$, —OC(=O)OR$^b$, —NR$^f$C(=O)R$^a$, —NR$^f$S(=O)$_2$R$^e$, —C(=O)NR$^c$R$^d$, —S(=O)$_2$NR$^c$R$^d$, —S(=O)$_2$R$^e$, —SR$^e$ or —S(=O)R$^e$, wherein the C$_{1-6}$ alkyl is unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
R$^2$ is F, Cl, Br, I, C$_{1-6}$ alkyl, —C(=O)OR$^b$, —C(=O)R$^a$, —OC(=O)R$^a$, —OC(=O)OR$^b$, —NR$^f$C(=O)R$^a$, —NR$^f$S(=O)$_2$R$^e$, —C(=O)NR$^c$R$^d$, —S(=O)$_2$NR$^c$R$^d$, —S(=O)$_2$R$^e$, —SR$^e$ or —S(=O)R$^e$, wherein the C$_{1-6}$ alkyl is unsubstituted or substituted with 1, 2, 3 or 4 substituents, the substituent is independently selected from D, F, Cl, Br, I, CN, NO$_2$, —OH, NH$_2$, C$_{1-6}$ alkyl, C$_{1-6}$ haloalkyl, C$_{1-6}$ alkoxy, C$_{1-6}$ alkylamino or C$_{1-6}$ haloalkoxy;
each of R$^3$ and R$^4$ is independently H, D, C$_{1-6}$ alkyl, C$_{1-6}$ haloalkyl, C$_{3-6}$ cycloalkyl, 3- to 6-membered heterocyclyl, C$_{6-10}$ aryl, 5- to 6-membered heteroaryl or

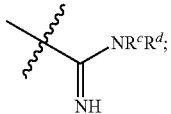

wherein each of the C$_{1-6}$ alkyl, C$_{1-6}$ haloalkyl, C$_{3-6}$ cycloalkyl, 3- to 6-membered heterocyclyl, C$_{6-10}$ aryl and 5- to 6-membered heteroaryl is independently unsubstituted or substituted with 1, 2, 3 or 4 substituents, the substituent is independently selected from D, F, Cl, Br, I, CN, —OH, NH$_2$, C$_{1-6}$ alkyl, C$_{1-6}$ haloalkyl, C$_{1-6}$ alkoxy or C$_{1-6}$ alkylamino;
or, R$^3$ and R$^4$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, C$_{1-6}$ alkyl, C$_{1-6}$ haloalkyl, C$_{1-6}$ alkoxy or C$_{1-6}$ alkylamino;
each R$^a$, R$^b$, R$^c$, R$^d$, R$^e$ and R$^f$ is independently H, D, —OH, C$_{1-6}$ haloalkyl, C$_{1-6}$ alkyl, C$_{1-6}$ alkoxy, C$_{2-6}$ alkenyl, C$_{2-6}$ alkynyl, C$_{3-6}$ cycloalkyl, C$_{3-6}$ cycloalkyl-C$_{1-4}$ alkylene, 3- to 6-membered heterocyclyl, (3- to 6-membered heterocyclyl)-C$_{1-4}$ alkylene, C$_{6-10}$ aryl, C$_{6-10}$ aryl-C$_{1-4}$ alkylene, 5- to 6-membered heteroaryl or (5- to 6-membered heteroaryl)-C$_{1-4}$ alkylene, wherein each of the C$_{1-6}$ haloalkyl, C$_{1-6}$ alkyl, C$_{1-6}$ alkoxy, C$_{2-6}$ alkenyl, C$_{2-6}$ alkynyl, C$_{3-6}$ cycloalkyl, C$_{3-6}$ cycloalkyl-C$_{1-4}$ alkylene, 3- to 6-membered heterocyclyl, (3- to 6-membered heterocyclyl)-C$_{1-4}$ alkylene, C$_{6-10}$ aryl, C$_{6-10}$ aryl-C$_{1-4}$ alkylene, 5- to 6-membered heteroaryl and (5- to 6-membered heteroaryl)-C$_{1-4}$ alkylene is independently unsubstituted or substituted with 1, 2, 3 or 4 substituents, the substituent is independently selected from D, F, Cl, Br, I, CN, —OH, NH$_2$, C$_{1-6}$ alkyl, C$_{1-6}$haloalkyl, C$_{1-6}$ alkoxy or C$_{1-6}$ alkylamino;
or, R$^c$ and R$^d$ together with the nitrogen atom to which they are attached, form 3- to 6-membered heterocyclyl or 5- to 6-membered heteroaryl, wherein each of the 3- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, C$_{1-6}$ alkyl, C$_{1-6}$ haloalkyl, C$_{1-6}$ alkoxy or C$_{1-6}$ alkylamino;

n is 0, 1, 2, 3 or 4;

t is 0, 1, 2, 3 or 4;

with the exception of the compounds:

6-[(E)-2-(aminomethyl)-3-fluoro-allyloxy]-3,4-dihydro-2H-isoquinolin-1-one,

6-[(Z)-2-(aminomethyl)-3-fluoro-allyloxy]-3,4-dihydro-2H-isoquinolin-1-one,

7-[(E)-2-(aminomethyl)-3-fluoro-allyloxy]-3,4-dihydro-2H-isoquinolin-1-one,

7-[(Z)-2-(aminomethyl)-3-fluoro-allyloxy]-3,4-dihydro-2H-isoquinolin-1-one,

5-[(Z)-2-(aminomethyl)-3-fluoro-allyloxy]isoindolin-1-one,

5-[(E)-2-(aminomethyl)-3-fluoro-allyloxy]isoindolin-1-one,

7-[(E)-2-(aminomethyl)-3-fluoro-allyloxy]-2,3,4,5-tetrahydro-2-benzoazepin-1-one, 7-[(Z)-2-(aminomethyl)-3-fluoro-allyloxy]-2,3,4,5-tetrahydro-2-benzoazepin-1-one,

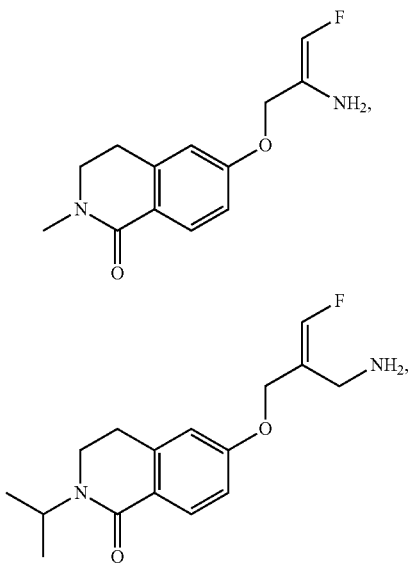

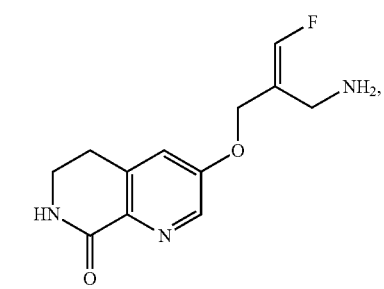

-continued

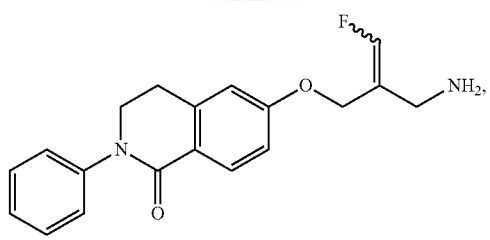

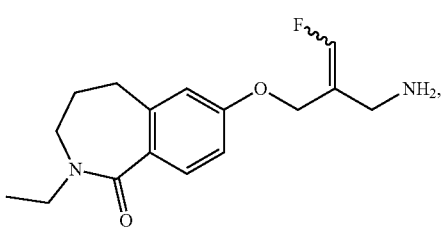

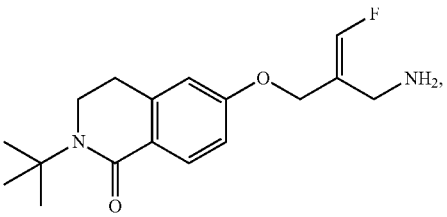

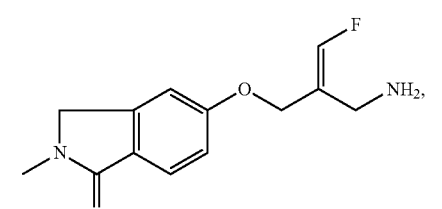

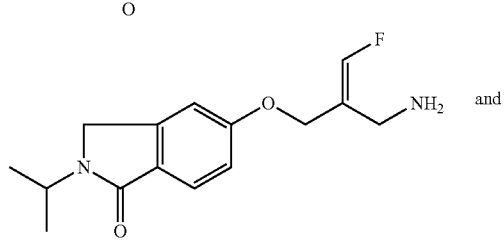

and

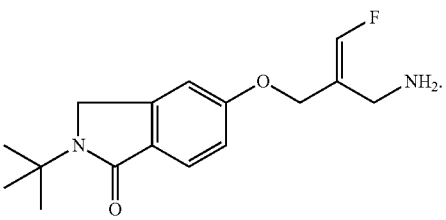

2. The compound of claim 1, wherein ring Cy is 5-membered heterocyclyl, or 6-membered heterocyclyl.

3. The compound of claim 1, wherein ring Cy is

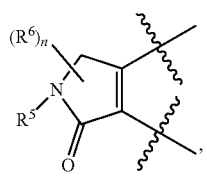 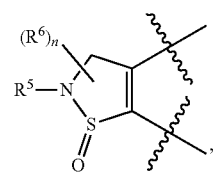

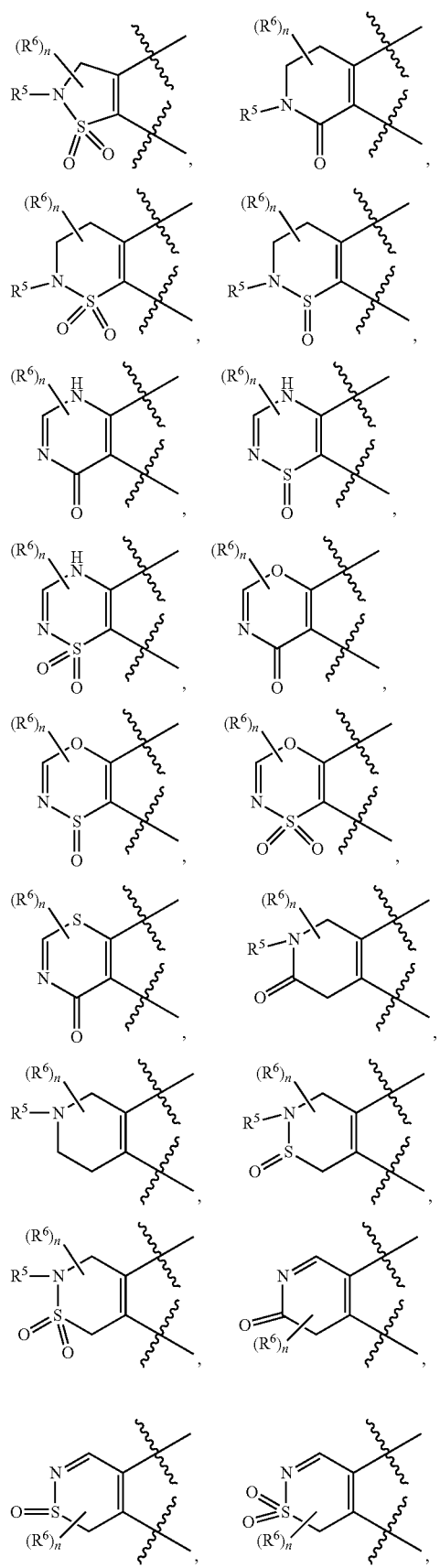
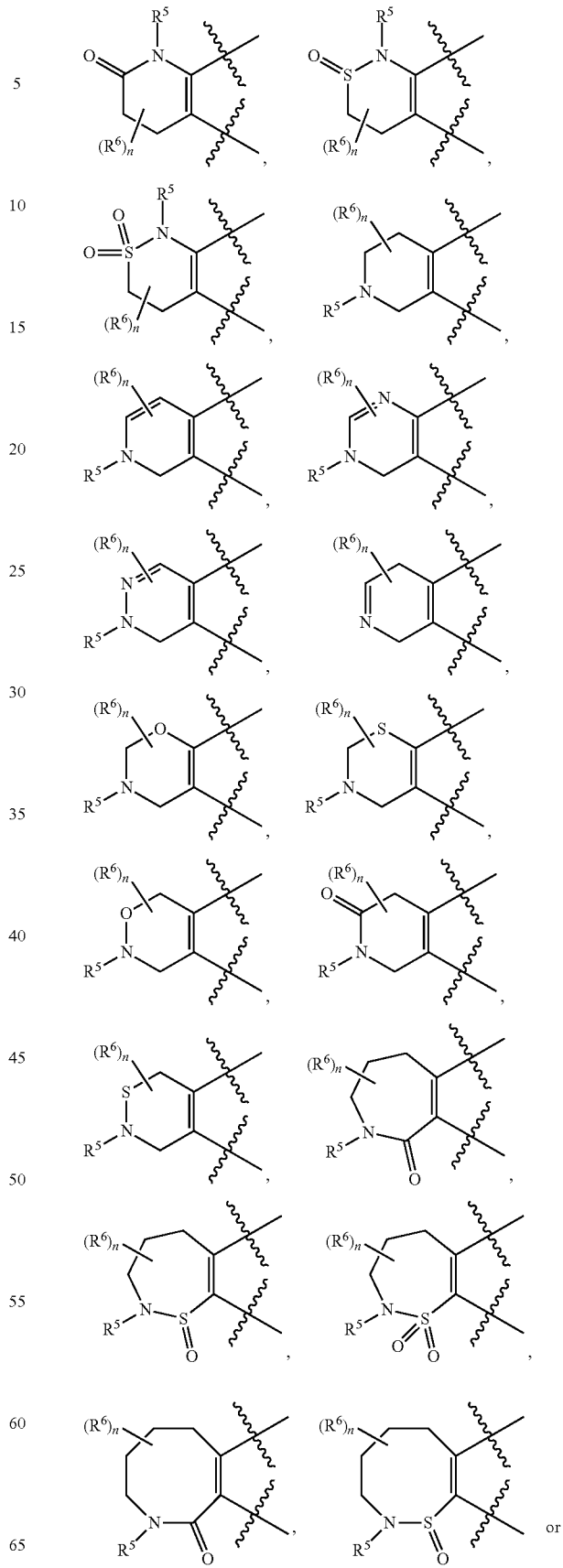
or

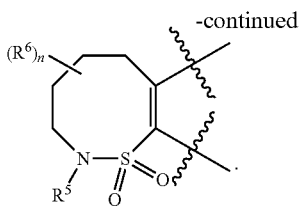

4. The compound of claim 1, wherein $R^5$ is H, D, F, Cl, Br, I, CN, NO$_2$, =O, —C(=O)R$^a$, —C(=O)OR$^b$, —C(=O)NR$^c$R$^d$, —SR$^e$, —S(=O)$_2$R$^e$, —S(=O)R$^e$, —S(=O)$_2$NR$^c$R$^d$, —NR$^f$C(=O)R$^a$, —NR$^f$S(=O)$_2$R$^e$, —NR$^c$R$^d$, —OR$^b$, R$^b$O—C$_{1-2}$ alkylene, R$^b$O—C(=O)—C$_{1-2}$ alkylene, R$^d$R$^c$N—C$_{1-2}$ alkylene, C$_{1-4}$ haloalkyl, C$_{1-4}$ alkyl, C$_{2-4}$ alkenyl, C$_{2-4}$ alkynyl, C$_{3-6}$ cycloalkyl-C$_{1-2}$ alkylene, 3- to 6-membered heterocyclyl, (3- to 6-membered heterocyclyl)-C$_{1-2}$ alkylene, 5- to 6-membered heteroaryl or (5- to 6-membered heteroaryl)-C$_{1-2}$ alkylene, wherein each of the C$_{2-4}$ alkenyl, C$_{2-4}$ alkynyl, C$_{3-6}$ cycloalkyl-C$_{1-2}$ alkylene, 3- to 6-membered heterocyclyl, (3- to 6-membered heterocyclyl)-C$_{1-2}$ alkylene, 5- to 6-membered heteroaryl and (5- to 6-membered heteroaryl)-C$_{1-2}$ alkylene is independently unsubstituted or substituted with 1, 2, 3 or 4 substituents, the substituent is independently selected from D, F, Cl, Br, I, CN, NO$_2$, —OR$^b$, —NR$^c$R$^d$, —C(=O)OR$^b$, C$_{1-4}$ alkyl, C$_{3-6}$ cycloalkyl, 3- to 6-membered heterocyclyl, C$_{6-10}$ aryl, 5- to 6-membered heteroaryl, C$_{1-4}$ haloalkyl, C$_{1-4}$ alkoxy, C$_{1-4}$ alkylamino or C$_{1-4}$ haloalkoxy; each of the C$_{1-4}$ alkyl and is independently substituted with 1, 2, 3 or 4 substituents, the substituent is independently selected from D, F, Cl, Br, I, CN, NO$_2$, —OR$^b$, —NR$^c$R$^d$, —C(=O)OR$^b$, C$_{1-4}$ alkyl, C$_{3-6}$ cycloalkyl, 3- to 6-membered heterocyclyl, 5- to 6-membered heteroaryl, C$_{1-4}$ haloalkyl, C$_{1-4}$ alkoxy, C$_{1-4}$ alkylamino or C$_{1-4}$haloalkoxy.

5. The compound of claim 1, wherein $R^5$ is H, D, F, Cl, Br, I, CN, NO$_2$, =O, —C(=O)R$^a$, —C(=O)OH, —C(=O)OCH$_3$, —C(=O)OCH$_2$CH$_3$, —C(=O)OCH$_2$CH$_2$CH$_3$, —C(=O)OCH(CH$_3$)$_2$, —C(=O)NH$_2$, —SR$^e$, —S(=O)$_2$R$^e$, —S(=O)R$^e$, —S(=O)$_2$NR$^c$R$^d$, —NHC(=O)R$^a$, —NHS(=O)$_2$R$^e$, NH$_2$, —OH, R$^b$O—C$_{1-2}$alkylene, R$^b$O—C(=O)—C$_{1-2}$ alkylene, trifluoromethyl, methyl, ethyl, n-propyl, i-propyl, vinyl, propynyl, C$_{3-6}$ cycloalkyl-C$_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-C$_{1-2}$ alkylene, C$_{6-10}$ aryl-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl or (5- to 6-membered heteroaryl)-C$_{1-2}$ alkylene, wherein each of the vinyl, propynyl, C$_{3-6}$cycloalkyl-C$_{1-2}$ alkylene, tetrahydrofuranyl, tetrahydrothienyl, tetrahydropyranyl, piperidinyl, morpholinyl, thiomorpholinyl, piperazinyl, (3- to 6-membered heterocyclyl)-C$_{1-2}$ alkylene, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl and (5- to 6-membered heteroaryl)-C$_{1-2}$alkylene is independently unsubstituted or substituted with 1, 2, 3 or 4 substituents, the substituent is independently selected from D, F, Cl, Br, I, CN, NO$_2$, —OH, —OCH$_3$, —OCH$_2$CH$_3$, —O— methylene-phenyl, NH$_2$, —C(=O)OH, —C(=O)OCH$_3$, —C(=O)OCH$_2$CH$_3$, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, phenyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy; each of the methyl, ethyl, n-propyl, and i-propyl, is independently unsubstituted or substituted with 1, 2, 3 or 4 substituents, the substituent is independently selected from D, F, Cl, Br, I, CN, NO$_2$, —OH, —OCH$_3$, —OCH$_2$CH$_3$, —O-methylene-phenyl, NH$_2$, —C(=O)OH, —C(=O)OCH$_3$, —C(=O)OCH$_2$CH$_3$, —C(=O)OCH$_2$CH$_2$CH$_3$, —C(=O)OCH(CH$_3$)$_2$, —C(=O)OCH$_2$CH$_2$CH$_2$CH$_3$, —C(=O)OC(CH$_3$)$_3$, —C(=O)OCH$_2$Ph, methyl, ethyl, n-propyl, i-propyl, cyclopropyl, cyclobutyl, cyclopentyl, cyclohexyl, tetrahydrofuranyl, tetrahydrothienyl, tetrahydropyranyl, piperidinyl, morpholinyl, thiomorpholinyl, piperazinyl, furyl, pyrrolyl, pyridyl, pyrazolyl, imidazolyl, triazolyl, tetrazolyl, oxazolyl, isoxazolyl, oxadiazolyl, 1,3,5-triazinyl, thiazolyl, thienyl, pyrazinyl, pyridazinyl, pyrimidyl, trifluoromethyl, methoxy, ethoxy, methylamino, trifluoromethoxy or difluoromethoxy.

6. The compound of claim 1, wherein each of $R^8$ and $R^9$ is independently H, D, Br, I, CN, NO$_2$, —C(=O)R$^a$, —C(=O)OR$^b$, —C(=O)NR$^c$R$^d$, —OH, NH$_2$, R$^b$O—C$_{1-2}$ alkylene, R$^d$R$^c$N—C$_{1-2}$ alkylene, C$_{1-4}$ alkyl, C$_{1-4}$ haloalkyl, C$_{1-4}$ haloalkoxy, C$_{3-6}$ cycloalkyl, 3- to 6-membered heterocyclyl, C$_{6-10}$ aryl or 5- to 6-membered heteroaryl, wherein each of the C$_{1-4}$ alkyl, C$_{1-4}$ haloalkyl, C$_{1-4}$ haloalkoxy, C$_{3-6}$ cycloalkyl, 3- to 6-membered heterocyclyl, C$_{6-10}$ aryl and 5- to 6-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-4}$ alkyl, C$_{1-4}$ haloalkyl, C$_{1-4}$ alkoxy, C$_{1-4}$ alkylamino or C$_{1-4}$ haloalkoxy;

$R^7$ is H, D, F, Cl, Br, I, CN, NO$_2$, —C(=O)R$^a$, —C(=O)OR$^b$, —C(=O)NR$^c$R$^d$, —OH, NH$_2$, R$^b$O—C$_{1-2}$ alkylene, R$^d$R$^c$N—C$_{1-2}$ alkylene, C$_{1-4}$ alkyl, C$_{1-4}$ haloalkyl, C$_{1-4}$ haloalkoxy, C$_{3-6}$ cycloalkyl, 3- to 6-membered heterocyclyl, C$_{6-10}$ aryl or 5- to 6-membered heteroaryl, wherein each of the C$_{1-4}$ alkyl, C$_{1-4}$ haloalkyl, C$_{1-4}$ haloalkoxy, C$_{3-6}$ cycloalkyl, 3- to 6-membered heterocyclyl, C$_{6-10}$ aryl and 5- to 6-membered heteroaryl is independently unsubstituted or substituted with 1, 2, 3 or 4 substituents, the substituent is independently selected from D, F, Cl, Br, I, CN, NO$_2$, —OH, NH$_2$, C$_{1-4}$ alkyl, C$_{1-4}$ haloalkyl, C$_{1-4}$ alkoxy, C$_{1-4}$ alkylamino or C$_{1-4}$ haloalkoxy.

7. The compound of claim 1, wherein each $R^8$ and $R^9$ is independently H, D, Br, I, CN, NO$_2$, —C(=O)R$^a$, —C(=O)OH, —C(=O)OCH$_3$, —C(=O)OCH$_2$CH$_3$, —C(=O)NH$_2$, —OH, NH$_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, NO$_2$, —OH, NH$_2$, methyl, ethyl, n-propyl, i-propyl, trifluoromethyl, methoxy, ethoxy, methylamino, trifluoromethoxy or difluoromethoxy;

$R^7$ is H, D, F, Cl, Br, I, CN, NO$_2$, —C(=O)R$^a$, —C(=O)OH, —C(=O)OCH$_3$, —C(=O)OCH$_2$CH$_3$, —C(=O)NH$_2$, —OH, NH$_2$, methyl, ethyl, n-propyl, i-propyl, trifluoromethyl, trifluoromethoxy, cyclopropyl, cyclobutyl, cyclopentyl, cyclohexyl, 3- to 6-membered heterocyclyl, phenyl or 5- to 6-membered heteroaryl, wherein each of the methyl, ethyl, n-propyl, i-propyl, cyclopropyl, cyclobutyl, cyclopentyl, cyclohexyl, 3- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, NO$_2$, —OH, NH$_2$, methyl, ethyl, n-propyl, i-propyl, trifluoromethyl, methoxy, ethoxy, methylamino, trifluoromethoxy or difluoromethoxy.

8. The compound of claim 1, wherein R$^1$ is H, D, F, Cl, Br, I, methyl, ethyl, i-propyl, n-propyl, —C(=O)OH, —C(=O)OCH$_3$, —C(=O)OCH$_2$CH$_3$, —C(=O)R$^a$, —OC(=O)R$^a$ or —OC(=O)OR$^a$, wherein each of the methyl, ethyl, i-propyl and n-propyl is independently unsubstituted or substituted with 1, 2, 3 or 4 substituents, the substituent is independently selected from D, F, Cl, Br, I, CN, NO$_2$, —OH, NH$_2$, methyl, ethyl, n-propyl or i-propyl;

R$^2$ is F, Cl, Br, I, methyl, ethyl, i-propyl, n-propyl, —C(=O)OH, —C(=O)OCH$_3$, —C(=O)OCH$_2$CH$_3$, —C(=O)R$^a$, —OC(=O)R$^a$ or —OC(=O)OR$^a$, wherein each of the methyl, ethyl, i-propyl and n-propyl is independently unsubstituted or substituted with 1, 2, 3 or 4 substituents, the substituent is independently selected from D, F, Cl, Br, I, CN, NO$_2$, —OH, NH$_2$, methyl, ethyl, n-propyl or i-propyl.

9. The compound of claim 1, wherein each of R$^3$ and R$^4$ is independently H, D, methyl, ethyl, n-propyl, i-propyl, C$_{1-4}$ haloalkyl, cyclopropyl, cyclobutyl, 5- to 6-membered heterocyclyl, phenyl or 5- to 6-membered heteroaryl or

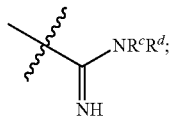

wherein each of the methyl, ethyl, n-propyl, i-propyl, C$_{1-4}$ haloalkyl, cyclopropyl, cyclobutyl, 5- to 6-membered heterocyclyl, phenyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

or, R$^3$ and R$^4$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy.

10. The compound of claim 1, wherein each R$^a$, R$^b$, R$^c$, R$^d$, R$^e$ and R$^f$ is independently H, D, —OH, trifluoromethyl, difluoromethyl, methyl, ethyl, i-propyl, n-propyl, n-butyl, t-butyl, methoxy, ethoxy, cyclopropyl, cyclobutyl, cyclopentyl, cyclohexyl, C$_{3-6}$ cycloalkyl-C$_{1-2}$alkylene, 5- to 6-membered heterocyclyl, (5- to 6-membered heterocyclyl)-C$_{1-2}$ alkylene, phenyl, phenyl-methylene, 5- to 6-membered heteroaryl or (5- to 6-membered heteroaryl)-C$_{1-2}$ alkylene, wherein each of the difluoromethyl, methyl, ethyl, i-propyl, n-propyl, n-butyl, t-butyl, methoxy, ethoxy, cyclopropyl, cyclobutyl, cyclopentyl, cyclohexyl, C$_{3-6}$ cycloalkyl-C$_{1-2}$alkylene, 5- to 6-membered heterocyclyl, (5- to 6-membered heterocyclyl)-C$_{1-2}$ alkylene, phenyl, phenyl-methylene, 5- to 6-membered heteroaryl and (5- to 6-membered heteroaryl)-C$_{1-2}$ alkylene is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy;

or, R$^c$ and R$^d$ together with the nitrogen atom to which they are attached, form 5- to 6-membered heterocyclyl or 5- to 6-membered heteroaryl, wherein each of the 5- to 6-membered heterocyclyl and 5- to 6-membered heteroaryl is independently unsubstituted or substituted with 1, 2, 3 or 4 substituents, the substituent is independently selected from D, F, Cl, Br, I, CN, —OH, NH$_2$, methyl, ethyl, n-propyl, i-propyl, trifluoromethyl, methoxy or ethoxy.

11. The compound of claim 1 having Formula (II):

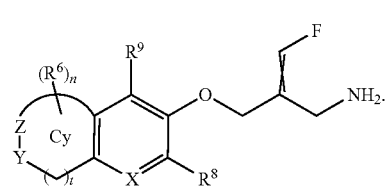

(II)

12. A compound having one of the following structures:

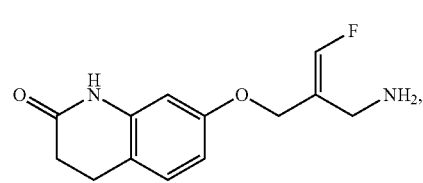

(1)

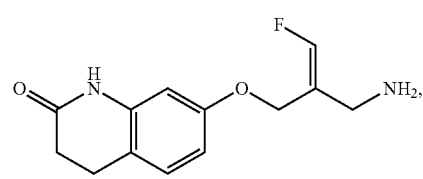

(2)

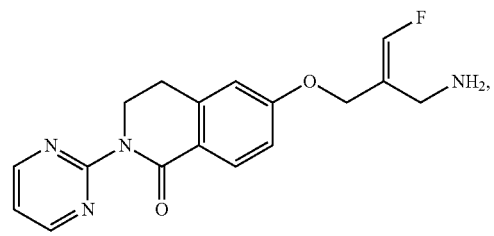

(7)

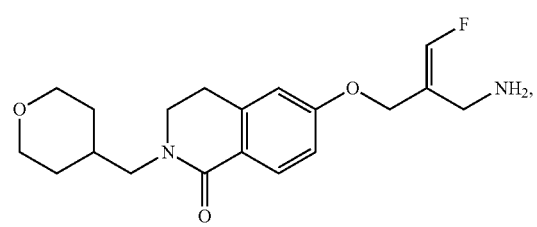

(10)

(11)
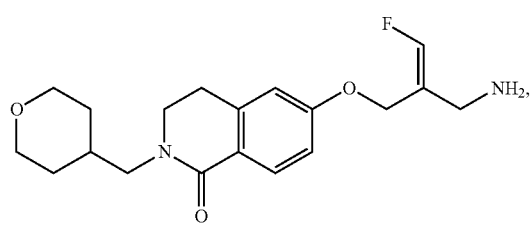
(12)
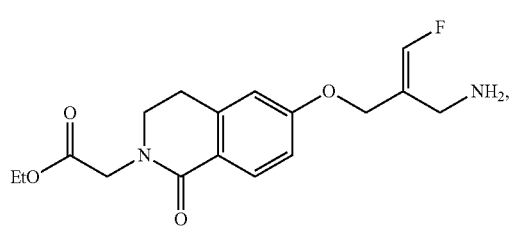
(13)
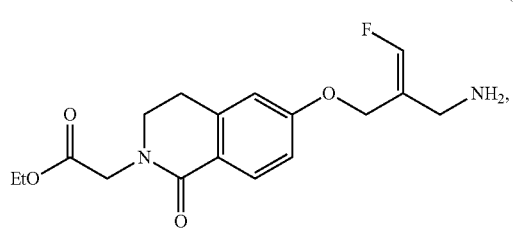
(16)
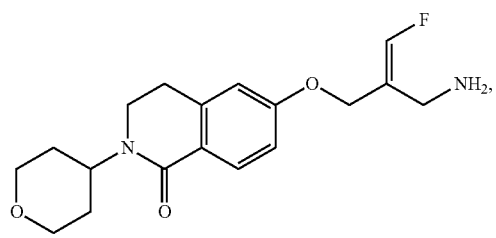
(17)
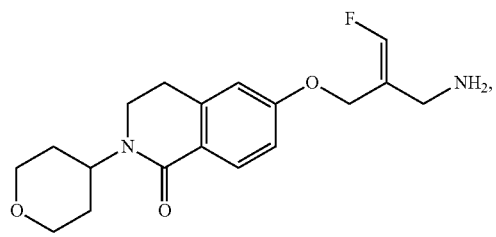
(18)
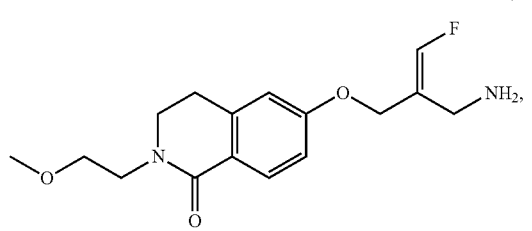
(19)
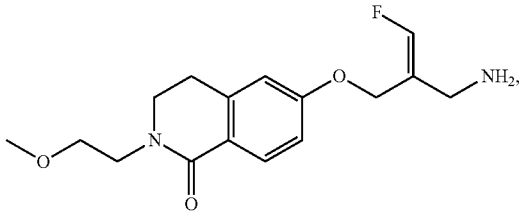
(20)
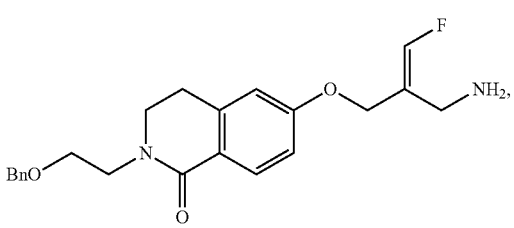
(21)
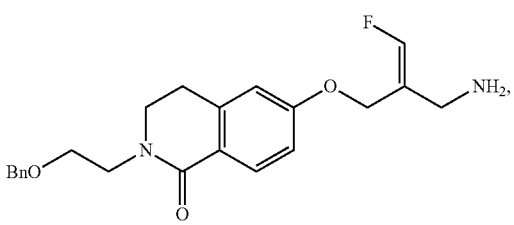
(28)
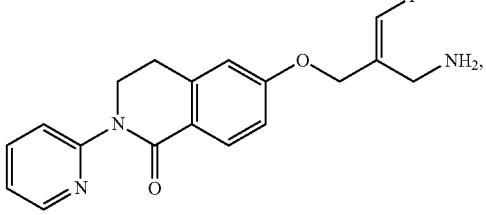
(29)
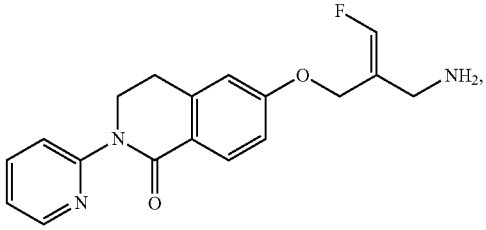
(30)
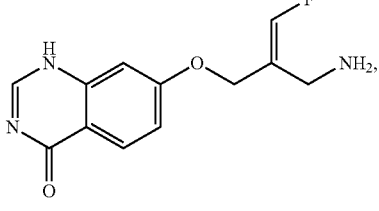
(31)
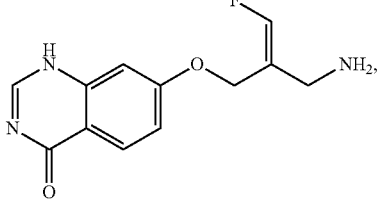

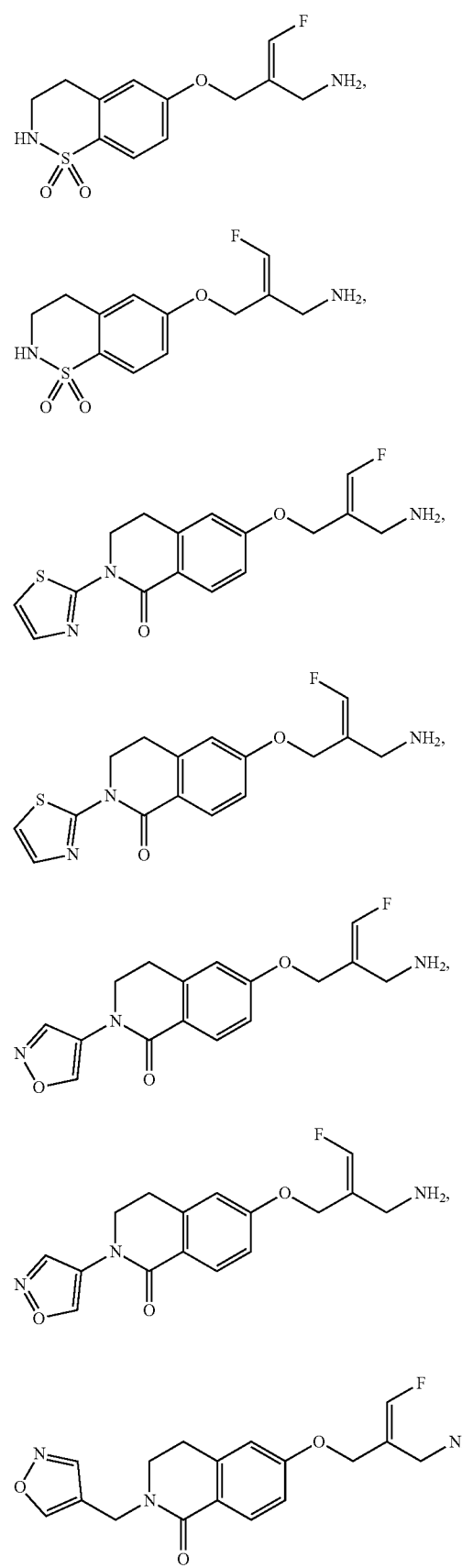
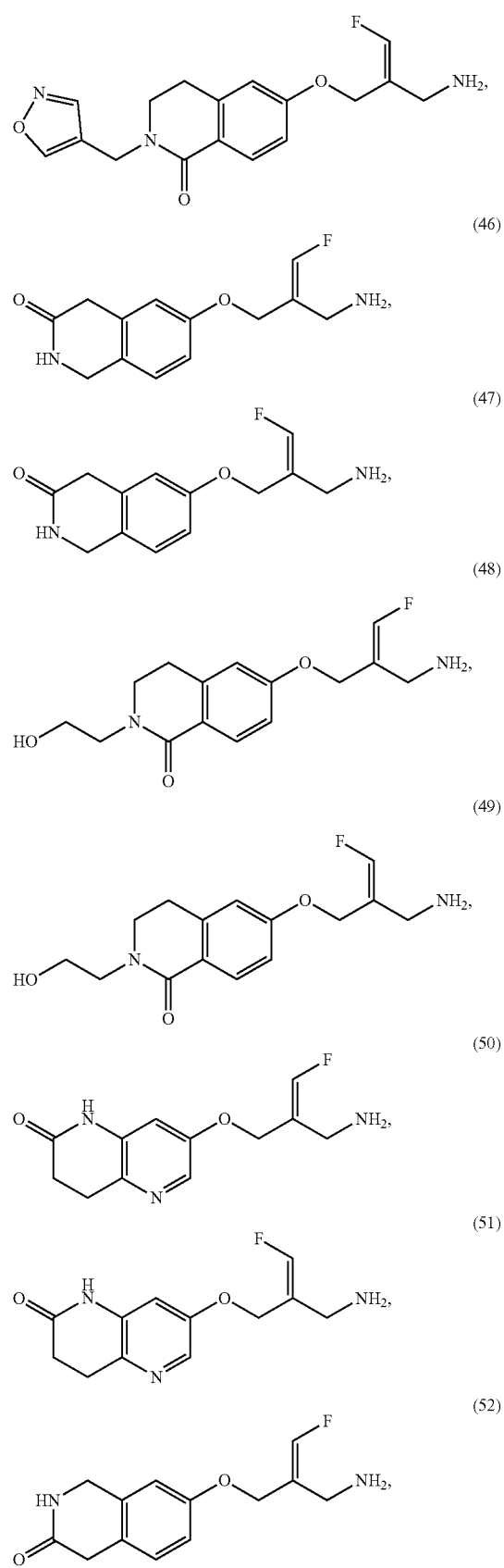

(53) 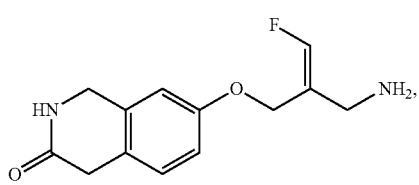
(54) 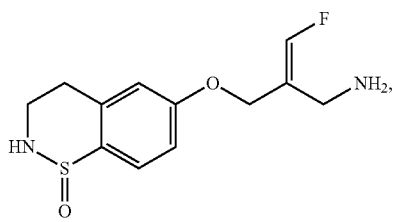
(55) 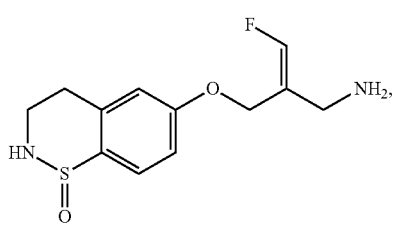
(56) 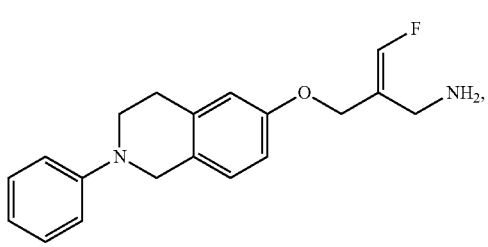
(57) 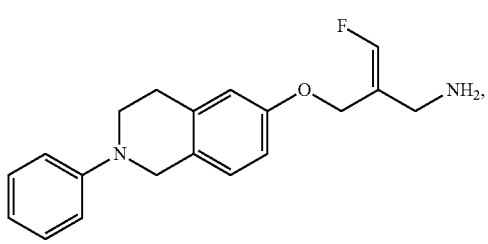
(58) 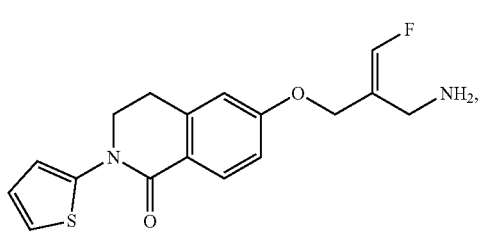
(59) 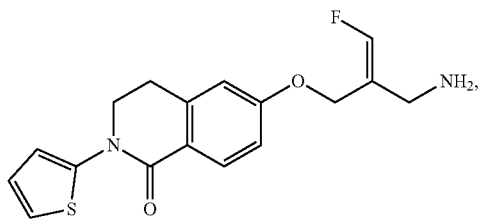
(60) 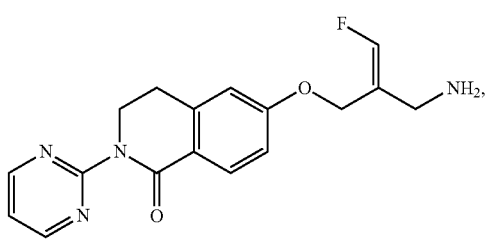
(61) 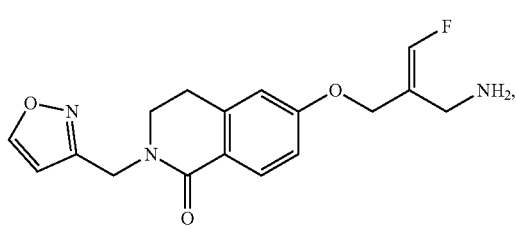
(62) 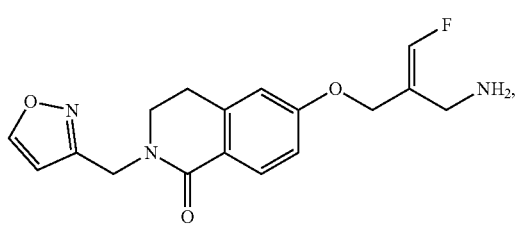
(63) 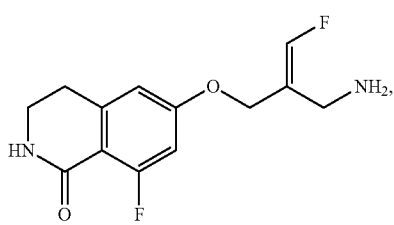
(64) 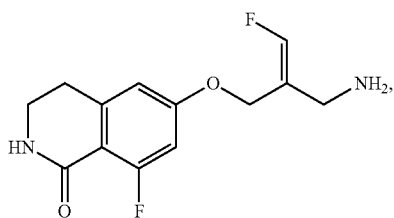
(71) 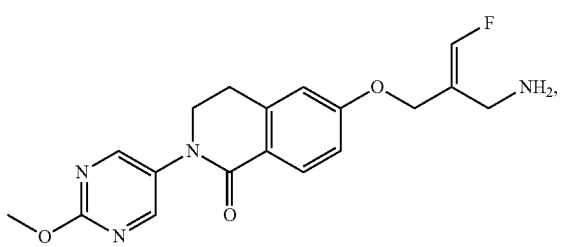

-continued

-continued (85)

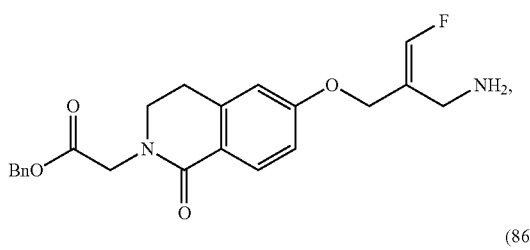

(86)

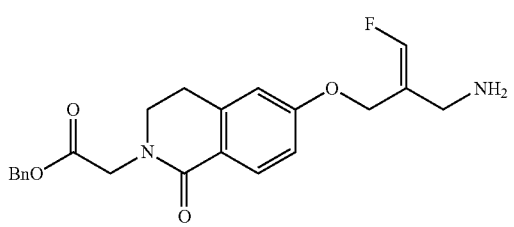

or a stereoisomer, a geometric isomer, a tautomer, an N-oxide, a solvate, a pharmaceutically acceptable salt or a prodrug thereof.

13. The compound of claim 1, wherein the pharmaceutically acceptable salt is hydrochloride, hydrobromide or mesylate.

14. A pharmaceutical composition comprising the compound of claim 1, and a pharmaceutically acceptable carrier, excipient, adjuvant, vehicle or a combination thereof.

15. A method of inhibiting SSAO/VAP-1, or treating or lessening a disease related to SSAO/VAP-1 protein or regulated by SSAO/VAP-1 in a subject comprising administering to the subject a therapeutically effective amount of the compound according to claim 1.

16. The method of claim 15, wherein the disease related to SSAO/VAP-1 protein or regulated by SSAO/VAP-1 is inflammation and/or a disease related inflammation, diabetes and/or a disease related diabetes, a mental disorder, an ischemic disease, a vascular disease, fibrosis or tissue transplant rejection.

17. The method of claim 16, wherein the inflammation and/or a disease related inflammation is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis; the diabetes and/or a disease related diabetes is type I diabetes, type II diabetes, X syndrome, diabetic retinopathy, diabetic nephropathy, diabetic neuropathy or diabetic macular edema; the mental disorder is severe depression, bipolar depression or attention deficit hyperactivity disorder; the ischemic disease is apoplexia and/or a complication thereof, myocardial infarction and/or a complication thereof or damage of inflammatory cells to tissues after apoplexia; the fibrosis is hepatic fibrosis, cystic fibrosis, renal fibrosis, idiopathic pulmonary fibrosis or radiation-induced fibrosis; the vascular disease is atherosclerosis, chronic heart failure or congestive heart failure.

18. The method of claim 17, wherein the arthritis is osteoarthritis, rheumarthritis, rheumatoid arthritis or juvenile rheumatoid arthritis; the systemic inflammatory response syndrome is systemic inflammatory sepsis; the inflammatory bowel disease is irritable bowel syndrome; the hepatopathy is a liver autoimmune disease, autoimmune hepatitis, primary biliary cirrhosis, sclerosing cholangitis, autoimmune cholangitis, an alcoholic liver disease or a non-alcoholic fatty liver disease; the respiratory disease is asthma, acute lung injury, acute respiratory distress syndrome, lung inflammation, a chronic obstructive pulmonary disease, bronchitis or bronchiectasis; the eye disease is uveitis, iritis, retinitis, autoimmune ophthalmia, inflammation driven by angiogenesis and/or lymphogenesis, macular degeneration; the skin disease is contact dermatitis, skin inflammation, psoriasis or eczema; the neuritis is Parkinson's disease, Alzheimer's disease, vascular dimentia, multiple sclerosis, chronic multiple sclerosis;

wherein the non-alcoholic fatty liver disease is nonalcoholic simple fatty liver, nonalcoholic steatohepatitis, cryptogenic cirrhosis or primary liver cancer related to nonalcoholic fatty liver disease.

19. A method of inhibiting SSAO/VAP-1, or treating or lessening a disease related to SSAO/VAP-1 protein or regulated by SSAO/VAP-1 in a subject comprising administering to the subject a therapeutically effective amount of the pharmaceutical composition according to claim 14.

20. The method of claim 19, wherein the disease related to SSAO/VAP-1 protein or regulated by SSAO/VAP-1 is inflammation and/or a disease related inflammation, diabetes and/or a disease related diabetes, a mental disorder, an ischemic disease, a vascular disease, fibrosis or tissue transplant rejection.

21. The method of claim 20, wherein the inflammation and/or a disease related inflammation is arthritis, systemic inflammatory response syndrome, pyemia, synovitis, a Crohn's disease, ulcerative colitis, an inflammatory bowel disease, hepatopathy, a respiratory disease, an eye disease, a skin disease or neuritis; the diabetes and/or a disease related diabetes is type I diabetes, type II diabetes, X syndrome, diabetic retinopathy, diabetic nephropathy, diabetic neuropathy or diabetic macular edema; the mental disorder is severe depression, bipolar depression or attention deficit hyperactivity disorder; the ischemic disease is apoplexia and/or a complication thereof, myocardial infarction and/or a complication thereof or damage of inflammatory cells to tissues after apoplexia; the fibrosis is hepatic fibrosis, cystic fibrosis, renal fibrosis, idiopathic pulmonary fibrosis or radiation-induced fibrosis; the vascular disease is atherosclerosis, chronic heart failure or congestive heart failure.

22. The method of claim 21, wherein the arthritis is osteoarthritis, rheumarthritis, rheumatoid arthritis or juvenile rheumatoid arthritis; the systemic inflammatory response syndrome is systemic inflammatory sepsis; the inflammatory bowel disease is irritable bowel syndrome; the hepatopathy is a liver autoimmune disease, autoimmune hepatitis, primary biliary cirrhosis, sclerosing cholangitis, autoimmune cholangitis, an alcoholic liver disease or a non-alcoholic fatty liver disease; the respiratory disease is asthma, acute lung injury, acute respiratory distress syndrome, lung inflammation, a chronic obstructive pulmonary disease, bronchitis or bronchiectasis; the eye disease is uveitis, iritis, retinitis, autoimmune ophthalmia, inflammation driven by angiogenesis and/or lymphogenesis, macular degeneration; the skin disease is contact dermatitis, skin inflammation, psoriasis or eczema; the neuritis is Parkinson's disease, Alzheimer's disease, vascular dimentia, multiple sclerosis, chronic multiple sclerosis;

wherein the non-alcoholic fatty liver disease is nonalcoholic simple fatty liver, nonalcoholic steatohepatitis, cryptogenic cirrhosis or primary liver cancer related to nonalcoholic fatty liver disease.

* * * * *